United States Patent
Wong et al.

(10) Patent No.: US 9,840,522 B2
(45) Date of Patent: Dec. 12, 2017

(54) MULTI-MODAL BIOPROBE FOR BLADDER CANCER IMAGING AND PHOTODYNAMIC THERAPY

(71) Applicant: Hong Kong Baptist University, Hong Kong (HK)

(72) Inventors: Ka Leung Wong, Hong Kong (HK); Wai Kwok Wong, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 15/352,561

(22) Filed: Nov. 15, 2016

(65) Prior Publication Data

US 2017/0107238 A1   Apr. 20, 2017

Related U.S. Application Data

(63) Continuation-in-part of application No. 14/934,140, filed on Nov. 5, 2015, now Pat. No. 9,522,925.

(60) Provisional application No. 62/404,222, filed on Oct. 5, 2016, provisional application No. 62/077,312, filed on Nov. 9, 2014.

(51) Int. Cl.
*C07F 5/00*    (2006.01)
*A61K 41/00*   (2006.01)
*A61N 5/06*    (2006.01)

(52) U.S. Cl.
CPC .......... *C07F 5/003* (2013.01); *A61K 41/0071* (2013.01); *A61N 5/062* (2013.01)

(58) Field of Classification Search
CPC ...... C07F 5/003; A61N 5/062; A61K 41/0071
See application file for complete search history.

(56) References Cited

PUBLICATIONS

Zhang et. al., "In vivo selective cancer-tracking gadolinium eradicator as new-generation photodynamic therapy agent" PNAS, 2014, E5492-E5497.
Zhang et. al., "Identification of a bladder cancer-specific ligand using a combinatorial chemistry approach" Urologic Oncology: Seminars and Original Investigations 30 (2012) 635-645.

*Primary Examiner* — Joseph R Kosack
(74) *Attorney, Agent, or Firm* — Spruson & Ferguson (HK)

(57) ABSTRACT

The present invention relates to a new generation of PDT agents based on porphyrin-lanthanide complexes with specific functional groups which can specifically localize on particular tumors, and their PDT processes can be monitored via NIR emission from erbium. In particular, the present invention provides a multi-modal lanthanide-porphyrin PDT agent (Er—$R_3$) that are capable of killing the bladder tumor cells selectivity via $^1O_2$ from porphyrin moiety and affording the fluorescence imaging simultaneously upon Er—$R_3$ binding with the integrin $\alpha_v\beta_3$ isoform in bladder cancer cells.

18 Claims, 73 Drawing Sheets a)

Group 1: Yb-N+laser    Group 3: Yb-RhB+laser
Group 2: Gd-N+laser    Group 4: Gd-Rhb+laser b)

C)

(D)

| Photo-IC$_{50}$/mM (Dark-IC$_{50}$/mM) | T24 | HeLa | MRC-5 |
|---|---|---|---|
| Er-R$_1$ | 38 (817) | 271 (937) | 489 (922) |
| Yb-R$_1$ | 63 (1414) | 287 (1297) | 264 (1382) |
| Er-R$_2$ | 35 (932) | 392 (1184) | 497 (1073) |
| Yb-R$_2$ | 60 (1551) | 499 (1422) | 434 (1601) |
| Er-R$_3$ | 31 (1044) | 343 (1302) | 345 (1127) |
| Yb-R$_3$ | 56 (1766) | 393 (1683) | 473 (1884) |
| ALA | 260 (929) | 375 (1043) | 744 (1547) |

(G)

(A)

(C)

(D)

C)

$R_n=R_1:\{Ahx\}$-(D-Cys)-Gln-Asp-Gly-Arg-Met-Gly-Phe-(D-Cys)

D)

$R_n$=N:

SEQUENCE LISTING

```
<160> NUMBER OF SEQ ID NOS: 5

<210> SEQ ID NO 1
<211> LENGTH: 10
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: DISULFID
<222> LOCATION: (2)..(10)
<223> OTHER INFORMATION: The side chain of C in position two taken
      together with the side chain of C in position ten form a disulfide
      bond
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: MISC_FEATURE
<222> LOCATION: (10)..(10)
<223> OTHER INFORMATION: C in position ten is a D-amino acid

<400> SEQUENCE: 1

Xaa Cys Gly Asp Gly Arg Met Gly Phe Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide sequence incorporating non-naturally
``` occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: MISC_FEATURE
<222> LOCATION: (2)..(2)
<223> OTHER INFORMATION: C in position two is a D-amino acid
<220> FEATURE:
<221> NAME/KEY: DISULFID
<222> LOCATION: (2)..(10)
<223> OTHER INFORMATION: The side chain of C in position two taken
      together with the side chain of C in position ten form a disulfide
      bond
<220> FEATURE:
<221> NAME/KEY: MISC_FEATURE
<222> LOCATION: (10)..(10)
<223> OTHER INFORMATION: C in position ten is a D-amino acid

<400> SEQUENCE: 2

Xaa Cys Gly Arg Leu Lys Glu Lys Lys Cys
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: Xaa in position one is 6-aminocaproic acid
<220> FEATURE:
<221> NAME/KEY: MISC_FEATURE
<222> LOCATION: (4)..(4)
<223> OTHER INFORMATION: R in position four is a D-amino acid
<220> FEATURE:
<221> NAME/KEY: MISC_FEATURE
<222> LOCATION: (6)..(6)
<223> OTHER INFORMATION: Xaa in position six is 6-aminocaproic acid
<220> FEATURE:
<221> NAME/KEY: MISC_FEATURE
<222> LOCATION: (7)..(7)
<223> OTHER INFORMATION: C in position seven is a D-amino acid
<220> FEATURE:
<221> NAME/KEY: DISULFID
<222> LOCATION: (7)..(15)
<223> OTHER INFORMATION: The side chain of C in position seven taken
      together with the side chain of C in position fifteen form a
      disulfide bond
<220> FEATURE:
<221> NAME/KEY: MISC_FEATURE
<222> LOCATION: (15)..(15)
<223> OTHER INFORMATION: C in position fifteen is a D-amino acid

<400> SEQUENCE: 3

Xaa Arg Arg Arg Lys Xaa Cys Gly Arg Leu Lys Glu Lys Lys Cys
1               5                   10                  15

<210> SEQ ID NO 4
<211> LENGTH: 4
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<223> OTHER INFORMATION: The R is the second position is a D-amino acid
<220> FEATURE:
<221> NAME/KEY: MISC_FEATURE
<223> OTHER INFORMATION: The R in the second position is a D-amino acid

```
<400> SEQUENCE: 4

Arg Arg Arg Lys
1

<210> SEQ ID NO 5
<211> LENGTH: 9
<212> TYPE: PRT
<213> ORGANISM: Artificial Sequence
<220> FEATURE:
<223> OTHER INFORMATION: Peptide sequence incorporating non-naturally
      occuring amino acids synthesized in the lab
<220> FEATURE:
<221> NAME/KEY: MISC_FEATURE
<222> LOCATION: (1)..(1)
<223> OTHER INFORMATION: C in position one is a D-amino acid
<220> FEATURE:
<221> NAME/KEY: DISULFID
<222> LOCATION: (1)..(9)
<223> OTHER INFORMATION: The side chain of C in position one taken
      together with the side chain of C in position nine form a
      disulfide bond
<220> FEATURE:
<221> NAME/KEY: MISC_FEATURE
<222> LOCATION: (9)..(9)
<223> OTHER INFORMATION: C in position nine is a D-amino acid

<400> SEQUENCE: 5

Cys Gly Arg Leu Lys Glu Lys Lys Cys
1               5
```

MULTI-MODAL BIOPROBE FOR BLADDER CANCER IMAGING AND PHOTODYNAMIC THERAPY

CROSS-REFERENCE TO RELATED APPLICATIONS

The present application claims the benefit of U.S. Provisional Application No. 62/404,222 filed on Oct. 5, 2016, and is also a continuation-in-part application of U.S. non-provisional application Ser. No. 14/934,140 filed on Nov. 5, 2015 which claims priority from U.S. provisional application No. 62/077,312 filed on Nov. 9, 2014. All of the foregoing applications are hereby incorporated by reference in their entirety.

TECHNICAL FIELD

The present invention relates to a new generation of photodynamic therapy agents based on porphyrin-lanthanide complexes, and the photodynamic therapy processes that can be monitored via NIR emission from erbium. In particular, the present invention provides a multi-modal lanthanide-porphyrin photodynamic therapy agent that are capable of killing bladder tumor cells.

BACKGROUND

Photodynamic Therapy (PDT) is emerging as a novel cancer treatment modality to help patients to live longer and to improve their quality of life without causing long-term side-effects. PDT is still failing to obtain deserved popularity in society due to current technological constraints and absence of practical advances as it is only offered in some treatment center and studied with little clinical trials. Recently, a renaissance of PDT has commenced with its wide recognition as a valuable treatment option for localized cancers (i.e. non-metastatic cancers), as well as pre-cancers of the skin and in the mouth, after three PDT photosensitizing agents have been approved by the United States Food and Drug Administration (FDA), e.g. Aminolevulinic acid (ALA). Nevertheless, conventional PDT still has from several limitations and drawbacks: (i) it is only able to treat diseased areas where light can be reached, that is, on or just under the skin; (ii) currently-used PDT drugs could leave people very sensitive to light, and therefore special precautions must be taken after the drugs are put in or on the body; (iii) adverse in-vitro/in-vivo reactions occur due to the variation in physiological conditions and notched distribution of cytotoxic singlet oxygen; and (iv) non-specific therapeutic nature may jeopardize normal cells during PDT treatment.

In this regard, porphyrin-based moieties, another novel class of promising PDT agents, have been investigated extensively by scientists worldwide to develop photodynamic therapy can be available and effective to other types of cancers and diseases particularly in the skin, bladder, mouth, and brain. As far as the light penetration depth for the singlet oxygen ($^1O_2$) generation is concerned, several porphyrin moieties have successfully showed the possibility to achieve near-infrared (NIR) excitation (via multi-photon/Second harmonic generation). NIR photons can penetrate deep and emit expeditiously from tissues without causing cell damage with their strong two-photon absorption properties being at ~860 nm. In the literature and referenced patent filing, a porphyrinato metal complex is disclosed which can serve as an in-vivo anti-cancer torpedo equipped with visible-to-NIR emission for imaging and discriminating radar for tumor cell selectivity, and $^1O_2$ explosive ammunition. However, the cancer selectivity of these PDT agents are still not yet solved and there exists a need to provide PDT agents with better cancer selectivity.

It is an objective of the present invention to provide for PDT probes that can specifically localize on particular tumors, and their PDT processes can be monitored via NIR emission.

SUMMARY OF THE INVENTION

In a first aspect of the present invention there is provided a composition for photodynamic therapy and imaging of cancer cells comprising gadolinium porphyrinate complex (Gd—N) of Formula (I):

Formula (I)

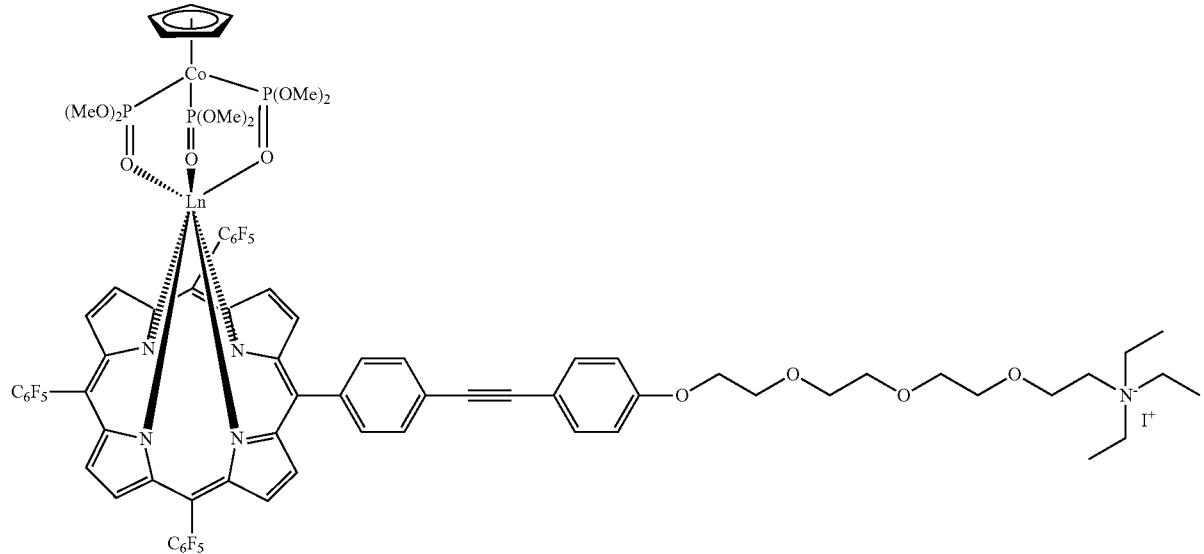

wherein Ln=Gd, or a pharmaceutically acceptable salt thereof.

In a first embodiment of the first aspect of the present invention there is provided a composition for photodynamic therapy and imaging of cancer cells wherein the cancer cells have anionic cell membranes.

In a second aspect of the present invention there is provided a method of photodynamic therapy and imaging of cancer cells comprising administering to a subject in need thereof the composition according to the first aspect of the present invention and irradiating a radiation source to the cancer cells in the subject in need thereof.

In a first embodiment of the second aspect of the present invention, the administration of said composition is performed intravenously or by injection to site of said cancer cells.

In a second embodiment of the second aspect of the present invention there is provided a method of photodynamic therapy and imaging of cancer cells comprising administering to a subject in need thereof a composition according to the first aspect of the present invention and irradiating the cancer cells in the subject in need thereof with a radiation source, wherein said radiation source is a light source of about 860 nm in wavelength.

In a third aspect of the present invention there is provided a method of synthesizing the compound of Formula (I) comprising steps according to scheme 1:

Scheme 1

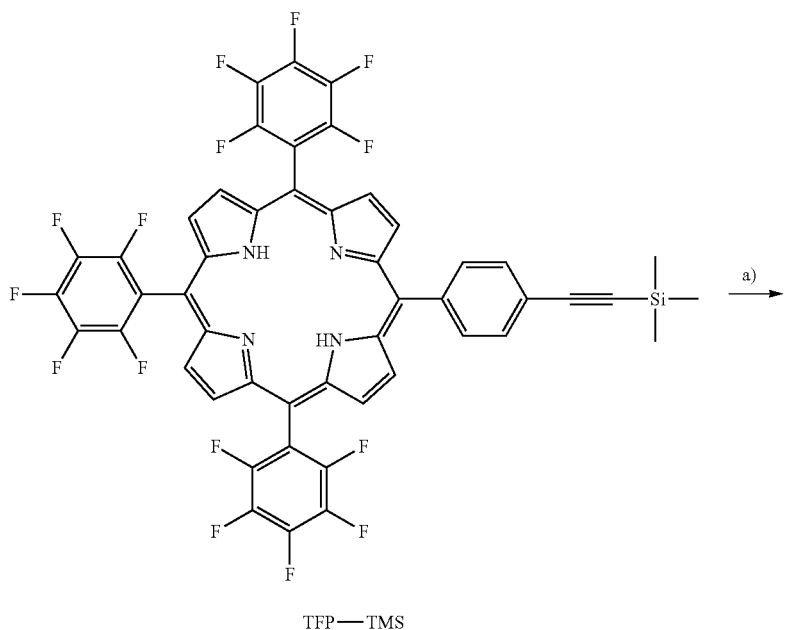

TFP—TMS

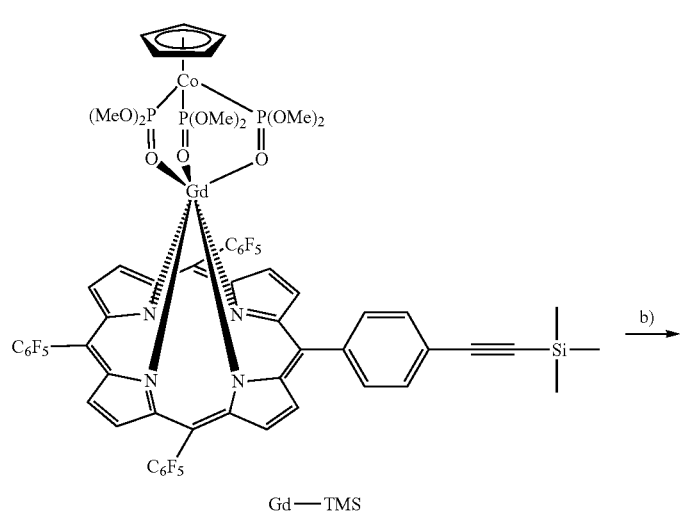

Gd—TMS

-continued

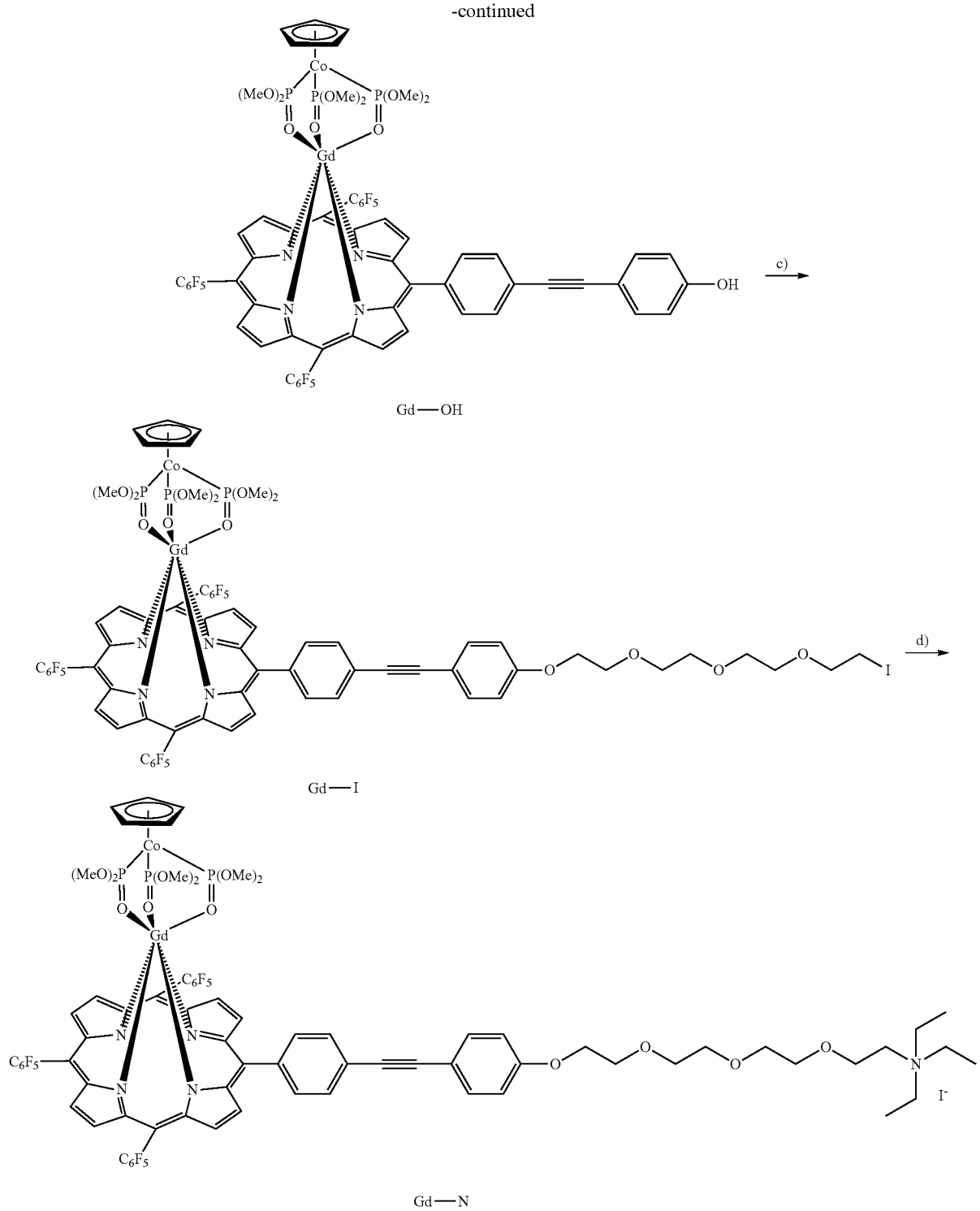

a) (i) Gd[N(SiMe$_3$)$_2$]$_3$·[LiCl(THF)$_3$]$_x$, toluene, reflux, 12 h; (ii) Na{(η$^5$-C$_5$H$_5$)Co[P(=O)(OMe)$_2$]$_3$}, toluene, rt, 1 h; b) (i) TBAF (THF, 1M), CH$_2$Cl$_2$, rt, 30 min;
(ii) a) 4-iodophenol, Pd(PPh$_3$)$_4$, CuI, THF, NEt$_3$, 40° C., 12 h; c) Tetraethyleneglycol diiodide, DMF, K$_2$CO$_3$, 80° C., 8 h; d) Triethylamine, DMF, 85° C., 24 h.

wherein
Step a): Removing solvent from a solution of Gd[N(SiMe$_3$)$_2$]$_3$·[Li(THF)$_3$Cl]$_x$ to form a precipitation of LiCl; adding dichloromethane (CH$_2$Cl$_2$) to the precipitation of LiCl to form a first mixture wherein the first mixture is centrifuged to separate a clear layer from said first mixture; transferring the clear layer to a porphyrin free base trifluoropropyl-trimethoxysilane (TFP-TMS) dissolved in toluene solution to form a second mixture; refluxing the second mixture until the porphyrin free base is coordinated with a metal ion to form a refluxed second mixture; cooling the refluxed second mixture to room temperature to form a cooled refluxed second mixture; adding dry Na{(η$^5$-C$_5$H$_5$)Co[P(=O)(OMe)$_2$]$_3$} to the cooled refluxed second mixture to form a third mixture; stirring the third mixture; removing solvent from the third mixture to form a first residue; dissolving the first residue in CH$_2$Cl$_2$ to form a fourth mixture; filtering and column chromatographing the fourth mixture using CH$_2$Cl$_2$/Hexane as eluent to produce Gd-TMS; Step b): Adding Tetrabutylammonium fluoride to a solution of the Gd-TMS in CH$_2$Cl$_2$, and stirring the Gd-TMS solution to create a chemical reaction; after completion of the chemical reaction, the solution is passed through column chromatography to form a fifth mixture; removing solvent

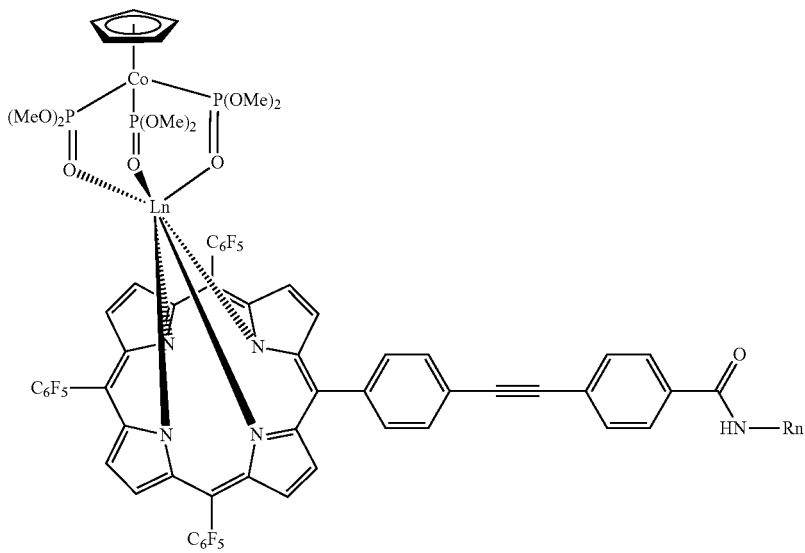

from the fifth mixture to obtain an intermediate; dissolving the intermediate and 4-iodophenol in dry tetrahydrofuran and triethylamine to form a sixth mixture; mixing the sixth mixture with nitrogen to form a nitrogenized sixth mixture; adding Pd(PPh$_3$)$_4$ and CuI to said nitrogenized sixth mixture to form a seventh mixture; stirring the seventh mixture at least 35° C. for at least 10 hours under a nitrogen atmosphere to produce a stirred seventh mixture; removing solvent from the stirred seventh mixture to produce a second residue; purifying the second residue using column chromatography with CH$_2$Cl$_2$/Methanol as eluent to produce Gd—OH; Step c): Adding anhydrous K$_2$CO$_3$ to a solution of Gd—OH and tetraethyleneglycol diiodide in dry N,N-Dimethylmethanamide to form an eighth mixture; heating said eighth mixture to at least 80° C. for at least 8 hours under a nitrogen atmosphere to form a heated eighth mixture; removing solvent from the heated eighth mixture to form a first crude product; purifying the first crude product using column chromatography eluented by CH$_2$Cl$_2$/CH$_3$OH to produce Gd—I, and Step d): Adding anhydrous Net$_3$ to a solution of Gd—I in dry DMF to form a ninth mixture; heating the ninth mixture to at least 85° C. for at least 24 hours under nitrogen atmosphere to form a heated ninth mixture; removing the solvent from the heated ninth mixture to obtain a second crude product; purifying the second crude product using column chromatography with CH$_2$Cl$_2$/CH$_3$OH as the eluent to remove unreacted Gd—I and other impurities, and further purifying with CH$_2$Cl$_2$/CH$_3$OH as the eluent to obtain Gd—N.

In a fourth aspect of the present invention there is provided a multi-modal lanthanide-porphyrin PDT agent (Er—R$_3$) that are capable of killing bladder tumor cells selectivity via $^1$O$_2$ from porphyrin moiety and affording fluorescence imaging simultaneously upon Er—R$_3$ binding with integrin α$_v$β$_3$ isoform in bladder cancer cells.

In a fifth aspect of the present invention there is provided a composition for photodynamic therapy and imaging of cancer cells comprising Erbium porphyrin based complexes or Ytterbium porphyrin based complexes or Gadolinium porphyrin based complexes represented by the molecular formula:

wherein Ln is Er, Yb, or Gd; and

R$_n$ is a polypeptide having an amino acid sequence selected from the group consisting of SEQ ID NO: 1; SEQ ID NO: 2; and SEQ ID NO: 3; or a water-soluble porphyrin-based Gadolinium complex represented by a molecular formula selected from the group consisting of Gd$_1$, Gd$_2$, Gd$_3$, Gd$_4$, and Gd$_5$:

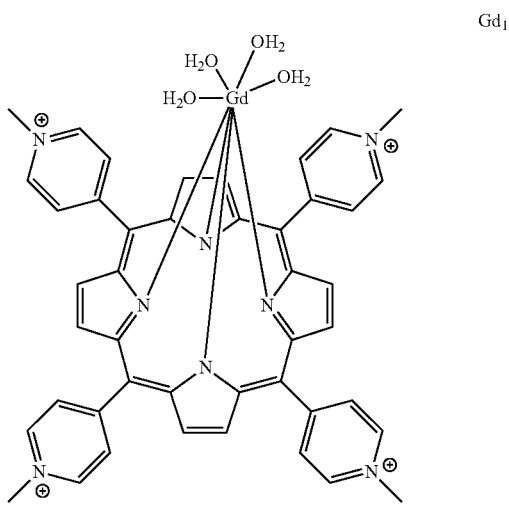

Gd$_1$

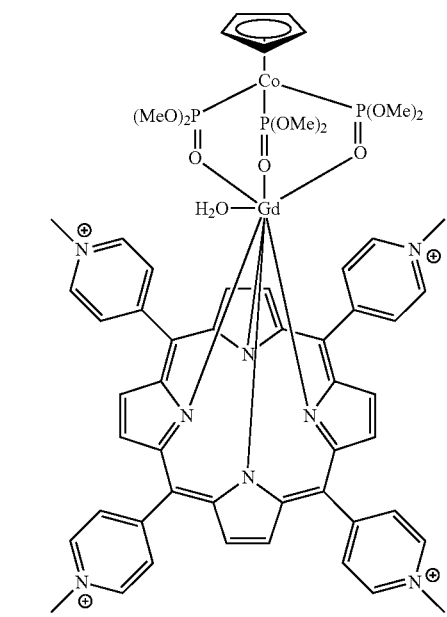
Gd₂
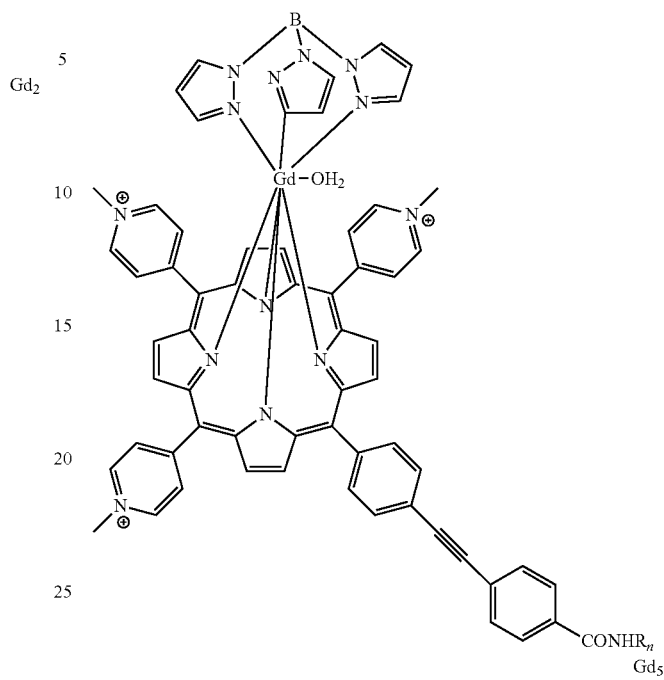
Gd₄
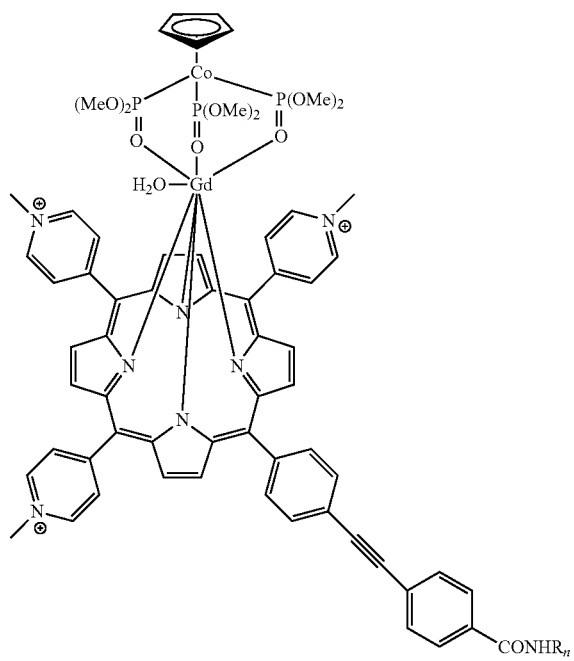
Gd₃
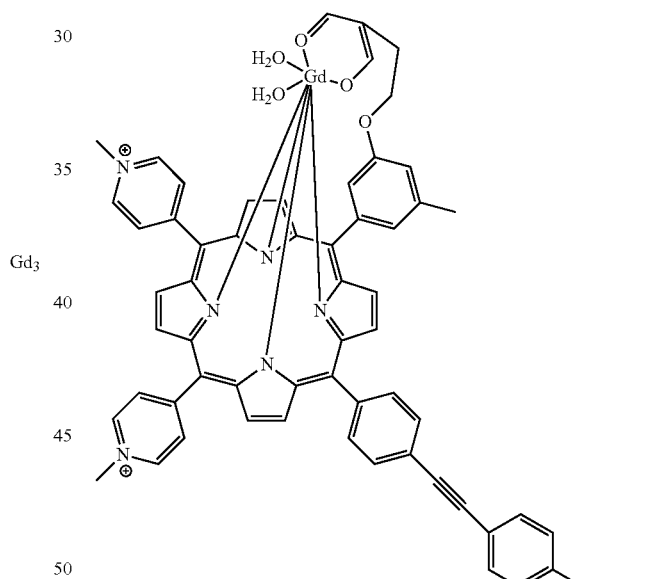
Gd₅
wherein R$_n$ is
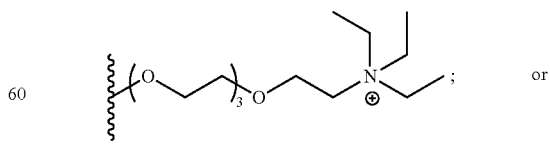
; or
a polypeptide having an amino acid sequence selected from the group consisting of SEQ ID NO: 1; SEQ ID NO: 2; and SEQ ID NO: 3 or a pharmaceutically acceptable salt thereof.

In a first embodiment of the fifth aspect of the present invention there is provided a composition wherein the Erbium porphyrin based complexes are conjugated with integrin $\alpha_v\beta_3$ isoform-specific peptides.

In a second embodiment of the fifth aspect of the present invention there is provided a composition wherein the Erbium porphyrin based complexes are conjugated with peptide RrRk (SEQ ID NO: 4).

In a third embodiment of the fifth aspect of the present invention there is provided a composition wherein the Erbium porphyrin based complexes are conjugated with integrin isoform specific peptide sequence (-cGRLKEKKc-) (SEQ ID NO: 5).

In a fourth embodiment of the fifth aspect of the present invention there is provided a composition wherein the Erbium porphyrin based complexes are conjugated with both peptide RrRk (SEQ ID NO: 4) and integrin $\alpha_v\beta_3$ isoform specific peptide sequence (-cGRLKEKKc-) (SEQ ID NO: 5).

In a fifth embodiment of the fifth aspect of the present invention there is provided a composition comprising the Erbium porphyrin based complex represented by the molecular formula:

In a sixth aspect of the present invention there is provided a method of photodynamic therapy and imaging of cancer cells comprising administering to a subject in need thereof the composition and irradiating the cancer cells in the subject in need thereof with a radiation source.

In a first embodiment of the sixth aspect of the present invention there is provided a method wherein the administration of said composition is performed intravenously or by injection to site of said cancer cells.

In a second embodiment of the sixth aspect of the present invention there is provided a method wherein said radiation source is a light source with a wavelength in the Q band of porphyrin.

In a third embodiment of the sixth aspect of the present invention there is provided a method wherein said radiation source is a light source with a wavelength beyond 550 nm or is at 860 nm.

In a fourth embodiment of the sixth aspect of the present invention there is provided a method wherein the imaging is performed using fluorescent imaging, NIR imaging or MRI imaging In a fifth embodiment of the sixth aspect of the present invention there is provided a method wherein the imaging is

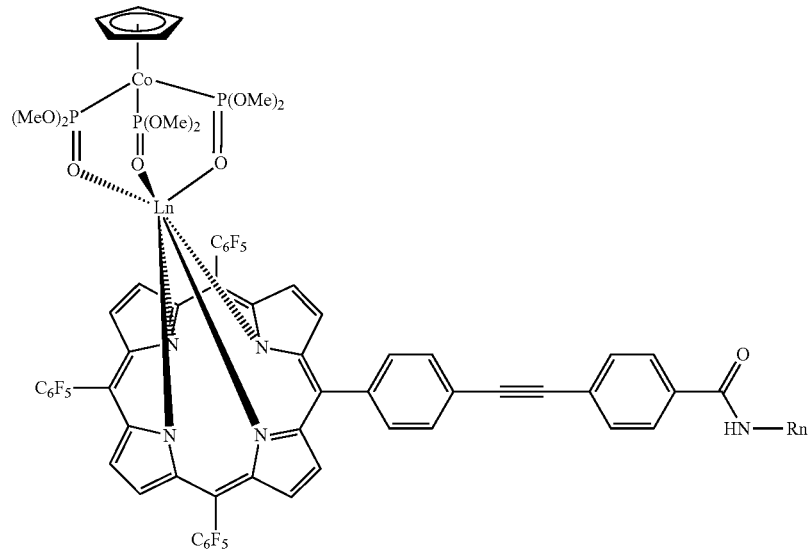

wherein Ln is Er and $R_n$ is a polypeptide having an amino acid sequence of SEQ ID NO: 3.

In a sixth embodiment of the fifth aspect of the present invention there is provided a composition wherein the cancer cells comprising of bladder cancer cells, cervical cancer cells and lung cancer.

performed using MRI imaging when Ln is Gd, or Ln is $Gd_1$, $Gd_2$, $Gd_3$, $Gd_4$, or $Gd_5$.

In a seventh aspect of the present invention there is provided a method of synthesizing the composition according to claim 1 wherein Ln=Er or Ln=Yb comprising steps according to the following scheme:

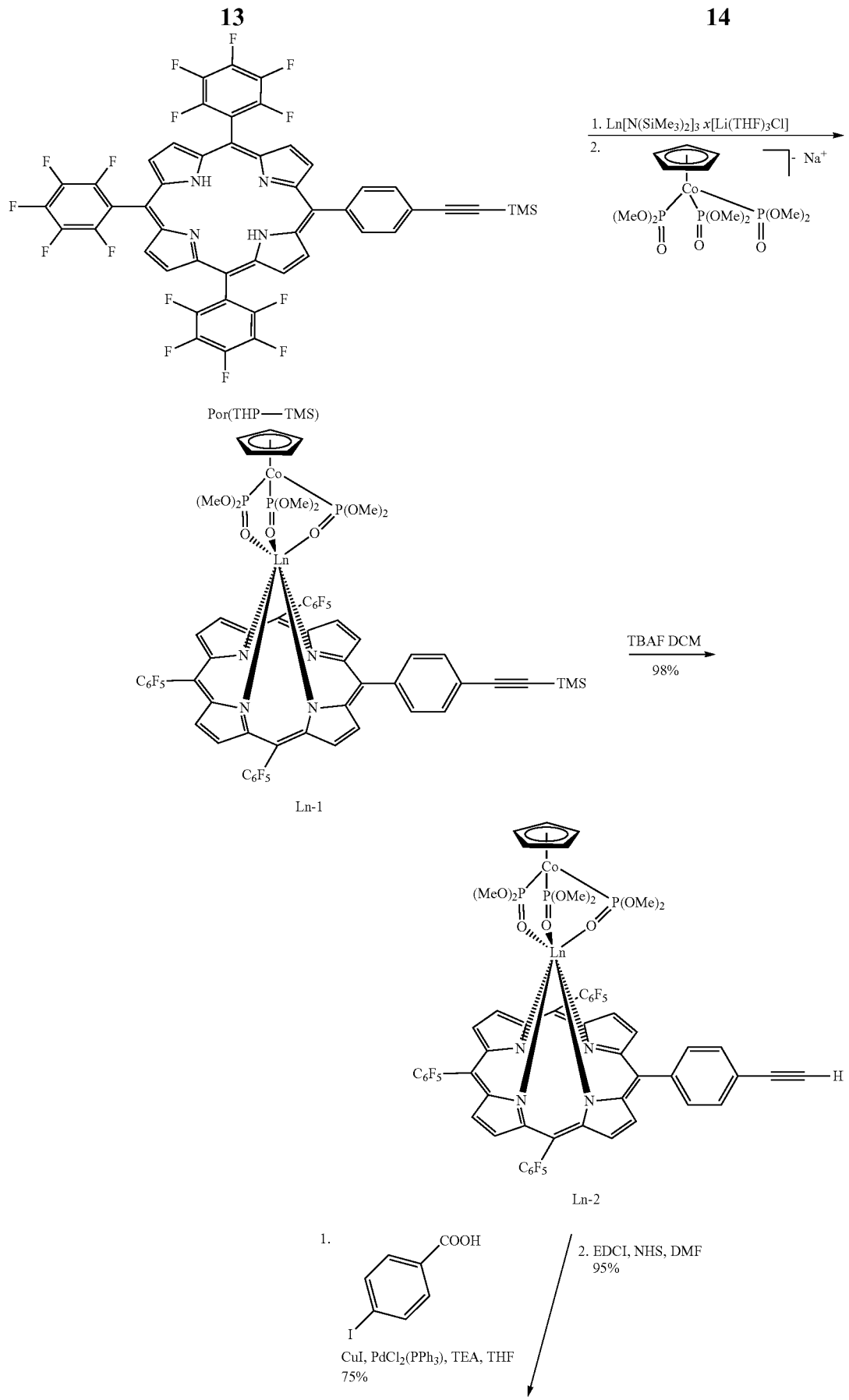

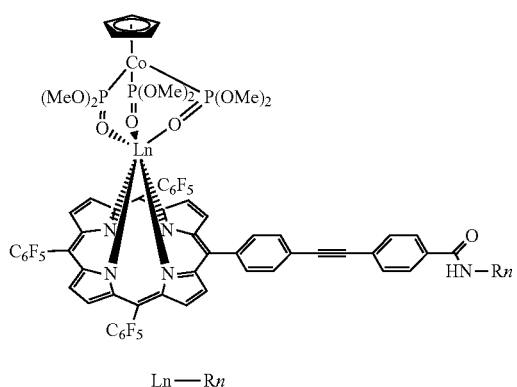 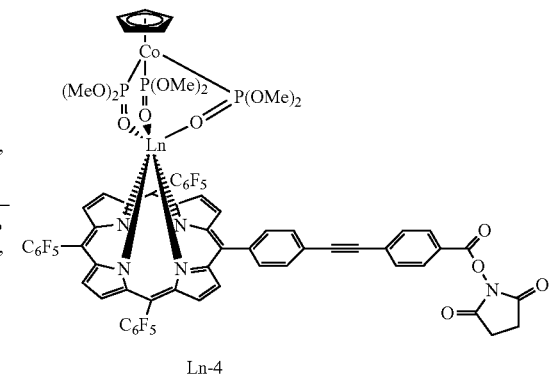

R1 = cQDGRMGFc
R2 = cGRLKEKKc
R3 = RrRkcGRLKEKKc wherein
said compound Por(THP-TMS) is synthesized via steps comprising:
dissolving Pyrrole, pentafluorobenzaldehyde and 4-[2-(trimethylsilyl)ethynyl]benzaldehyde 6 in $CH_2Cl_2$ under an argon atmosphere to produce a first solution;
leaving the first solution for at least 10 minutes;
adding $BF_3 \cdot O(Et)_2$ to the first solution;
stirring the first solution for at least 1 hour at room temperature;
adding DDQ (2,3-Dichloro-5,6-dicyano-1,4-benzoquinone) to the first solution;
stirring the first solution for at least another 1 hour at room temperature;
removing the solvent from the first solution in vacuo to produce a first mixture;
passing the first mixture through a silica column (hexanes-$CH_2Cl_2$) concentrated under reduced pressure to produce 5,10,15-Tris(pentafluorophenyl)-20-[4-{2-(trimethylsilyl)ethynyl}phenylporphyrin] or Por(THP-TMS);
said compound Ln-1 is synthesized via steps comprising:
dissolving $Ln[N(SiMe_3)2]_3 \cdot x[LiCl(THF)_3]$: $HN(SiMe_3)_2$ in THF at about 0 degrees Celcius to produce a second solution;
adding n-BuLi slowly over at least 30-minutes period to the second solution; stirring the second solution for at least 12 hours;
transferring the second solution to a Schlenk flask with $LnCl_3$ suspended in THF to produce a second mixture;
stirring the second mixture for at least 24 hours until all of the solid $LnCl_3$ disappeared to produce $Ln[N(SiMe_3)2]_3 \cdot x[Li(THF)_3Cl]$ (x=3~5) wherein Ln=Er or Ln=Yb;
said compound Yb-1 is further synthesized via steps comprising:
transferring $Yb[N(SiMe_3)2]_3 \cdot x[Li(THF)_3Cl]$ (x=3~5) to a Schlenk flask;
removing the solvent from $Yb[N(SiMe_3)2]_3 \cdot x[Li(THF)_3Cl]$ (x=3~5) under vacuum to produce a first residue;
adding $CH_2Cl_2$ to the first residue for the precipitation of LiCl to produce a third mixture;
centrifuging the third mixture until a clear layer is produced;
transferring the clear layer to another Schlenk flask with dry Por(THP-TMS) free base dissolved in toluene to produce a third solution;
refluxing the third solution until most of the free base coordinated with the metal ion;
adding dry NaLOMe [LOMe-((cyclopentadienyl)tris(dimethylphosphito)-cobaltate or an anionic tripodalligand) to the third solution to produce a fourth mixture;
stirring the fourth mixture for at least another 12 hours;
cooling down the fourth mixture to room temperature;
removing the solvent from the fourth mixture in vacuum to produce a second residue;
dissolving the second residue in $CHCl_3$;
filtering and chromatographing the dissolved second residue on silica gel using $CHCl_3$/petroleum ether as eluent;
further dissolving the output from chromatography in $CH_2Cl_2$; and filtering the solution to produce compound Yb-1.
Said compound Er-1 is further synthesized via steps comprising:
the same steps as for Yb-1, replacing $Yb[N(SiMe_3)2]_3 \cdot x[Li(THF)_3Cl]$ (x=3~5) with $Er[N(SiMe_3)2]_3 \cdot x[Li(THF)_3Cl]$ (x=3~5);
said compound Ln-2 wherein Ln=Yr is synthesized via steps comprising:
adding TBAF to a solution of Yb-1 in $CH_2Cl_2$ to produce a fifth solution;
stirring the fifth solution for at least 30 minutes;
monitoring the progress of the reaction of the fifth solution by TLC;
after completion of the reaction, passing the fifth solution through a short of silica gel column;
removing the solvent from the fifth solution to produce Yr-2;
said compound Er-2 is further synthesized via steps comprising:
the same steps as for Yb-2, replacing Yb-1 with Er-1;
said compound Ln-4 wherein Ln=Yr is synthesized via steps comprising:
mixing $Pd(PPh_3)_4$, CuI, Yb-2 and 4-iodobenzoic acid in a dried flask under nitrogen to produce a fifth mixture;
adding THF and $Net_3$ to the fifth mixture and degassing said fifth mixture with nitrogen;
stirring said fifth mixture at least 40° C. for at least 12 hours;
removing the solvent from said fifth mixture under reduced pressure to produce a third residue;

purifying the third residue by chromatography;
eluting the purified third residue with $CH_2Cl_2$/Methanol to produce an eluted compound;
mixing the eluted compound, EDCI, NHS in a dried flask and under nitrogen to produce a sixth mixture;
adding dry DMF to the sixth mixture;
stirring the sixth mixture at room temperature for at least 48 hours;
removing the solvent from the stirred sixth mixture to produce a fourth residue;
recrystallizing the fourth residue by diethyl ether and drying the crystals to produce Yb-4;
said compound Er-4 is further synthesized via steps comprising:
the same steps as for Yb-4, replacing Yb-2 with Er-2;
said compound Yb—$R_1$ is synthesized via steps comprising:
mixing a stirred solution of Yb-4 in anhydrous DMF with N,N'-diisopropylethylamine (DIPEA) to produce a seventh mixture;
adding peptide $R_1$ to the seventh mixture;
leaving the seventh mixture to react at room temperature for at least 24 hours;
removing the solvent from the seventh mixture under vacuum to produce a dry fifth residue;
recrystallizing the dry fifth residue by diethyl ether for at least three times;
drying the recrystallized dry fifth residue to produce Yb—$R_1$;
said compound Yb—$R_2$ is further synthesized via steps comprising:
the same steps as for Yb—$R_1$, replacing $R_1$ with $R_2$;
said compound Yb—$R_3$ is further synthesized via steps comprising:
the same steps as for Yb—$R_1$, replacing $R_1$ with $R_3$;
said compound Er—$R_1$ is further synthesized via steps comprising:
the same steps as for Yb—$R_1$, replacing Yb-4 with Er-4;
said compound Er—$R_2$ is further synthesized via steps comprising:
the same steps as for Yb—$R_2$, replacing Yb-4 with Er-4;
said compound Er—$R_3$ is further synthesized via steps comprising:
the same steps as for Yb—$R_3$, replacing Yb-4 with Er-4.

In a eighth aspect of the present invention there is provided a method of synthesizing the composition according to claim 1 comprising steps according to the following scheme:

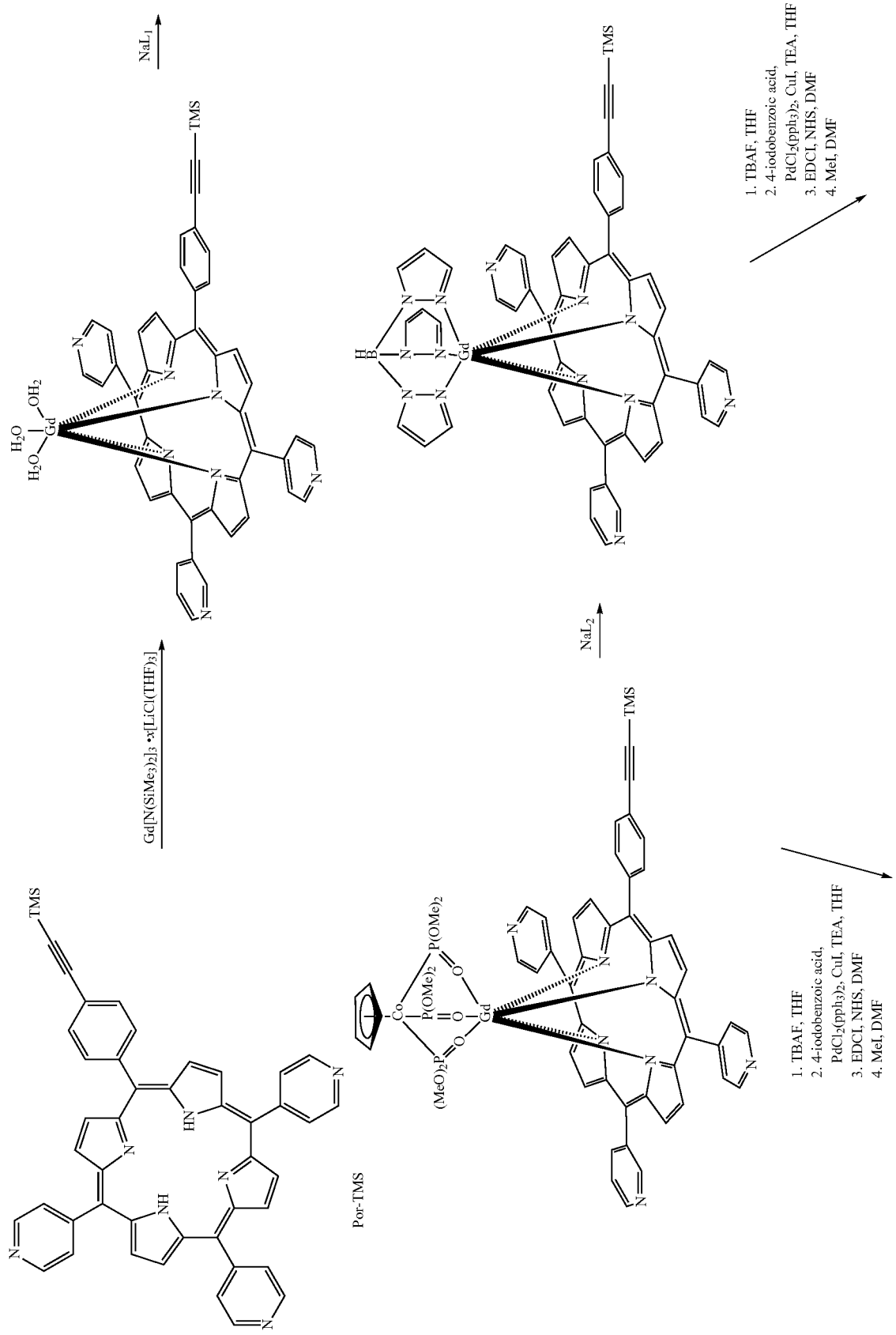

-continued
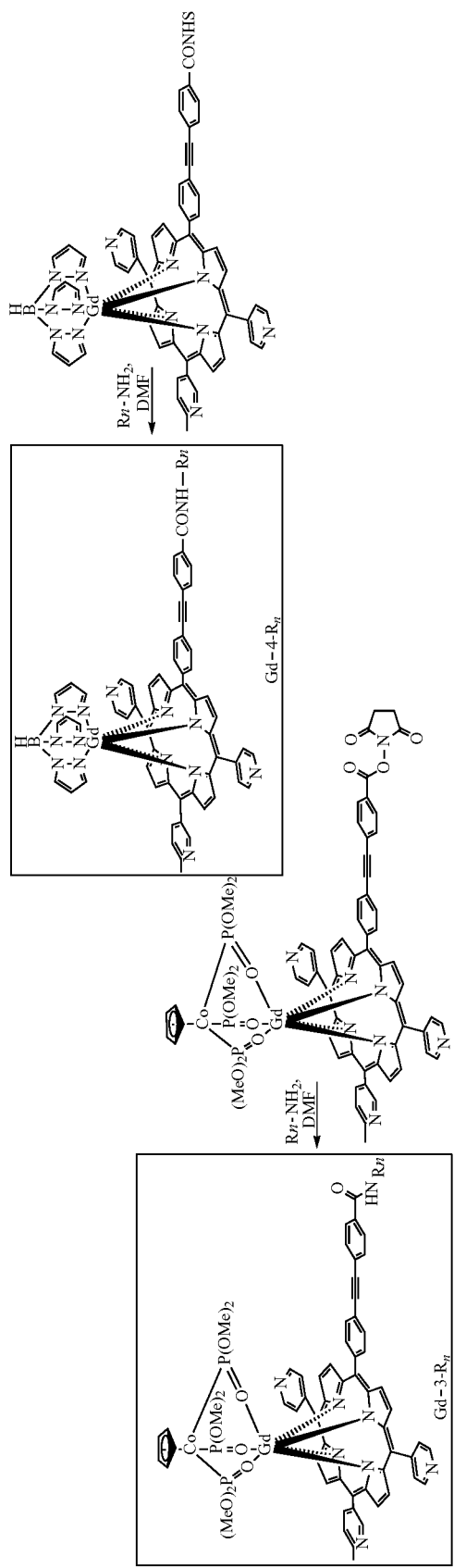

wherein
said compound Por-TMS is synthesized via steps comprising:
mixing 4-((trimethylsilyl)ethynyl)benzaldehyde with Pyridine-4-carboxaldehyde in propionic acid to produce an eighth mixture;
stirring the eighth mixture for at least half an hour in at least 130° C.;
adding pyrrole dropwise into the eighth mixture with the temperature increased to at least 140° C.;
stirring the eighth mixture for at least 30 minutes in open air;
cooling down the eighth mixture to room temperature;
removing the solvent from the eighth mixture under reduce pressure to produce a crude product;
dissolving the crude product in $CH_2Cl_2$ to produce a sixth solution;
purifying the sixth solution by column chromatography on silica gel column $CH_2Cl_2$/Methanol to produce Por-TMS;
said compound $Gd[N(SiMe_3)_2]_3 \cdot x[LiCl(THF)_3]$ is synthesized via steps comprising:
dissolving $HN(SiMe_3)_2$ in THF at about 0 degrees Celcius to produce a seventh solution;
adding n-BuLi to the seventh solution over at least a 30-minutes period;
stirring the seventh solution at least for 12 hours until a clear pale yellow solution was obtained;
transferring the seventh solution a Schlenk flask with $GdCl_3$ suspended in THF to produce a ninth mixture;
stirring the ninth mixture for at least 24 hours until all of the solid $GdCl_3$ disappeared to produce the resultant solution $Gd[N(SiMe_3)_2]_3 \cdot x[LiCl(THF)_3]$ (x=3~5);
said compound Gd-1-L1 is synthesized via steps comprising:
transferring $Gd[N(SiMe_3)_2]_3 \cdot x[LiCl(THF)_3]$ (x=3~5) to a Schlenk flask and removing the solvent therein under vacuum to produce a sixth residue;
adding $CH_2Cl_2$ to the sixth residue for the precipitation of LiCl to produce a tenth mixture;
centrifuging the tenth mixture until a clear layer is produced;
transferring the clear layer to another Schlenk flask with dry Por-TMS free base dissolved in toluene to produce an eighth solution;
refluxing the eighth solution until most of the free base coordinated with the metal ion;
adding dry $NaL_1$ (0.1 g, 0.22 mmol) [$L_1$-((cyclopentadienyl)tris(dimethylphosphito)-cobaltate, an anionic tripodal ligand) to the eighth solution to produce an eleventh mixture;
stirring the eleventh mixture for at least another 12 hours;
cooling down the eleventh mixture to room temperature;
removing the solvent from the eleventh mixture in vacuum to produce a seventh residue;
dissolving the seventh residue in $CHCl_3$;
filtering and chromatographing the dissolved second residue on silica gel using $CHCl_3$/$CH_3OH$ ether as eluent;
further dissolving the output from chromatography in $CH_2Cl_2$; and filtering the dissolved output to produce compound Gd-1-L1.
Said compound Gd-1-L2 is synthesized via steps comprising:
the same steps as for Gd-1-L1, replacing $NaL_1$ with $KL_2$ (potassium tris(1-pyrazolyl) borohydride);
said compound Gd-3 is synthesized via steps comprising:
adding TBAF to a solution of Gd-1-L1 in DCM to produce a ninth solution;
stirring the ninth solution for at least 30 minutes;
monitoring the reaction of the ninth solution by TLC;
passing the ninth solution through a short of silica gel column using DCM to remove the solvent therein to produce a pure product;
placing the pure product and $Pd(PPh_3)_4$, CuI, 4-iodobenzoic acid in a dried flask and under nitrogen to produce a twelfth mixture;
adding THF and $Net_3$ to the twelfth mixture;
degassing the twelfth mixture with nitrogen;
stirring the twelfth mixture at a temperature at least 40° C. for at least 12 hours;
removing the solvent from the twelfth mixture under reduced pressure to produce an eighth residue;
purifying the eighth residue by chromatography;
eluting the purified eighth residue with $CH_2Cl_2$/Methanol;
placing the eluted purified eighth residue, EDCI, NHS in a dried flask and under nitrogen to produce a thirteenth mixture;
adding dry DMF to the thirteenth mixture;
stirring the thirteenth mixture at room temperature for at least 48 hours;
removing the solvent from the thirteenth mixture to produce a ninth residue;
recrystallizing the ninth residue by diethyl ether and dried said crystals to produce Gd-3;
dissolving the Gd-3 in DMF;
adding $CH_3I$ to the dissolved Gd-3;
stirring the dissolved Gd-3 for at least 5 hours;
removing the solvent from the stirred dissolved Gd-3 to produce a tenth residue;
washing the tenth residue with ether .DCM. to produce pure Gd-3;
said compound Gd-4 is synthesized via steps comprising:
the same steps as for Gd-3, replacing Gd-1-L1 with Gd-1-L2;
said compound Gd-3-Rn is synthesized via steps comprising:
mixing a stirred solution of Gd-3 in anhydrous DMF with N,N'-diisopropylethylamine (DIPEA) to produce a fourteenth mixture;
adding peptide Rn to the fourteenth mixture;
reacting the fourteenth mixture at room temperature for at least 24 hours;
removing the solvent from the fourteenth mixture under vacuum to produce a dry eleventh residue;
recrystallizing the dry eleventh residue by diethyl ether for at least three times and further dry the result to produce Gd-3-Rn;
said compound Gd-4-Rn is synthesized via steps comprising:
the same steps as for Gd-3-Rn, replacing Gd-3 with Gd-4.
Features, integers, characteristics, compounds, chemical moieties or groups described in conjunction with a particular aspect, embodiment or example of the present invention are to be understood to be applicable to any other aspect, embodiment or example described herein unless incompatible therewith.
Those skilled in the art will appreciate that the present invention described herein is susceptible to variations and modifications other than those specifically described.
The present invention includes all such variation and modifications. The present invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

The present invention is not to be limited in scope by any of the specific embodiments described herein. The following embodiments are presented for exemplification only.

Figure 1A:
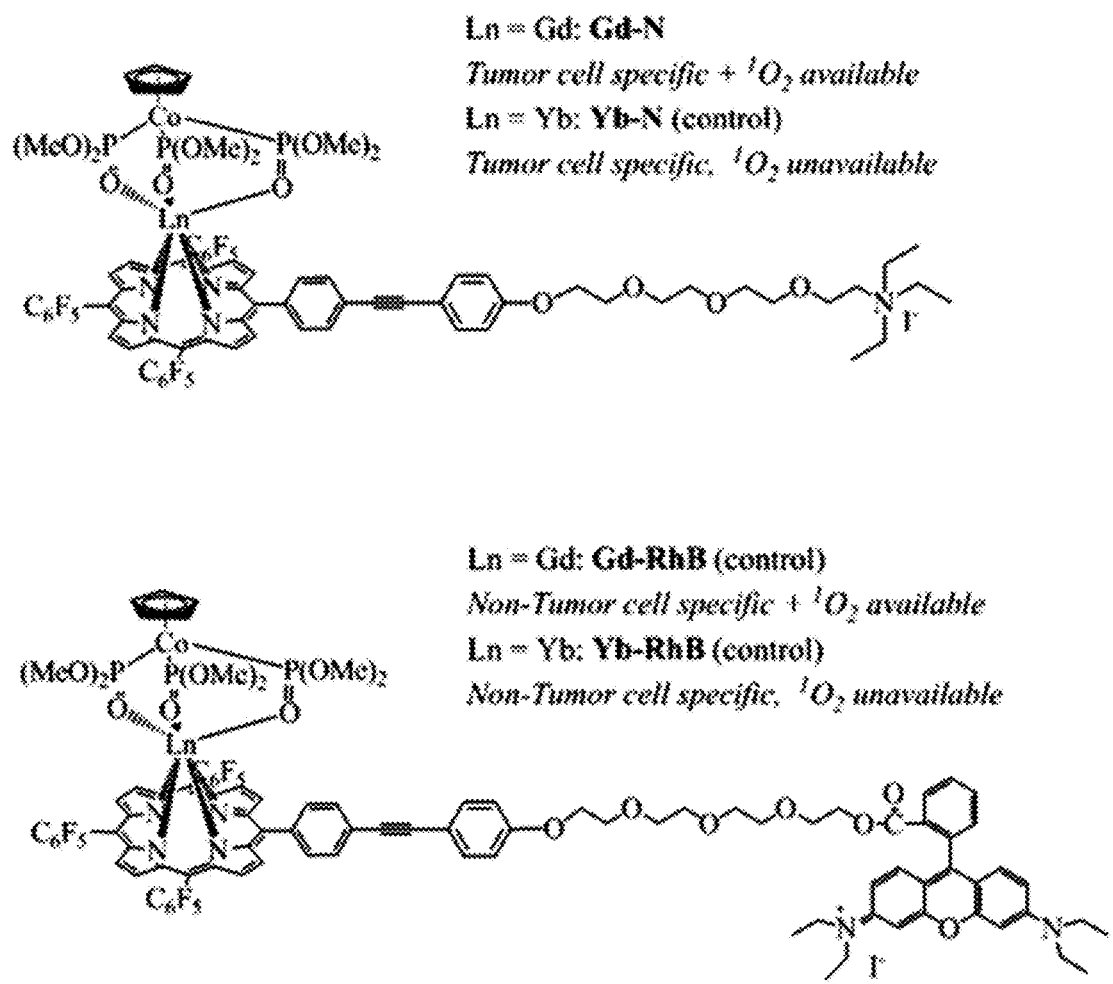
FIG. 1A shows molecular structure of the cancer cells specific photodynamic therapy agent (Gd—N) and their control analogues Yb—N, Gd—RhB and Yb—RhB.

Without wishing to be bound by theory, the inventors of the present invention have developed gadolinium porphyrinate (Gd—N; FIG. 1A), a PDT agent which is synthesized on the basis of Yb—N and shown 51% singlet oxygen quantum yield with characteristic NIR emission of porphyrin upon photoexcitation. (FIG. 1B-D) Comprehensive studies have revealed that Gd—N can recognize tumor cells by their anionic phosphotidylserine membrane in the first six hours after administration. Upon administration of Gd—N, laser-irradiation at certain wavelengths, Gd—N enters the tumor cells and produce $^1$O$_2$ in addition to exhibiting TP-induced NIR emission. Results of the in vivo mouse models and biodistribution assays further illustrates that Gd—N is found to be located in the tumor after simple injection of Gd—N into the blood vessel. Upon $^1$O$_2$ releasing from the porphyrin, the solid tumor is found to be reduced after 24-hour treatment. To the best of current knowledge in the art, there is a lack of in vivo lanthanide-based PDT agents. The present invention provide a novel PDT agent, Gd—N, and the use thereof for practical cancer tracking, imaging and treatment.

Results and Discussion

Figure 2:
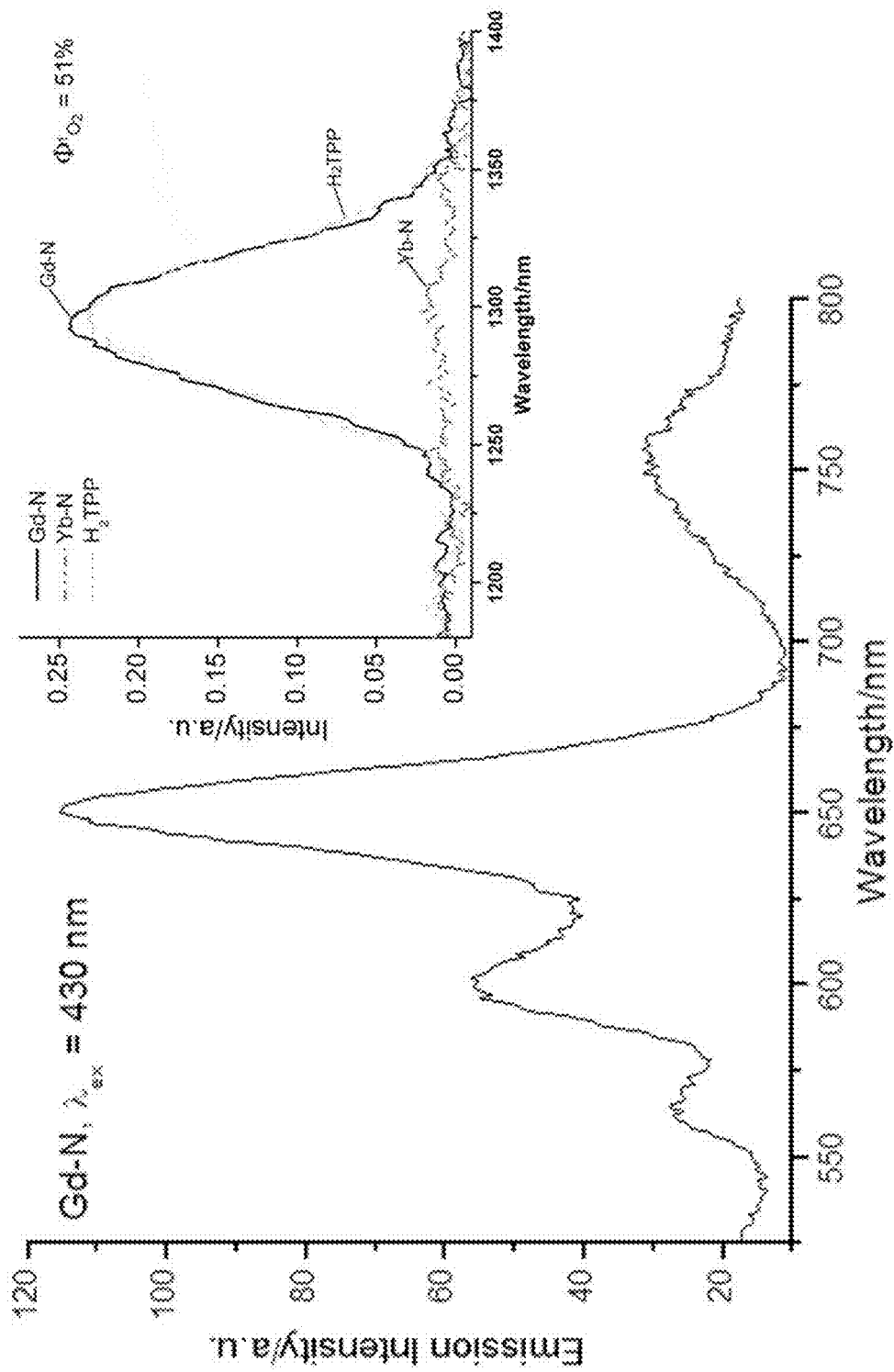
FIG. 2 shows emission spectra of Gd—N(HEPES buffer solution, 10 μM, $\lambda_{ex}$=0.430 nm, pH=7.4) and $^1O_2$ quantum yield measurement (Near-IR phosphorescence spectra of $^1O_2CHCl_3$, 10 μM, $\lambda_{ex}$=430 nm, abs($\lambda_{ex}$)=0.03). Yb—N and $H_2TPP$ are measured similarly as control.
Figure 8:
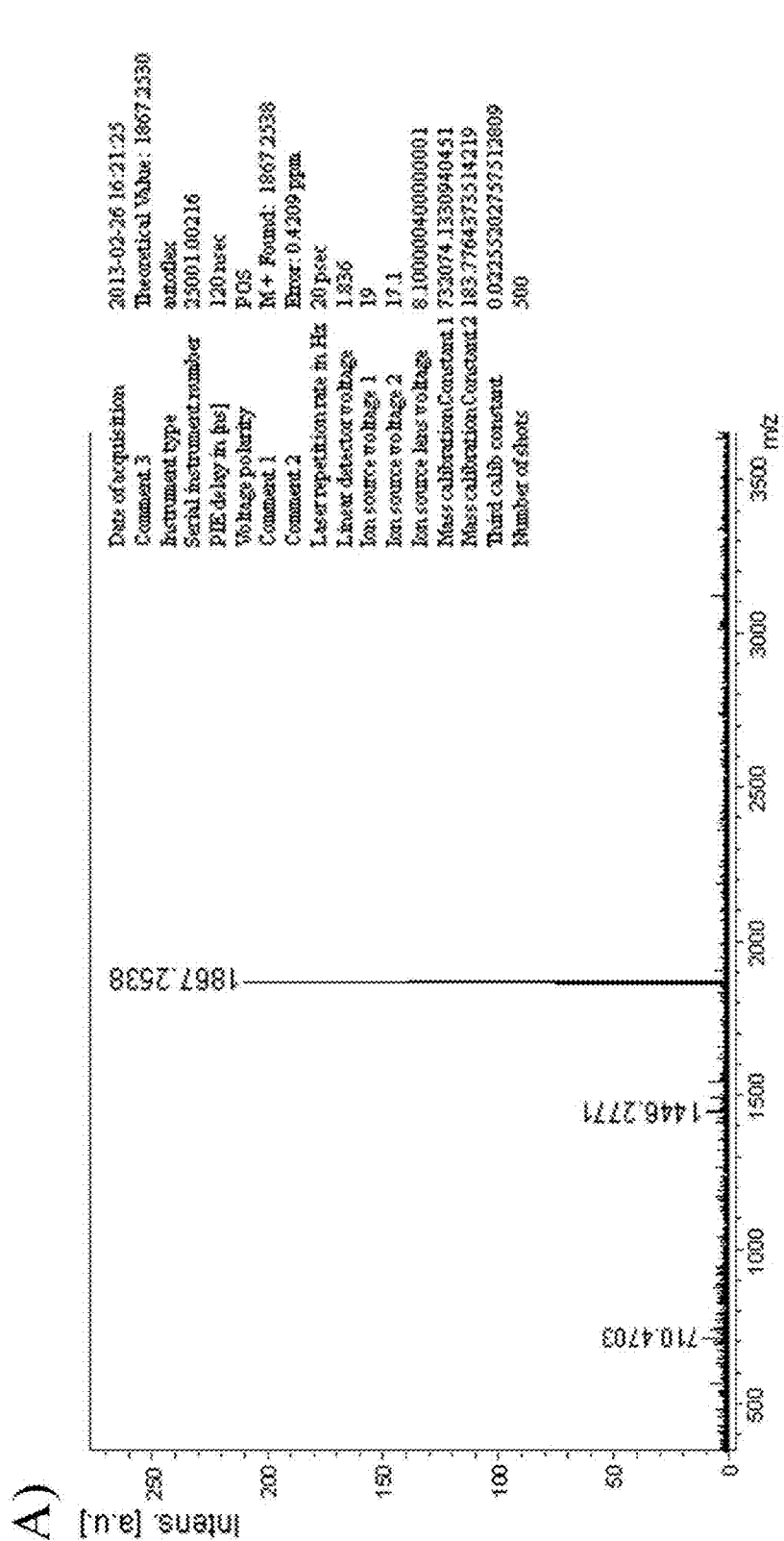
FIG. 8 shows A) High-resolution MALDI-TOF mass spectrum of Gd—N; B) Isotopic patterns for the molecular ion Gd—N; C) Calculated MS patterns of the molecular ion Gd—N(using the software: IsoPro 3.0).
Figure 8:
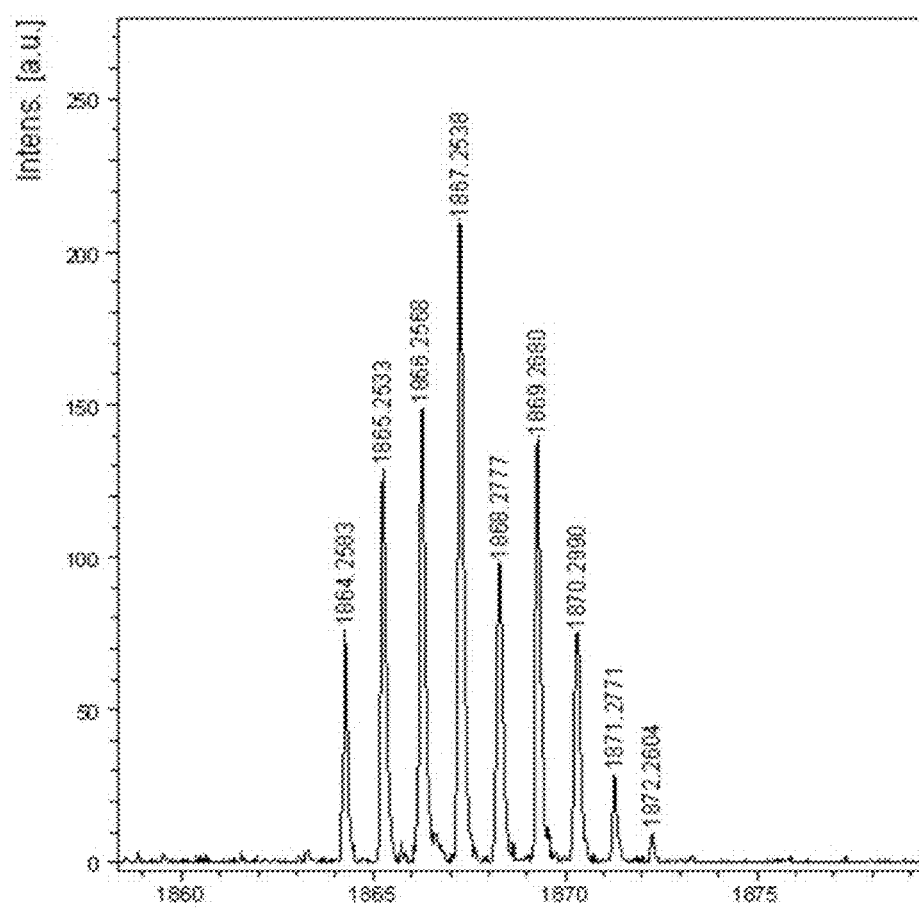
Figure 8:
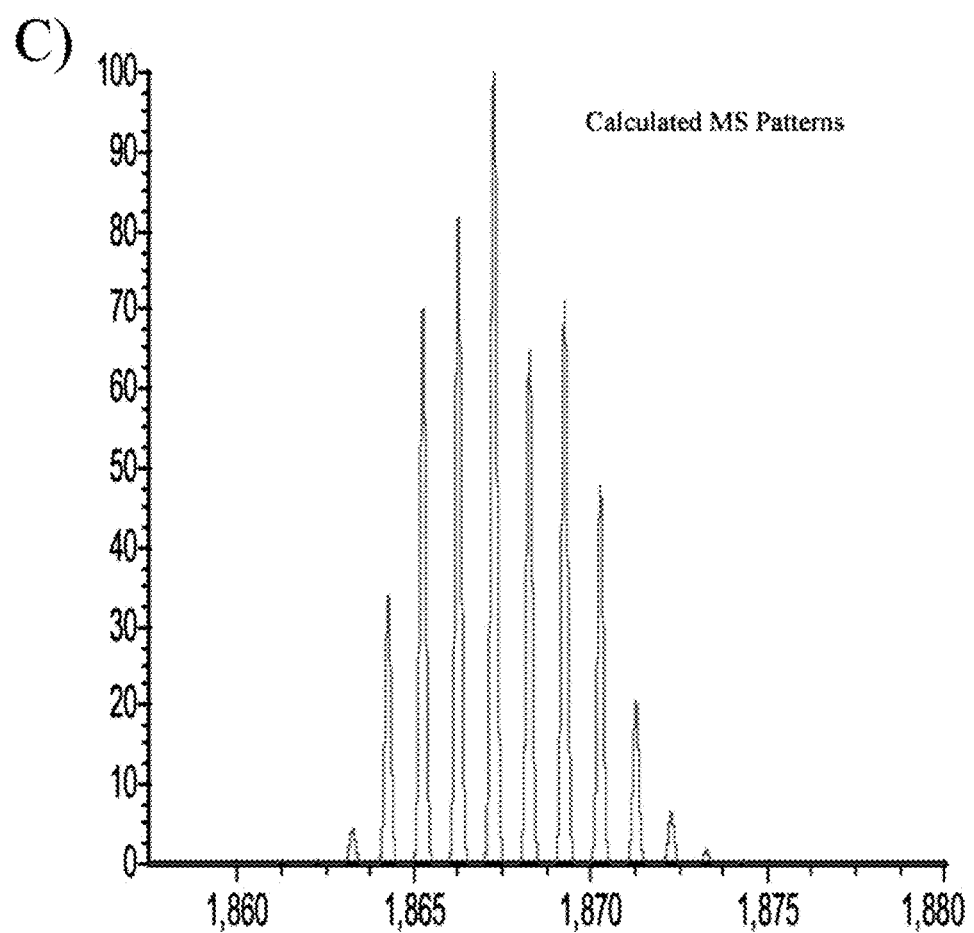
Figure 9:
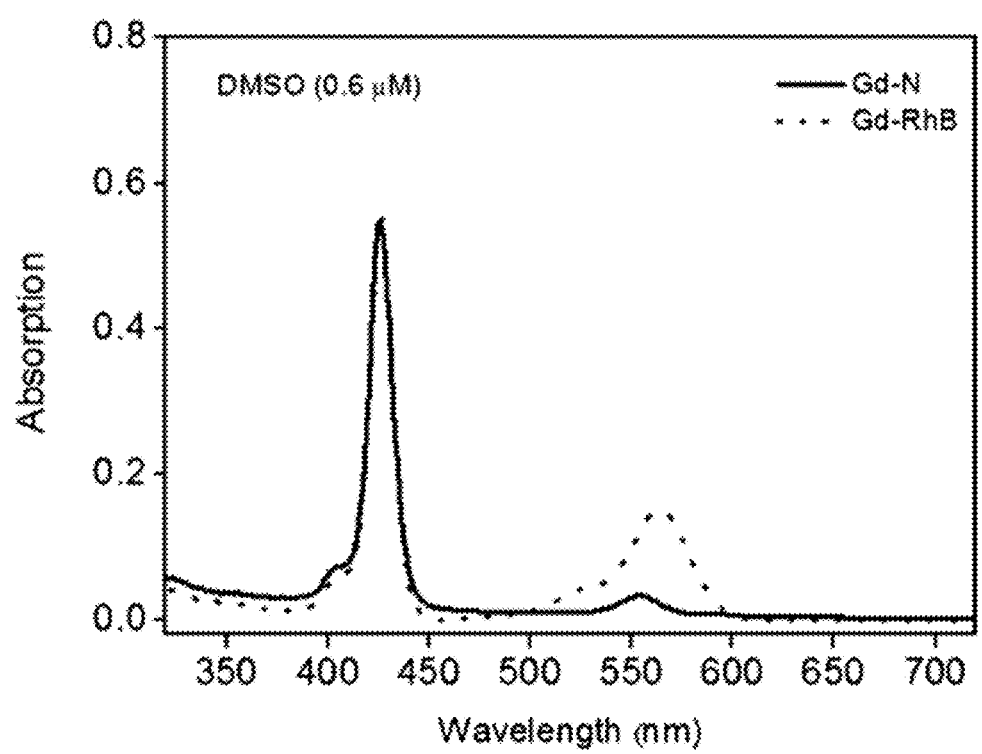
FIG. 9 shows the absorption spectra of Gd—N and Gd—RhB.
Figure 10:
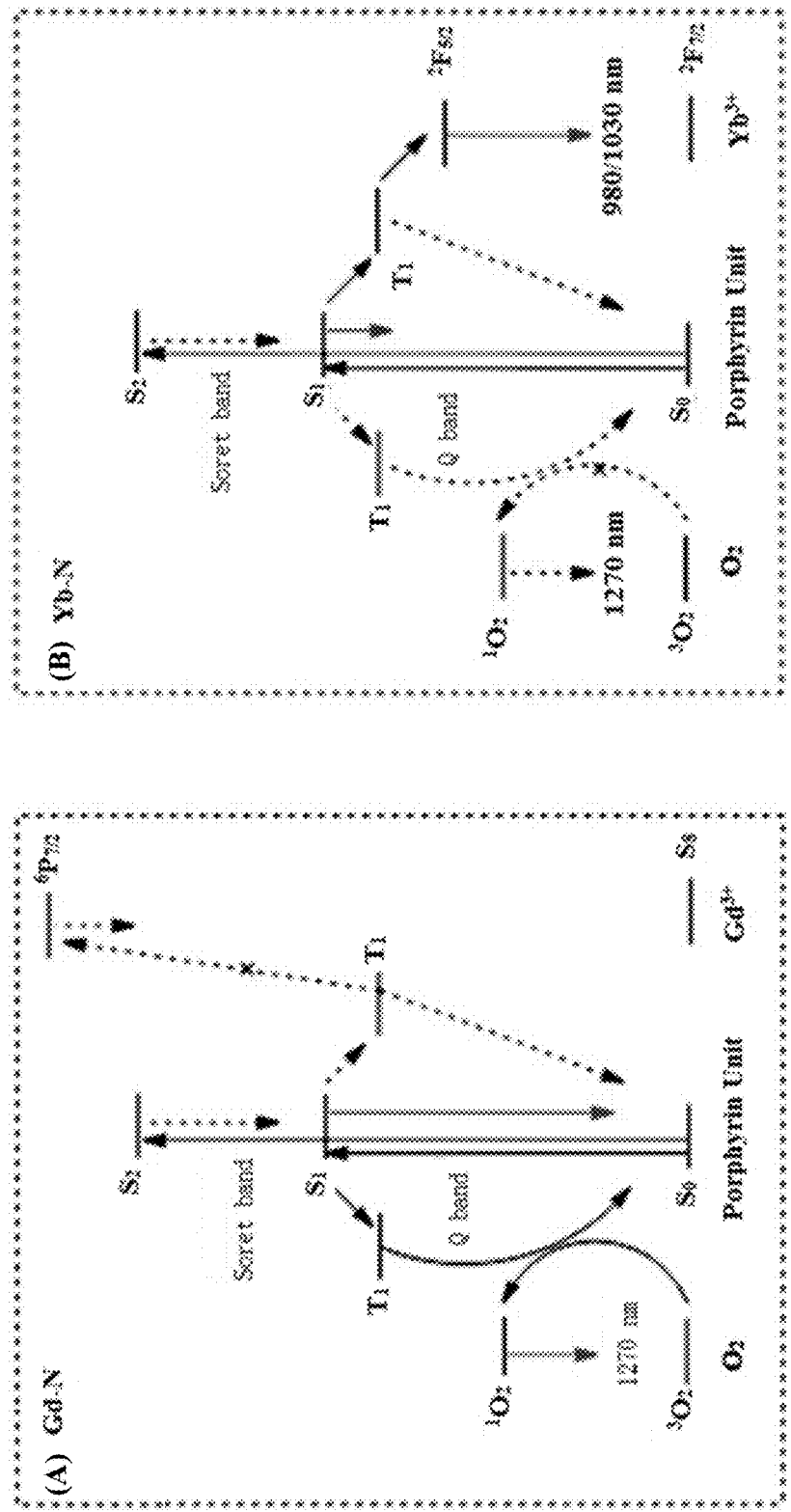
FIG. 10 shows the schematic representation of energy absorption, migration and emission (indicated by — · — · —▶) processes in the (A) gadolinium porphyrinate complex (Gd—N) and (B) ytterbium porphyrinate complex (Yb—N).
Figure 11:
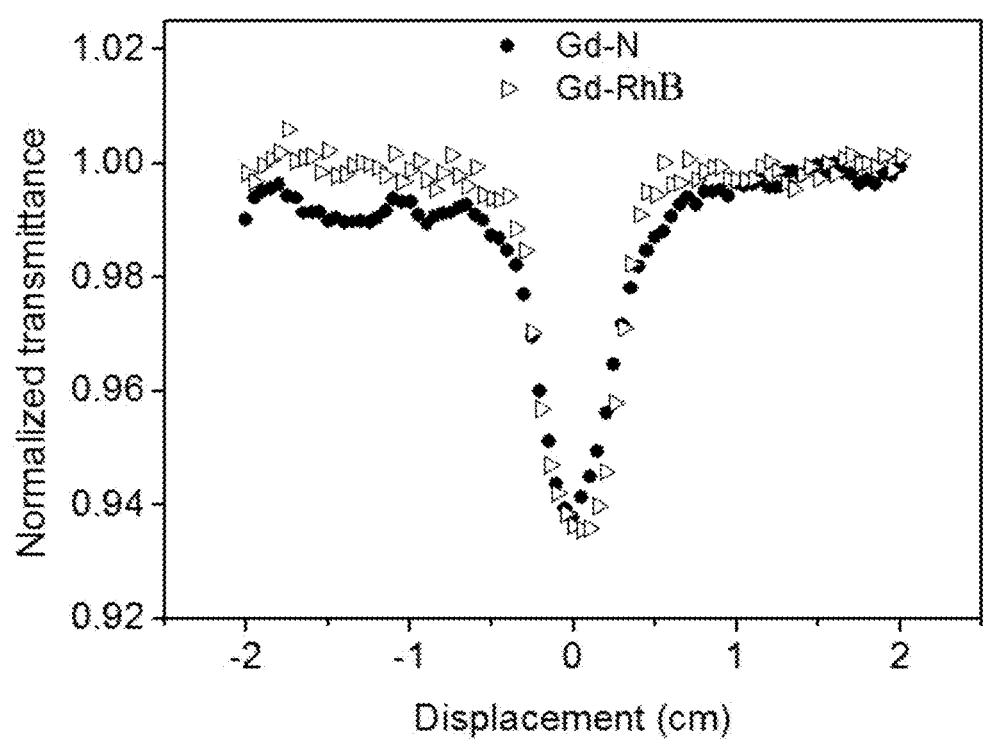
FIG. 11 shows the open-aperture Z-scan trace of Gd—N (351 GM) and Gd—RhB (418 GM) excited at 800 nm in DMSO (5 μM). The average power of the laser beam is 0.271 mW.

The detailed synthesis and characterization of Gd—N, which is the motif structure of the ytterbium complex (Yb—N) reported in the inventors' previous work, are shown in Scheme 1 and FIG. 8. Gd—N and Yb—N are structurally different in the lanthanide ion present in the complex (the vector ligated to Gd—N is also the same as Yb—N). It is self-evident that porphyrin's coordination with different lanthanides can cause changes not only in the NIR emission, but also the $^1$O$_2$ generation. (FIG. 2 and FIG. 9) Such phenomena, in principle, arise from the fact that better orbital overlapping between the metal center and the ligand results in better energy transfer (i.e. the bonding orbitals of Yb which consists of a smaller atomic radius than Gd is thus overlap more preferably and compatibly with the porphyrin's orbitals). The heavy atom effect exerted by the lanthanide can also augment the triplet-state decay rate and lead to higher triplet-state quantum yields of the porphyrin system. According to spectroscopic studies, the singlet oxygen quantum yield of Yb—N is measured to be 0% and Gd—N is determined to be 51%. The calculations are based on (i) the NIR phosphorescence intensity of the $^1O_2$ (at 1270 nm) produced from the two complexes and (ii) the lowest excited states of ytterbium $^2F_{5/2}$ (~10200 cm$^{-1}$) and gadolinium $^6P_{7/2}$ (~32000 cm$^{-1}$) respectively. It should be noted that the latter energy level of $^6P_{7/2}$ is much higher than the singlet/triplet levels of the porphyrin unit (singlet states=~23200 and 15300 cm$^{-1}$; triplet state=12500 cm$^{-1}$). A large energy gap between porphyrin and Gd, there is no energy transfer from porphyrin to Gd; the energy gained can therefore purely be either dissipated in the form of light or employed to form singlet oxygen, making direct determination of $^1O_2$ quantum yield feasible. (FIG. 10(A)) This is entirely not the same case for Yb. As the energy gap between porphyrin and Yb is small, most of the energy absorbed by the porphyrin unit would just be simply transferred to the ytterbium efficiently (via heavy atom effect) and afford the characteristic f-f emission exclusively. (FIG. 10(B)) The two percentages have clearly showcased that nearly half of the energy absorbed by the porphyrin of Gd—N would be involved in the $^1O_2$ generation, while the rest will be normally used for the porphyrin's NIR emissions; in contrast, for Yb—N, ytterbium's f-f luminescence at 1.08 μm is the dominant process of energy consumption under the same photoexcitation. (Linear and two-photon excitation at 430 nm and 860 nm respectively; the two-photon absorption cross section of Gd—N and Yb—N are similar to be ~351 GM (FIG. 11).

Figure 1B:
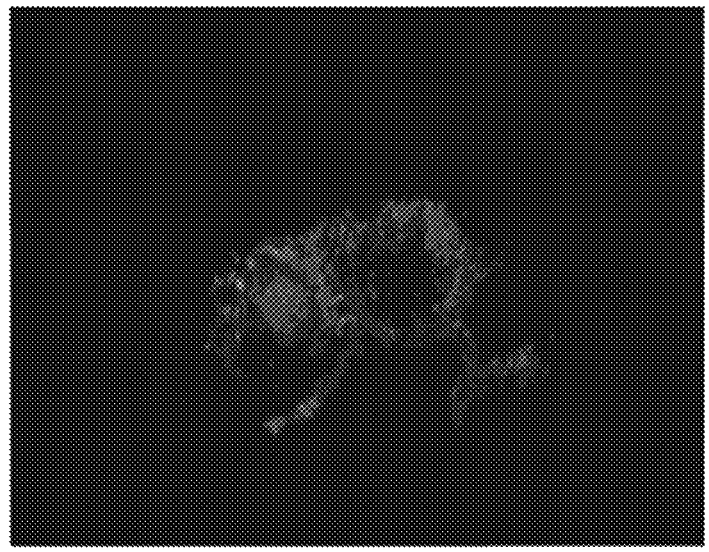
FIG. 1B is 3D in vitro imaging of Gd—N after 15-hour incubation in HeLa cells.
Figure 1C:
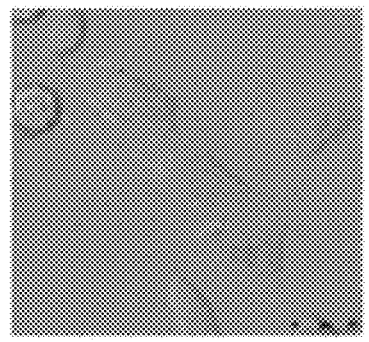
FIG. 1C and FIG. 1D show difference in subcellular localization of Gd—N in cancer cells (HeLa) and normal cells. (WPMY-1), respectively.
Figure 1D:
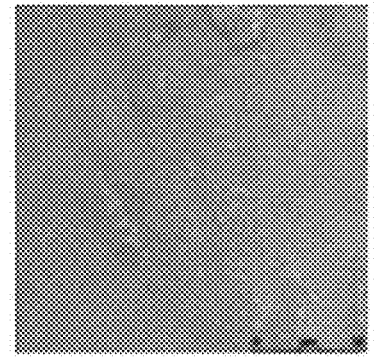
Figure 3:
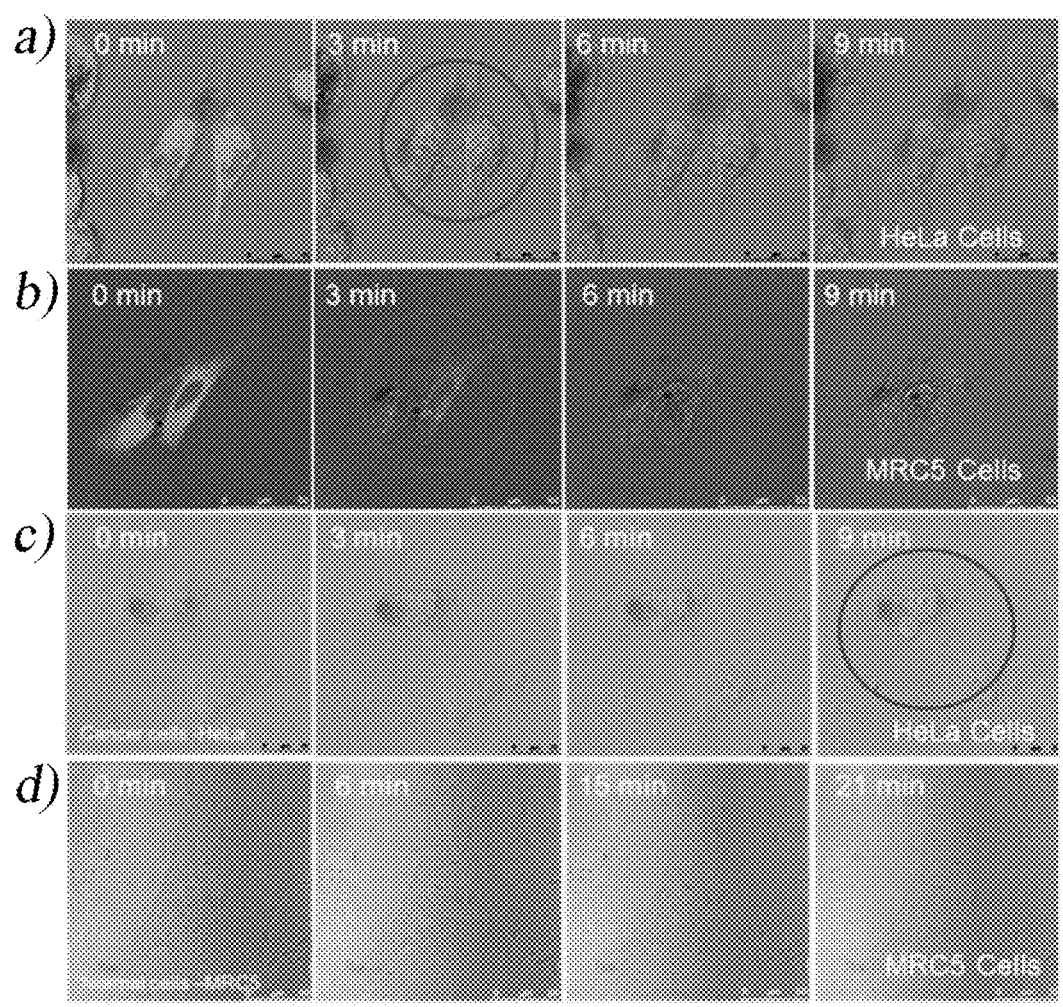
FIG. 3 shows in vitro imaging of Gd—N and Gd—RhB in tumor cells—HeLa and normal cells—MRC5 (as the controls) after 2-hour incubation. PDT effect is triggered upon 860 nm excitation. A) Gd—RhB in HeLa; b) Gd—RhB in MRC-5; c) Gd—N in HeLa; d) Gd—N in MRC-5 (1 μM).

Investigations with relation to real PDT-applications of Gd—N in vitro and, particularly, in vivo had been accomplished in terms of tumor selectivity, cytotoxicity and photocytotoxicity, imaging, PDT efficiency, as well as biodistribution. The selectivity of Gd—N against tumor and normal cells are superiorly distinct. As shown in FIG. 1B-1D, in the HeLa cancer cell, strong red emission from the porphyrin of Gd—N can be observed on the periphery, that is, the membrane surface, after 2-hour incubation. Upon incubation with more than 15 hours, several red emission enter and scatter internally to the cytoplasm. In the normal cell MRC-5, however, no emission can be detected on the surface of or inside the cell even after the 12 hours of incubation. In order to have a fair comparison, Gd—RhB had been synthesized for the control experiments. Rhodamine B (RhB) is a well-known mitochondria vector common for conjugation. Under the same experimental condition (incubation time, concentration, cell lines and laser power), the inventors find Gd—RhB's emission in both normal and cancer cells' mitochondria, and this very observation becomes the clear, cognizant, and convincing evidence of the tumor-specific property of the Gd—N. (FIG. 3) Through the MTT assays, the cytotoxicity of the three complexes, Gd—N, Yb—N and Gd—RhB in dark can be subsequently determined against the two kinds of cell lines. The IC$_{50}$ values of them are 0.78, 0.80, and 0.65 mM in cancer cells (HeLa) and 0.70, 0.70, and 0.45 mM in normal cells (MRC-5) respectively. The underlying reason of the vast difference in the dark cytotoxicity of Gd—RhB towards cancer/normal cells compared with Gd—N and Yb—N can be largely due to Gd—RhB's non-selectivity. Again, Gd—N of the present invention exhibits crucial tumor selectivity. The in vitro PDT effect of the three complexes is evaluated using in vitro confocal microscopy and photocytotoxicity assays. Gd—N, Yb—N and Gd—RhB complexes are dosed in HeLa cells and MRC-5 cells for 6 hours, and then subjected to excitation at 860 nm for triggering any PDT effect. (Three complexes are all available for TP-induced in vitro imaging with TP cross-section ~351 GM; given the limitation of the confocal spectroscope, the emission from porphyrin had only been monitored from 600 nm to 750 nm only) In FIG. 3, the emission of Gd—RhB can be noticed in the mitochondria. Upon suitable laser-induction, only small quantities of $^1O_2$ are produced but the cancer cells are killed within a few minutes; in effect, the normal cells are also killed rapidly under the same conditions. The PDT effect of Gd—RhB is therefore efficient enough but obviously non-selective and undesirable; it accumulates inside the mitochondria of cancer and normal cells, annihilating them unselectively. Although Yb—N is cancer-specific, its incapability to produce any $^1O_2$ imposes a restriction on any PDT practice. The red emissive Gd—N, not only it recognizes and localizes on the anionic membrane of tumor cells, but also access to certain parts of cytoplasm and induce cancer apoptosis via $^1O_2$ upon 9-minutes light dose flashing 5 seconds per minute. More time is required to trigger cancer cell death by Gd—N after definite laser irradiation; however, there is no significant cell death in the normal cells, far outweighing its slow-response drawback.

Figure 4:
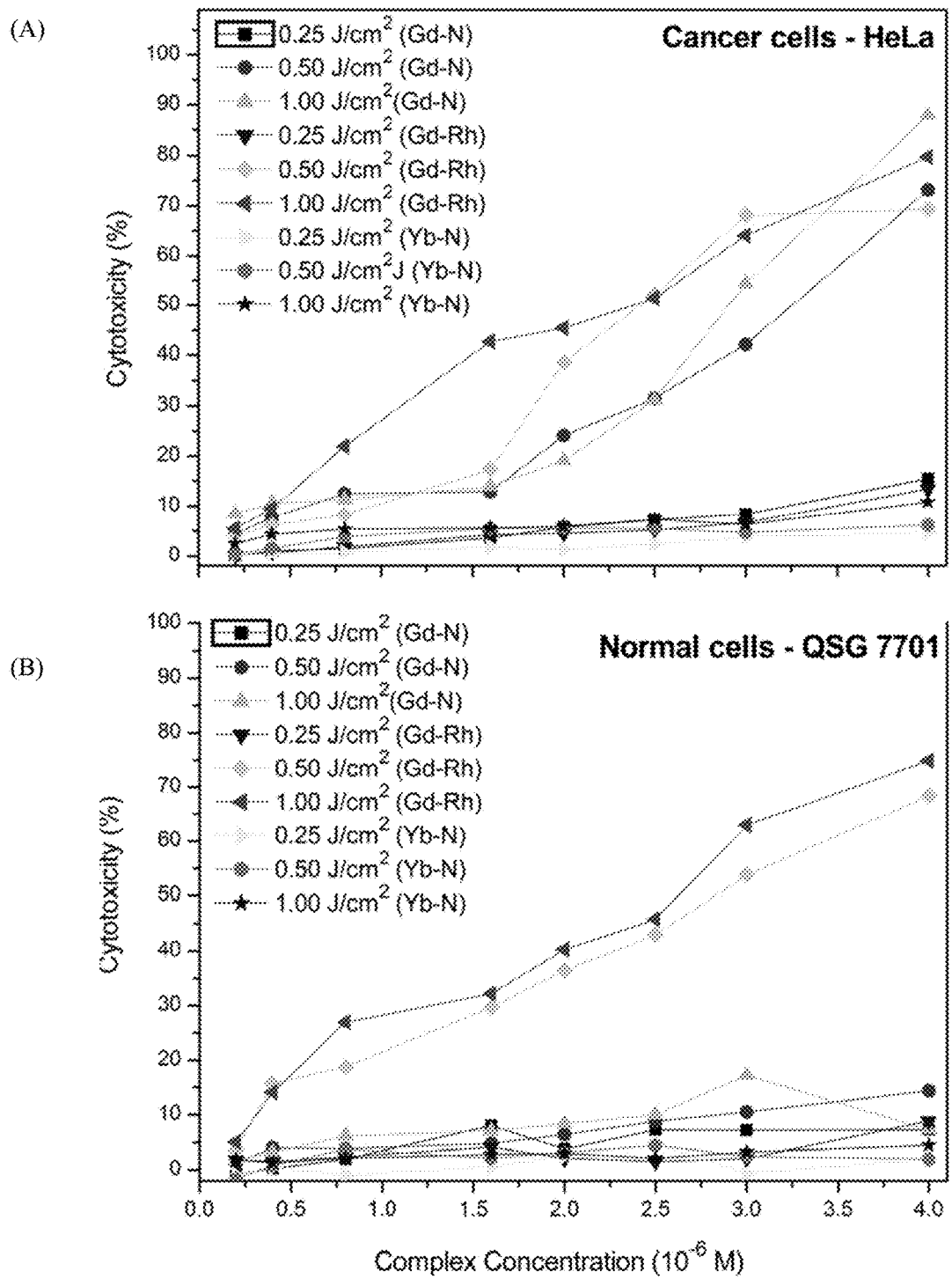
FIG. 4 shows photocytotoxicities of Gd—N, Gd—RhB (control) and Yb—N (control) towards (A) cancer cell (HeLa) and (B) normal cell (QSG 7701). Gd—N ($^1O_2$ available, tumor specific, strong photocytotoxicity in cancer cells, but no photocytotoxicity in normal cells), Gd—RhB (control —$^1O_2$ available, non tumor specific, strong cancer and normal cell photocytotoxicity) and Yb—N (control, $^1O_2$ not available, no photocytotoxicity in both cancer and normal cells). Photocytotoxicity curves are obtained using 1 μM of conjugates and various light doses from 0 to 1 J/cm$^2$; MTT assays are carried out after incubation for 24 hours. (37° C., 5% $CO_2$).
Figure 5:
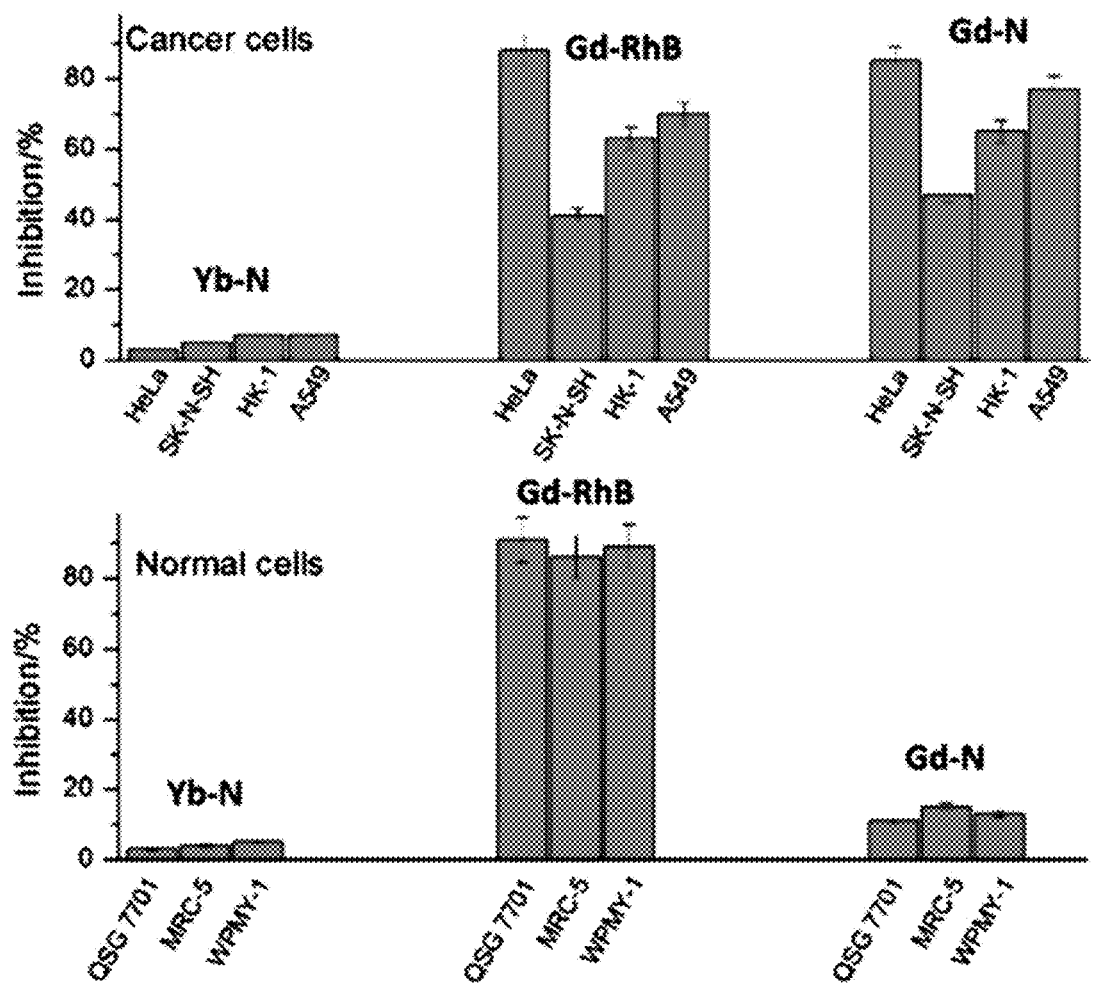
FIG. 5 shows the in vitro photocytotoxicity=430 nm) of the tumor-specific Gd—N in four tumor cell lines (HeLa, SK-N-SH, HK-1 and A549) and three normal cell lines (QSG 7701, MRC-5, WPMY-1), as well as the two controls—Yb—N and Gd—RhB.

The concentration-dependent photocytotoxicity of Gd—N, Yb—N and Gd—RhB, ranging from 0.2 to 1 μM dosage, are measured under varying light doses from 0.25 to 1 J/cm$^2$ in cancer cells and normal cells. The light dose-response curves obtained are displayed in FIG. 4. In HeLa cancer cells, Gd—RhB and Gd—N exhibit strong photocytotoxicity, whereas Yb—N (without singlet oxygen) has no photocytotoxcity (FIG. 4 (A)). From FIG. 4(B), in normal cell QSG 7701, no photocytotoxicty is found from Gd—N, while Gd—RhB gives very similar results as it behaved in the cancer cells. Such trend correlates with the selective cellular uptake of Gd—N by cancer and normal cells. The inventors had extended the studies with the use of more cancer cell and normal cell lines, and the results are shown in FIG. 5—Gd—N maintains its good tumor selectivity towards total of 7 cell lines (four cancer cells and three normal cells), thereby acting as an outstanding and specific PDT agent.

Figure 6:
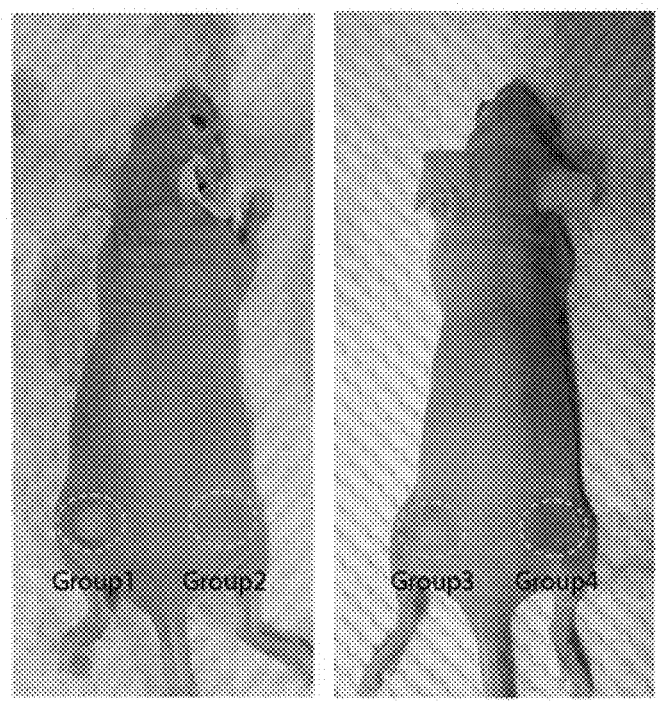
FIG. 6 shows in vivo studies of Gd—N as the cancer cell-specific PDT agent. A) the representative gross images of tumors after PDT using 860 nm laser for excitation, and candidates are divided into four groups (Group 1: Yb—N; Group 2: Gd—N; Group 3: Yb—RhB; Group 4: Gd—RhB); b) the measurement of tumor volume in a); c) In vivo biodistribution of Gd—N via ICP-MS studies; d) Two-photon microscopic images of tumor samples in c); e) In vivo tumor inhibition assays of Gd—N; f) In vivo tumor inhibition via Gd—N induced $^1O_2$ through caudal vein injection.
Figure 6:
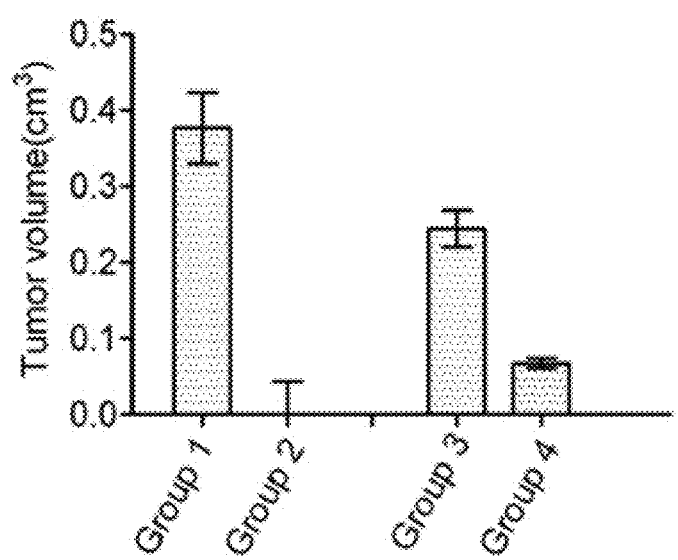
Figure 6:
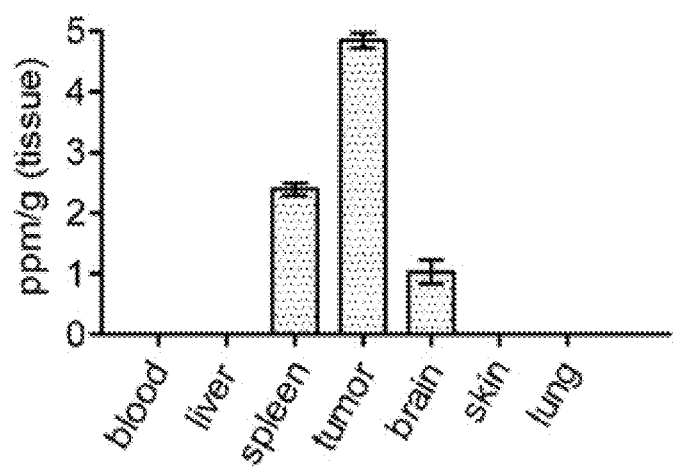
Figure 6:
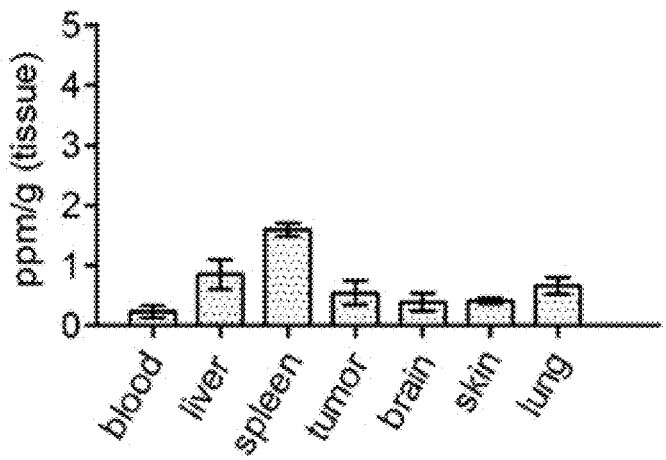
Figure 6:
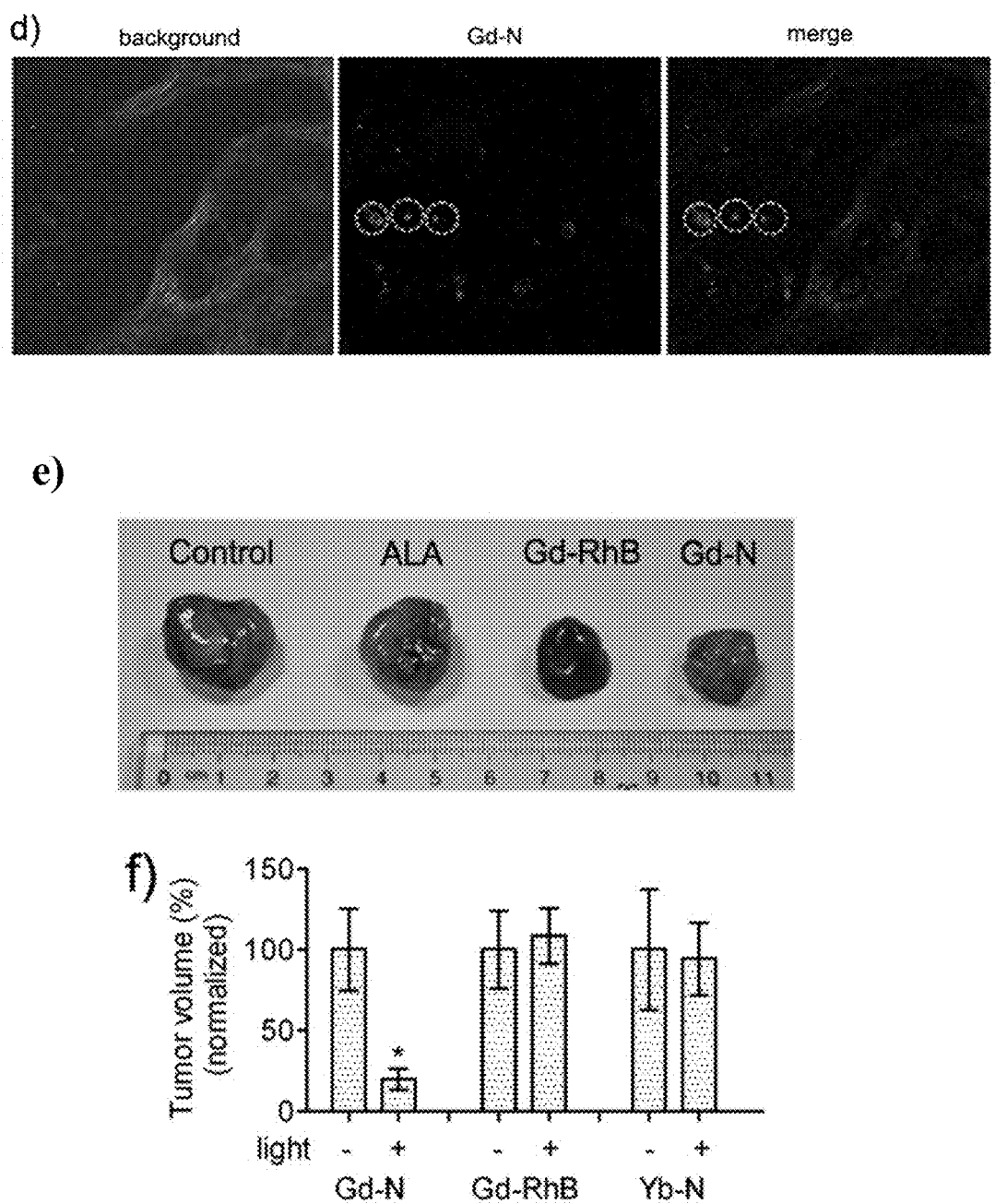

To demonstrate in vivo uptakes of complexes of the present invention, studies of biodistribution on these complexes' specialty towards infections of particular organs are carried out via xenograft mouse models and ICP-MS. Four complexes are classified into four groups. HeLa cells pre-incubated separately with Gd—N, Yb—N, Gd—RhB and Yb—RhB, and are subcutaneously injected into BALB/c nude mice and then irradiated the injected sites with 860 nm laser. Two weeks later, mice are pictured and the tumor volumes are measured (picture of the mice and measurement of tumor volumes are shown in FIGS. 6 *a*) and 6*b*), respectively). The tumors are found effectively inhibited in the groups of Gd—N and Gd—RhB, compared with their counterparts Yb—N and Yb—RhB; Gd—N, among the four complexes, is the best in vivo PDT agent that devastate the tumor with 100% efficiency. In biodistribution study, BALB/c nude mice with tumor xenograft attaining a size of approximately 0.1 cm$^3$ are caudal vein injected with Gd—N (1.0 mg/kg). Two days after administration, concentrations of Gd—N and Gd—RhB in different tissues or circulating blood are examined using ICP-MS. As seen in FIG. 6 *c*), tumors have the largest enrichment of Gd—N (4.84 ppm/g), demonstrating the specific recognition of the Gd—N towards tumor cells.

This result is also confirmed by two-photon microscopic imaging of the tumor tissues extracted from Gd—N administrated BALB/c nude mice. There are obvious two-photon microscopic signal from Gd—N(image of Gd—N, circled points), while the control image (showed as background, imaged by bright field shows no specific signal. The merge image is the overlap photon of Background and Gd—N which is shown FIG. 6 d). Further verification of the inhibiting effect of Gd—N and Gd—RhB towards tumor growth in tumor-bearing mice is done by intratumorally injecting BALB/c nude mice of HeLa xenograft tumor of approximately 0.3 cm³ with Gd—N (2.0 mg/kg), Gd—RhB (2.0 mg/kg) and ALA (60 mg/kg) (5-aminolevulinic acid, which can produce protoporphyrin in living cells and herein serve as the control PDT chemical), and irradiating with 860 nm light for three hours after injection. The total light dosage to tumor is 50 J/cm². Tumors are then allowed for growth for another 7 days and subjected for final extraction and picturing. As shown in FIG. 6 e), Gd—N is capable of tremendously inhibiting and even reducing the size of solid tumor by half from 2 cm to 1 cm within a short period of time.

Alternatively, mice with xenograft tumor are caudal vein injected with Gd—N and Gd—RhB (2.0 mg/kg body weight) and allowed for full circulation for 6 hours. Then tumors are irradiated with 860 nm light similarly as above. The tumor with light untreated serves as a control. The treatments are repeated for three times in the following days in a one-time-per-day manner. Consistently, it is found that Gd—N plus light treated tumors are inhibited compared to their opposite flank controls of tumor or Gd—RhB groups. Pharmacokinetics analyses also show that Gd—N persisted in animals for longer time with a larger MRT (mean resistance time) value (12.50 hours), while Gd—RhB is fast cleared (with MRT of 5.04 hours) (results are illustrated in FIG. 6 f) and Table 1).

TABLE 1

Pharmacokinetic parameters of Gd-N and Gd-RhB in plasma after caudal vein injections of 20 nmol of Gd—N (37.34 ug) or Gd—RhB (44.28 µg) to BALB/c nude mice (n = 3), respectively.

| Parameters | Gd—N | Gd—RhB |
| --- | --- | --- |
| Equation | $C_{(t)} = 138.61\ e^{-0.08t}$ | $C_{(t)} = 176.08\ e^{-0.1986t}$ |
| $AUC_{(0-t)}$ (µg/mL × h) | 1732.63 | 886.61 |
| $MRT_{(0-t)}$ (h) | 12.50 | 5.04 |
| $t_{1/2}$ (h) | 8.66 | 3.49 |
| $V_d$ (mL) | 0.269 | 0.251 |

AUC, area under the concentration-time curve; MRT, mean residence time; $t_{1/2}$, statistical half life; $V_d$, volume of distribution.

Figure 7:
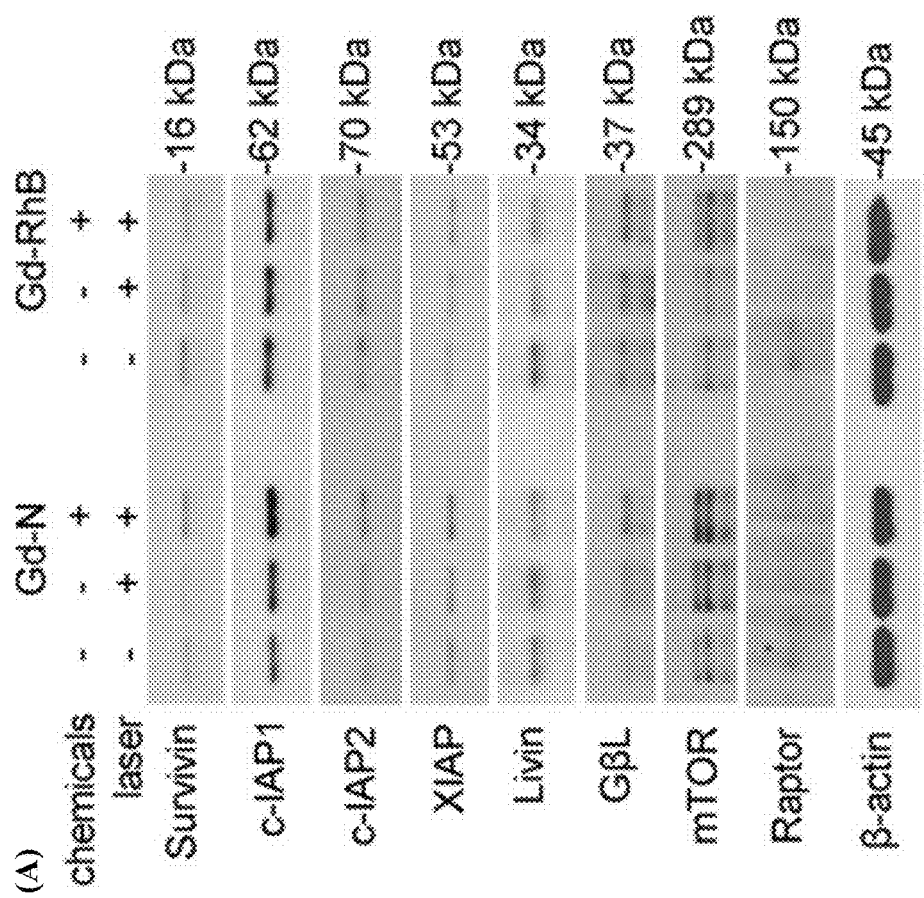
FIG. 7 shows Gd—N and Gd—RhB induced $^1O_2$ activated the inhibitor of apoptosis protein family and mTOR pathway. (A) western blot of HeLa cells dosed with 1 μM Gd—N or Gd—RhB and irradiated with 0.5 J/cm$^2$. Untreated or free of chemicals samples are served as the controls. (B) Cellular protein changes are semi-quantitatively measured using Gel-Pro Analyzer software of western blotting bands in (A) and showed as the ratio to β-actin (loading control of total proteins). P values are calculated between untreated and Gd—N or Gd—RhB plus laser groups by One-way Analysis of Variance.
Figure 7:
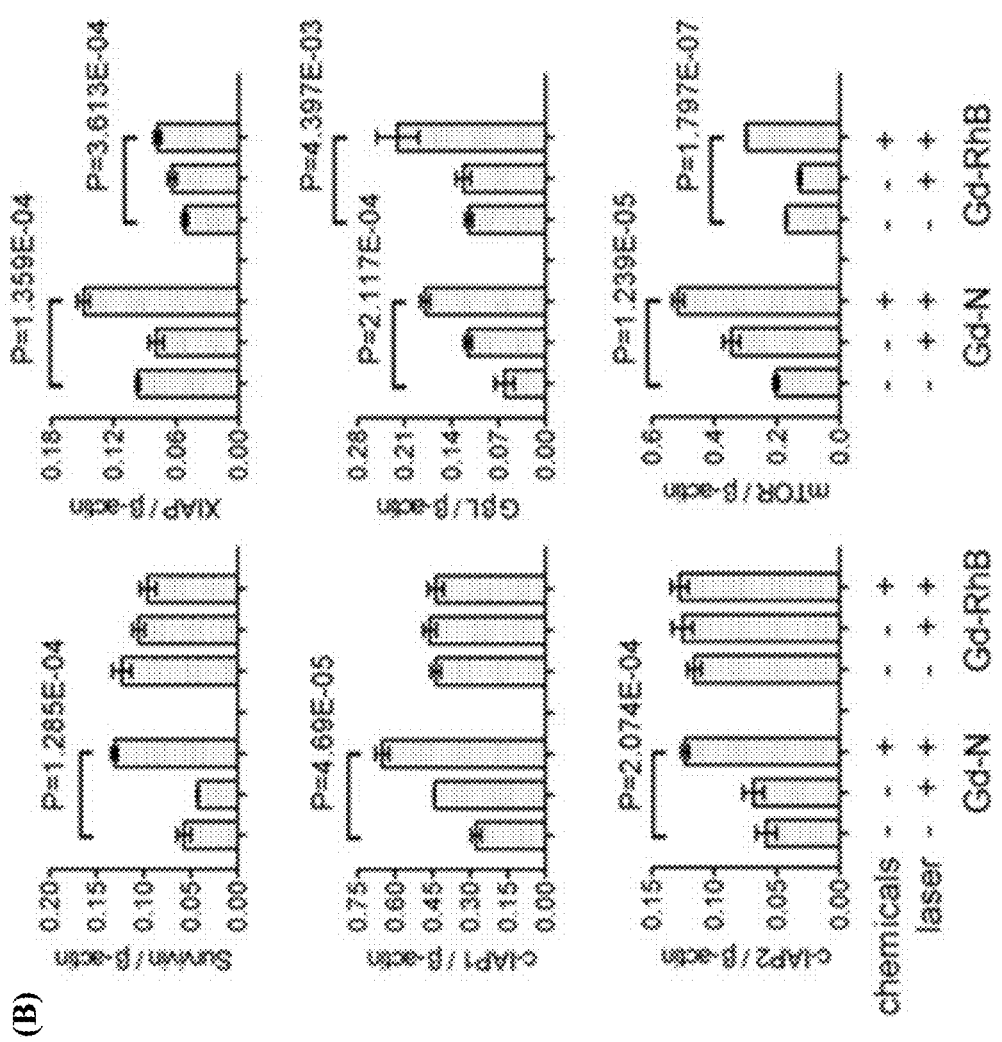

Molecular mechanism of PDT, protein levels of cellular surviving and inhibitors of apoptosis protein family (IAP) in protein lysates of PDT-treated HeLa cells are also investigated. Survivin and the IAP family members, c-IAP1, c-IAP2 and XIAP, are all remarkably expressed in Gd—N plus laser-treated samples. mTOR pathway is found to be involved in response to the PDT treatment of the cancer cells. The levels of two critical members, mTOR and GβL, are obviously elevated upon Gd—N or Gd—RhB induced $^1O_2$ stress stimulus. These results demonstrate the successful cell killing effect of Gd—N promoted photodynamic therapy at the molecular level and may also shed new light on the design and improvement of current PDT agents (FIG. 7).

Conclusion

The present invention provides theranostic gadolinium complex Gd—N for use as an anti-cancer agent which is equipped with visible-to-NIR emission for imaging, tumor cell selectivity, and $^1O_2$ generation. Through a string of in vitro and in vivo studies, the effectiveness and advantages of Gd—N of the present invention for use as smart dual-functional PDT agent is shown. The present invention also provides a method of tracking and imaging long-term live cancer cell, using Gd—N, as well as selective photodynamic therapy.

Experimentation Methods

Linear Induced Photophysical Properties

UV-Visible absorption spectra (ranging from 200 to 1100 nm) and single-photon luminescence spectra are recorded with an HP UV-8453 spectrophotometer and an Edinburgh Instrument FLS920 Combined Fluorescence Lifetime and Steady state spectrophotometer equipped with a UV-to-NIR-sensitive photomultiplier inside a nitrogen flow cooled housing. The Inventors had corrected all the spectra from the detector response and stray background light phosphorescence, measuring the quantum yields of the lanthanide complexes by a demountable 142 mm (inner) diameter barium sulphide-coated integrating sphere supplied with the two access ports in Edinburgh Instrument FLS920.

Singlet Oxygen Quantum Yield

With phosphorescence at 1270 nm, the singlet oxygen with an InGaAs detector on the PTI QM4 luminescence spectrometer are detected, and the quantum yields ($\Phi_\Delta$) of all compounds in $CHCl_3$ through comparing the $^1O_2$ emission intensity of the sample solution to that of a reference material[4] ($H_2TPP$, $\Phi_\Delta$=0.55 in $CHCl_3$) are determined and as illustrated in the following equation:

$$\Phi_\Delta^S = \Phi_\Delta^{REF} \times \left(\frac{n_S}{n_{REF}}\right)^2 \frac{G_\Delta^S}{G_\Delta^{REF}} \times \frac{A_{REF}}{A_S}$$

where $\Phi_\Delta$ denotes the singlet oxygen quantum yield, $G_\Delta$ indicates the integrated emission intensity, A represents the absorbance at the operation excitation wavelength, n reflects the solvent's refractive index, given that the Superscripts REF and S stand for the reference and sample respectively. In all cases, the inventors had measured the $^1O_2$ emission spectra upon due excitation. To reduce the impacts of re-absorption of the emitted light, all absorbance were set at 0.05 as well.

Cell Culture

Human HeLa (cervical carcinoma) and WPMY-1 (normal prostate stroma immortalized cell) cells are grown in DMEM medium; A549 (lung adenoma) are maintained in a mixture of Ham's F12K medium and L-glutamine (N3520, Sigma, St. Louis, Mo., USA); QSG 7701 (normal liver cell), HK-1, HONE1 (nasopharyngeal carcinoma) are grown in RMPI-1640 medium; MRC-5 (normal lung fibroblasts) and SK-N-SH (neuroblastoma) cells are grown in MEM medium. (i) 10% (v/v) fetal bovine serum (FBS), (ii) 100 µg/ml streptomycin, and (iii) 100 units/ml penicillin are also added in the all the medium.

In Vitro Imaging

To test the suitability of the water-soluble complexes of the present invention as bioprobes, a commercial confocal laser scanning microscope, Leica TCS SP5, equipped with a Ti:Sapphire laser (Libra II, Coherent) as well as a 980 nm wavelength laser for excitation are used to in vitro image HeLa/WPMY-1/MRC-5 cells incubated with the five complexes of the present invention.

MTT Cell Viability Assay

After 24 hours, the water-soluble complexes and the treated cells are incubated further with 3-(4, 5-dimethylthiazol-2-yl)-2,5-diphenyltetrazolium bromide (MTT) (0.5 mg/ml) for 4 hours, so that formazan is formed along with the cell's metabolic pathways. Then, the formazan are extracted and dissolved by dimethyl sulfoxide (DMSO), with the absorbance of the subsequent solutions being measured in a Bio-Rad iMark microplate reader (490 nm).

Quadruplicates are performed and the data are interpreted and analyzed by plottings using the GraphPad Prism 5 software.

Photodynamic Treatment (PDT) Assay

On a 96-well plate, cancer cells ($2 \times 10^4$/well) are first incubated overnight and then treated with complexes of the present invention and control analogues for 6 hours in dark. After the old medium being replaced with the fresh one, the cells are accordingly exposed to yellow light (1-8 J/cm$^2$) generated from a 400 W tungsten lamp fitted with a heat-isolation filter and a 500 nm long-pass filter under the fluency rate of mW/cm2. After 24 hours, post-PDT cell viability is examined by MTT assay. Cell monolayers are rinsed with PBS prior to incubation with 250 μg/mL MTT solution at 37° C. for 3 hours. The formazan crystals formed and dissolved in DMSO then undergo absorbance measurement at 540 and 690 nm by a 96-well plate reader (Elx800 Absorbance Microp late Reader).

Animals:

All the experiments entailing animal models are performed on athymic nude mice (BALB/c-nu/nu) which are all obtained from Guangdong Medical Lab Animal Center (license number: SCXK-2008-0002). Mice are raised and operated according to the strict protocol the National Standard of Animal Care and Use Procedures (20080820).

Pharmacokinetics Analysis:

Gd—N and Gd—RhB (1.0 μmol/kg body weight each) are caudal vein injected into the mice. Then sera are collected at different time points from 0-20 hours as indicated. The concentrations of Gd—N and Gd—RhB are measured by PerkinElmer EnVision Multilabel Reader 2104 at 570 nm, and calculated using standard absorptions via concentration curve. Pharmacokinetic parameters ($t_{1/2}$, Vd, MRT, AUC) are calculated by fitting with one compartment model.

In Vivo Bio Distribution Via ICP-MS

Biodistribution studies of In vivo uptakes of complexes of the present invention in particular organs/bacterial infections are carried out via ICP-MS. Gd—N and Gd—PhB are administered to mice at a dosage of 1.0 μmol/kg body weight when tumor xenograft attains a size of approximately 0.1 cm$^3$. 2 days later, around 0.02-0.04 gram of sample tissues are collected in tumor, liver, lung, kidney, spleen, brain, prostate, skin and blood (80-90 μL). All samples are incubated with 500 μL nitric acid at 37° C. for releasing the metal ions for further ICP-MS examinations, in addition to dissolving the interfering organic molecules.

In Vivo Photodynamic Therapy Studies

For the establishment of mouse tumor xenograft mode, cells are trypsinized, harvested and suspended in the culture medium. $1 \times 10^6$ cells in 100 μL, volume are s.c. injected into the flanks of female athymic nude mice (with 5-week old) and waited for 10-15 days. When the tumor volume reaches to size of 100-150 mm$^3$, the animals are randomly divided into different groups for further experiments. Tumor volume is measured by calipers (accuracy of 0.02 mm) and then calculated independently on the basis of the equation $V=(L \times W^2)/2$, where L and W correspond to the larger and smaller dimensions, respectively. One-way analysis of variance towards statistical significances between groups is assessed by the GraphPad Prism 5.0 software.

Materials and Methods

All chemicals used are of reagent-grade and are purchased from Sigma-Aldrich and used without further purification. Preparations of intermediates Yb[N(SiMe$_3$)$_2$]$_3$.[LiCl (THF)$_3$][1] and starting porphyrin free base TFP-TMS[2] are performed according to the literature procedures. Preparations of the control compounds Gd—RhB, Yb—RhB[4] and Yb—N[5] are accomplished according to the inventors' previous procedures. All analytical-grade solvents are dried by standard procedures, distilled and deaerated before use. High-resolution mass spectra, reported as m/z, are obtained on a Bruker Autoflex MALDI-TOF mass spectrometer. Elemental analyses carried out at the School of Chemical Engineering, Northwest University, P. R. China. The synthetic route of intermediates and Gd—N is shown in Scheme 1:

Scheme 1

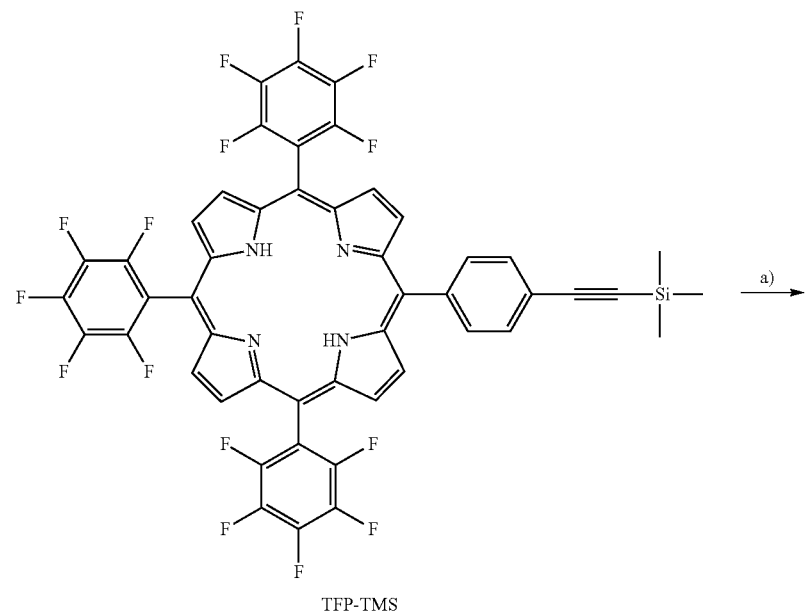

TFP-TMS

-continued
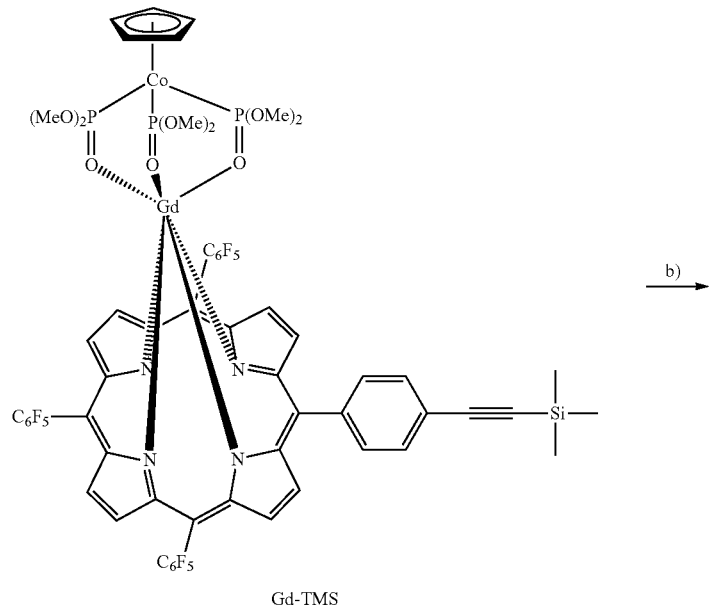
Gd-TMS
b) →
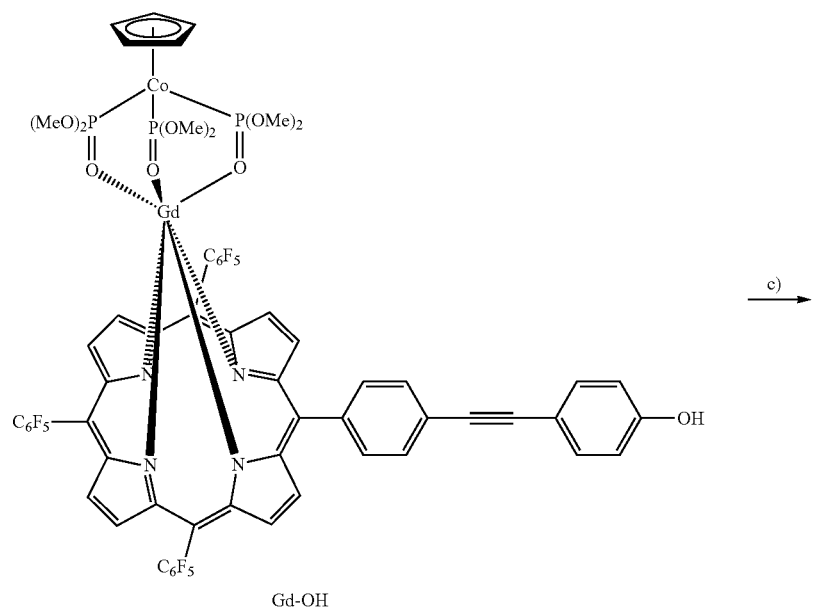
Gd-OH
c) →

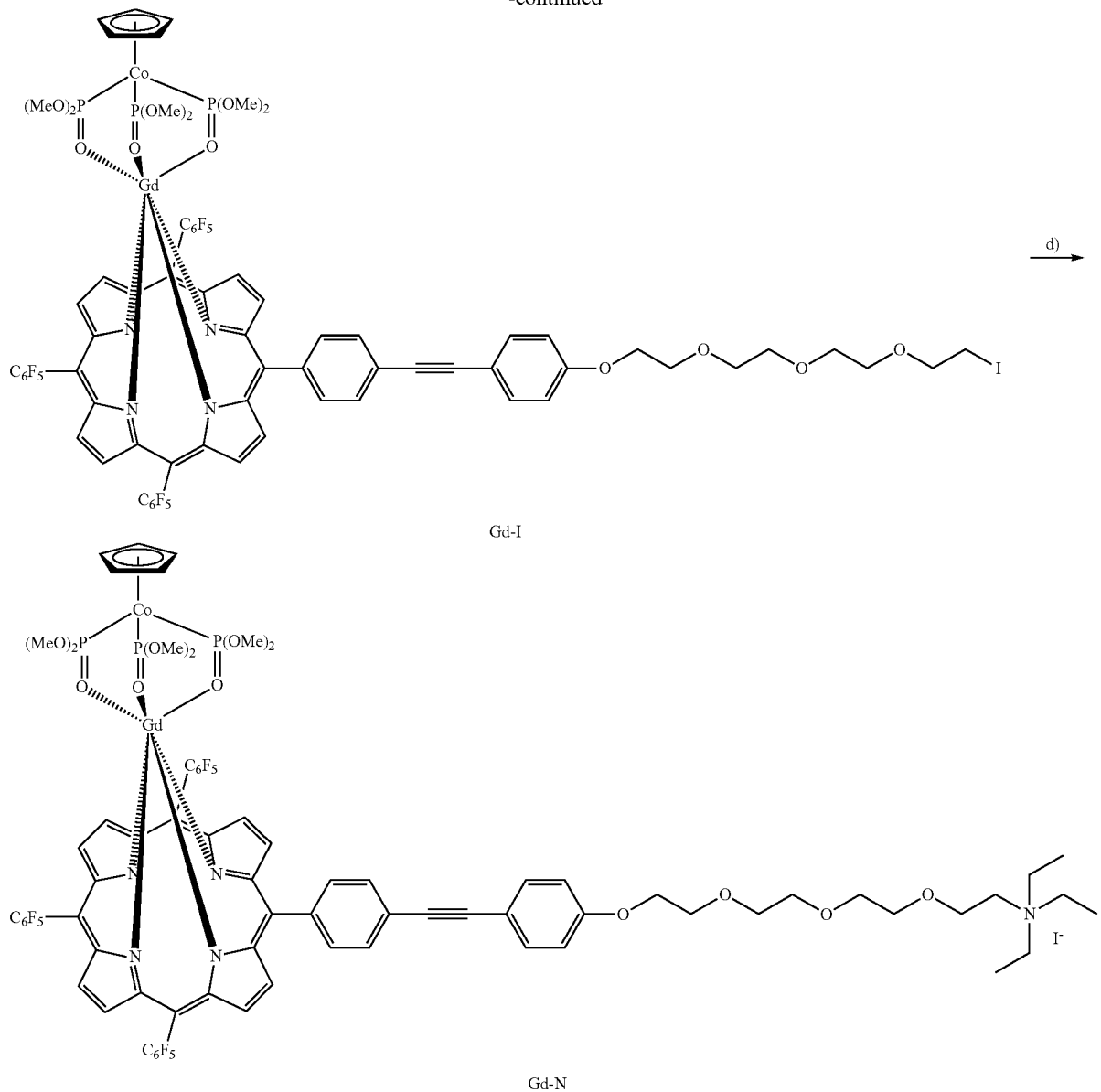

Gd-I

Gd-N

The synthetic routes of Gd-NGd-TMS: A solution of Gd[N(SiMe$_3$)$_2$]$_3$·[Li(THF)$_3$Cl]$_x$ (5.0 ml, 0.6 mmol Gd) is transferred to a Schlenk flask and the solvent is removed under vacuum. Then 10 ml dichloromethane (CH$_2$Cl$_2$) is added for the precipitation of LiCl. The mixture is centrifuged and the clear layer is transferred to another Schlenk flask with the porphyrin free base TFP-TMS (196 mg, 0.2 mmol) dissolved in 20 ml toluene. The resulting solution is refluxed for 12 hours until most of the free base are coordinated with the metal ion. The reaction solution is cooled to room temperature. Then dry Na{η$^5$-C$_5$H$_5$)Co[P(=O)(Ome)$_2$]$_3$} (104 mg 0.22 mmol) is added to the mixture which is magnetically stirred for another 1 hour. After the reaction was complete, the solvent is removed under vacuum and the residue dissolved in CH$_2$Cl$_2$, filtered and chromatographed on silica gel using CH$_2$Cl$_2$/Hexane as eluent to afford the pure product as a red solid. Yield: 86%; MALDI-TOF MS: calcd. For [M$^+$]: M. p. > 300° C.; 1587.1965, found: 1587.2154; Anal. Calc. For[C$_{60}$H$_{44}$CoF$_{15}$N$_4$O$_9$P$_3$SiGd]: C, 45.40; H, 2.79; N, 3.53%, Found: C, 45.46; H, 2.83; N, 3.51%; UV/Vis (DMSO, 25° C.): $\lambda_{max}$ (log ε) = 427 (5.68), 558 (4.34), 597 (3.29 dm$^3$ mol$^{-1}$cm$^{-1}$)

a) (i) Gd[N(SiMe$_3$)$_2$]$_3$·[LiCl(THF)$_3$]$_x$, toluene, reflux, 12 h; (ii) Na{(η$^5$-C$_5$H$_5$)Cd[P(=O)(OMe)$_2$]$_3$}, toluene, rt, 1 h; b) (i) TBAF (THF, 1M), CH$_2$Cl$_2$, rt, 30 min; (ii) a) 4-iodophenol, Pd(PPh$_3$)$_4$, CuI, THF, NEt$_3$, 40° C., 12 h; c) Tetraetyleneglycol diiodide, DMF, K$_2$CO$_3$, 80° C., 8 h; d) Triethylamine, DMF, 85° C., 24 h.

Gd—OH:

Tetrabutylammonium fluoride (TBAF, 1.0 M in THF, 200 µL, 0.2 mmol) is added to a solution of Gd-TMS (182 mg, 0.1 mmol) in 10 ml CH$_2$Cl$_2$, and the solution is stirred for 30 minutes. The progress of the reaction is monitored by TLC. After completion of the reaction, the mixture is passed through a short column of silica gel. After removal of the solvent, the intermediate is obtained and used for the next step without further purification. Then the obtained intermediate and 4-iodophenol (33 mg, 0.15 mmol) are dissolved in dry tetrahydrofuran (THF, 15 ml) and triethylamine (Net$_3$, 5 mL), and the mixture is bubbled with nitrogen for 30 minutes. After that, Pd(PPh$_3$)$_4$ (12 mg 0.01 mmol) and CuI (3.8 mg, 0.02 mmol) are added to the above solution. The reaction mixture is stirred at least 35° C. for at least 10 hours under a nitrogen atmosphere. Then the solvent is removed under reduced pressure. The residue is purified by column chromatography on silica gel using $CH_2Cl_2$/Methanol (50:1) as eluent to afford the pure product as a red solid. Yield: 73% (Table 2); M. p.>300° C.; MALDI-TOF MS: calcd. For [$M^+$]: 1607.0291. found: 1608.0308; Anal. Calc. For [$C_{63}H_{40}CoF_{15}N_4O_{10}P_3Gd$]: C, 47.08; H, 2.51; N, 3.49%. Found: C, 47.10; H, 2.49; N, 3.51%; UV/Vis (DMSO, 25° C.): $\lambda_{max}$ (log $\epsilon$)=426 (5.70), 555 nm (4.48 $dm^3$ $mol^{-1}$ $cm^{-1}$).

TABLE 2

Yield in different cross-coupling reaction condition(%). Considering both time and temprature, 40° C. and 12 hours is selected as the major reaction condition.

| Temperature (° C.) | Time (hours) | | |
|---|---|---|---|
| | 10 | 12 | 15 |
| 35 | 60 | 64 | 69 |
| 40 | 68 | 73 | 74 |
| 60 | 59 | 62 | 66 |

Gd—I:

To a solution of Gd—OH (161 mg, 0.1 mmol) and tetraethyleneglycol diiodide (207 mg, 0.5 mmol) in dry N,N-Dimethylmethanamide (DMF, 10 ml) is added anhydrous $K_2CO_3$ (69 mg, 0.5 mmol), and the mixture is heated to 80° C. for 8 hours under a nitrogen atmosphere. Then the solvent is removed under reduced pressure. The crude product is purified by column chromatography on silica gel eluented by $CH_2Cl_2$/$CH_3OH$ (v/v, 100:1) to afford the pure product as a red solid. Yield: 82%; M. p.>300° C.; MALDI-TOF MS: calcd. For [$M^+$]: 1893.2210. found 1893.1038; Anal. Calc. for [$C_{71}H_{55}CoF_{15}IN_4O_{13}P_3Gd$]: C, 45.04; H, 2.94; N, 3.11%. Found: C, 45.21; H, 2.99; N, 3.06%; UV/Vis (DMSO, 25° C.): $\lambda_{max}$ (log $\epsilon$)=425 (5.71), 555 nm (4.50 $dm^3$ $mol^{-1}$ $cm^{-1}$).

Gd—N:

To a solution of Gd—I (95 mg, 0.05 mmol) in dry (DMF, 10 ml), anhydrous Nets (1 ml, excess) is added, and the mixture is heated to 85° C. for 24 h under the nitrogen atmosphere. Then the solvent is removed under reduced pressure. The obtained crude product is purified by silica gel column chromatography using $CH_2Cl_2$/$CH_3OH$ (v/v, 80:1) as the eluent to remove unreacted Gd—I and other impurities, then using $CH_2Cl_2$/$CH_3OH$ (v/v, 10:1) to obtain the pure product as a red solid. Yield: 80%; M. p.>300° C.; MALDI-TOF MS: calcd. For [$M^+$]: 1867.5095. found 1867.2538; Anal. Calc. For [$C_{99}H_{85}CoF_{15}N_6O_{16}P_3Gd$]: C, 46.37; H, 3.54; N, 3.51%. Found: C, 46.40; H, 3.59; N, 3.48%; UV/Vis (DMSO, 25° C.): $\lambda_{max}$ (log $\epsilon$)=426 (5.74), 555 nm (4.53 $dm^3$ $mol^{-1}$ $cm^{-1}$).

Two-Photon-Absorption Measurements

The two-photon-absorption spectra (i.e., Z-scan traces) are measured at 800 nm by the open-aperture Z-scan method using 100 fs laser pulses with a peak power of 276 $GWcm^{-2}$ from an optical parametric amplifier operating at a repetition rate of 1 kHz generated from a Ti:sapphire regenerative amplifier system. The laser beam is split into two parts by a beam splitter. One is monitored by a photodiode (D1) as the incident intensity reference, $I_0$, and the other is detected as the transmitted intensity by another photodiode (D2). After passing through a lens with f=20 cm, the laser beam is focused and passed through a quartz cell. The position of the sample cell, z, is moved along the direction of the laser beam (z axis) by a computer-controlled translatable table so that the local power density within the sample cell could be changed under the constant incident intensity laser power level. Finally, the transmitted intensity from the sample cell is detected by the photodiode D2. The photodiode D2 is interfaced to a computer for signal acquisition and averaging. Each transmitted intensity datum represents the average of over 100 measurements. Assuming a Gaussian beam profile, the non-linear absorption coefficient, β, can be obtained by curve-fitting to the observed open-aperture traces, T(z), with Equation (1)[6], where $a_0$ is the linear absorption coefficient, l is the sample length (the 1 mm quartz cell) and $z_0$ is the diffraction length of the incident beam. After obtaining the nonlinear absorption coefficient, β, the 2 PA cross-section, $\sigma^{(2)}$, of the sample molecule (in units of 1 GM=$10^{-50}$ $cm^4$ $sphoton^{-1}$) can be determined by using Equation (2), where $N_A$ is Avogadro.'s constant, d is the concentration of the sample compound in solution, h is Planck's constant and v is the frequency of the incident laser beam.

$$T(z) = 1 - \frac{\beta I_0(1-e^{-a_0 l})}{2a_0(1+(z/z_0))^2} \quad (1)$$

$$\sigma_2 = \frac{1000\beta h v}{N_A d} \quad (2)$$

Further Embodiments of the Present Inventions

In a further embodiment of the present invention, new generation of PDT agents based on porphyrin-lanthanide complexes with specific functional groups are provided which can specifically localize on particular tumors, and their PDT processes can be monitored via NIR emission from erbium (Er). The newly developed erbium porphyrin complexes are conjugated with integrin $\alpha_v\beta_3$ isoform-specific peptides. The porphyrin and erbium emission from Er—$R_3$ show that Er—$R_3$ are able to significantly interrupt bladder cancer tumor growth that specific binds to "integrin $\alpha_v\beta_3$ isoform" with responsive emission for imaging.

The water solubility of Er porphyrin complexes are improved compared with previously reported analogues with conjugation of hydrophilic peptide RrRk (SEQ ID NO: 4). The integrin $\alpha_v\beta_3$ isoform specific peptide sequence (-cGRLKEKKc-) (SEQ ID NO: 5) is chosen to conjugate with RrRk (SEQ ID NO: 4) in different positions for the estimation of binding selectivity to integrin $\alpha_v\beta_3$ isoform in bladder cancer cells (Scheme 3). The amphiphilic character of the peptides is synthesized with the combination of hydrophilic RrRk (SEQ ID NO: 4) and hydrophobic cGRLKEKKc (SEQ ID NO: 5) to improve the cell permeability. The absorption coefficient (Porphyrin: Soret Band at 430 nm, 199,526 $cm^{-1}$) and emission quantum yield (Porphyrin: Soret Band and Er: $^2F_{5/2} \rightarrow {}^2F_{7/2}$) of Er—$R_1$, Er—$R_2$ and Er—$R_3$ are similar. The details of photophysical measurement of Ln-$R_n$ are shown in the Table 3. The Er moiety demonstrates stronger singlet oxygen quantum efficiency than Yb moiety due to the energy transfer from porphyrin to Yb for f-f emission which is much better than from porphyrin to Er f-f emission. All of the Er—$R_n$ porphyrin complexes and Yb—$R_n$ porphyrin

TABLE 3

Photophysical properties Summary of Ln—R$_n$ (Ln = Yb, Er, n = 1, 2, 3)

| Compound | Absorption ($\lambda_{max}$)[nm] Log($\epsilon$[dm$^3$mol$^{-1}$cm$^{-1}$])$^a$ | Excitation ($\lambda_{exc}$)[nm] | Emission($\lambda_{em}$) [nm]$^a$ ($\Phi_{em}$, $\tau$)$^{b,c}$ | $\Phi_\Delta{}^d$ |
|---|---|---|---|---|
| Yb-R$_1$ | 425 (5.37), 554 (4.09) | 430 | 656, 712 (0.012) 975 (29.86 s) | Not Found |
| Yb-R$_2$ | 425 (5.34), 554 (4.16) | 430 | 56, 712 (0.013) 975 (30.08 s) | Not Found |
| Yb-R$_3$ | 425 (5.27), 554 (4.04) | 430 | 656, 712(0.013) 975 (29.97 s) | Not Found |
| Er-R$_1$ | 426 (5.32), 554 (4.05) | 430 | 654, 715 (0.014), 1531 | 0.11 |
| Er-R$_2$ | 426 (5.50), 554 (4.53) | 430 | 654, 715 (0.014), 1531 | 0.12 |
| Er-R$_3$ | 426 (5.36), 554 (4.24) | 430 | 654, 715 (0.015), 1531 | 0.12 |

Complexes are characterized by $^1$H NMR and mass spectrometry (FIG. 17-36).
$^a$Absorption and Emission are measured in water (3% DMSO) at room temperature.
$^b$The emission quantum yield standard used in this study is tetraphenylporphyrin (H$_2$TPP) in anhydrous DCM ($\Phi$em = 0.120 at 298 K).
$^c$lifetime were measured in water (3% DMSO) at room temperature
$^d$The Singlet oxygen quantum yield standard used in this study was tetraphenylporphyrin (H$_2$TPP) in anhydrous DCM ($\Phi\Delta$ = 0.62 at 298 K).

Figure 12:
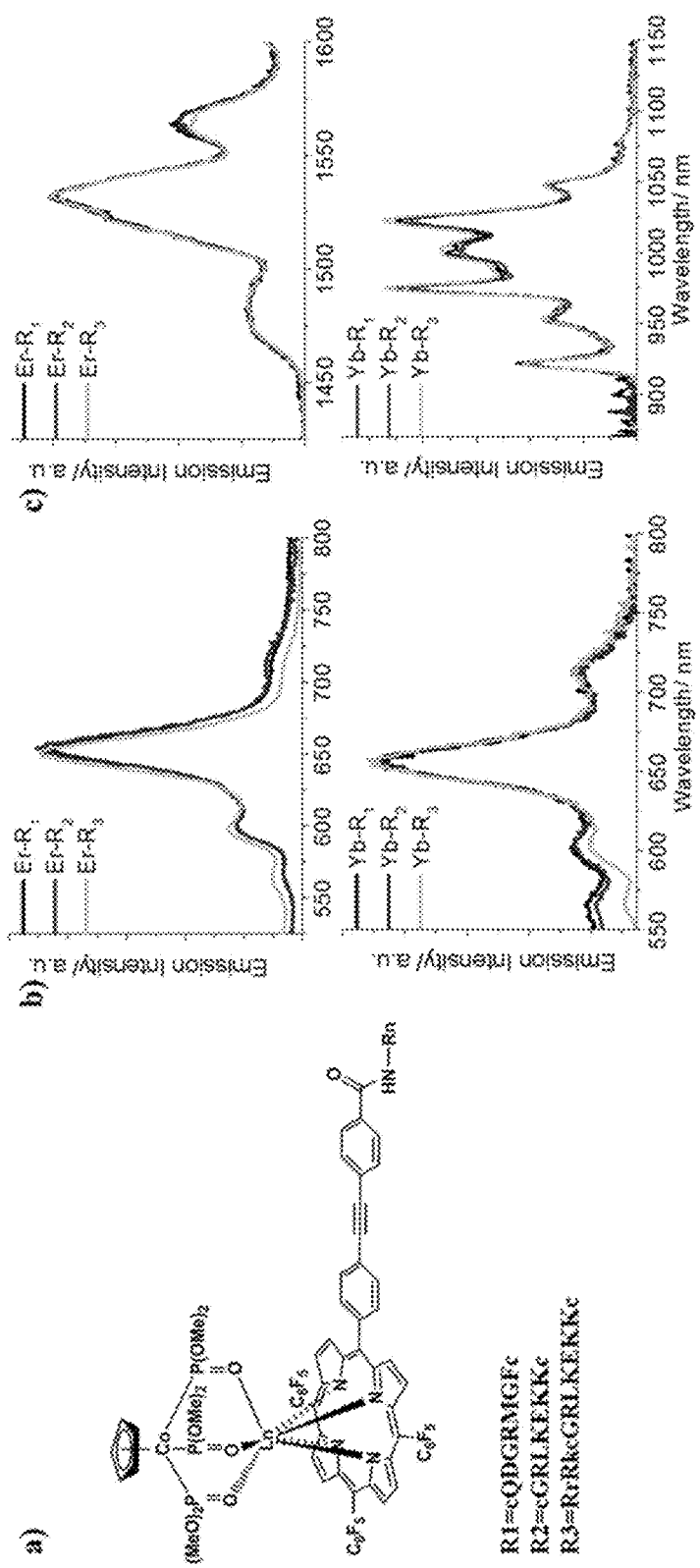
FIG. 12 shows (a) the molecular structures of Ln-R$_n$, (b) the visible spectra of Ln-R$_n$ in aqueous solution with 430 nm excitation (conc.=1 M, Ln=Er or Yb, n=1, 2 and 3) and (c) near-infrared emission spectra of Ln-R$_n$ in aqueous solution with 430 nm excitation (conc.=1M, Ln=Er or Yb, n=1, 2 and 3).
Figure 13:
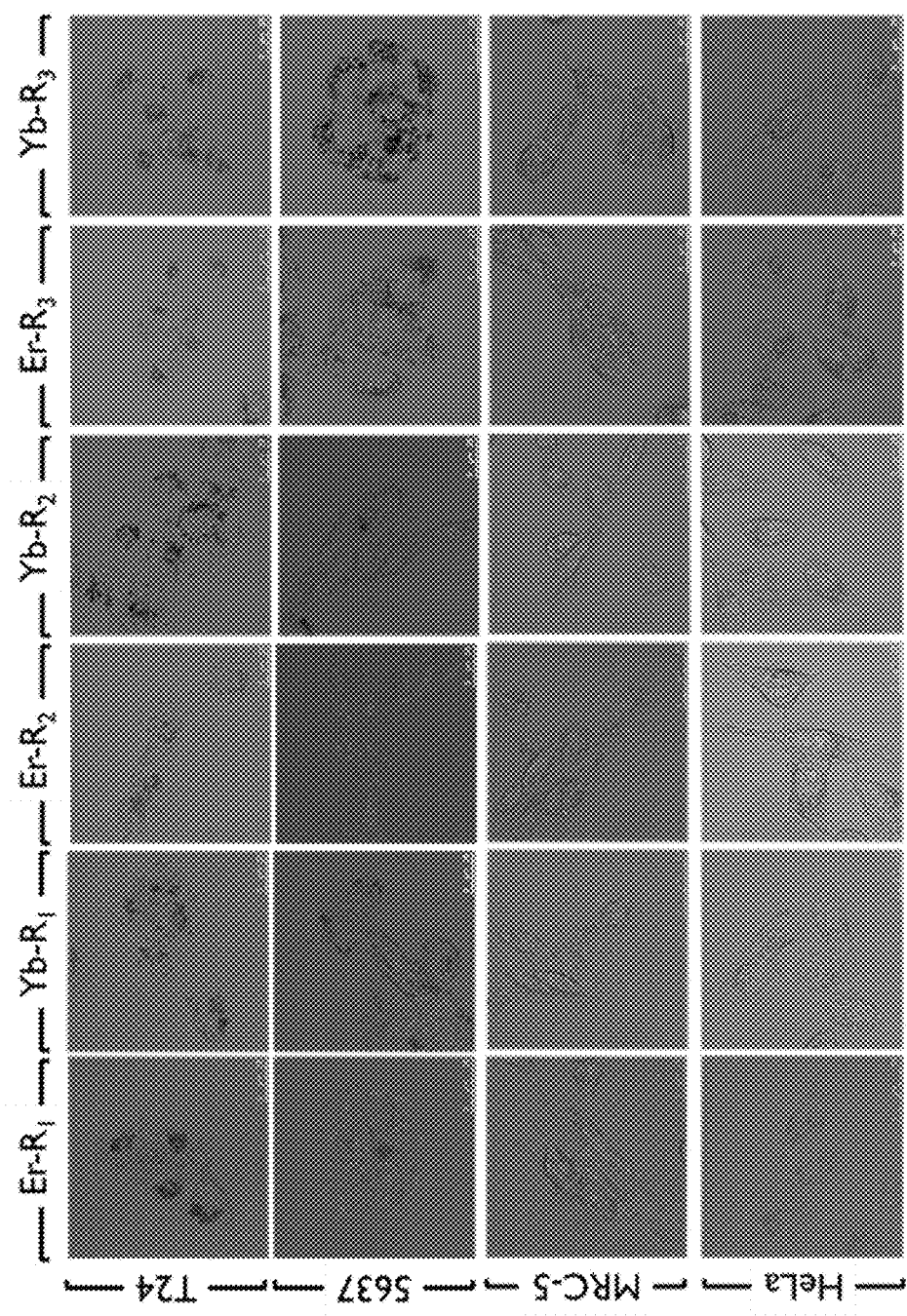
FIG. 13 shows subcellular localization of Er—R$_n$ and Yb—R$_n$ porphyrin complexes in human bladder carcinoma (T24 and 5637) cells, normal lung fibroblast (MRC-5) cells, and Human cervical carcinoma (HeLa) cells.
Figure 37:
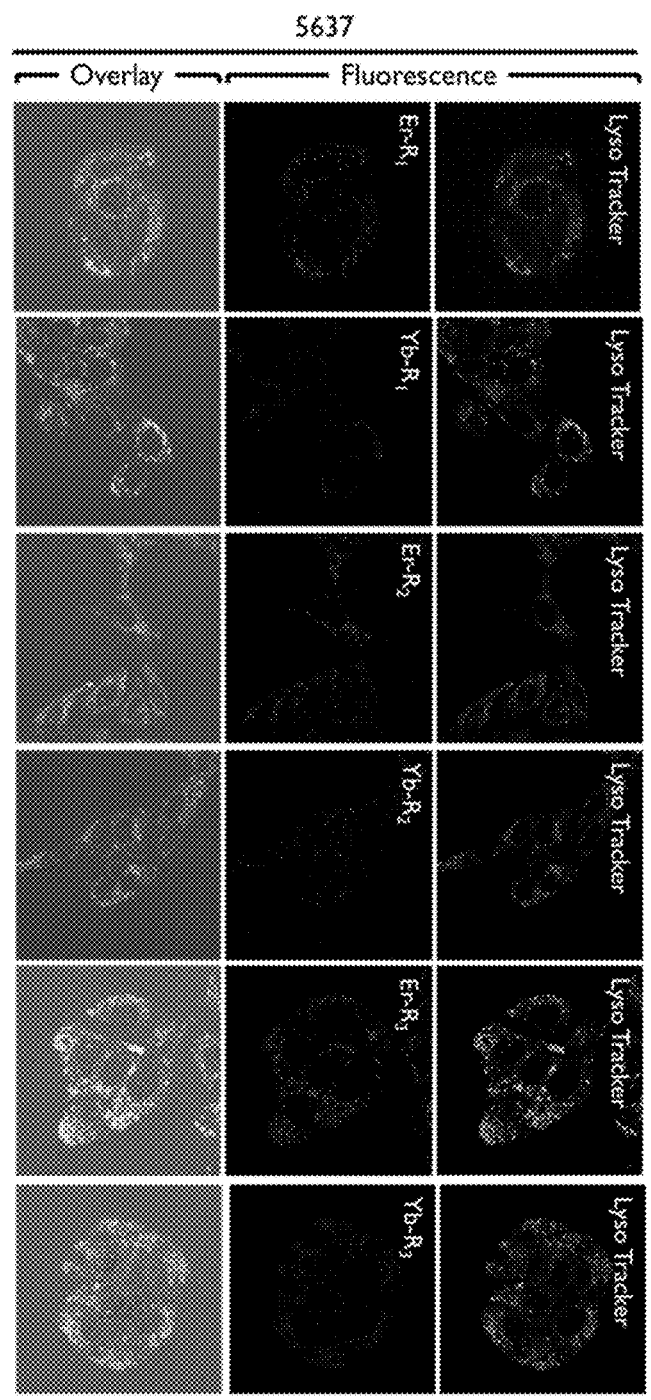
FIG. 37 shows the subcellular localization of Er—R$_n$ and Yb—R$_n$ porphyrin complexes by staining with Lyso Tracker green in (A) 5637 cells, (B) T24 cells, (C) HeLa cells and (D) MRC-5 cells.
Figure 37:
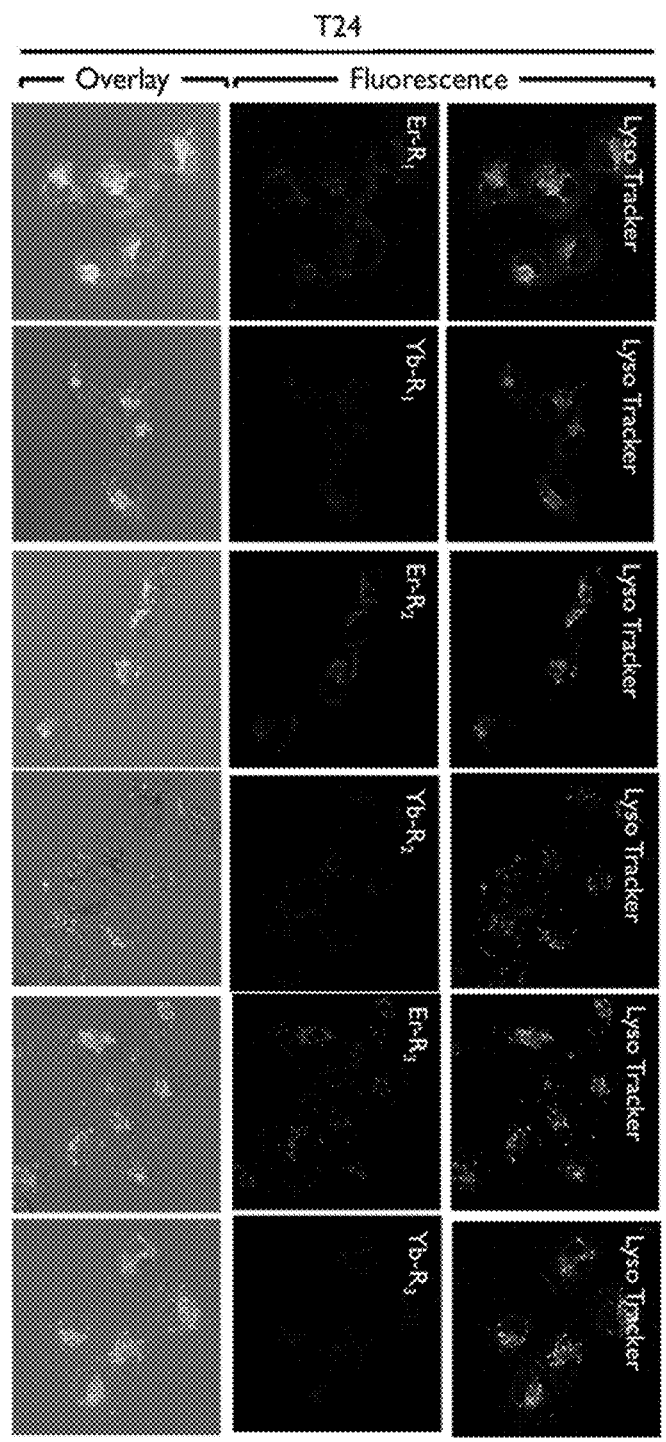
Figure 37:
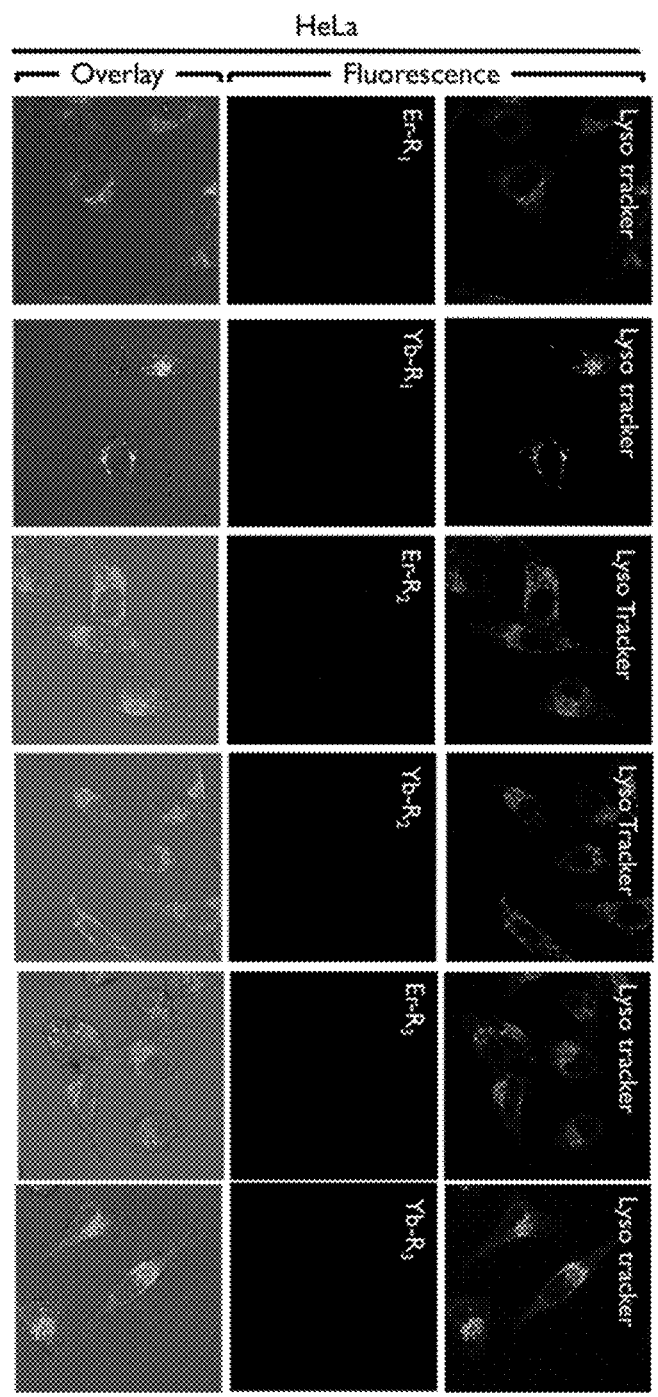
Figure 37:
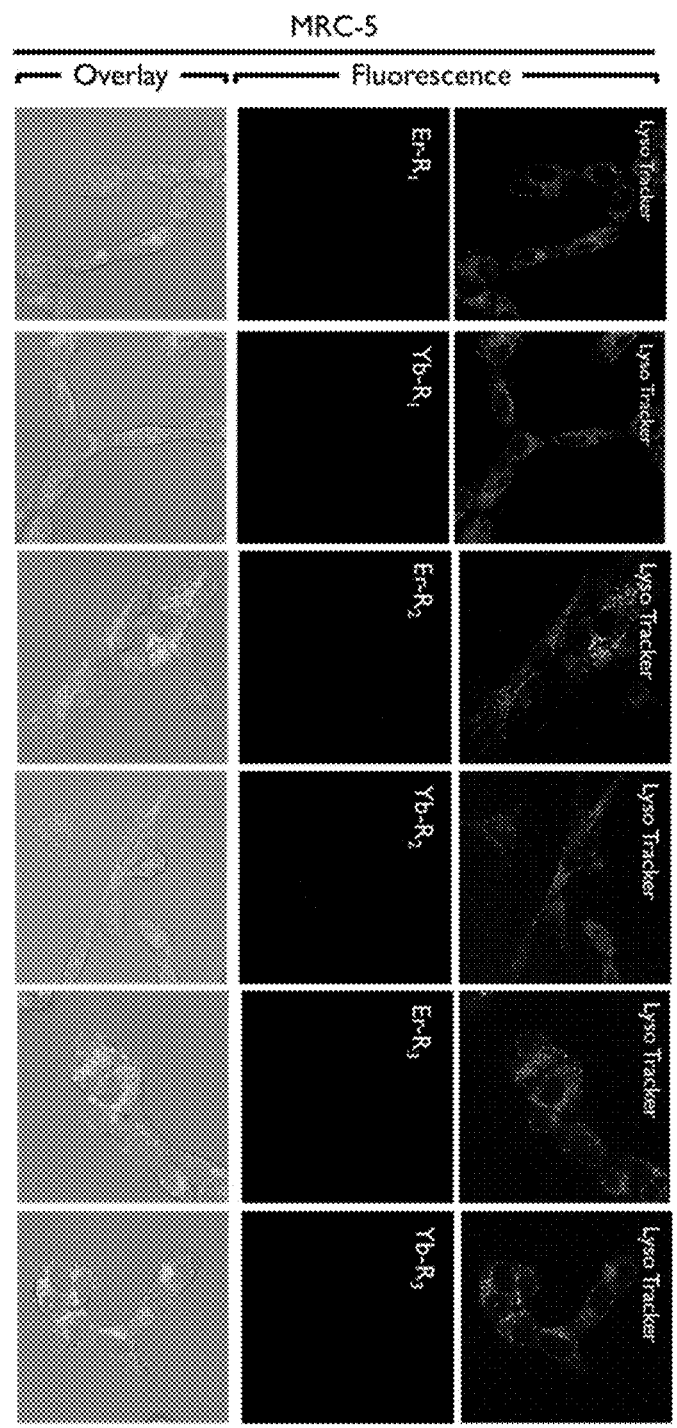

In FIG. 12, the photophysical properties of Er or Yb porphyrin based complexes are similar. However, the in vitro subcellular localization, uptake and toxicity (light and dark) are different due to the conjugation of the peptides. First of all, the subcellular localization of Er—Rn porphyrin complexes and Yb—Rn porphyrin complexes (Ln=Er or Yb; n=1, 2 and 3; R1=cQDGRMGFc={Ahx}-(D-Cys)-Gln-Asp-Gly-Arg-Met-Gly-Phe-(D-Cys) (SEQ ID NO: 1); R2=cGRLKEKKc={Ahx}-(D-Cys)-Gly-Arg-Leu-Lys-Glu-Lys-Lys-(D-Cys) (SEQ ID NO: 2); R3=RrRkcGRLKEKKc={Ahx}-Arg-Arg-(D-Arg)-Lys-{Ahx}-(D-Cys)-Gly-Arg-Leu-Lys-Glu-Lys-Lys-(D-Cys) (SEQ ID NO: 3) in bladder cancer cells-T24 and -5637, cervical cancer cells—HeLa and normal lung normal cells-MRC5 are different (FIG. 13, dosed concentration=5 µM, incubation time=6 hours). The in vitro fluorescent intensity of three erbium porphyrin complexes is higher than its ytterbium motif analogue due to efficient energy transfer from the porphyrin molecules to the Yb3+ ion and emits Yb near-infrared fluorescence. In bladder cancer cells T24 and 5637, red porphyrin emission from Er-R1 is found only on the cell membrane, however, the red emission of Er-R2 and Er-R3 are found inside the cells. Ytterbium analogues also show the same subcellular localization; emission of porphyrin Yb-R1 is found in the cell membrane. The co-localization experiments have been done with green Lyso tracker, the red emission form Er-R2, Er-R3, Yb-R2 and Yb-R3 overlap well with the green fluorescence from Lyso Tracker in T24 and 5637 cells in FIG. 37, but Er-R1 and Yb-R1 are not, indicating the Er-R2 porphyrin complexes, Er-R3 porphyrin complexes, Yb-R2 porphyrin complexes and Yb-R3 porphyrin complexes are mostly localized in the lysosome of T24 cells and 5637 cells and Er-R1 and Yb-R1 are localized in T24 and 5637 cell membrane. To further confirm, the peptides sequence in SEQ ID NO: 1, SEQ ID NO: 2, and SEQ ID NO: 3 can recognize the $\alpha_v\beta_3$ integrin. The in vitro imaging of Er—Rn porphyrin complexes and Yb—Rn porphyrin complexes (n=1, 2 and 3) have been done in the non-bladder cancer cells, HeLa and MRC-5 under the same experimental condition. Red emission signal is detected in neither HeLa cells nor MRC-5. The lack of $\alpha_v\beta_3$ integrin in HeLa and MRC-5 cells should limit the uptake of Er—Rn and Yb—Rn. The porphyrin complexes Er—Rn and Yb—Rn (n=1, 2 and 3) will not bind to HeLa and MRC-5 cells, so only green emission signal from Lyso tracker is shown in fluorescent staining experiment (FIG. 37).

Figure 14:
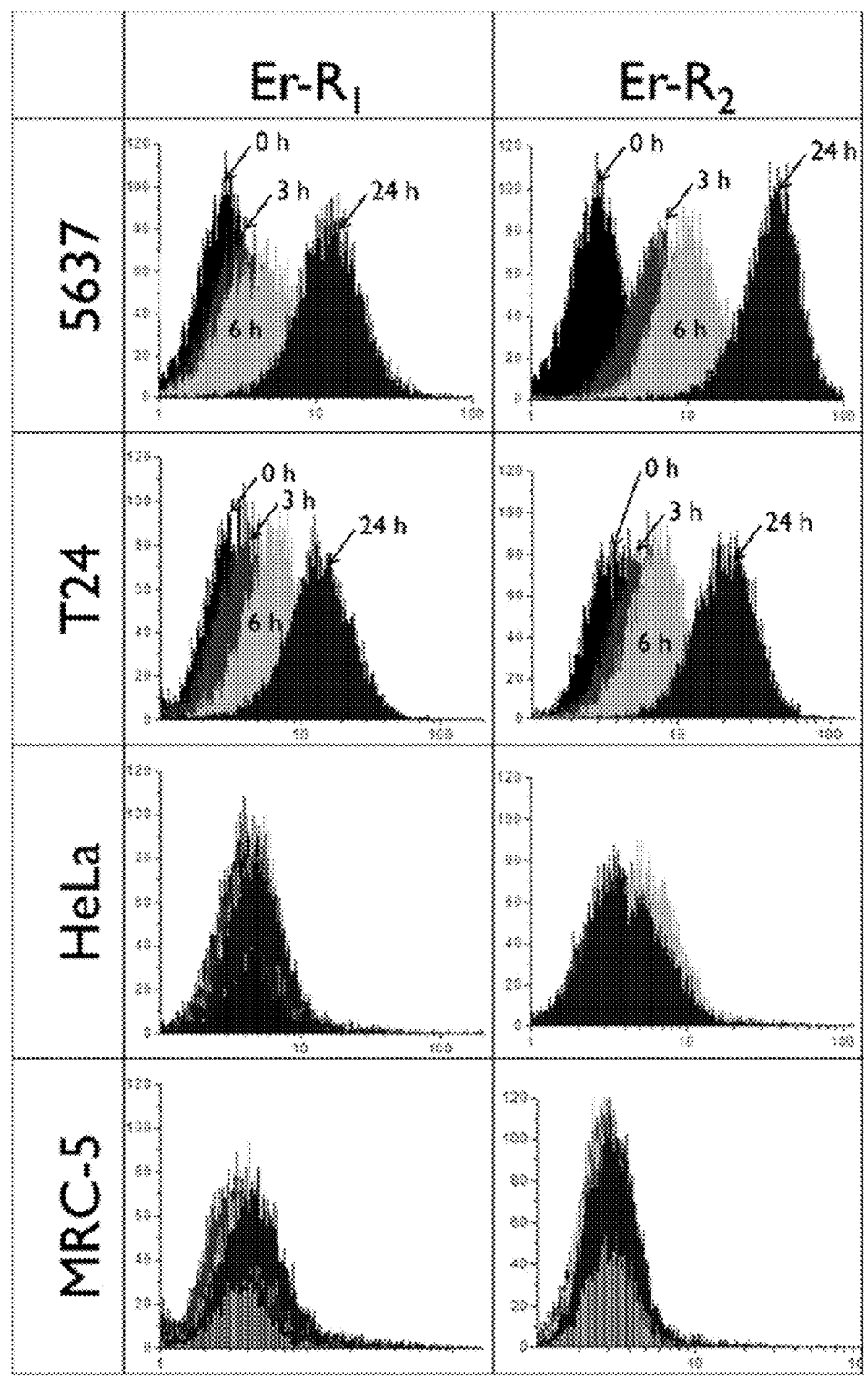
FIG. 14 shows the cellular uptake analyzed by flow cytometry of Er—R$_n$ and Yb—R$_n$ porphyrin complexes in 5637, T24, HeLa and MRC-5 cells incubated for 0, 3, 6, and 24 hours as indicated by arrows. The y-axis and x-axis are corresponding to cell counts and fluorescence intensity in FL3 channel (wavelength>650 nm).
Figure 14:
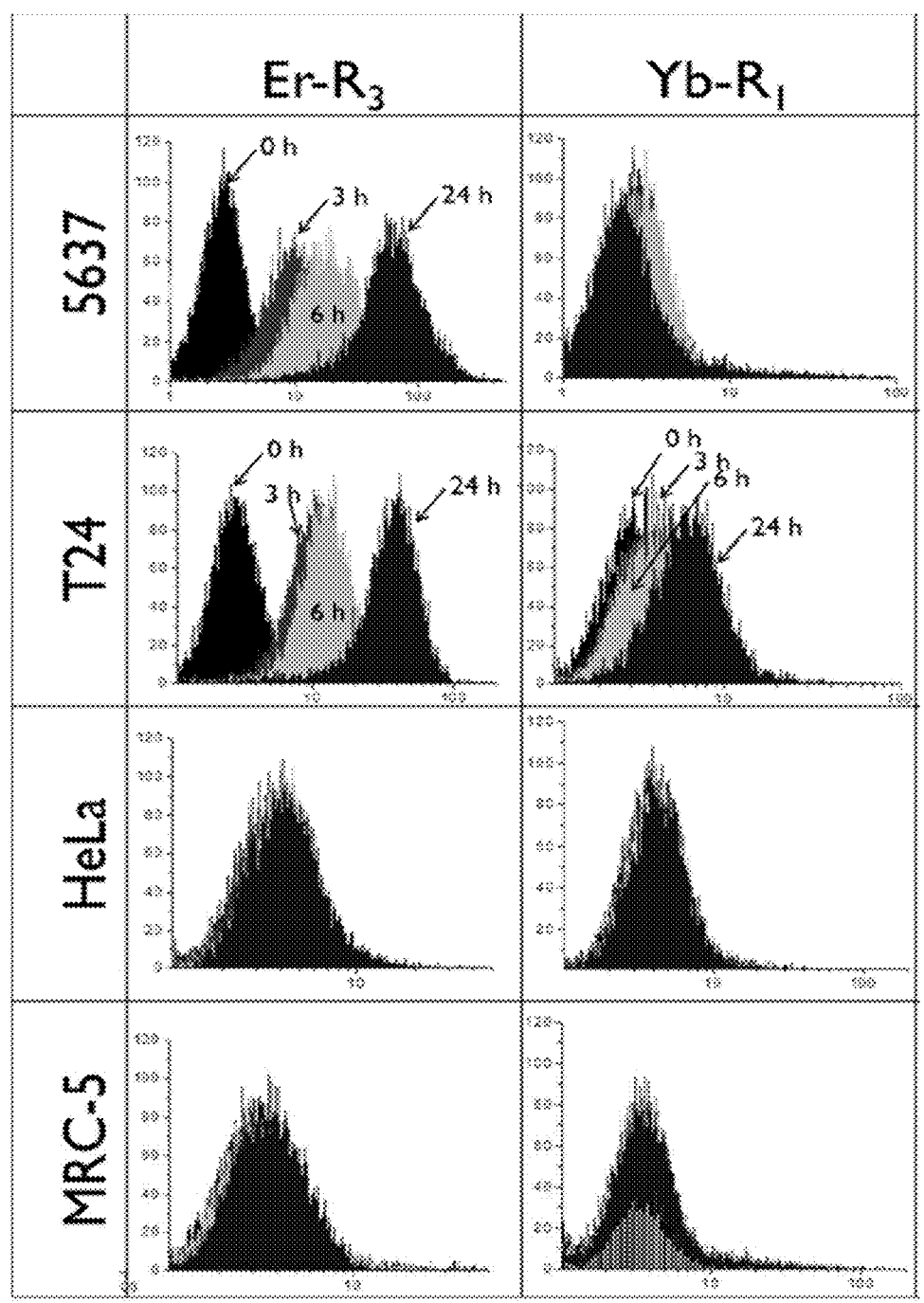
Figure 14:
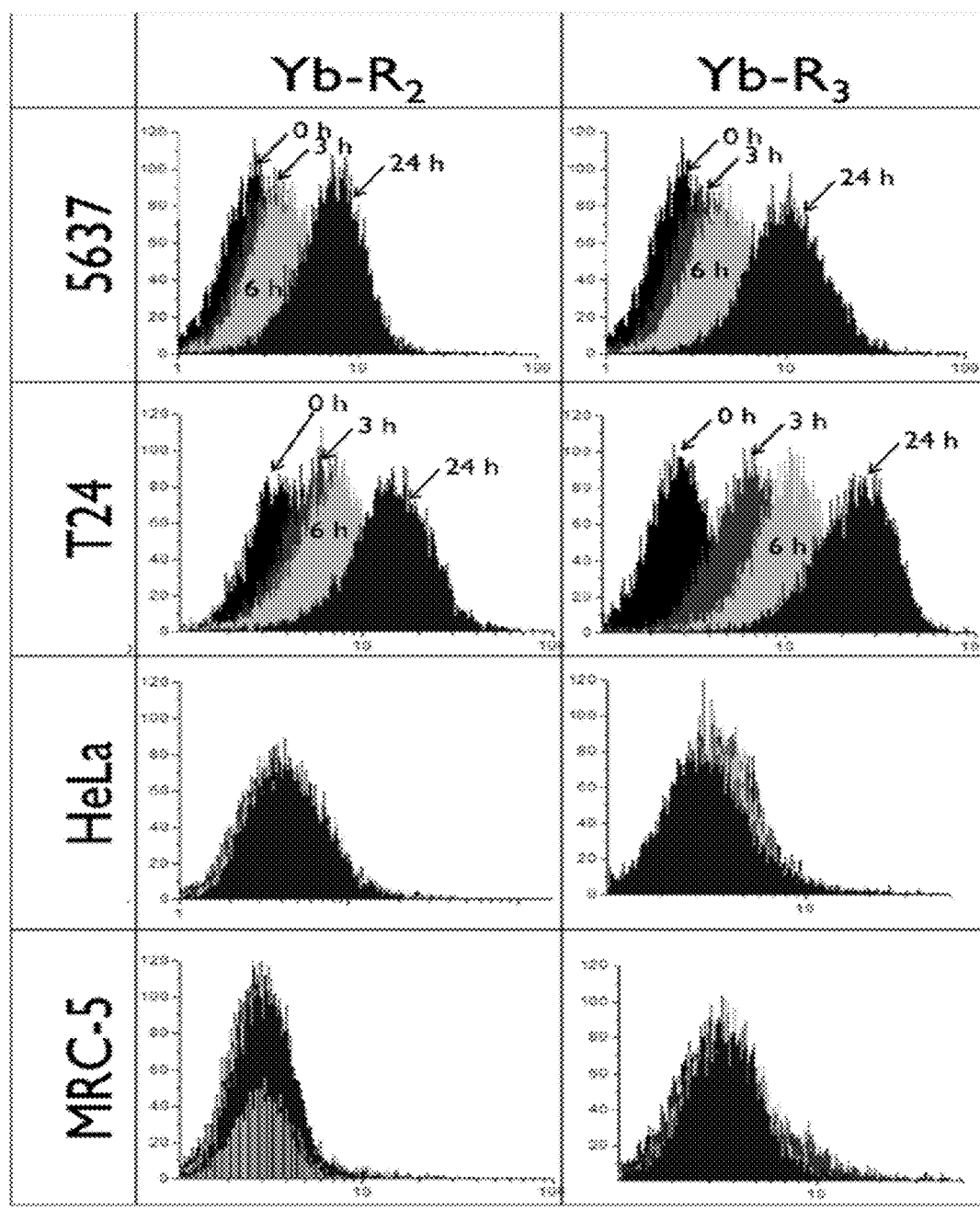

To further prove that the selective uptake of Er—Rn and Yb—Rn (n=1, 2 and 3) porphyrin complexes in bladder cancer cells was induced by the recognition of the $\alpha_v\beta_3$ integrin on the surface of the T24 through the tailor-made cyclic peptide R1, R2 and R3, the flow cytometry analysis of erbium (Er) and ytterbium (Yb) complexes in three cell lines is performed and the results are shown in the FIG. 14.

Molecular docking simulates the present porphyrin complexes and provides great steric hindrance to the peptides and facilitates interaction with the $\alpha_v\beta_3$ integrin. Zhang et al. (Urologic Oncol. 2012, 30, 635-645) have tested the peptides R$_1$ and R$_2$ of the complexes of the subject invention in different cell lines and screened through the OBOC combinatorial library to demonstrate the binding specificity towards blabber cancer. The amphiphilic peptide R$_3$ is the modification of R$_2$ by adding RrRk (SEQ ID NO: 4) to improve water solubility and cellular uptake. Therefore, as shown in FIG. 14, the T24 cells display significant fluorescence within a 6 hours incubation of Er—R$_n$ porphyrin complexes and Yb—R$_n$ porphyrin complexes in FL3 channel (Emission filter: 670 long-pass filter), whereas the HeLa and MRC-5 (cell surface $\alpha_v\beta_3$ integrin receptor-negative) incubated with Er—R$_n$ porphyrin complexes and Yb—R$_n$ porphyrin complexes show little fluorescence signal under similar experimental condition. In addition, the cellular uptake increases along with the incubation time in T24 cells which is quantified as median fluorescence intensity after 24-hour (Table 4).

TABLE 4

Summary of Er—R$_n$ porphyrin complexes and Yb—R$_n$ porphyrin complexes median fluorescence intensity in T24, HeLa and MRC-5 cells incubated for 24 hours.

| Median fluorescence intensity | T24 | HeLa | MRC-5 |
|---|---|---|---|
| Er—R$_1$ | 11.80 | 4.86 | 4.07 |
| Yb—R$_1$ | 6.68 | 4.31 | 3.56 |
| Er—R$_2$ | 21.21 | 4.11 | 3.09 |
| Yb—R$_2$ | 14.07 | 4.21 | 3.02 |
| Er—R$_3$ | 40.52 | 4.13 | 3.59 |
| Yb—R$_3$ | 26.07 | 3.36 | 3.33 |

Figure 15:
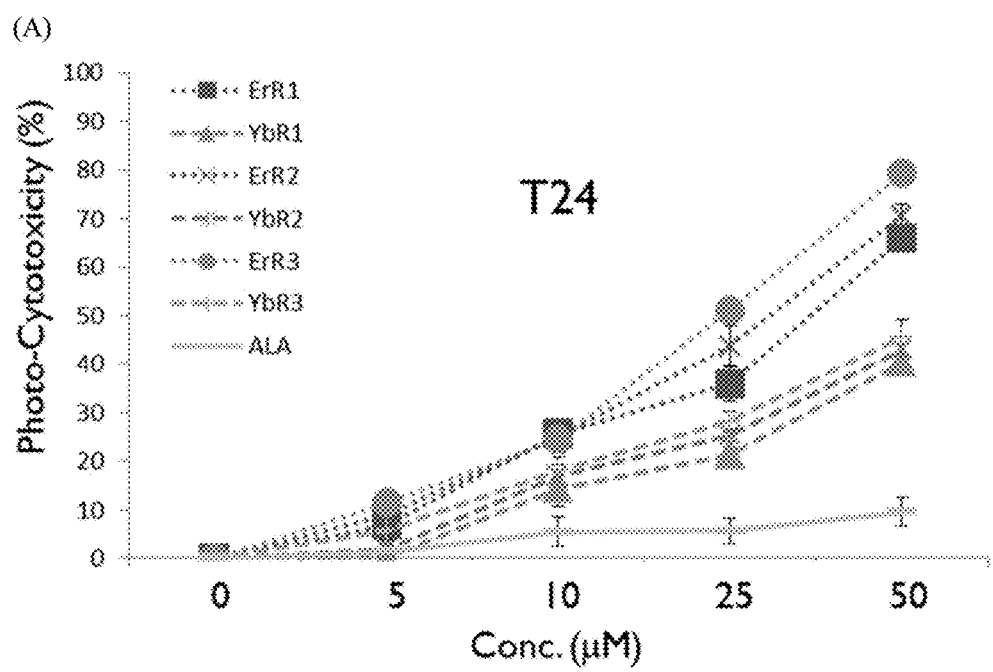
FIG. 15 shows the comparison of in vitro photo-cytotoxicity of Er—R$_n$ and Yb—R$_n$ porphyrin complexes with ALA in (A) T24, (B) HeLa and (C) MRC-5 cells irradiated at 10 J cm$^{-2}$ with 550 nm long-pass filter, D) Summary of IC$_{50}$ value of Er—R$_n$ and Yb—R$_n$ porphyrin complexes and ALA in the presence and absence of irradiation in T24, HeLa and MRC-5 cells.
Figure 15:
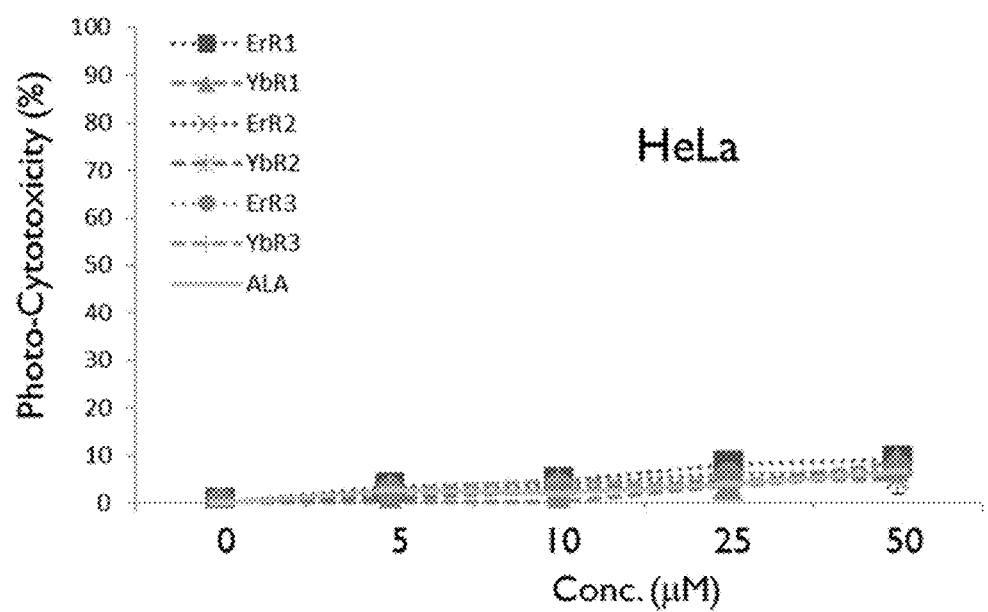
Figure 15:
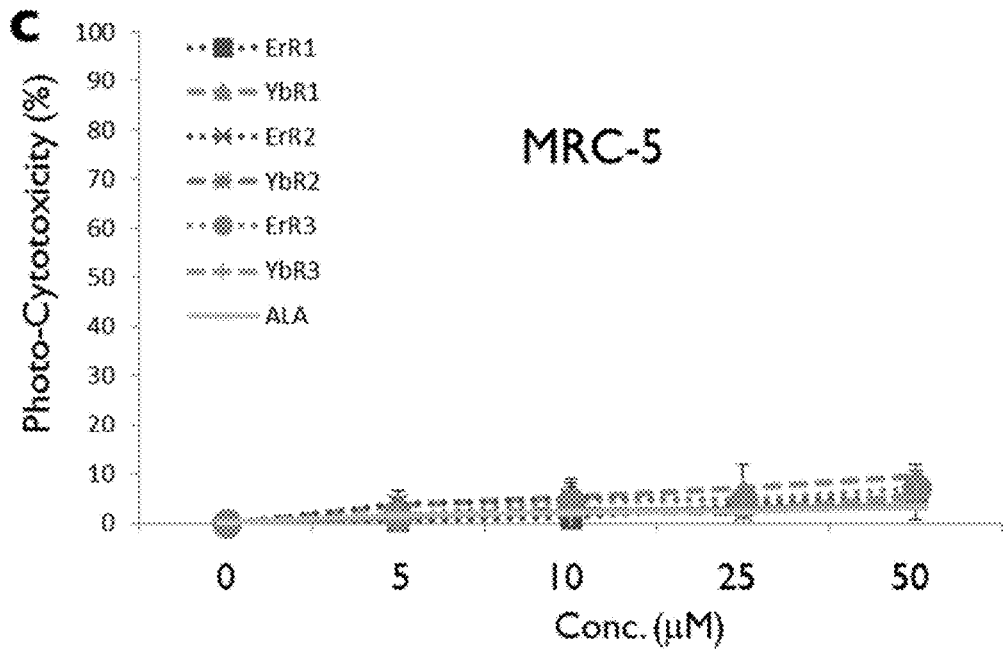

After verification of specific uptake of Er—R$_n$ porphyrin complexes and Yb—R$_n$ porphyrin complexes into T24 cells, in vitro PDT in various cell lines are carried out. Low-dark and high-light cytotoxicity are the necessary properties of a photosensitizer for the application in PDT. The cytotoxicity of Er—$R_n$ porphyrin complexes and Yb—$R_n$ porphyrin complexes to T24, HeLa and MRC-5 cells are examined in both presence (550 nm long-pass filter, 6 mW cm$^{-2}$, 28 minutes) and absence of irradiation using MTT assay. Er—$R_n$ and Yb—$R_n$ exhibit high photo-cytotoxicity under irradiation of 10 Jcm$^{-2}$. Furthermore, the photo-cytotoxicity increased along with the concentration of Er—$R_n$ porphyrin complexes and Yb—$R_n$ porphyrin complexes with a half lethal dose ($IC_{50}$) calculated in FIG. 15 after incubation for 24 hours. The $IC_{50}$ of Er—$R_n$ porphyrin complexes and Yb—$R_n$ porphyrin complexes to T24 is 8 to 10 times lower than HeLa and MRC-5 which demonstrates Er—$R_n$ porphyrin complexes and Yb—$R_n$ porphyrin complexes selectively kill bladder cancer. Attributed from the RrRK (SEQ ID NO:4) peptide sequence in Er—$R_3$ porphyrin complexes and Yb—$R_3$ porphyrin complexes, the cellular uptake of them is higher than Er—$R_1$ porphyrin complexes, Er—$R_2$ porphyrin complexes, Yb—$R_1$ porphyrin complexes and Yb—$R_2$ porphyrin complexes which lead to higher photo-cytotoxicity. Moreover, the excitation wavelength 550 nm is located in the Q band of porphyrin which would provide better tissue penetration in practice. However, it cannot trigger efficient PDT effect comparable to the FDA approved Aminolevulinic acid, (ALA). ALA is excited at 400-450 nm. In some embodiments of the present invention, Er—$R_n$ porphyrin complexes and Yb—$R_n$ porphyrin complexes cause more intense photo-cytotoxic effect than ALA when excited beyond 550 nm. Among all of the Er—$R_n$ porphyrin complexes and Yb—$R_n$ porphyrin complexes, Er—$R_3$ porphyrin complexes kill bladder cancer cells mostly effectively ($IC_{50}$ as low as 31 µM can be reached) due to brightest in vitro fluorescence and highest cellular uptake. However, in the absence of light, all of the Er—$R_n$ porphyrin complexes and Yb—$R_n$ porphyrin complexes are basically non-cytotoxic. ($IC_{50}$ over 1000 µM) Based on the results above, Er—$R_3$ porphyrin complexes is of the preferred embodiment for PDT agent to selectively kill bladder cancer.

In summary, the present invention provides a multi-modal lanthanide-porphyrin PDT agent that is capable of killing the tumor cells via $^1O_2$ from porphyrin moiety and affording the fluorescence imaging simultaneously. Er—$R_3$ porphyrin complexes are synthesized and shown to be highly selective to bladder cancer cells by specific targeting integrin $\alpha_v\beta_3$ isoform in bladder cancer cells with strong NIR and $^1O_2$ emission. The cancer cells selectivity uptake property of the porphyrin complexes of the present invention is confirmed by flow cytometry and in-vitro imaging and is able to significantly interrupt the bladder cancer cells growth with specific binding to "integrin $\alpha_v\beta_3$ isoform" of blabber cancer cells.

General Information about the Compound Synthesis.

All chemicals used are of reagent-grade and are purchased from Sigma-Aldrich and used without further purification. All analytical-grade solvents are dried by standard procedures, distilled and deaerated before use. NMR spectra are recorded on a Bruker Ultra shield 400 Plus NMR spectrometer. The $^1$H NMR chemical shifts are referenced to tetramethylsilane, TMS (d=0.00). High-resolution mass spectra, reported as m/z, are obtained on a Bruker Autoflex MALDI-TOF mass spectrometer. The synthetic Route of intermediates and Ln-Rn (Ln=Yb,Er, n=1, 2, 3) are shown in Scheme 2. All the Ln-Rn (Ln=Yb or Er, n=1, 2, 3) complexes are purified by High Performance Liquid Chromatography. The solvent system was shown in Table 5.

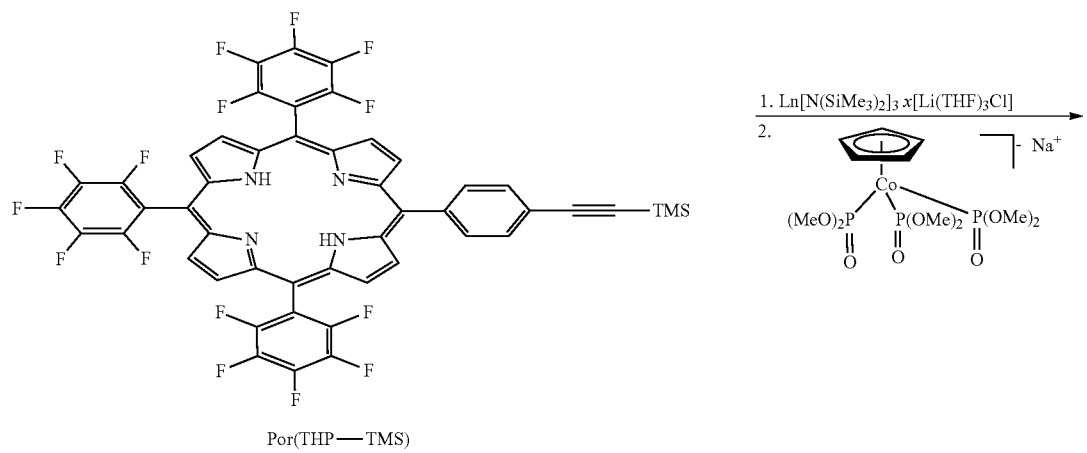

Scheme 2. The synthetic scheme of Ln—R*n*.
(Ln = Yb or Er, n = 1, 2, 3)

-continued
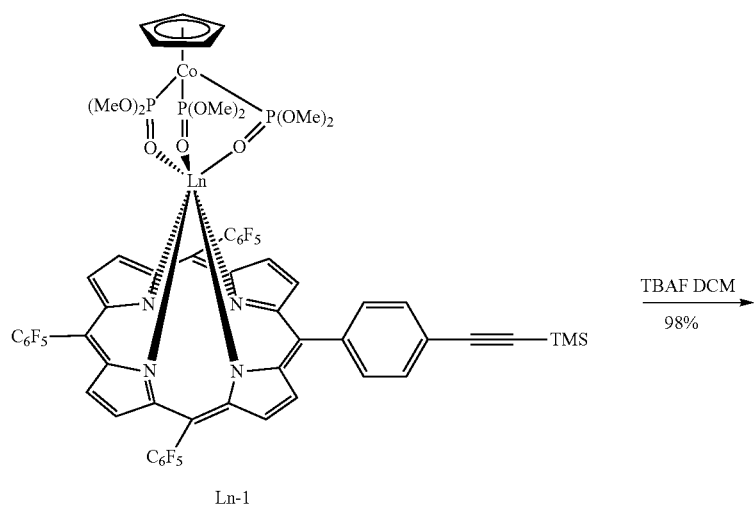
Ln-1
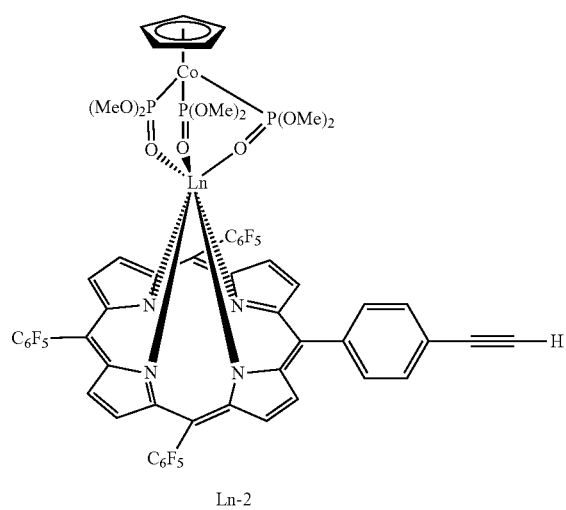
Ln-2
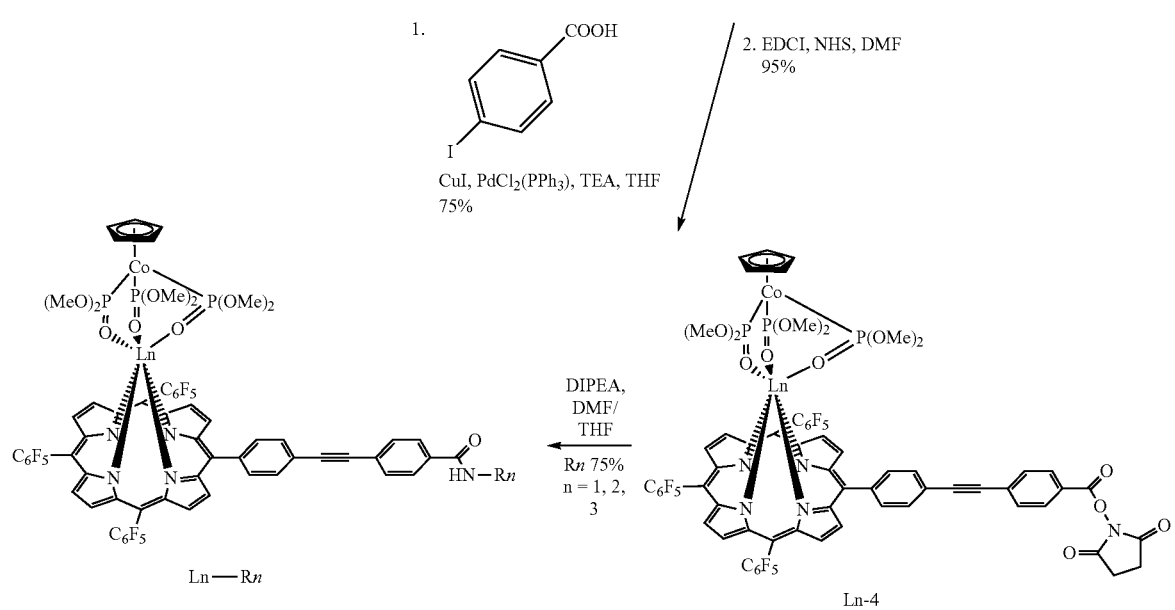
Ln—Rn
R1 = cQDGRMGFc
R2 = cGRLKEKKc
R3 = RrRkcGRLKEKKc Scheme 3. The molecular structures of bladder cancer peptides.
(SEQ ID NO: 1)
R1(PLZ 4)
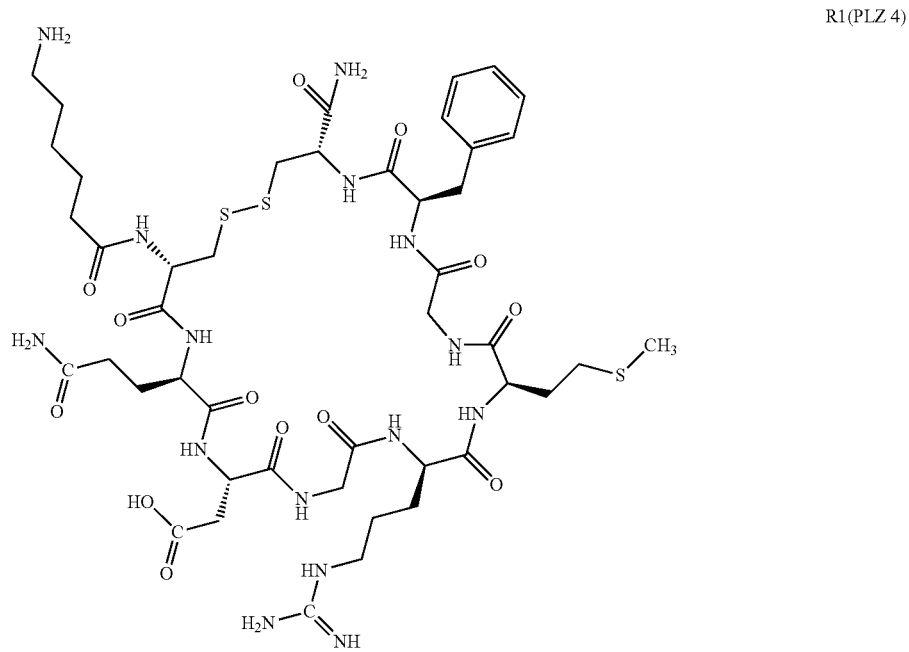
(SEQ ID NO: 2)
R2(PLZ 5)
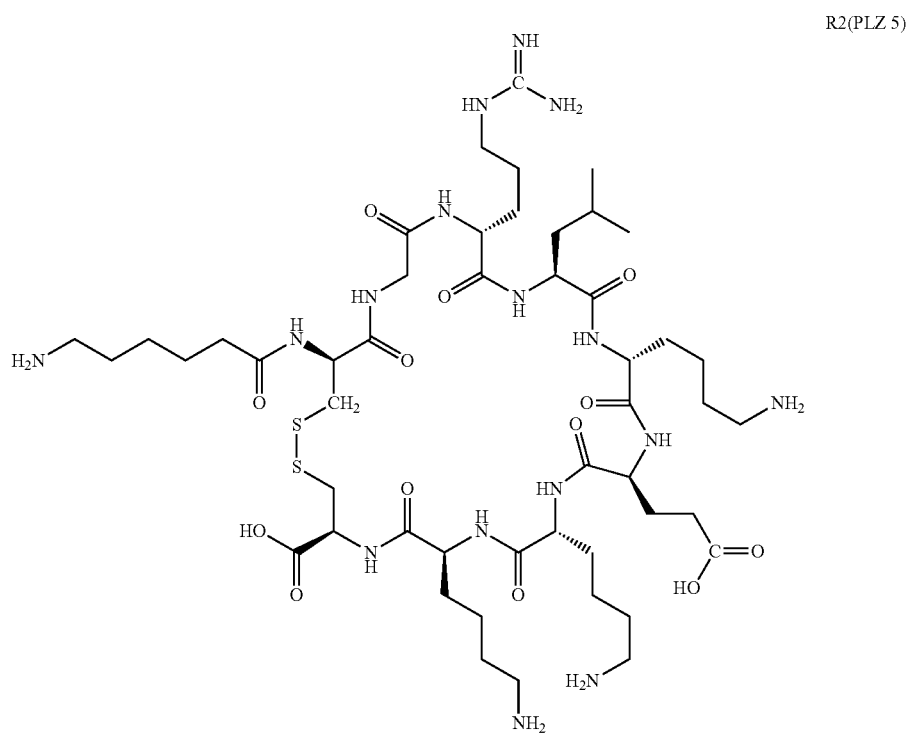

(SEQ ID NO: 3)

-continued

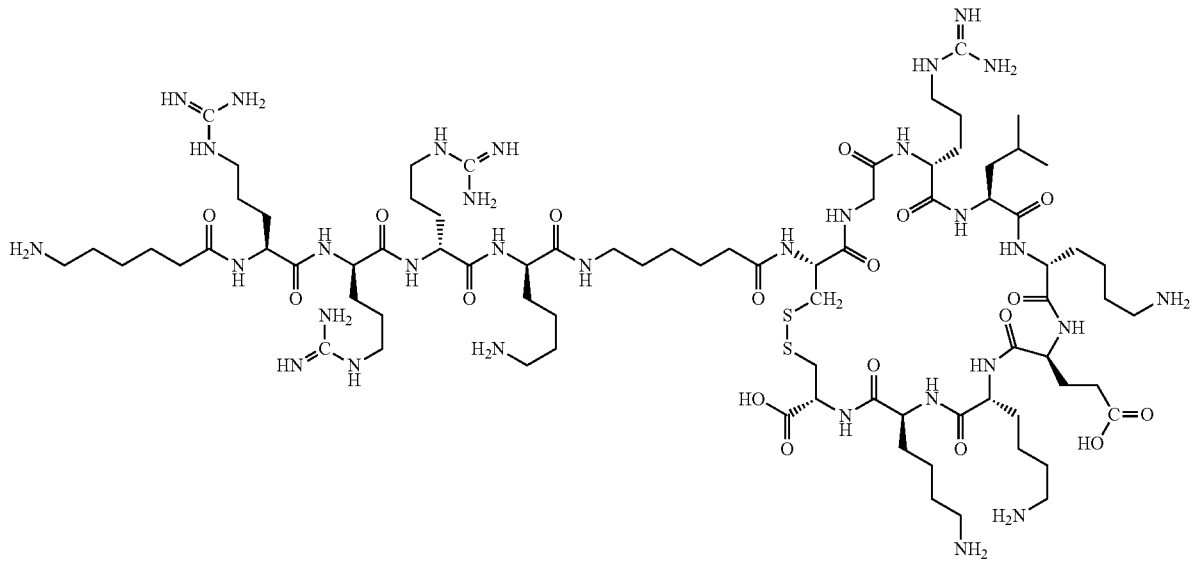

R3

Synthesis of the Intermediates and Ln-R$_n$ (Ln=Yb or Er, n=1, 2, 3)

Preparation of Compound Por(THP-TMS)

Pyrrole (280 uL, 4.0 mmol), pentafluorobenzaldehyde (588 mg, 0.3.0 mmol) and 4-[2-(trimethylsilyl)ethynyl]benzaldehyde 6 (202 mg, 1.0 mmol) are dissolved in 410 mL CH$_2$Cl$_2$ under an argon atmosphere. After 10 minutes BF$_3$O(Et)$_2$ (0.60 mL of 2.65M stock solution, 1.32 mmol) is added via syringe with vigorous stirring. After addition is complete, the reaction is left to stir for 1 hour at room temperature. DDQ (2,3-Dichloro-5,6-dicyano-1,4-benzoquinone) (0.68 g, 3.0 mmol) is added and after 1 hour stirring at room temperature the solvent is removed in vacuo. The crude reaction mixture is passed through a short silica column (hexanes-CH$_2$Cl$_2$ (9:1)) concentrated under reduced pressure, to give product 5,10,15-Tris(pentafluorophenyl)-20-[4-{2-(trimethylsilyl)ethynyl}phenylporphyrin], a pink/purple solid (238 mg, 22.8%); $^1$HNMR (CDCl$_3$): −2.87 (2H, s, NH), 7.91 (2H, d, J 8.1 Hz, Ar—H), 8.17 (2H, d, J 8.1 Hz, Ar—H), 8.89 (2H, d, J 4.7 Hz, P-pyrrole), 8.932 (4H, s, P-pyrrole), 8.94 (2H, d, J 4.7 Hz, P-pyrrole); 0.387 (9H, s) MS (MALDI) for [M]$^+$, calcd. for C$_{49}$H$_{23}$F$_{15}$N$_4$Si 980.1513. found 981.1519.

Preparation of Compound Ln-1

Ln[N(SiMe$_3$)2]$_3$.x[LiCl(THF)$_3$]: HN(SiMe$_3$)$_2$ (Ln=Yb or Er, 10.8 ml 0.050 mol) is dissolved in 20 ml of THF in ice bath, then n-BuLi (1.6 M in hexane) is added slowly over 30-minutes period. The resulting solution is magnetically stirred for 12 hours until a clear pale yellow solution is obtained. Then the solution is transferred slowly to a Schlenk flask with LnCl$_3$ (Ln=Yb or Er, 4.74 g, 0.017 mol) suspended in 20 ml THF. The resulting mixture is magnetically stirred for 24 hours until all of the solid LnCl$_3$ (Ln=Yb or Er,) disappear. The resultant solution Ln[N(SiMe$_3$)2]$_3$.x[Li(THF)$_3$Cl] (Ln=Yb or Er, x=3~5) is used for next synthetic step.

Yb-1:

Yb[N(SiMe$_3$)2]$_3$.x[Li(THF)$_3$Cl] (2.5 ml, 0.52 mmol of Yb) as prepared above is transferred to a Schlenk flask and the solvent is removed under vacuum. Then 10 ml CH$_2$Cl$_2$ is added, for the precipitation of LiCl. The mixture is centrifuged and the clear layer is transferred to another Schlenk flask with dry Por(THP-TMS) (0.1 g, 0.16 mmol) dissolved in 15 ml toluene. The resulting solution is refluxed until most of the free base coordinated with the metal ion. Then, dry NaLOMe (0.1 g, 0.22 mmol) [LOMe-((cyclopentadienyl)tris(dimethylphosphito)-cobaltate, an anionic tripodalligand) is added and magnetically stirred for another 12 hours before the reaction solution is cooled down to room temperature. Upon completion of the reaction, the solvent is removed in vacuum and the residue dissolved in CHCl$_3$, filtered and chromatographed on silica gel using CHCl$_3$/petroleum ether (V/V 1:1) as eluent. The product is dissolved in CH$_2$Cl$_2$ (5 ml) and the solution is filtered.

Yb-1:

Yield: 81%; $^1$HNMR (CDCl$_3$): δ −5.02 (s, 5H), 0.93 (s, 9H), 6.37 (s, 18H), 8.70 (s, 1H), 8.97 (d, J=4.96 Hz, 1H), 10.88 (s, 1H), 14.65 (s, 2H), 14.89 (s, 2H), 15.18 (s, 2H), 15.58 (s, 2H), 17.40 (s, 1H); MALDI-TOF MS: calcd. For C$_{60}$H$_{44}$CoF$_{15}$N$_4$O$_9$P$_3$SiYb [M]$^+$ 1603.0571. found: 1603.0556.

Er-1:

The same procedure with Yb-1, replace Yb[N(SiMe$_3$)2]$_3$.x[Li(THF)$_3$Cl] with Er[N(SiMe$_3$)2]$_3$.x[Li(THF)$_3$Cl]; Yield: 80%. $^1$HNMR (CDCl$_3$): δ −35.54 (s, 5H), 3.48 (s, 9H), 14.09 (s, 1H), 13.50 (s, 1H), 21.73 (s, 18H), 21.16 (s, 1H), 31.22 (s, 2H), 32.93 (s, 2H), 36.37 (s, 2H), 37.76 (s, 2H), 46.77 (s, 1H); MALDI-TOF MS: calcd. For C$_{60}$H$_{44}$CoErF$_{15}$N$_4$O$_9$P$_3$Si [M]$^+$ 1597.1878. found 1597.2927.

General Procedure for the Preparation of Ln-2

Yb-2:

TBAF (1.0 M in THF, 0.2 mL, 0.2 mmol) is added to a solution of Yb-1 (0.05 mmol 76.55 mg,) in 10 ml $CH_2Cl_2$, and the solution is stirred for 30 min. The progress of the reaction is monitored by Thin-layer Chromatography (TLC). After completion of the reaction, the mixture is passed through a short of silica gel column. After removal of solvent, pure product is obtained.

Yb-2:

Yield: 92%; $^1$HNMR ($CDCl_3$): δ −4.82 (s, 5H), 4.13 (s, 1H), 6.30 (s, 18H), 8.63 (s, 1H), 8.95 (d, J=4.44 Hz, 1H), 10.83 (s, 1H), 14.51 (s, 2H), 14.90 (s, 2H), 15.08 (s, 2H), 15.44 (s, 2H), 17.21 (s, 1H); MALDI-TOF MS: calcd. For $C_{57}H_{36}CoF_{15}N_4O_9P_3Yb$ $[M+Na+Cl]^+$ 1587.0176. found 1587.0514.

Er-2:

The same procedure with Yb-2, replace Yb-1 with Er-1; Yield: 92%; $^1$HNMR (CDCl3): δ −35.05 (s, 5H), 13.94 (s, 1H), 13.19 (s, 1H), 20.56 (s, 18H), 21.02 (s, 1H), 30.97 (s, 2H), 32.77 (s, 2H), 36.44 (s, 2H), 37.36 (s, 2H), 46.20 (s, 1H); MALDI-TOF MS: calcd. For $C_{57}H_{36}CoErF_{15}N_4O_9P_3$ $[M+H]^+$: 1525.0067. found: 1525.0143.

General Procedure for the Preparation of Ln-4

Yb-4:

$Pd(PPh_3)_4$ (22.16 mg 0.08 mmol), CuI (7.65 mg, 0.04 mmol), Yb-2 (30.62. mg, 0.02 mmol) and 4-iodobenzoic acid 5.087 mg are placed in a dried flask and under nitrogen. THF (15 mL) and $Net_3$ (5 mL) are added and the reaction mixture degassed with nitrogen. The reaction mixture is stirred at 40° C. for 12 hours. After that, the solvent is removed under reduced pressure. The residue is purified by chromatography. Elution with $CH_2Cl_2$/Methanol (12:1). The eluted compound (26 mg, 0.0157 mmol), EDCI (6.04 mg, 0.031 mmol), NHS (3.57 mg, 0.031 mmol) are placed in a dried flask and under nitrogen, 10 mL dry DMF is added. Stirred at room temperature for 48 hours, then remove the solvent. The residue is recrystallized by diethyl ether and dried to give Yb-4.

Yb-4:

Yield: 72%; $^1$HNMR ($CDCl_3$): δ −4.82 (s, 5H), 4.16 (s, 1H), 6.39 (s, 18H), 8.68 (s, 1H), 8.98 (d, J=4.44 Hz, 1H), 8.47 (s, J=4.44 Hz, 2H), 8.45 (s, J=4.44 Hz, 2H) 10.91 (s, 1H), 14.63 (s, 2H), 14.92 (s, 2H), 15.24 (s; 2H), 15.61 (s, 2H), 17.39 (s, 1H); MALDI-TOF MS: calcd. For $C_{68}H_{43}CoF_{15}N_5O_{13}P_3Yb$ $[M]^+$ 1748.0176. found 1748.0460. HPLC characterization: retention time=7.24 min (FIG. 16 (A)).

Er-4:

The same procedure with Yb-4, only replace Yb-2 with Er-2; Yield: 80%; $^1$HNMR ($CDCl_3$): δ −35.94 (s, 5H), 6.04 (s, 1H), 8.64 (d, J=7.96 Hz, 2H), 10.80 (d, J=5.12 Hz, 2H), 13.12 (s, 1H), 13.76 (s, 1H), 20.67 (s, 18H), 20.90 (s, 1H), 31.06 (s, 2H), 32.94 (s, 2H), 36.39 (s, 2H), 37.62 (s, 2H), 46.54 (s, 1H); MALDI-TOF MS: calcd. For $C_{68}H_{43}CoErF_{15}N_5O_{13}P_3$ $[M+Cl^-]$: 1777.2035. found: 1777.4591. HPLC characterization: retention time=7.23 min (FIG. 16 (B)).

General Procedure for the Preparation of Ln-Rn

Yb—$R_1$:

A stirred solution of Yb-4 (16 mg, 1 equiv.) in anhydrous DMF is mixed with N,N'-diisopropylethylamine (DIPEA) (1 equiv.). The mixture solution is added into a vial which contains peptide $R_1$ (1.3 equiv.) It was then reacted at room temperature overnight, after that, the solvent is removed under vacuum to get the dry compound. The residue is recrystallized by diethyl ether three times and dried to give Yb—$R_1$.

Figure 16:
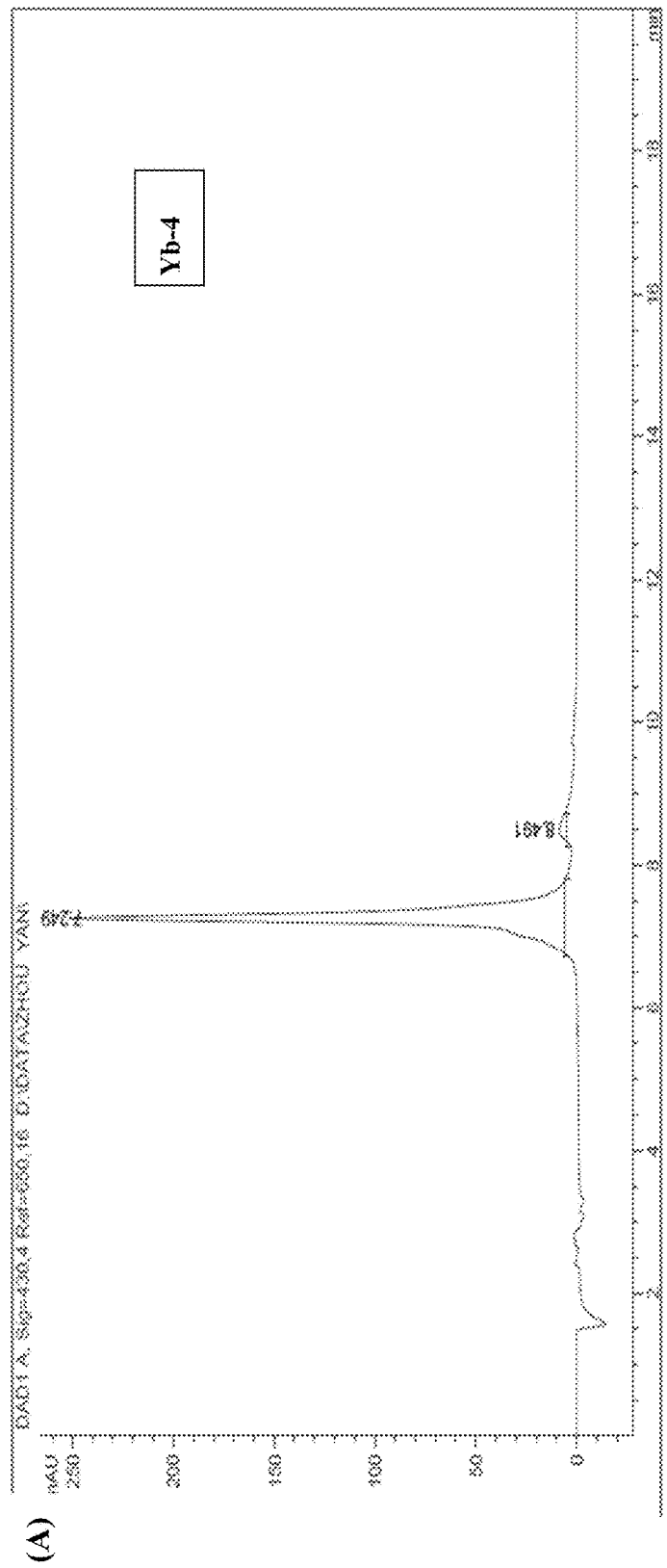
FIG. 16 shows HPLC chromatogram of the complexes. Elution conditions: column, Agilent ZORBAXSB-C18 (4.6×150 mm, particle size 5; flow rate, 1.0 mL/min; gradient elution; detection wavelength, 430 nm. Retention time: (A) Yb-4, 7.24 min; (B) Er-4, 7.23 min; (C) Yb—R$_1$, 10.00 min; (D) Yb—R$_2$, 10.21 min; (E) Yb—R$_3$, 10.01 min; (F) Er—R$_1$, 9.66 min; (G) Er—R$_2$, 10.09 min; and (H) Er—R$_3$, 9.80 min.
Figure 16:
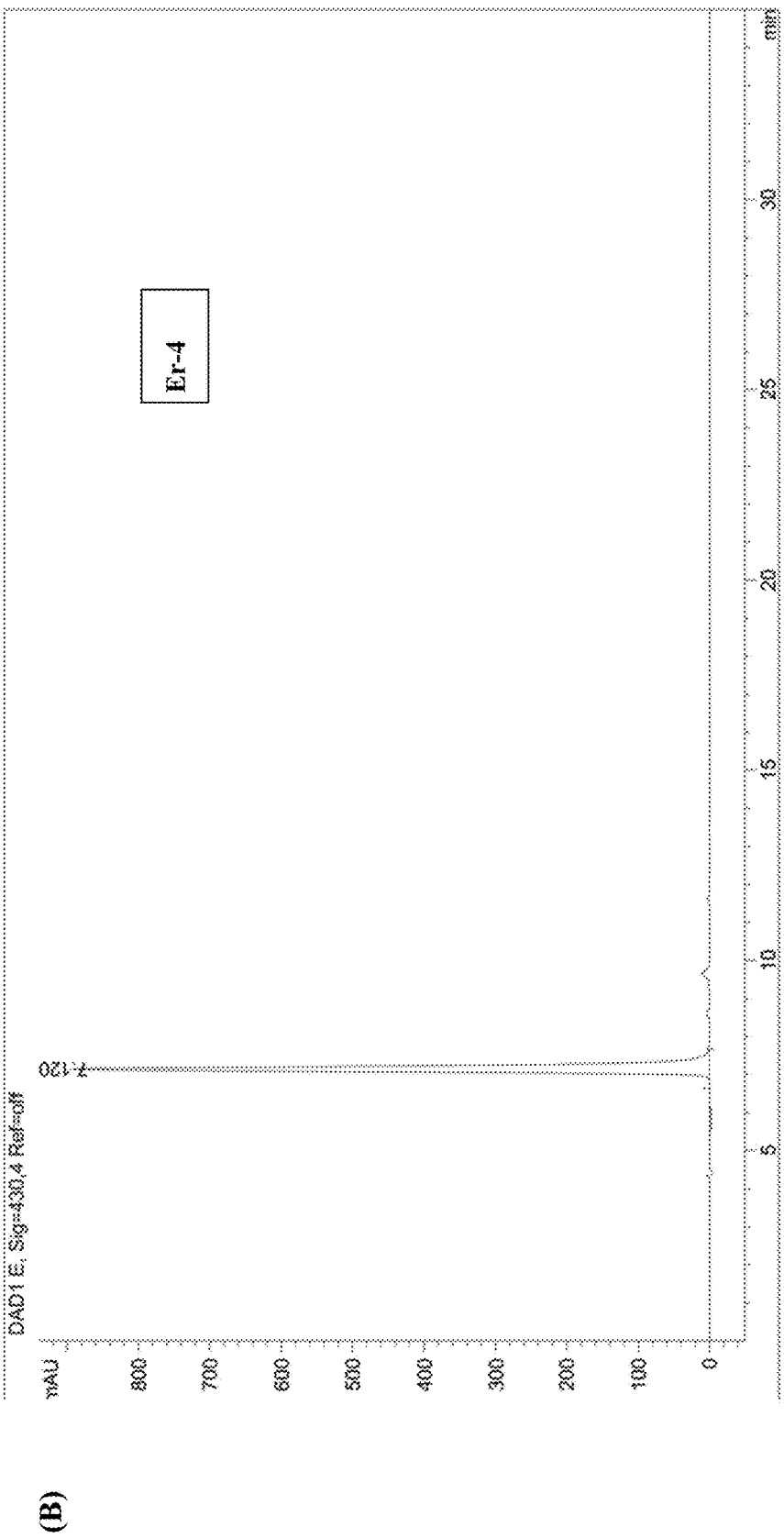
Figure 16:
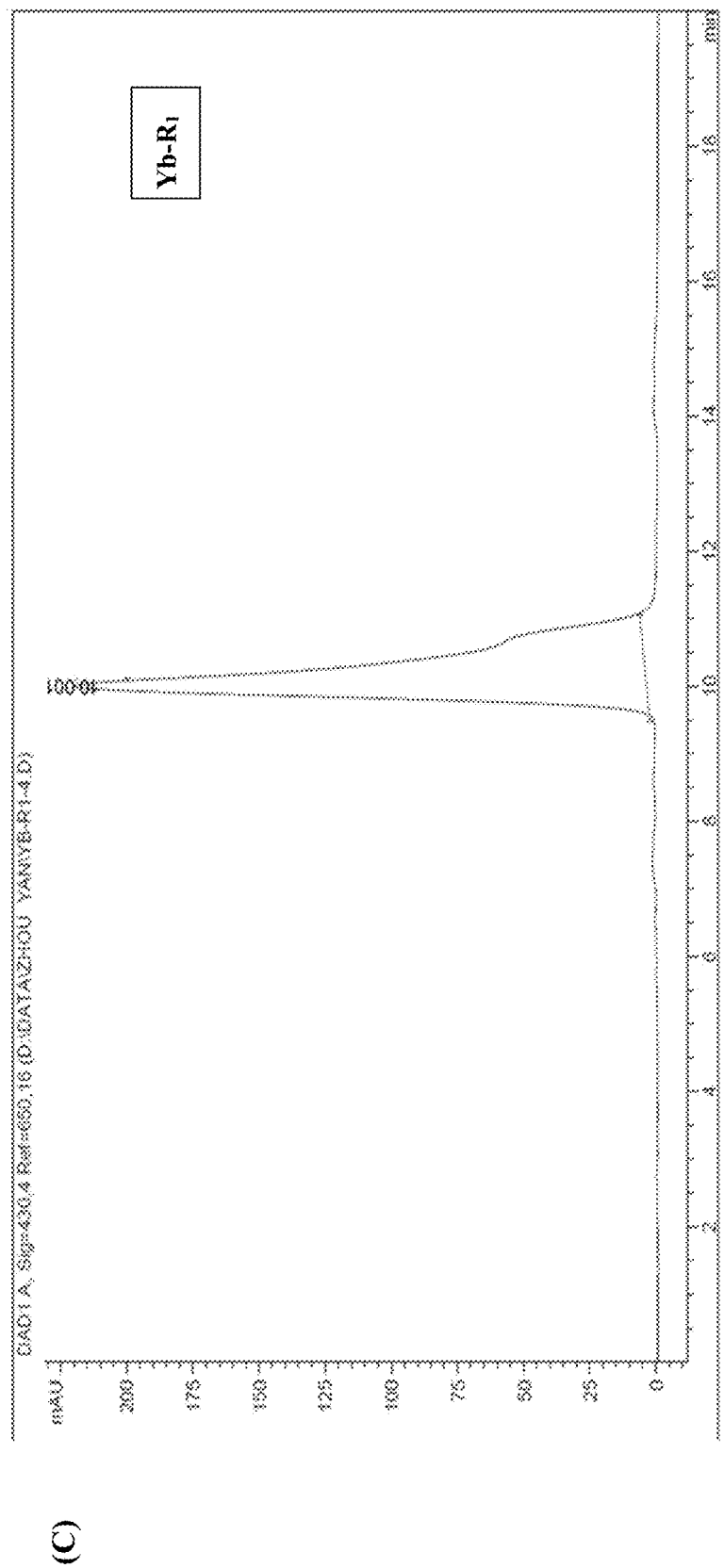
Figure 16:
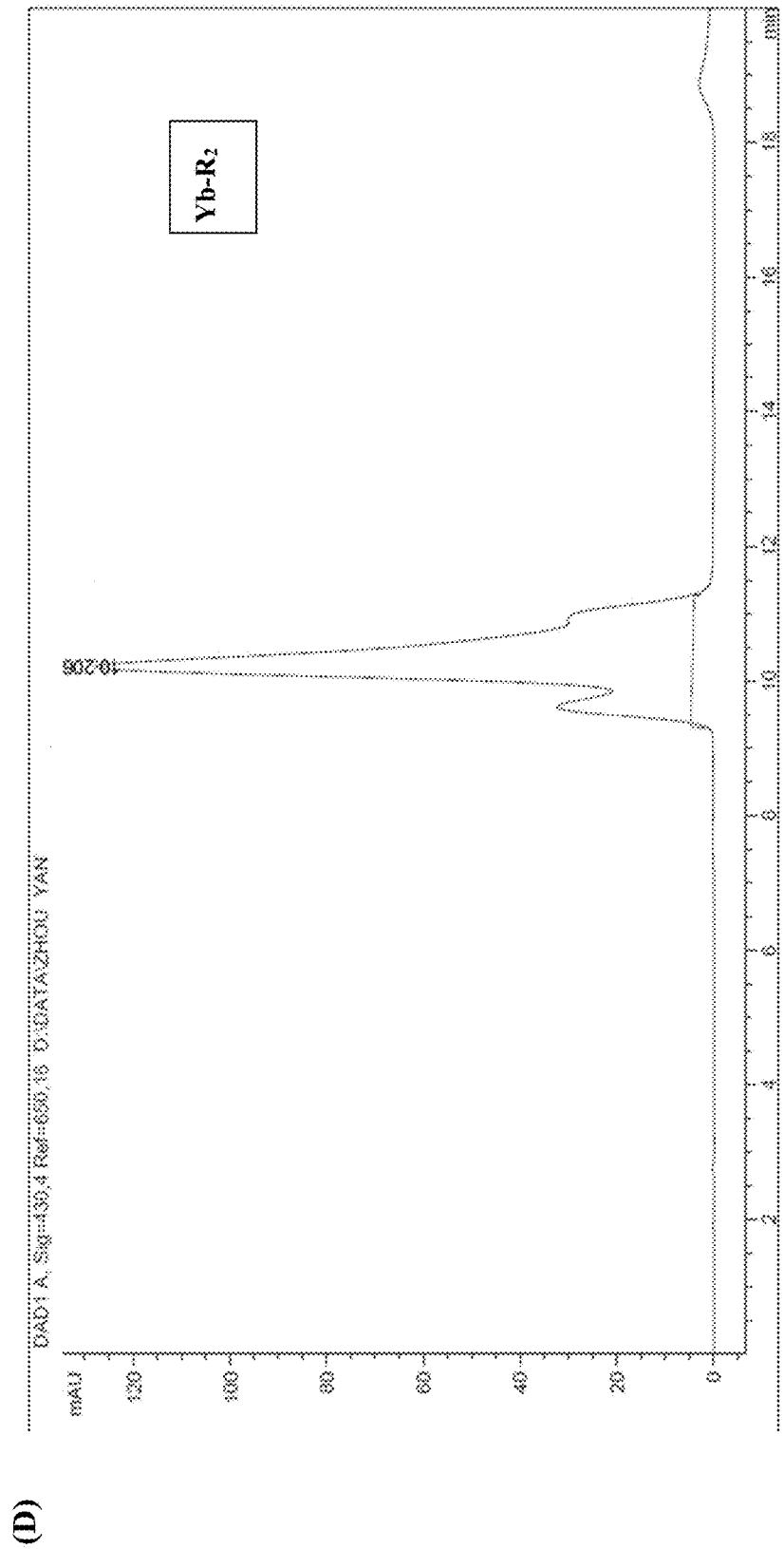
Figure 16:
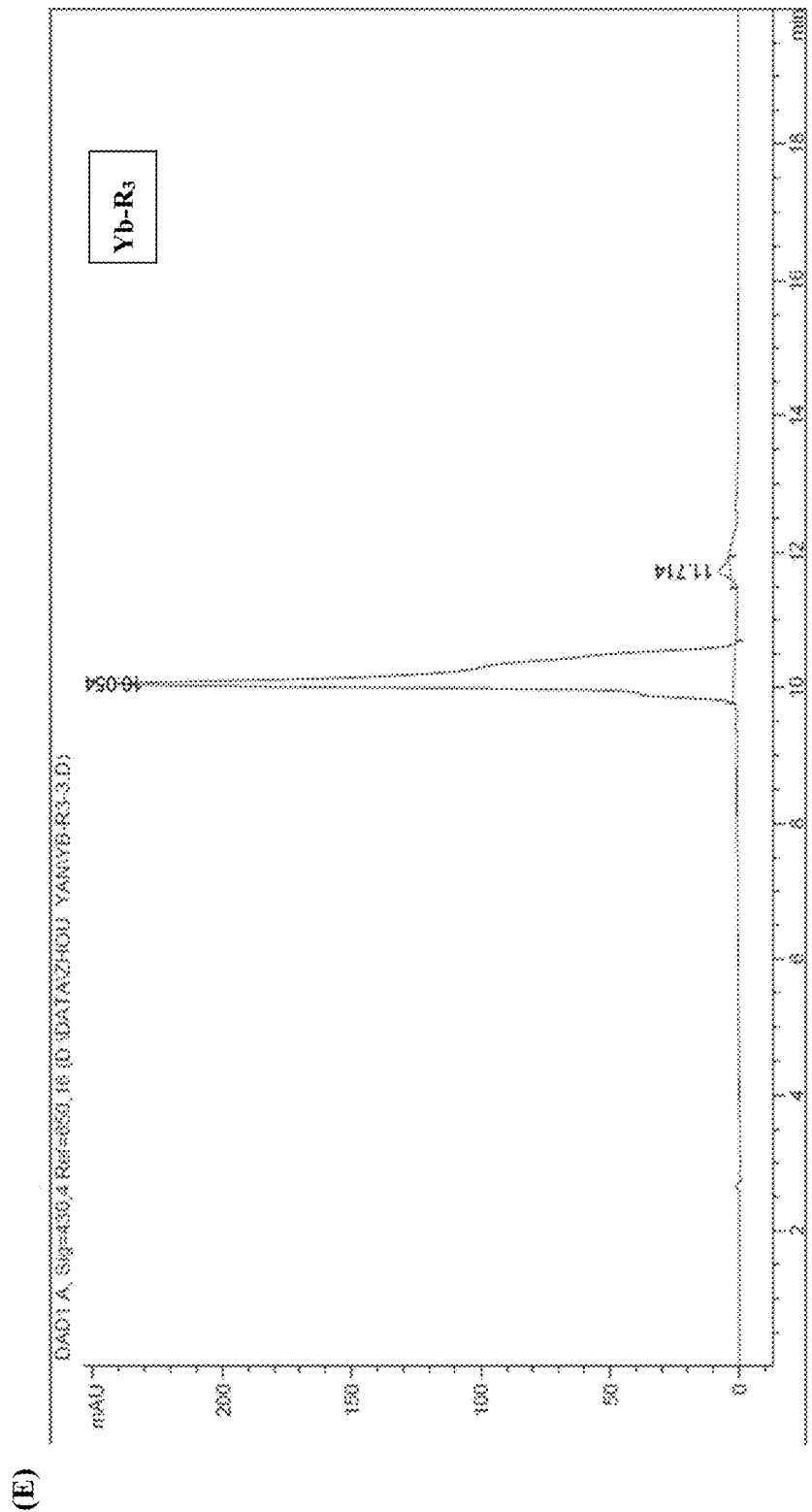
Figure 16:
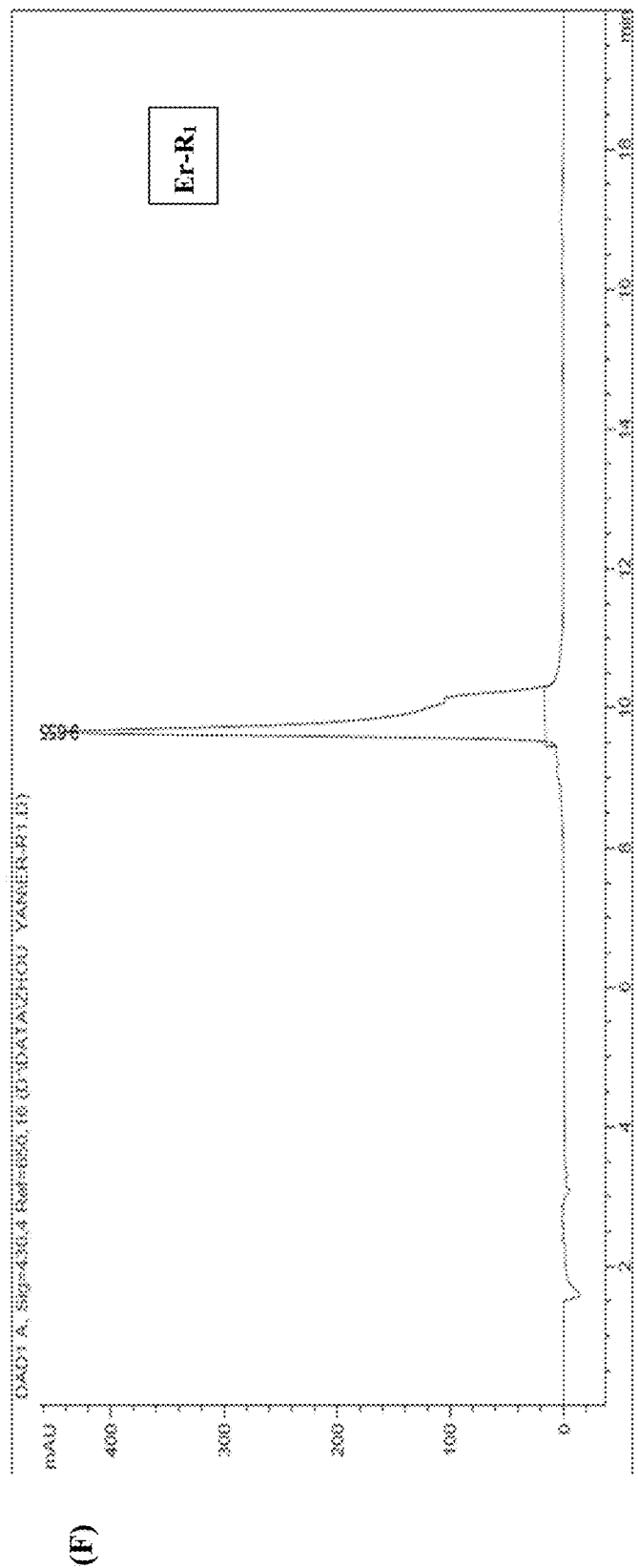
Figure 16:
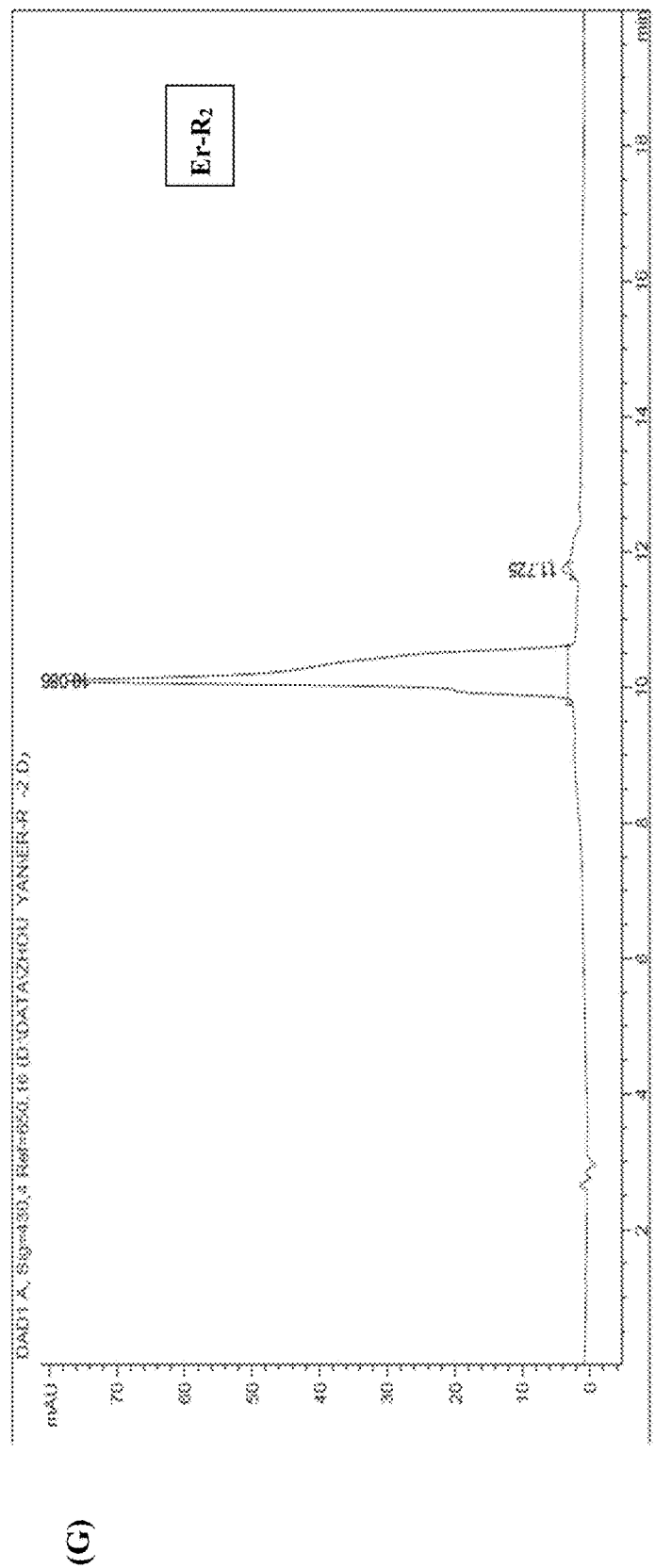
Figure 16:
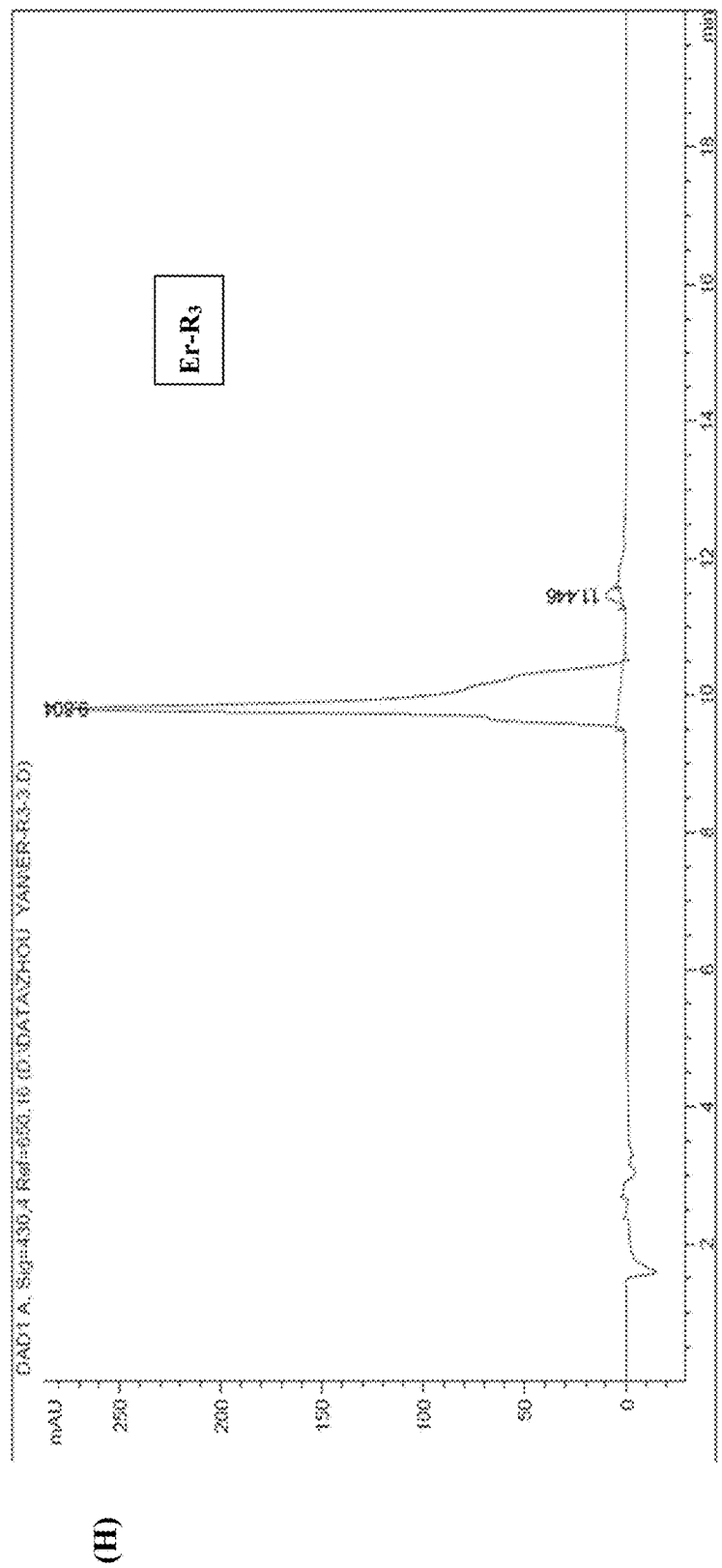
Figure 17:
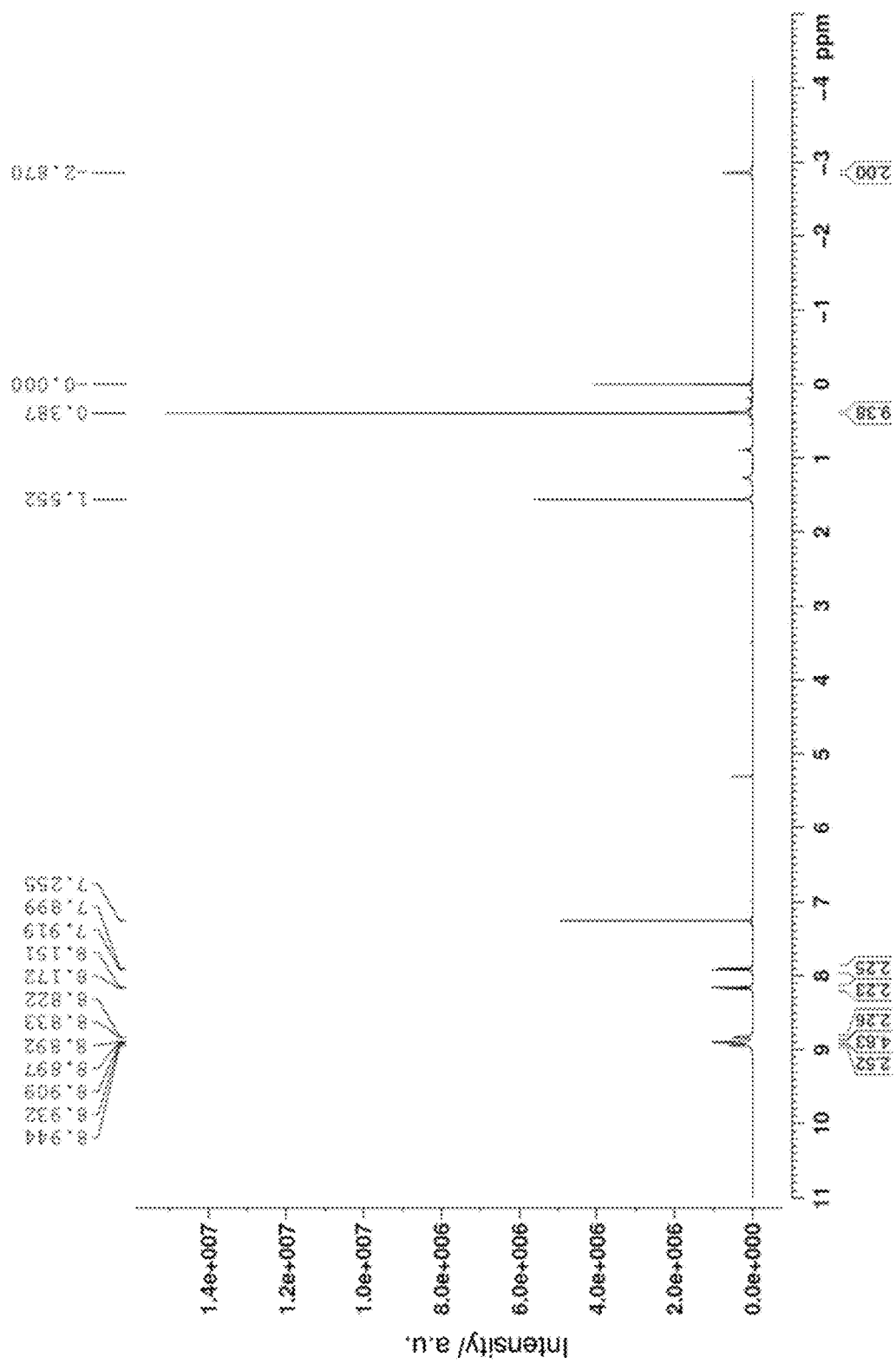
FIG. 17 shows the 400 MHz-$^1$H-NMR (CDCl$_3$) spectrum of Por(THP-TMS).
Figure 18:
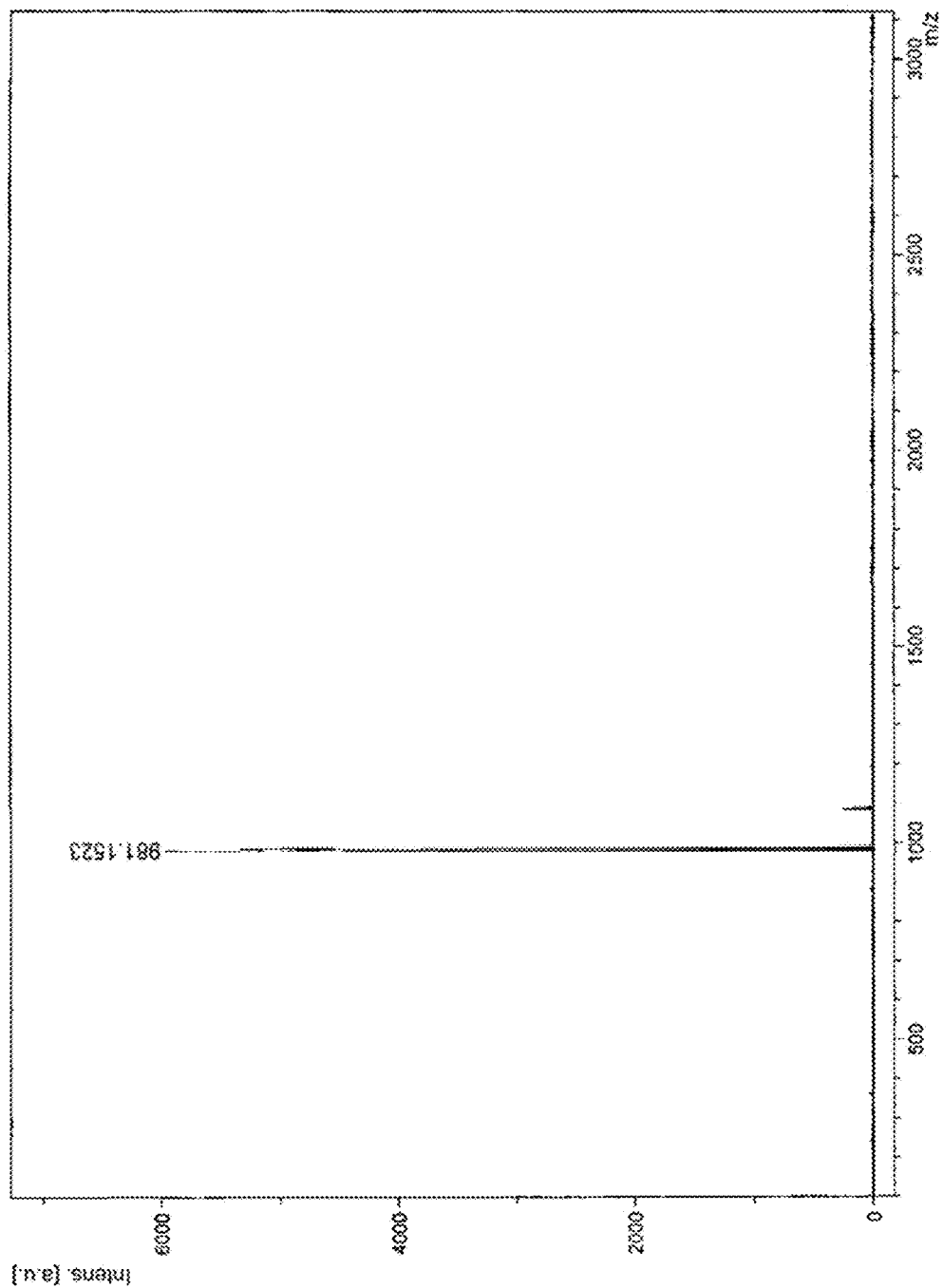
FIG. 18 shows the MALDI-TOF spectrum of Por(THP-TMS).
Figure 19:
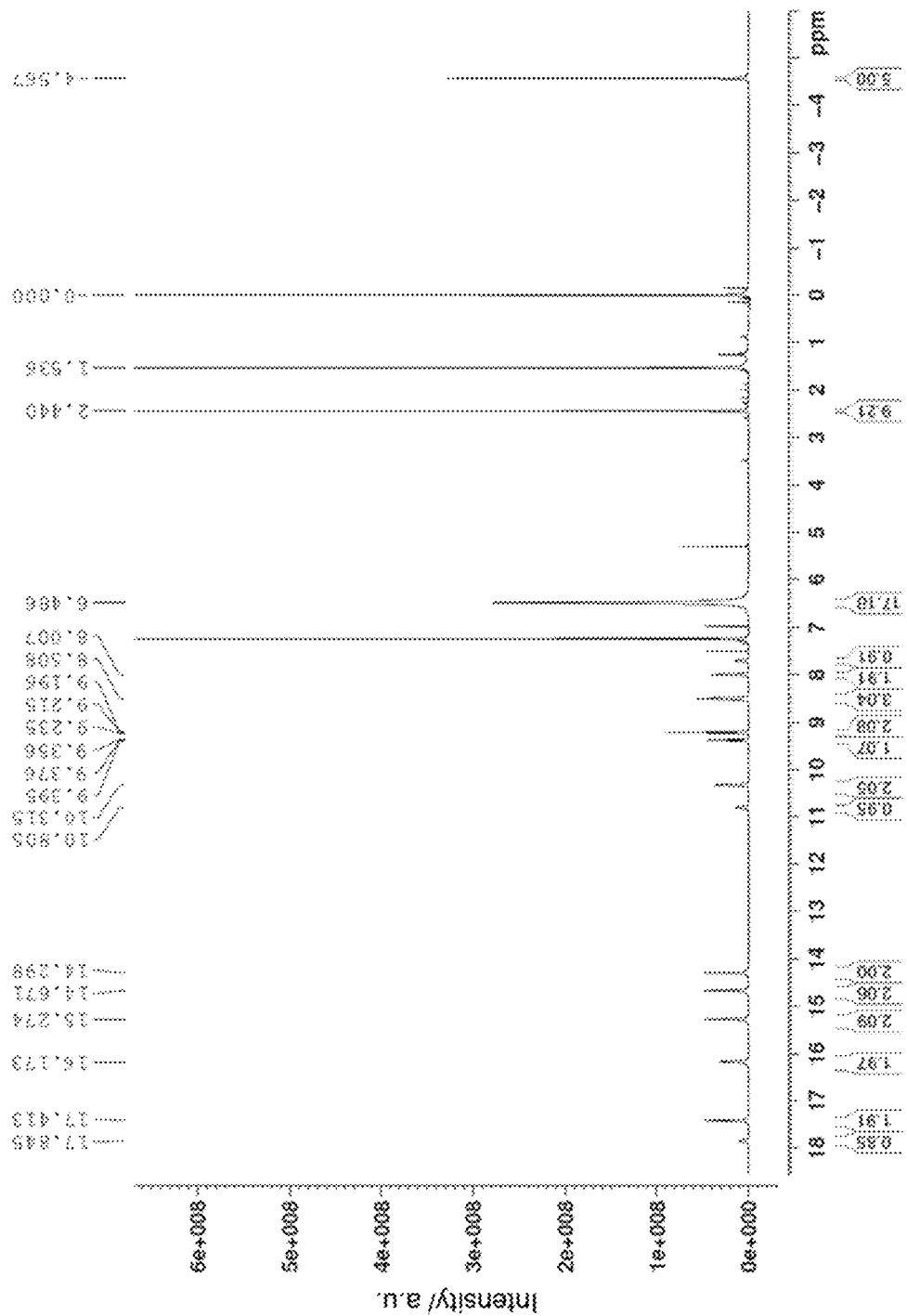
FIG. 19 shows the 400 MHz-$^1$H-NMR (CDCl$_3$) spectrum of Yb-1.
Figure 20:
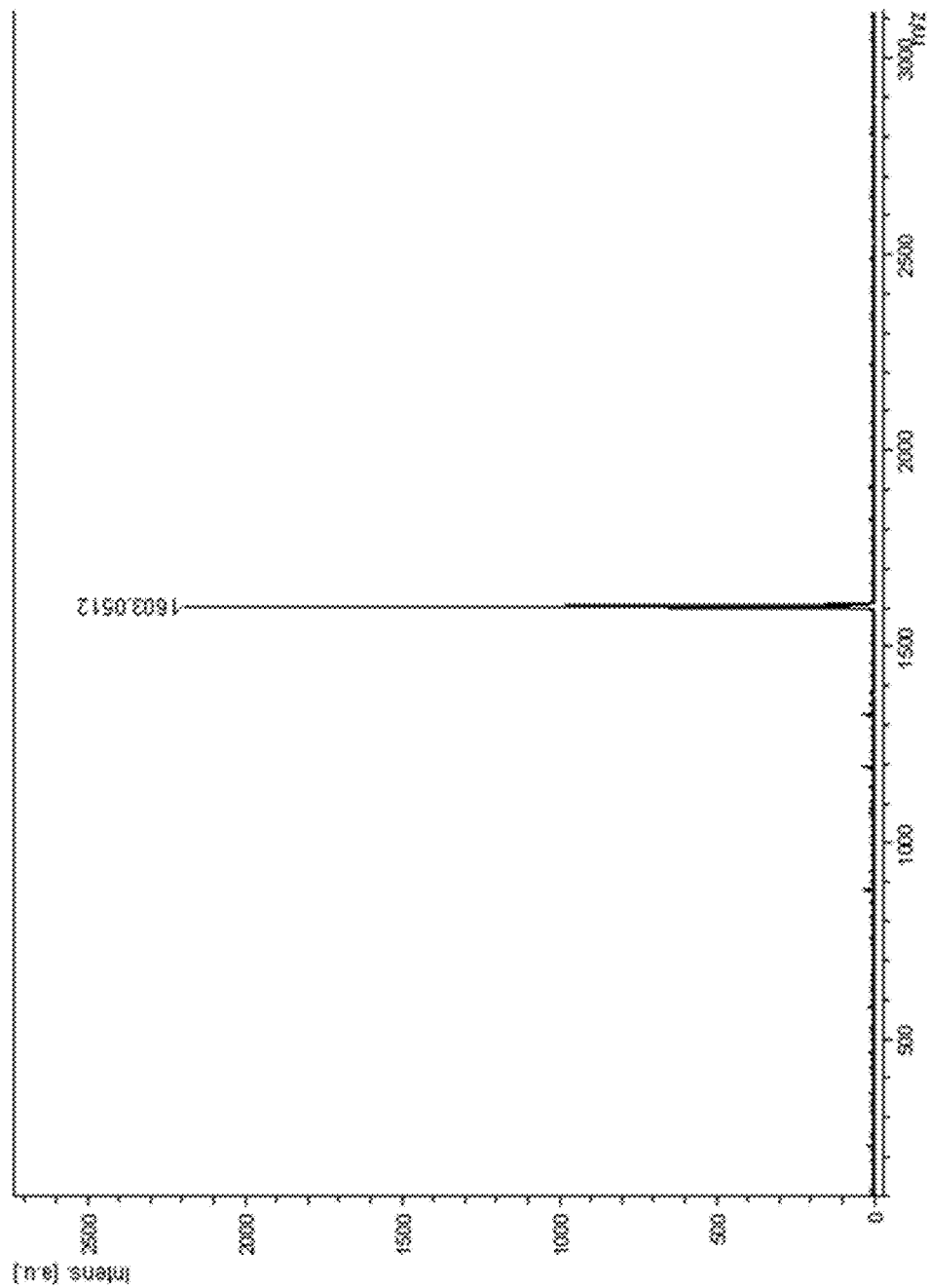
FIG. 20 shows the MALDI-TOF spectrum of Yb-1.
Figure 21:
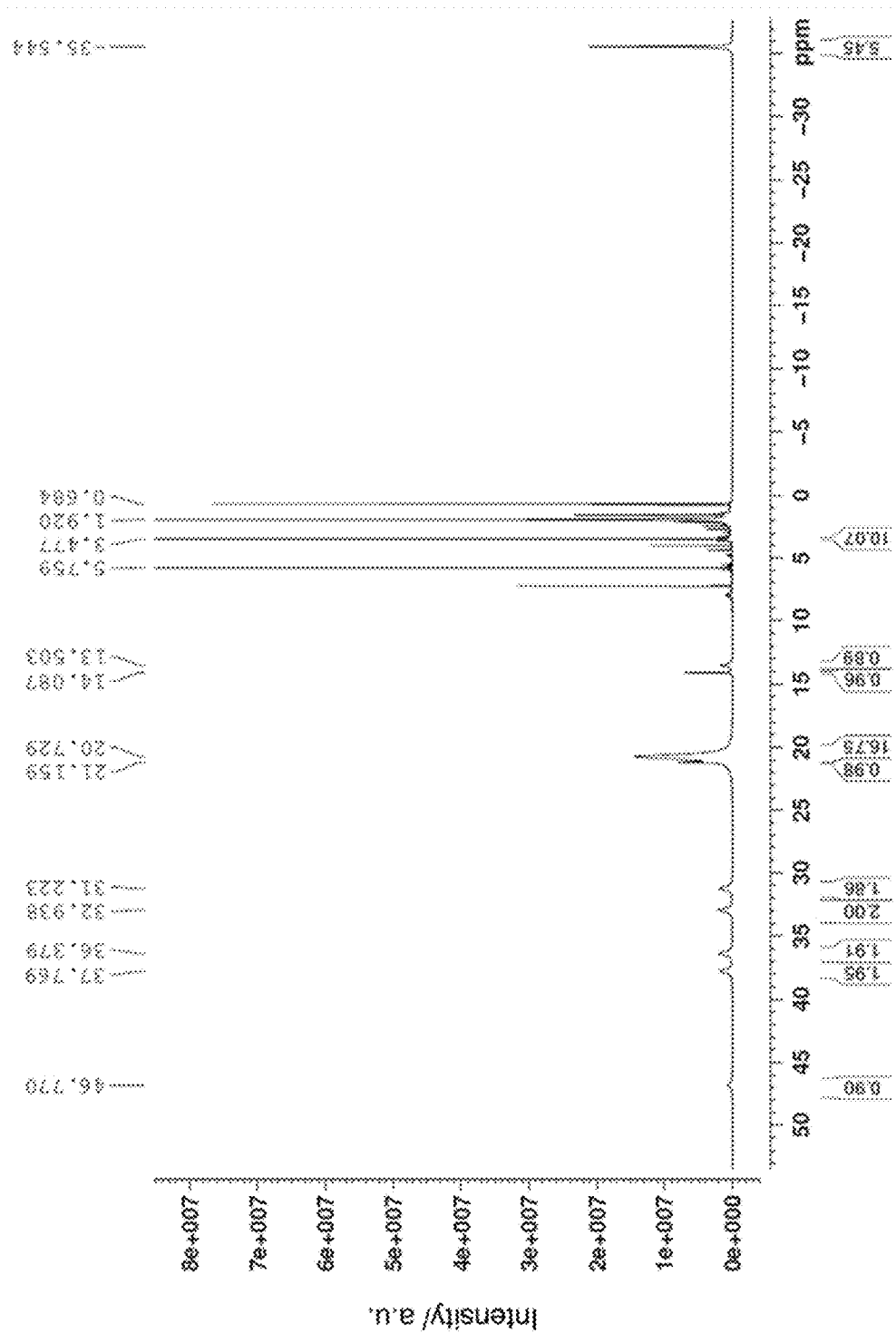
FIG. 21 shows the 400 MHz-$^1$H-NMR (CDCl$_3$) spectrum of Er-1.
Figure 22:
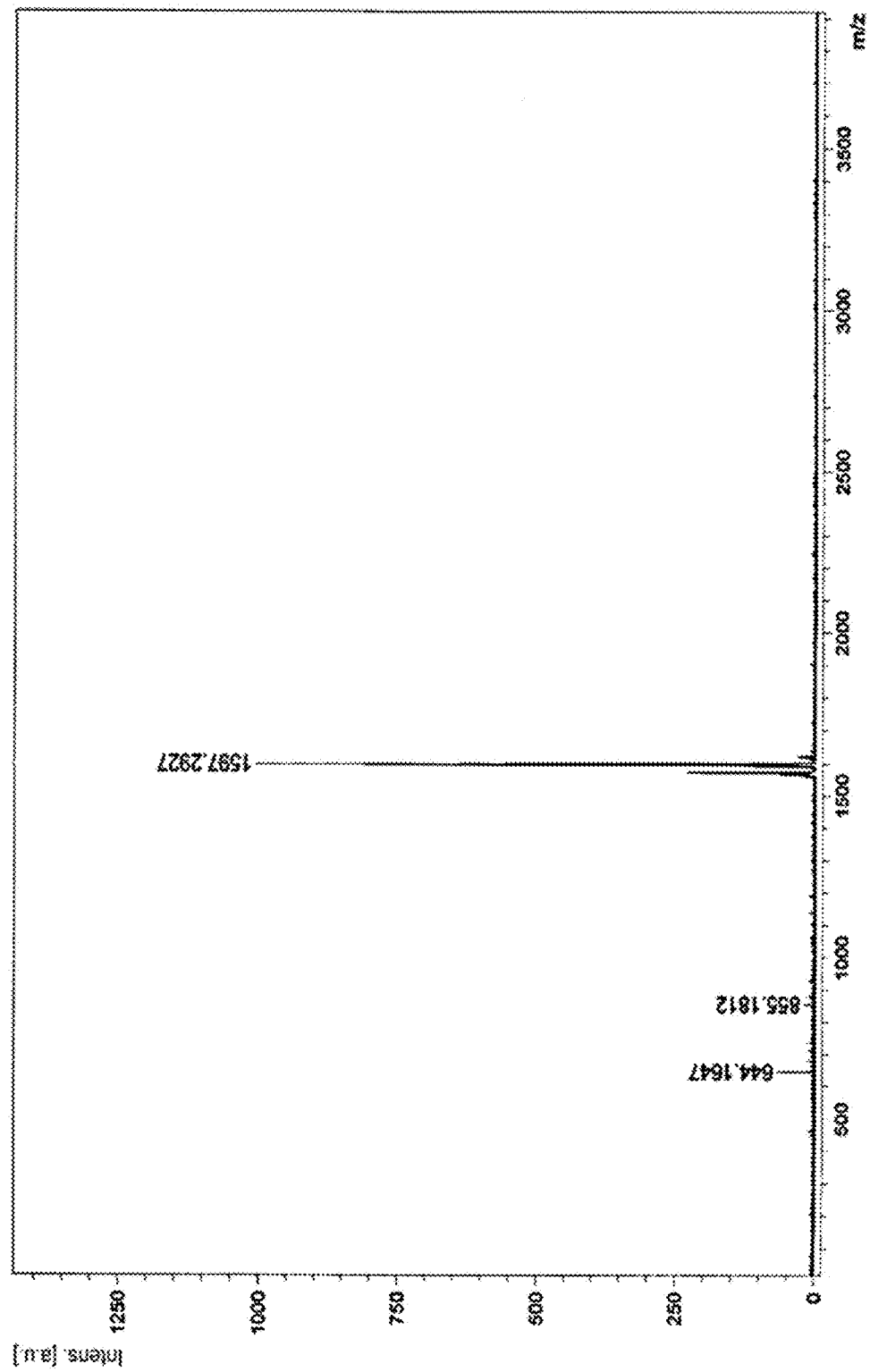
FIG. 22 shows the MALDI-TOF spectrum of Er-1.
Figure 23:
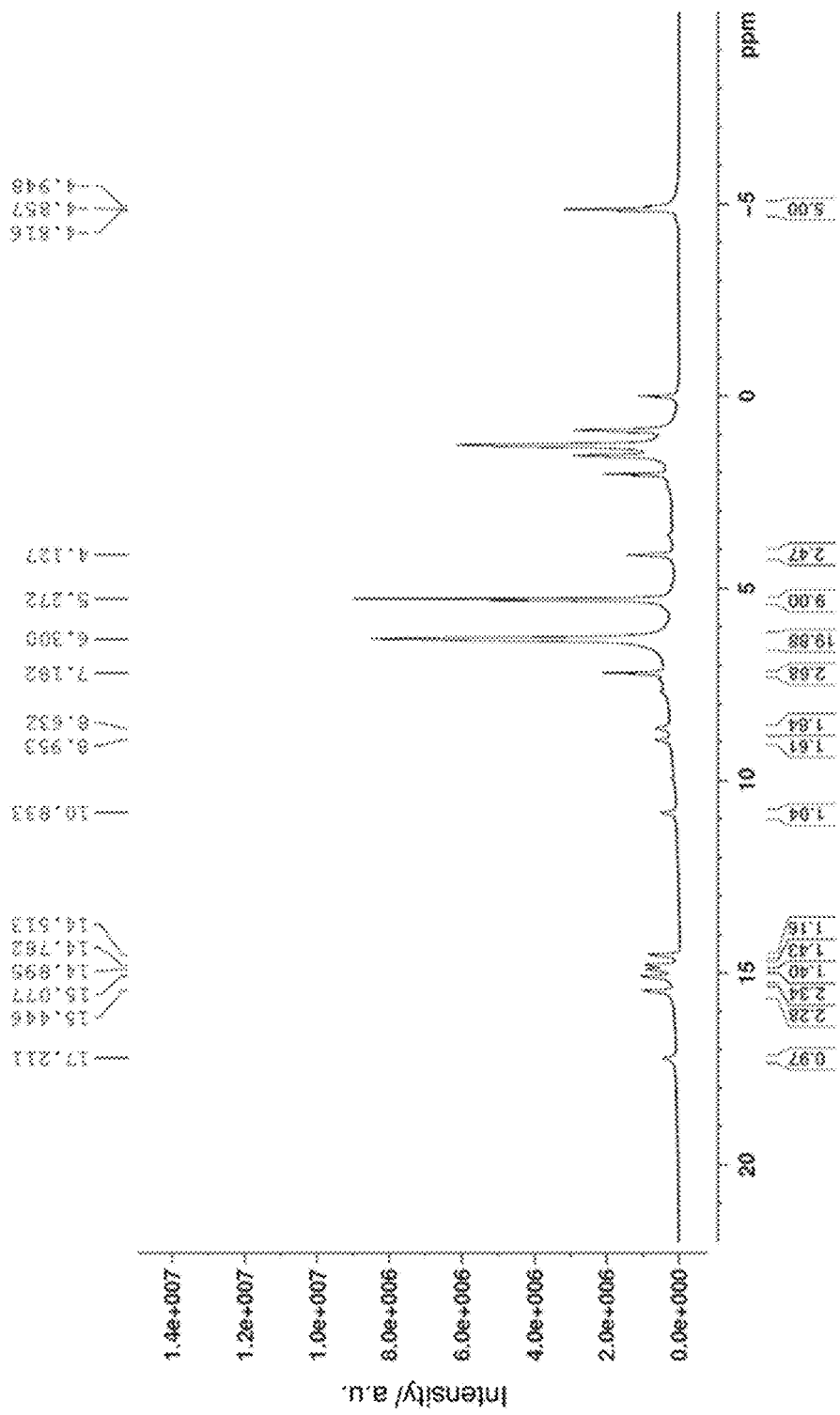
FIG. 23 shows the 400 MHz-$^1$H-NMR (CDCl$_3$) spectrum of Yb-2.
Figure 24:
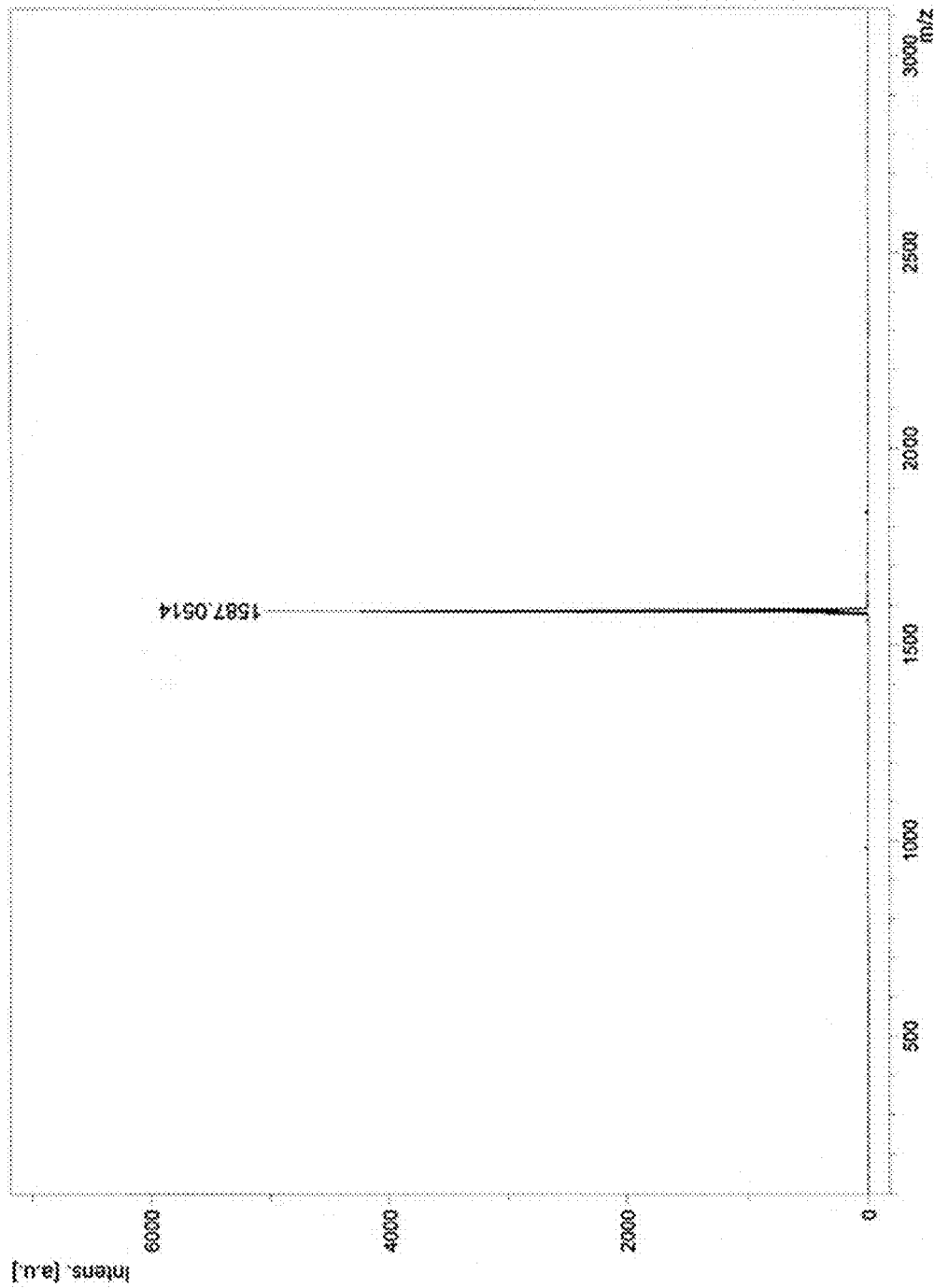
FIG. 24 shows the MALDI-TOF spectrum of Yb-2.
Figure 25:
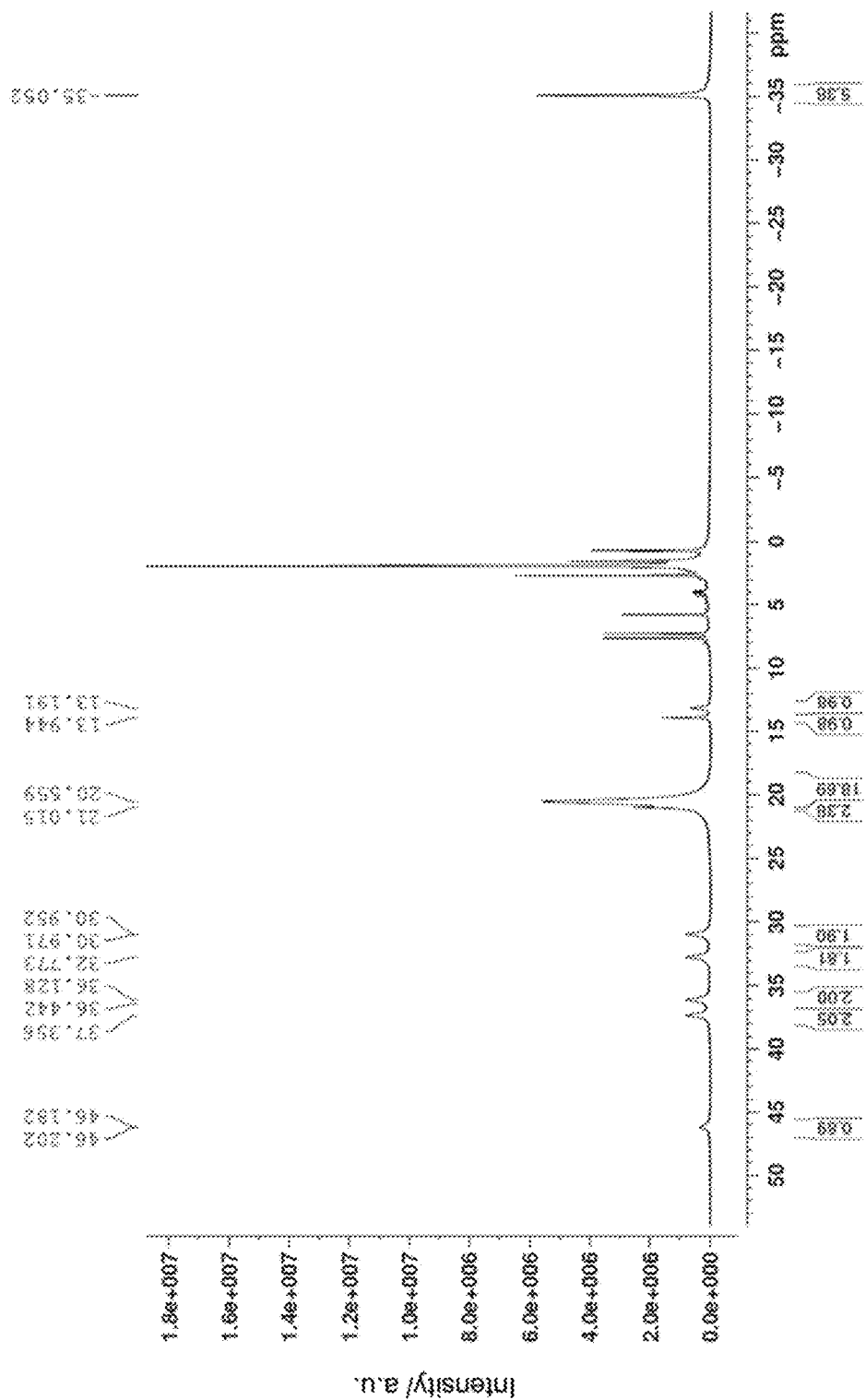
FIG. 25 shows the 400 MHz-$^1$H-NMR (CDCl$_3$) spectrum of Er-2.
Figure 26:
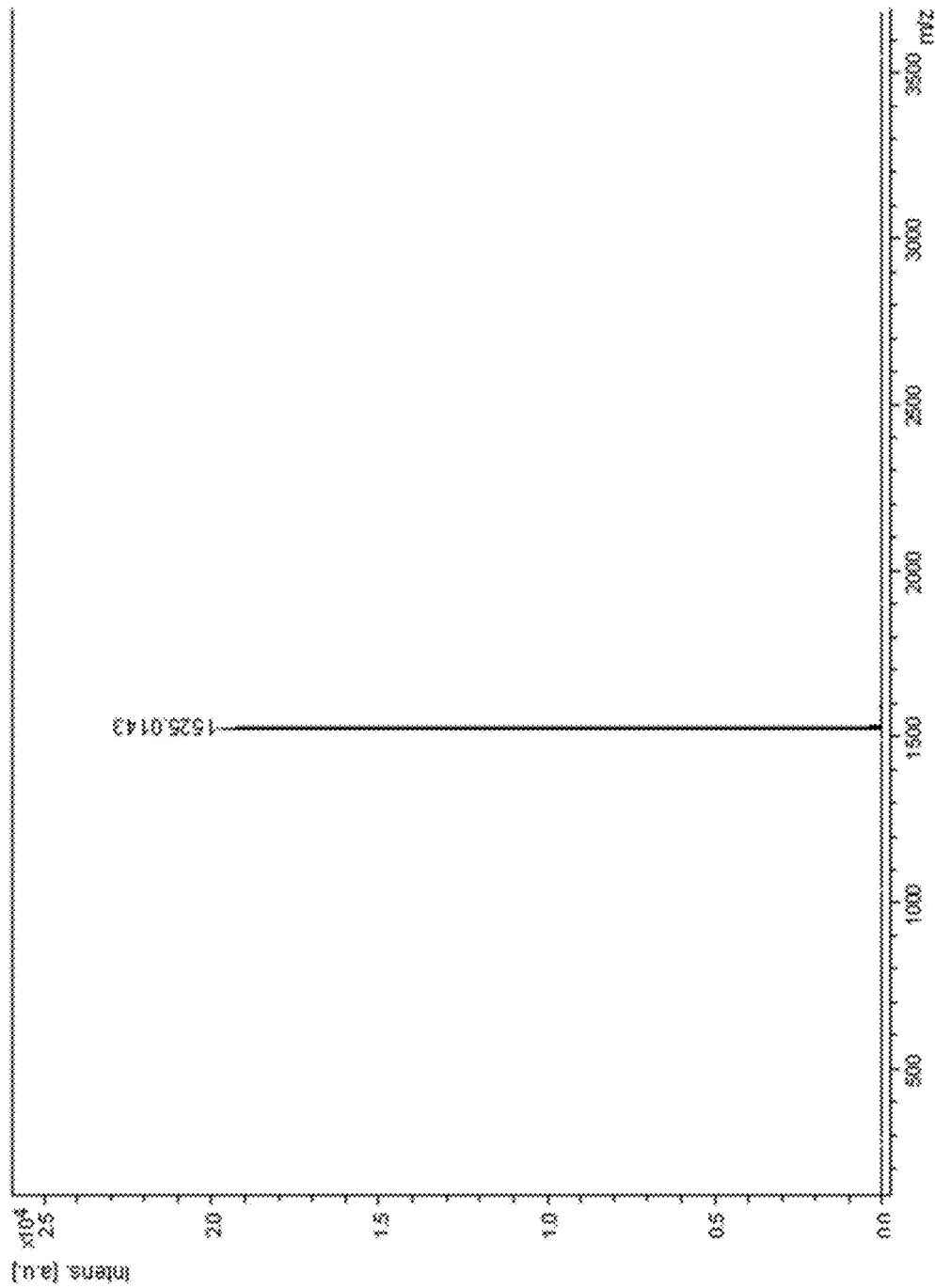
FIG. 26 shows the MALDI-TOF spectrum of Er-2.
Figure 27:
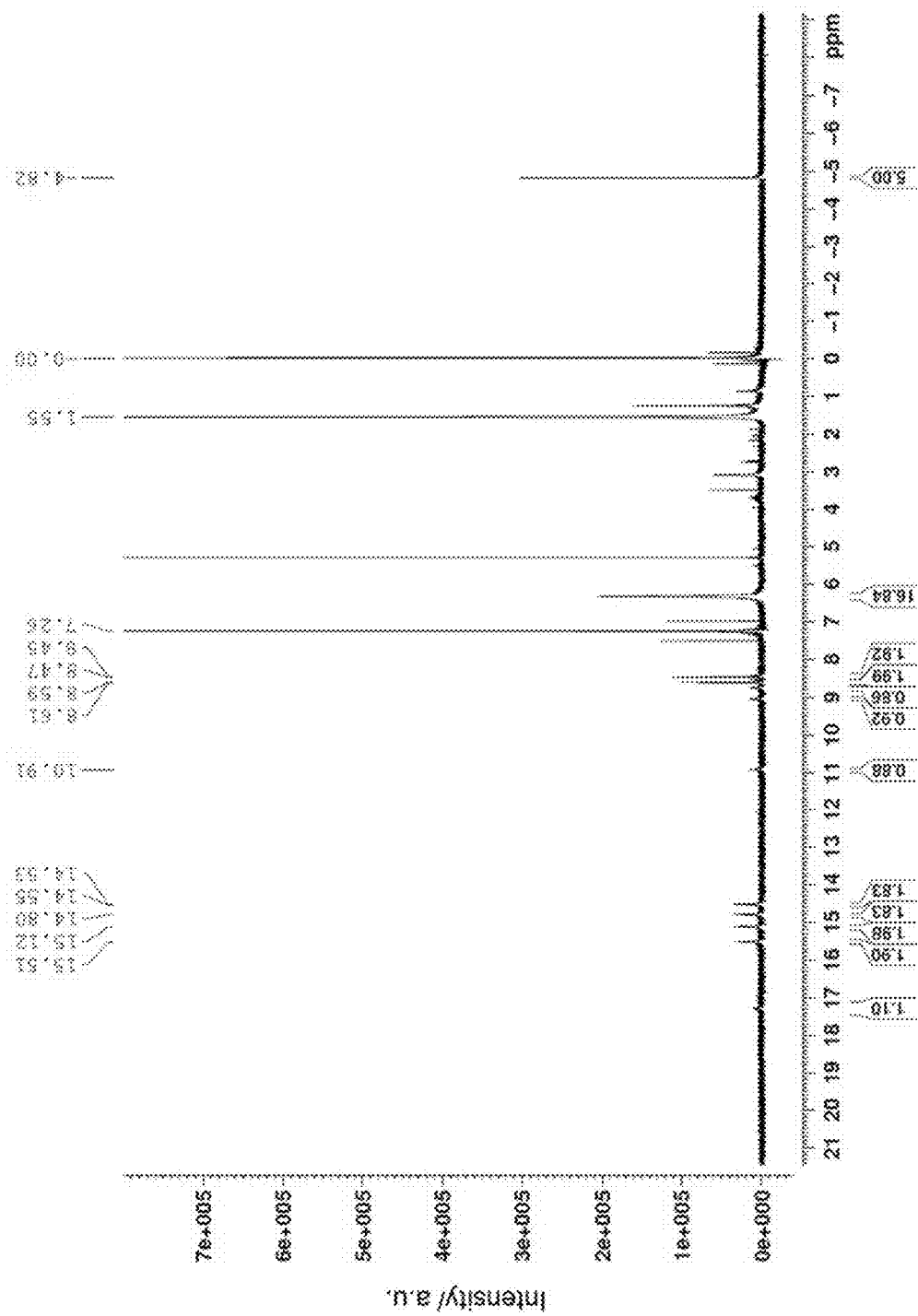
FIG. 27 shows the 400 MHz-$^1$H-NMR (CDCl$_3$) spectrum of Yb-4.
Figure 28:
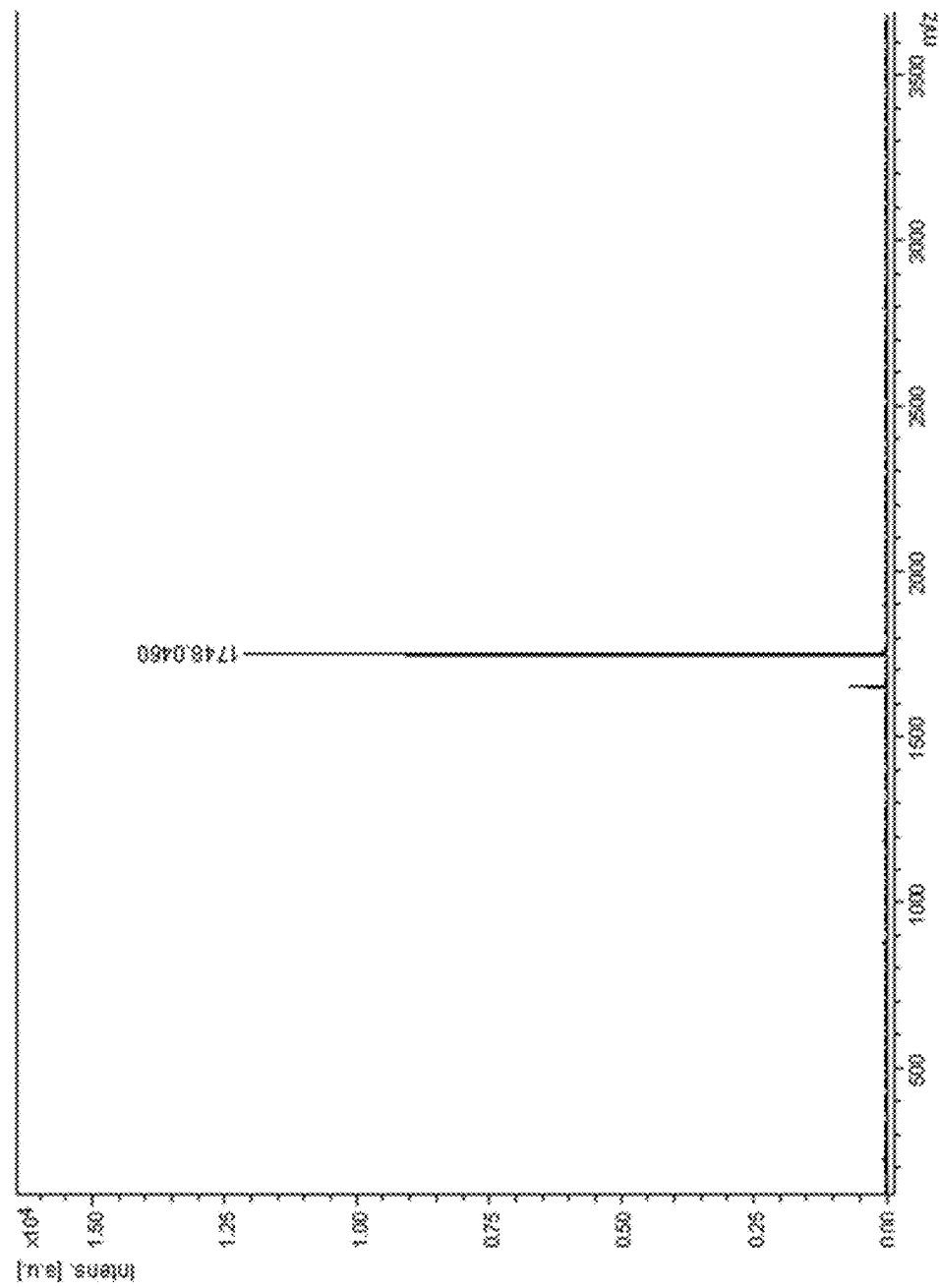
FIG. 28 shows the MALDI-TOF spectrum of Yb-4.
Figure 29:
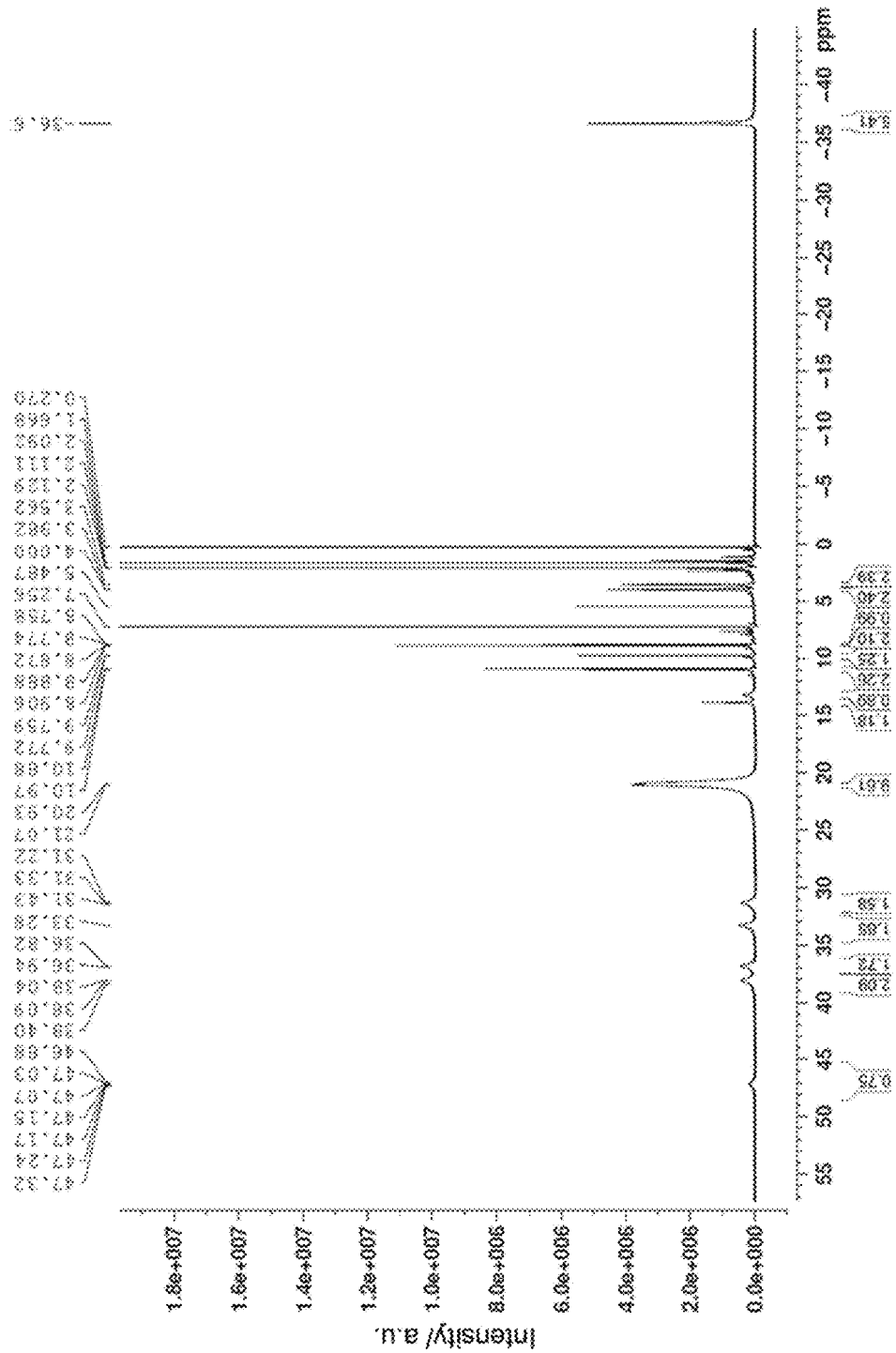
FIG. 29 shows the 400 MHz-$^1$H-NMR (CDCl$_3$) spectrum of Er-4.
Figure 30:
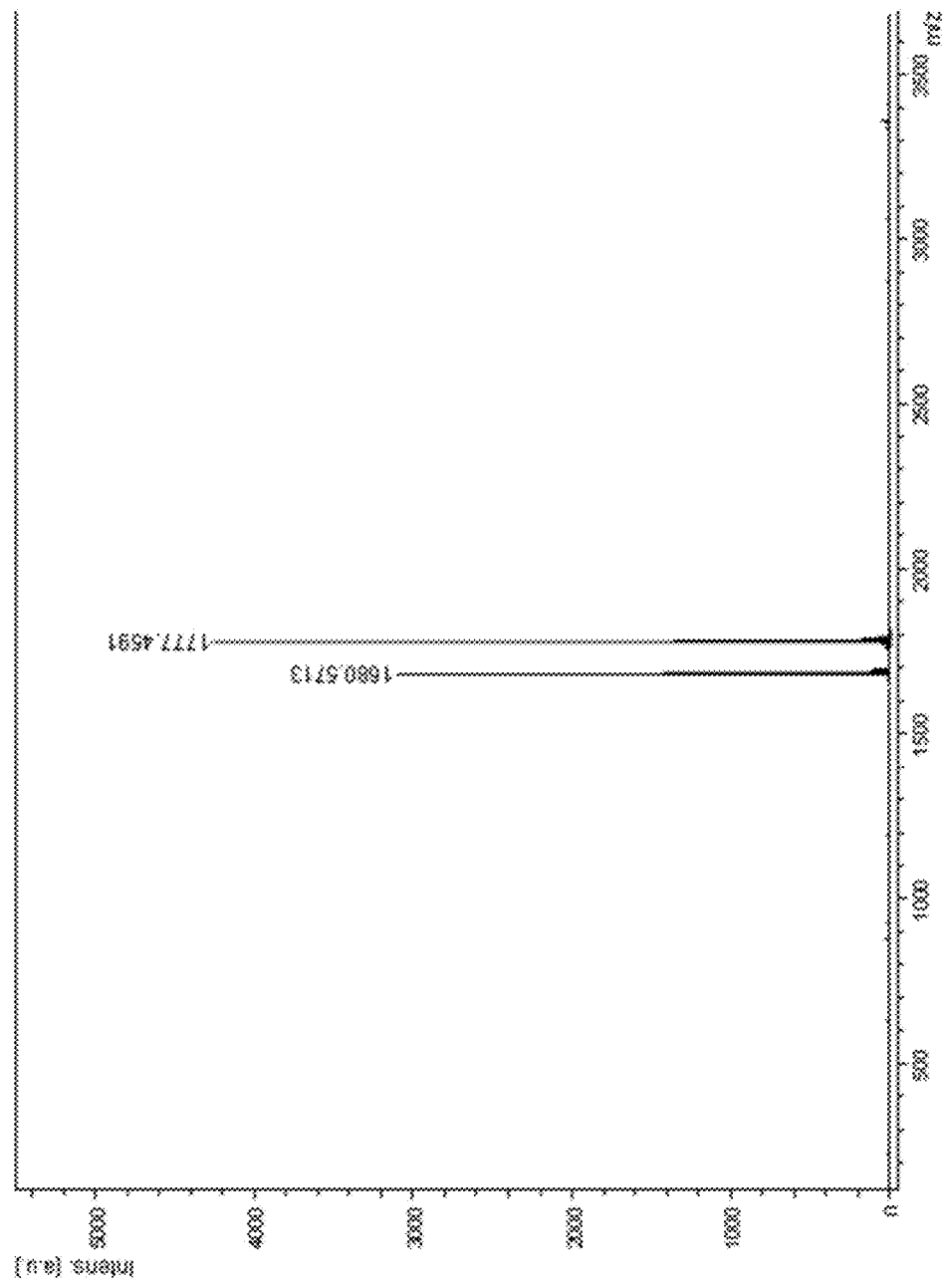
FIG. 30 shows the MALDI-TOF spectrum of Er-4.
Figure 31:
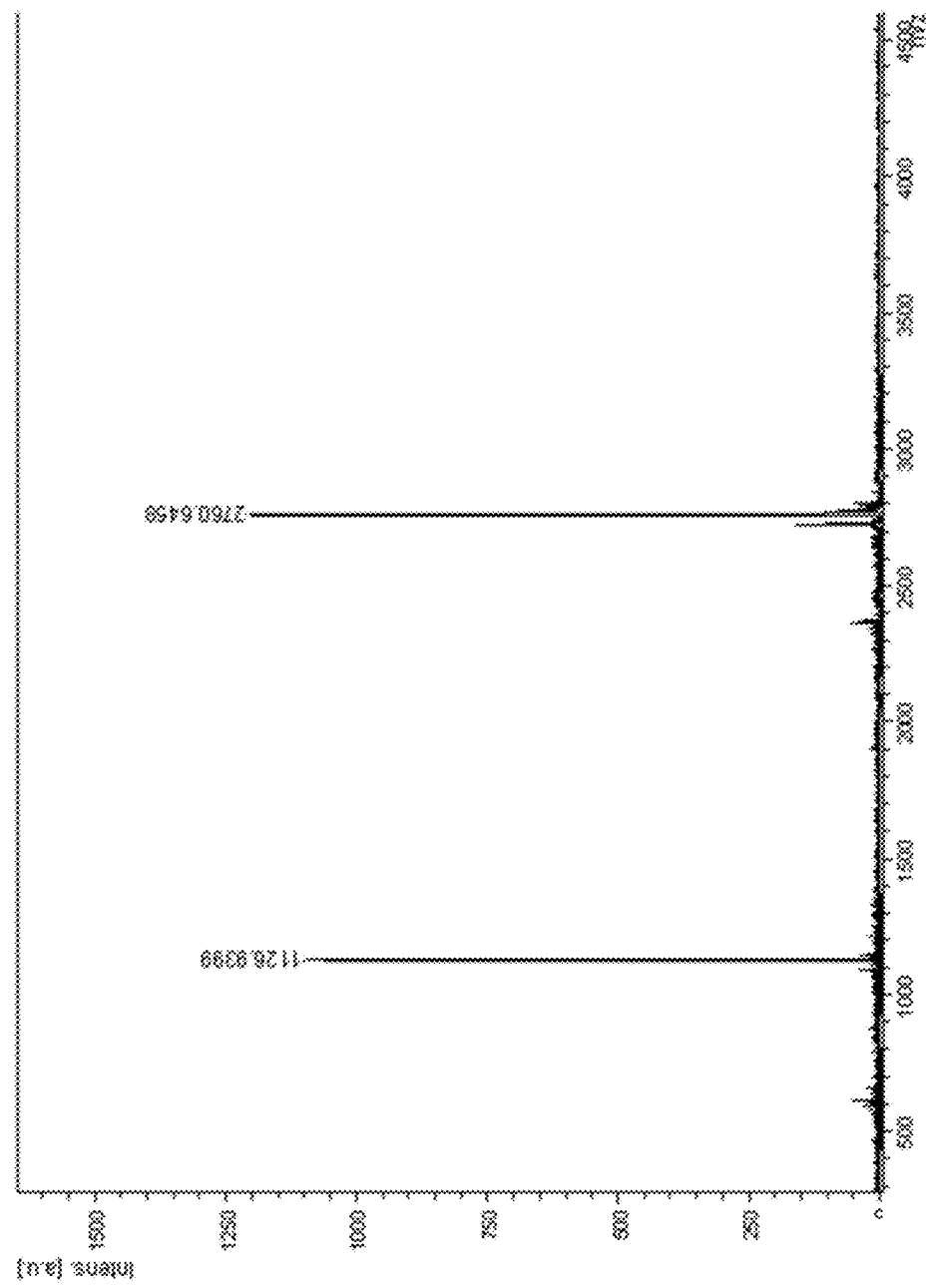
FIG. 31 shows the MALDI-TOF spectrum of Yb—R$_1$.
Figure 32:
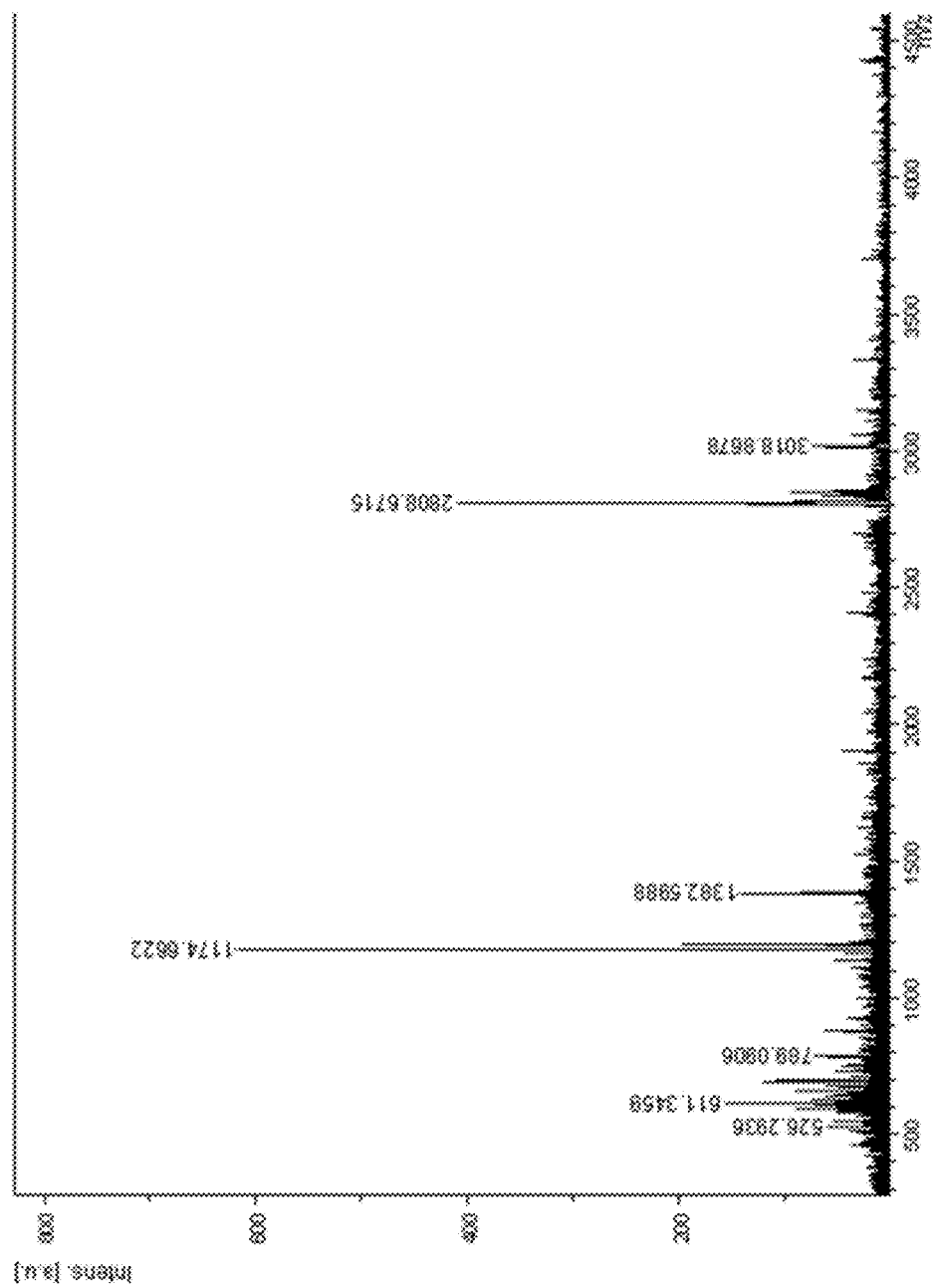
FIG. 32 shows the MALDI-TOF spectrum of Yb—R$_2$.
Figure 33:
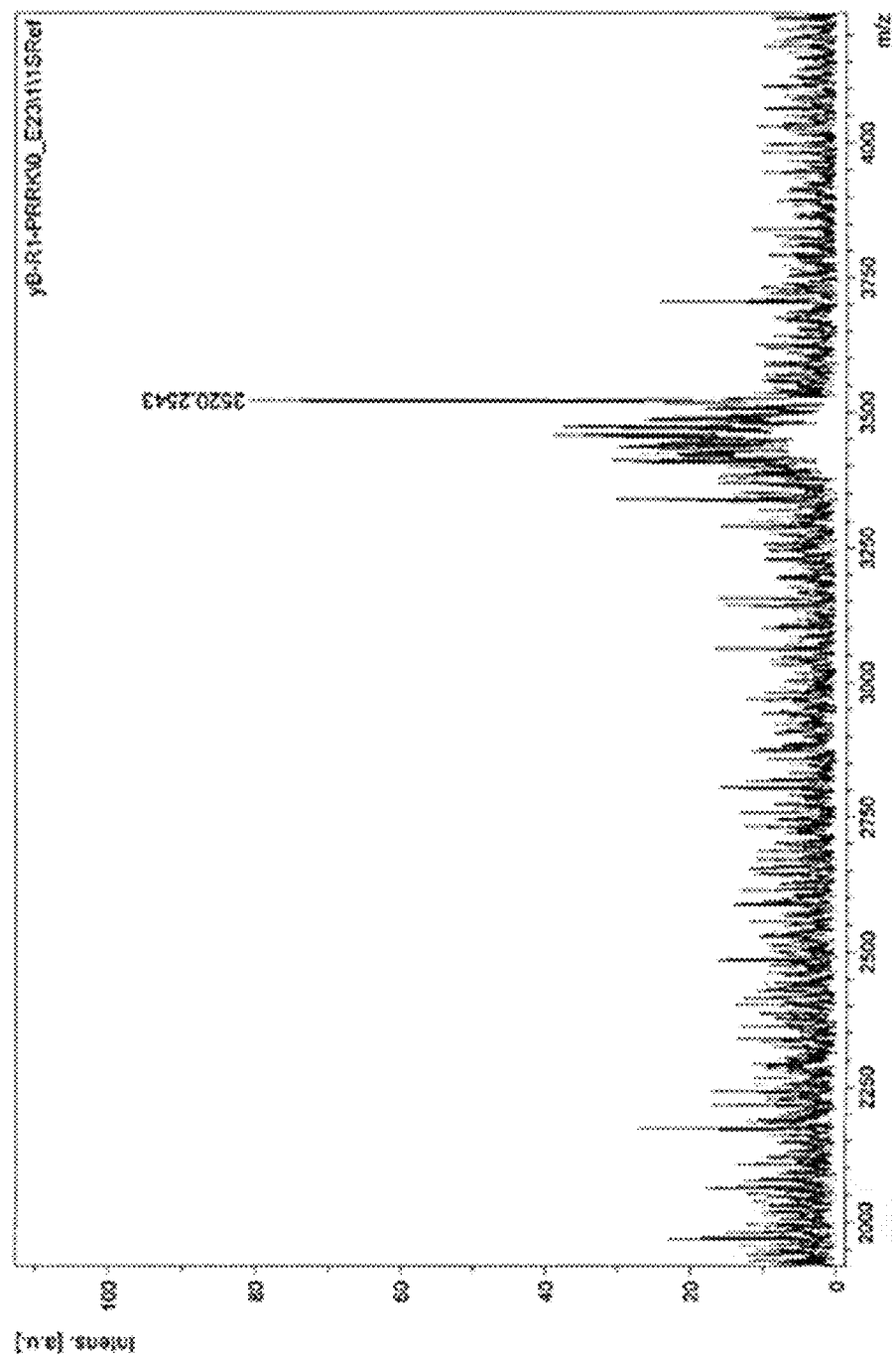
FIG. 33 shows the MALDI-TOF spectrum of Yb—R$_3$.
Figure 34:
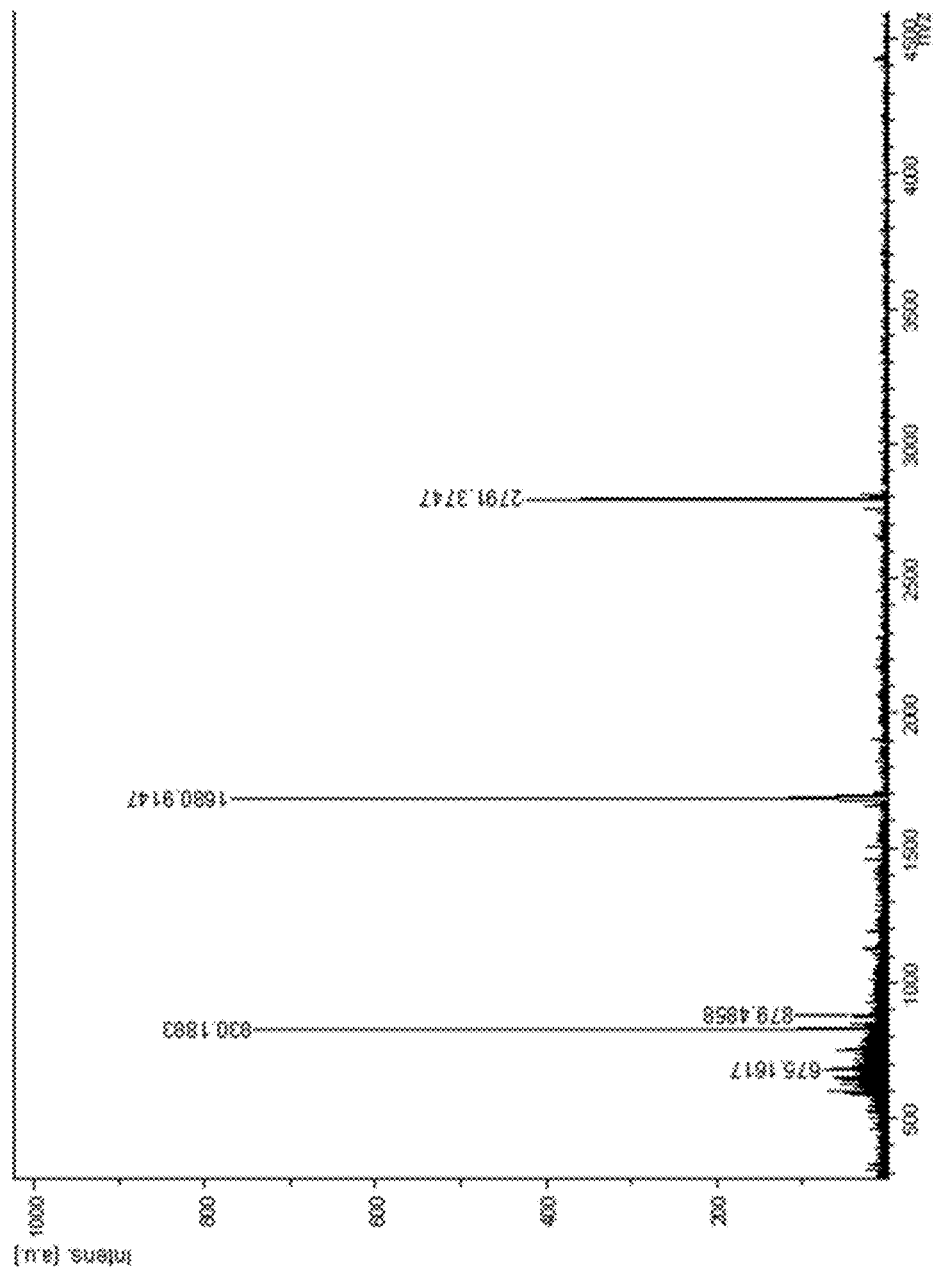
FIG. 34 shows the MALDI-TOF spectrum of Er—R$_1$.
Figure 35:
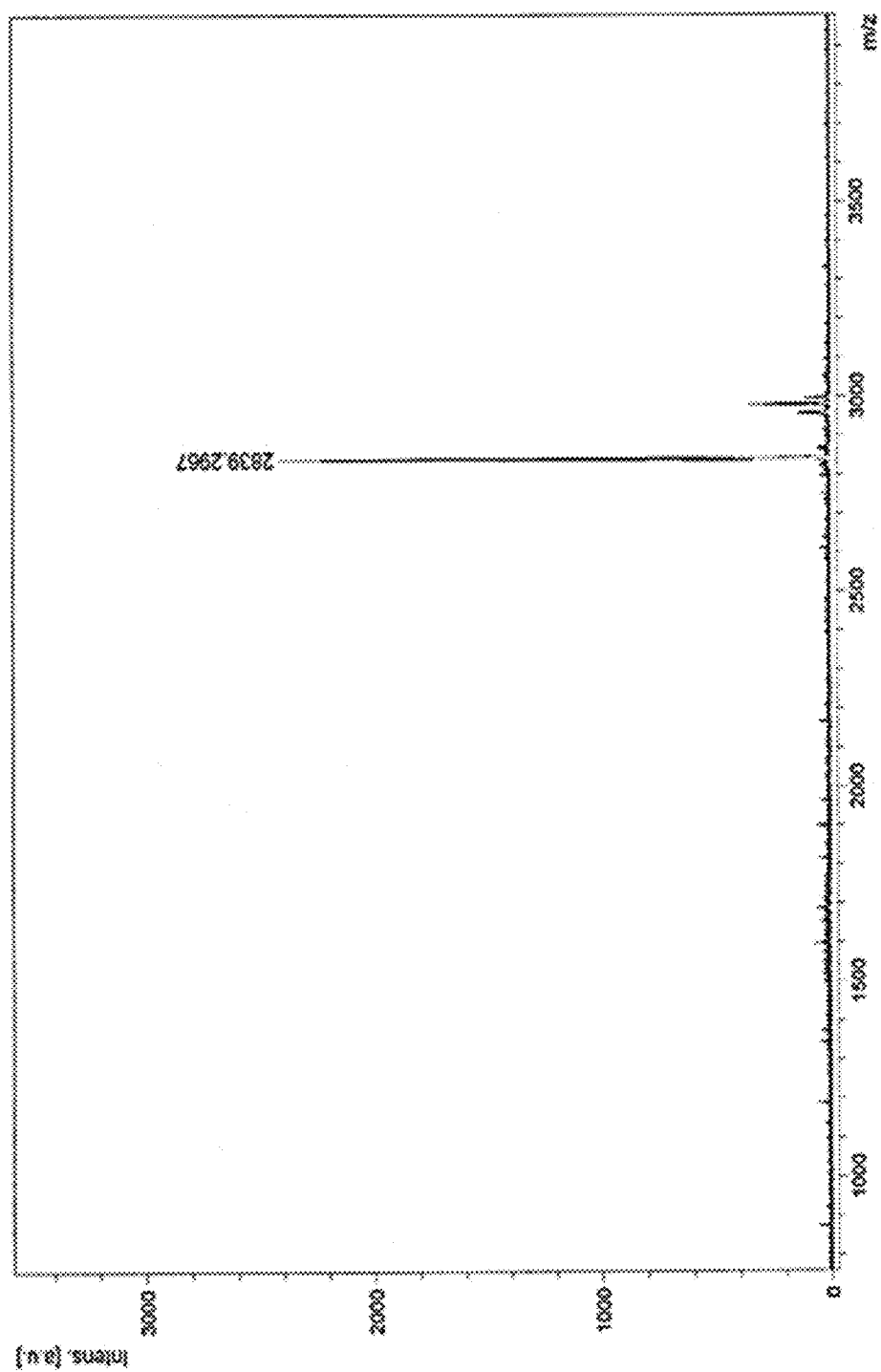
FIG. 35 shows the MALDI-TOF spectrum of Er—R$_2$.
Figure 36:
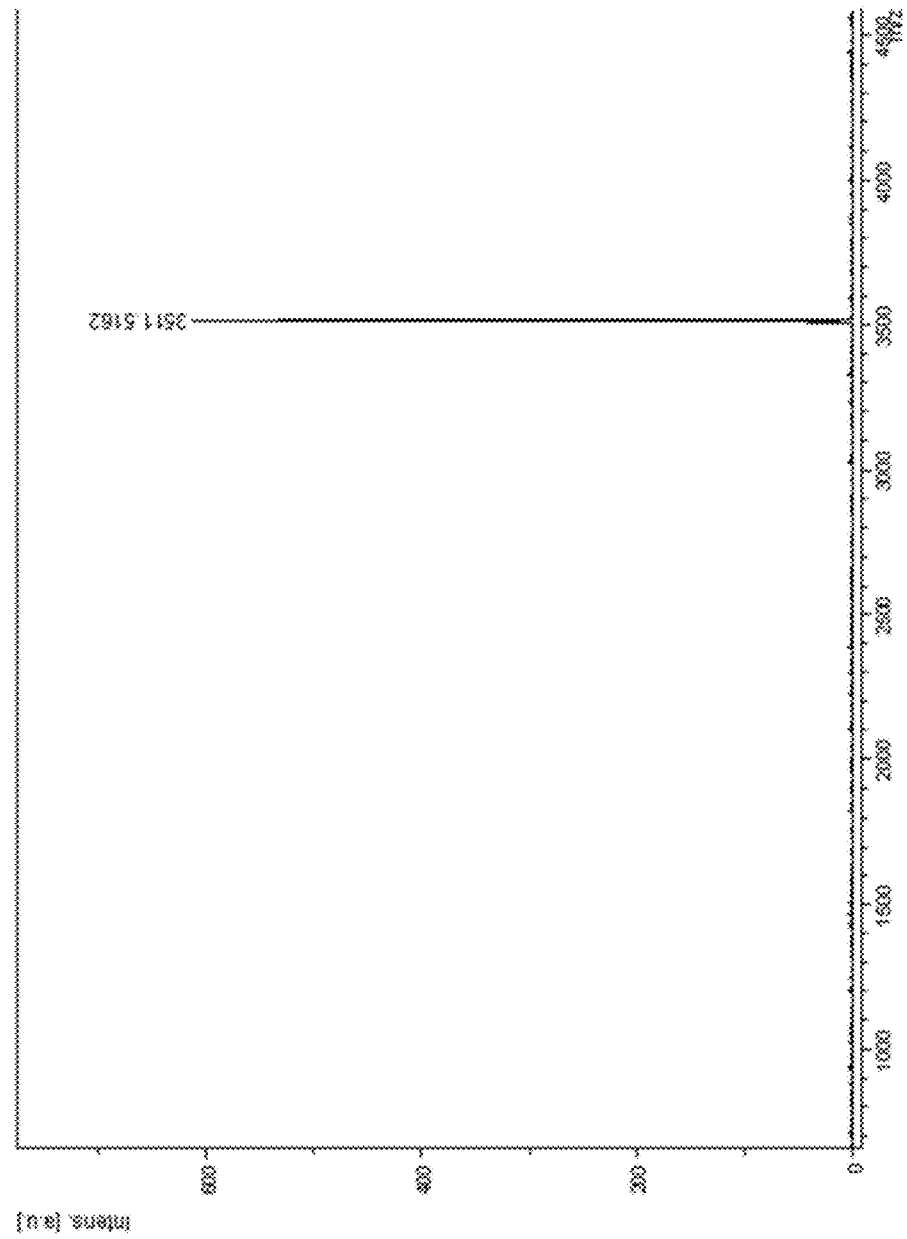
FIG. 36 shows the MALDI-TOF spectrum of Er—R$_3$.

Yb—$R_1$:

Yield: 69%. MALDI-TOF MS: calculated for $C_{109}H_{109}CoF_{15}N_{19}O_{23}P_3S_3Yb$ $[M+H]^+$: 2760.4878. found: 2760.6458. HPLC characterization: retention time=10.00 min (FIG. 16 I).

Yb—$R_2$:

The same procedure with Yb—$R_1$, peptide $R_2$ is used; Yield: 69% MALDI-TOF MS: calculated for $C_{113}H_{129}CoF_{15}N_{21}O_{22}P_3S_2Yb$ $[M+H]^+$ 2808.6835. found: 2808.6715. HPLC characterization: retention time=10.21 min (FIG. 16 (D)).

Yb—$R_3$:

The same procedure with Yb—$R_1$, peptide $R_3$ is used; Yield: 65% MALDI-TOF MS: calculated for $C_{143}H_{187}CoF_{15}N_{35}O_{28}P_3S_2Yb$ $[M+H]^+$ 3520.2985. found: 3520.2543. HPLC characterization: retention time=10.01 min (FIG. 16 (E)).

Er—$R_1$:

The same procedure with Yb—$R_1$, replace Yb-4 with Er-4; Yield: 75% MALDI-TOF MS: calculated for $C_{109}H_{109}CoErF_{15}N_{19}O_{23}P_3S_3$ $[M+K]^+$: 2791.4826. found: 2791.3747. HPLC characterization: retention time=9.66 min (FIG. 16 (F)).

Er—$R_2$:

The same procedure with Yb—$R_2$, replace Yb-4 with Er-4; Yield: 72% MALDI-TOF MS: calculated for $C_{113}H_{129}CoErF_{15}N_{21}O_{22}P_3S_2$ $[M+K]^+$: 2839.6015. found: 2839.2967. HPLC characterization: retention time=10.09 min (FIG. 16 (G)).

Er—$R_3$:

The same procedure with Yb—$R_3$, replace Yb-4 with Er-4; Yield: 70% MALDI-TOF MS: calculated for $C_{143}H_{187}CoErF_{15}N_{35}O_{28}P_3S_2$ $[M]^+$: 3511.4955. found: 3511.5162. HPLC characterization: retention time=9.80 min (FIG. 16 (H)).

Cell Culture

Human bladder carcinoma (T24) and (5637) cells are cultured in RPMI 1640 medium (Gibco) supplemented with 10% fetal bovine serum (FBS, Gibco) and antibiotics (penicillin, 50 $gmL^{-1}$; streptomycin, 50 $gmL^{-1}$). Human cervical carcinoma (HeLa) cells are cultured in DMEM (Gibco) supplemented with 10% FBS (Gibco) and antibiotics (penicillin, 50 $gmL^{-1}$; streptomycin, 50 $gmL^{-1}$). Human normal lung fibroblast (MRC-5) cells are maintained in minimum essential medium (MEM) supplemented with 10% FBS and 1% 50 $gmL^{-1}$ penicillin; 50 $gmL^{-1}$ streptomycin. All cells are incubated at 37° C. in a humidified environment with 5% $CO_2$.

Dark Cytotoxicity

T24, HeLa and MRC-5 cells ($1\times10^5$) are treated with Er—$R_n$ porphyrin complexes and Yb—$R_n$ porphyrin complexes for 24 hours at six concentrations (1, 5, 10, 50, 100, 500M). The cell monolayers are rinsed once with phosphate-buffered saline (PBS) and incubated with 500 gmL$^{-1}$ 3-(4,5-dimethylthiazol-2-yl)-2 and 5-diphenyltetrazolium bromide (MTT) solution. The cellular inhibitory potency of the complexes is examined by treating the cells with MTT for 3 hours to allow formazan production during cell metabolism. After that, the formazan crystals are fully dissolved in DMSO with oscillation. Finally, the absorbance of solution is measured with Biotek PowerWave XS microplate reader at the wavelengths of 570 and 690 nm.

Photo-Cytotoxicity

T24, HeLa and MRC-5 cells ($1\times10^5$) are treated with Er—R$_n$ porphyrin complexes and Yb—R$_n$ porphyrin complexes for 24 hours at four concentrations (1, 5, 10, 50M). Then, the cells are irradiated at 6 mWcm$^{-2}$ (equipped with 550 nm long pass filter) for about 27 minutes and further incubated for 24 hours. The cells are then treated according to the same protocol as the previous MTT assay.

In Vitro Confocal Microscopy

To investigate the suitability of the obtained complexes as bioprobes, T24, 5637, HeLa and MRC-5 cells ($1\times10^5$) are imaged. After incubation with the complexes at 5M for 24 hours, the cells are washed with PBS for three times before imaging. LysoTracker Green DND-26 was used as containing dye. Images were acquired on a Leica TCS SPE confocal laser-scanning microscope. The samples and LysoTracker were excited at wavelength of 561 and 488 nm respectively.

Flow Cytometry Measurements of Cellular Uptake

5637, T24, HeLa and MRC-5 cells ($1\times10^5$ per sample) are seeded onto 35 min Petri dishes and incubated overnight. Then the cells are incubated with the Er—R$_n$ and Yb—R$_n$ porphyrin complexes (5M) for 3, 6 and 24 hours. Cells are harvested with trypsin and washed twice with PBS. The uptake of the complexes by the 5637, T24, HeLa and MRC-5 cells is analyzed by flow cytometry. The cells are excited with a 488 nm argon laser and emission is collected in the FL-3 channel (with a 650 nm long-pass filter); 10000 events are analyzed.

HPLC Characterization of the Complexes.

TABLE 5

Solvent gradient for HPLC

| Time/min | 0.05% TFA in water/% | MeOH/% |
|---|---|---|
| 0 | 50 | 50 |
| 5 | 20 | 80 |
| 20 | 0 | 100 |

Figure 38A:
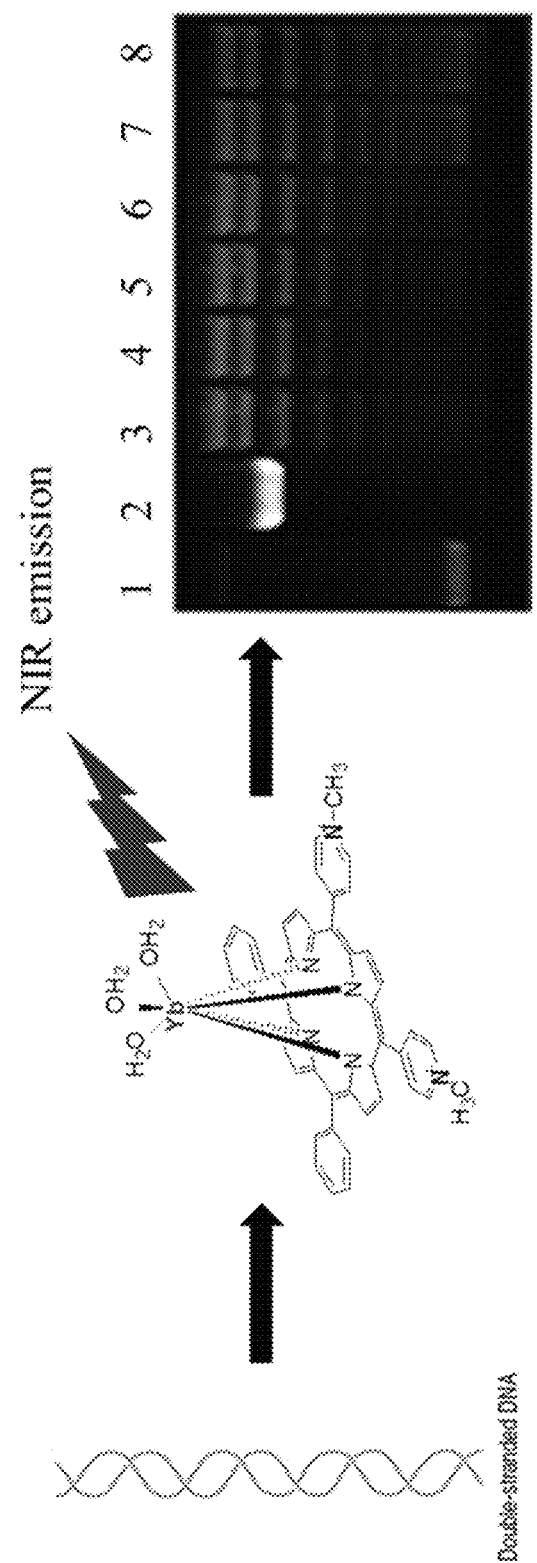
FIG. 38A shows NIR emission of existing organelle/DNA specific lanthanide complex. Meso-pyridinium-substituted porphyrin-based ytterbium complexes shows a responsive NIR emission upon the addition of DNA.
Figure 38B:
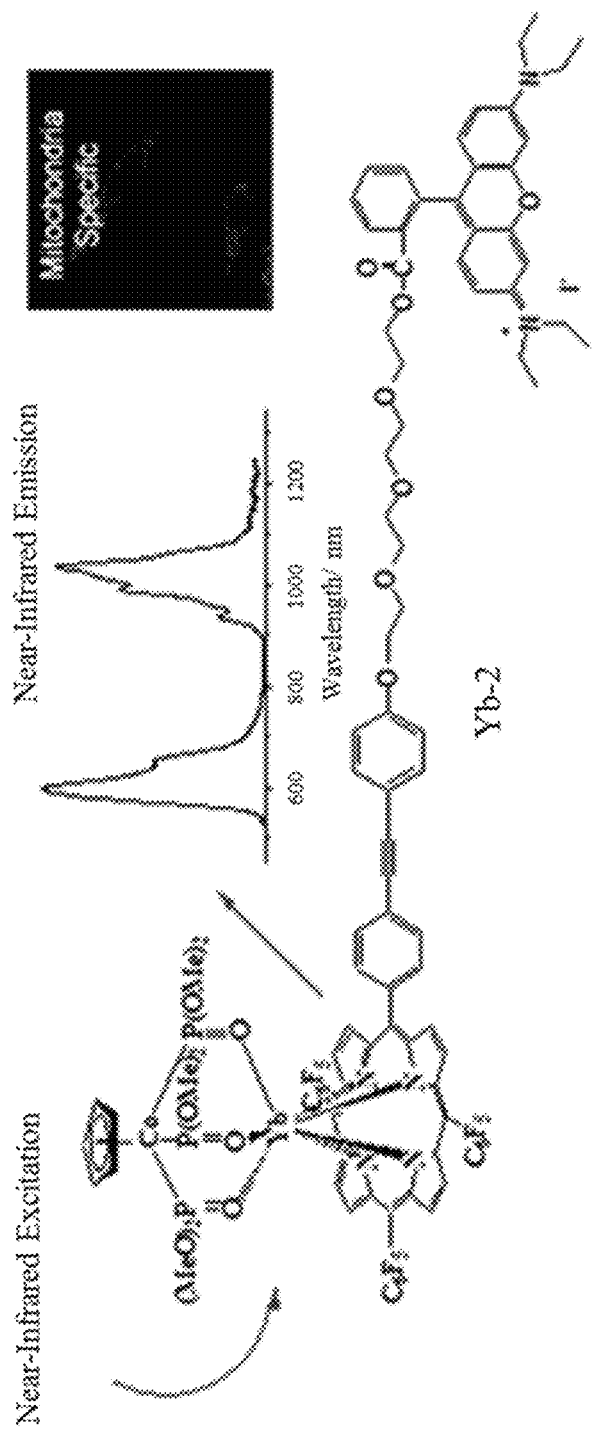
FIG. 38B shows NIR emission of water-soluble and mitochondria specific porphyrin-based Yb(III) complex (Yb-2).
Figure 39A:
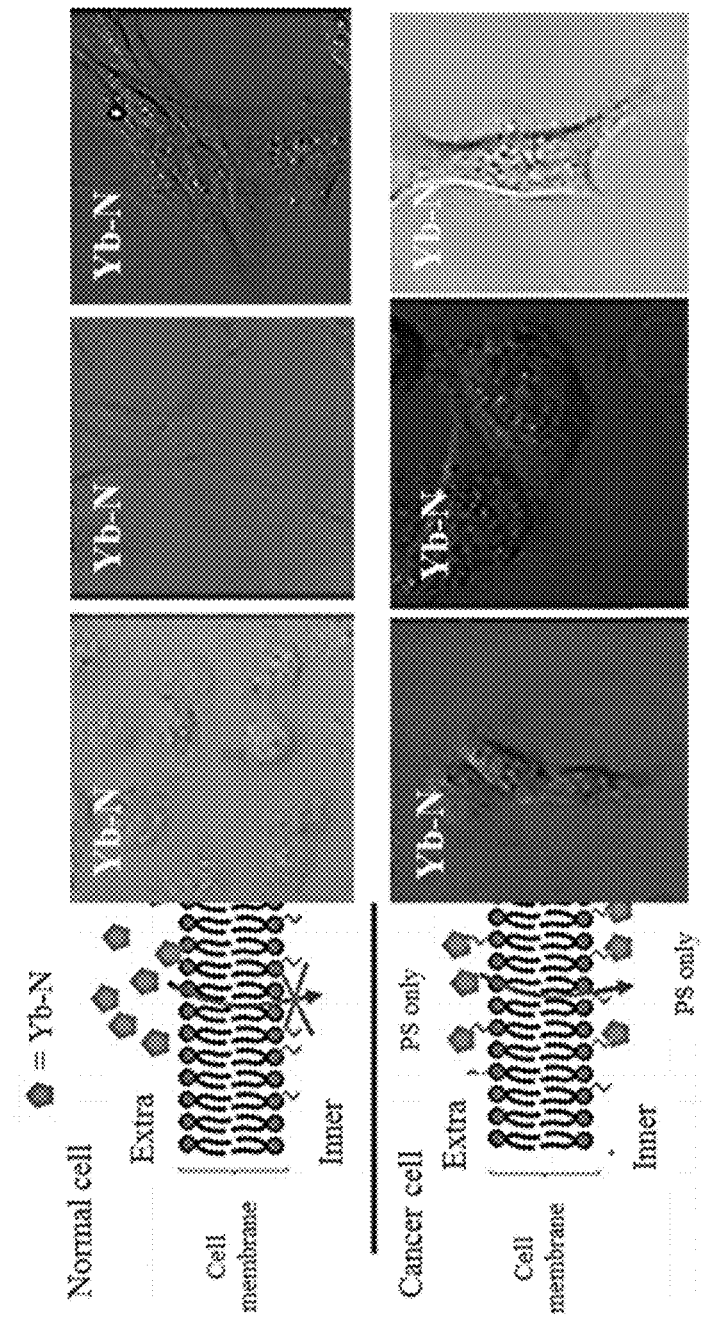
FIG. 39A shows affinity of Yb—N to phosphatidylserine and cancer cells; a strong binding to phosphatidylserine and the capability to differentiate of cancer cells via targeting the anionic phospholipid membrane.
Figure 39B:
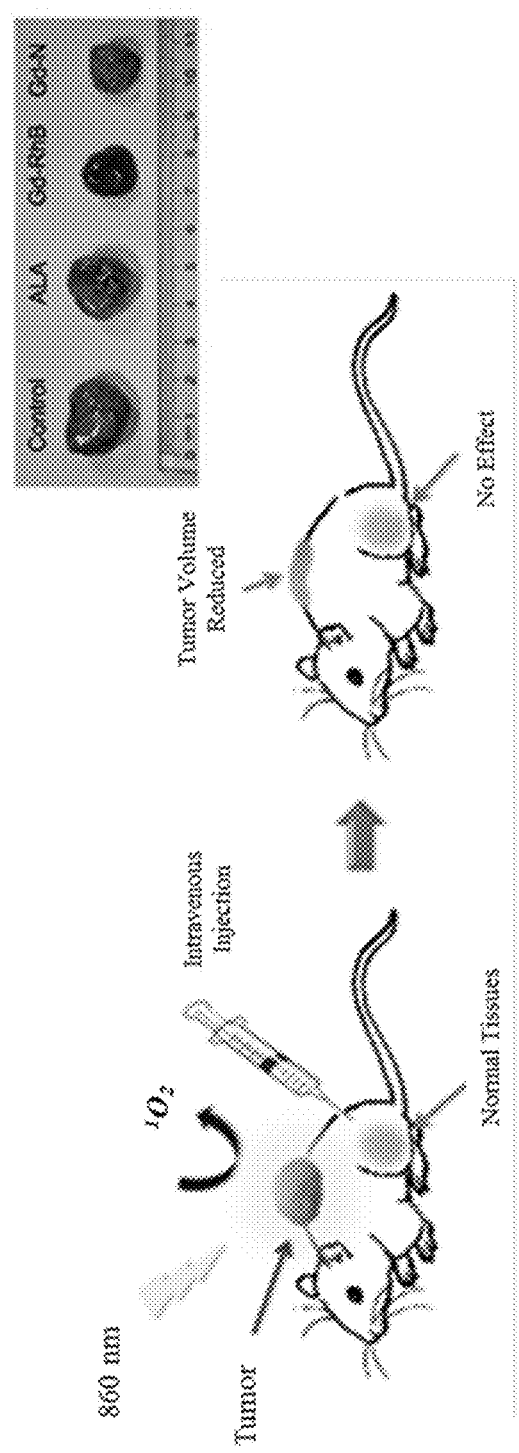
FIG. 39B shows the development of organometallic complexes as in vitro and vivo tumor specific PDT agents as PDT agents.

Another further embodiment of the present invention.

i. Development and Comprehensive Studies of Various Organometallic/Lanthanide Complexes for Biological Studies Another series of organometallic complexes are provided in the present invention and their structure-photophysical property relationship in multi-photon and non-linear processes are studied. These complexes are applicable for biological imaging. Water-soluble lanthanide(III) porphyrinate complexes and meso-pyridinium-substituted porphyrin are obtained by methylation of the corresponding pyridyl complexes with methyl iodide and unambiguously charac- terized. The binding interactions and photocleavage activities of these water-soluble lanthanide(III) porphyrinate complexes towards DNA are investigated (FIG. 38A). Additionally, the inventors reported a new water-soluble, mitochondria-specific porphyrinato Yb(III) complex (FIG. 38B) capped with a tripodal[($\eta^5$-C$_5$H$_5$)Co{(MeO)$_2$P=O}$_3$]$^-$ anion which showed a remarkable NIR emission quantum yield in water.

ii. Development of Organometallic Complexes as In Vivo Tumor Specific PDT Agents The present invention provides another set of novel organelle specific markers (for lysosome, mitochondria, Golgi apparatus). These complexes in-vitro simultaneously trigger the generation of $^1O_2$ in-vitro and give luminescent images of the organelles upon irradiation by visible/NIR excitation. Such behavior affords spatial control using dual laser excitations to damage selected cell compartments/components. Previously, the inventors reported a porphyrinato ytterbium complex which shows a strong binding to phosphatidylserine and the capability to differentiate of cancer cells via targeting the anionic phospholipid membrane (FIG. 39A) and recently, its motif structure (Gd—N) has demonstrated the availability as in vivo tumor specific PDT agents. (FIG. 39B).

In the present invention, another set of multi-modal porphyrinato lanthanide-based complexes for biological imaging are provided—NIR optical and t$_1$ magnetic resonance imaging—that bind strongly to the targets, phospholysation anionic membrane/integrin $\alpha_v\beta_3$ isoform, and generates $^1O_2$ as anticancer agents. The present invention provides (1) complexes for use as dual probe for optical and MRI imaging and cancer specific PDT effect, via the bio-conjugation with the known functional groups and peptides, and $^1O_2$ from porphyrin moieties; (2) in vitro anticancer effects via optical imaging and other typical protocols; (3) in vivo pharmacokinetics and bio-distribution of these complexes (with anticancer effects) by MRI imaging/ICPMS.

Figure 40:
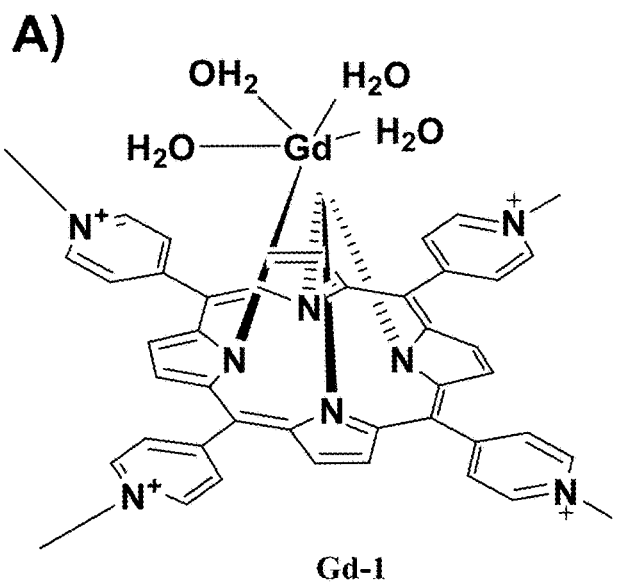
FIG. 40 shows the molecular structures of multi-modal porphyrin based metal complexes A) Gd-1, B) Gd-2, C) Gd-3-R$_1$ and D) Gd-3-N which are used as PDT, optical and MRI agents.
Figure 40:
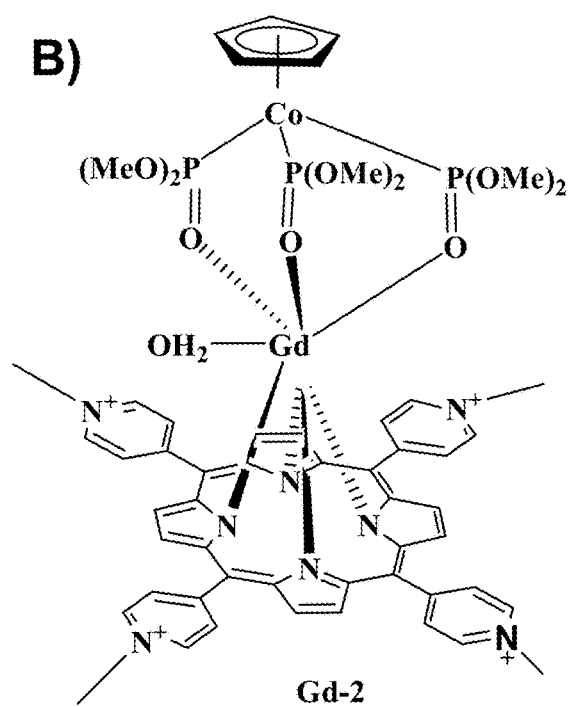
Figure 40:
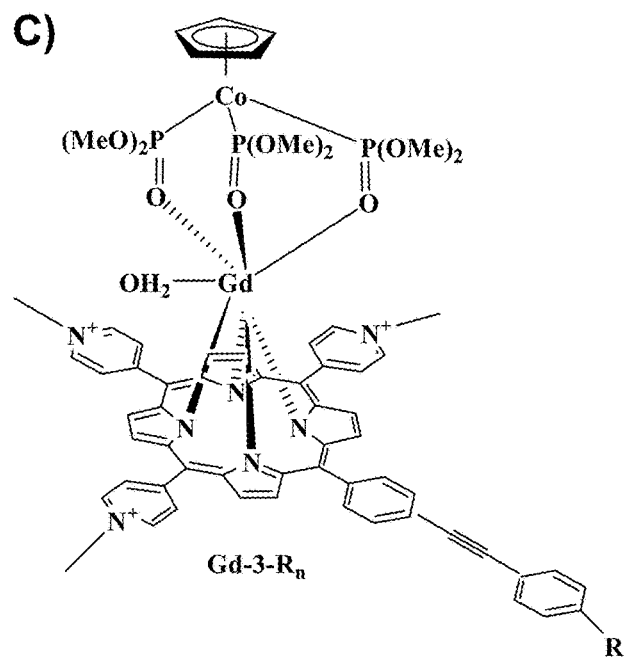
Figure 40:
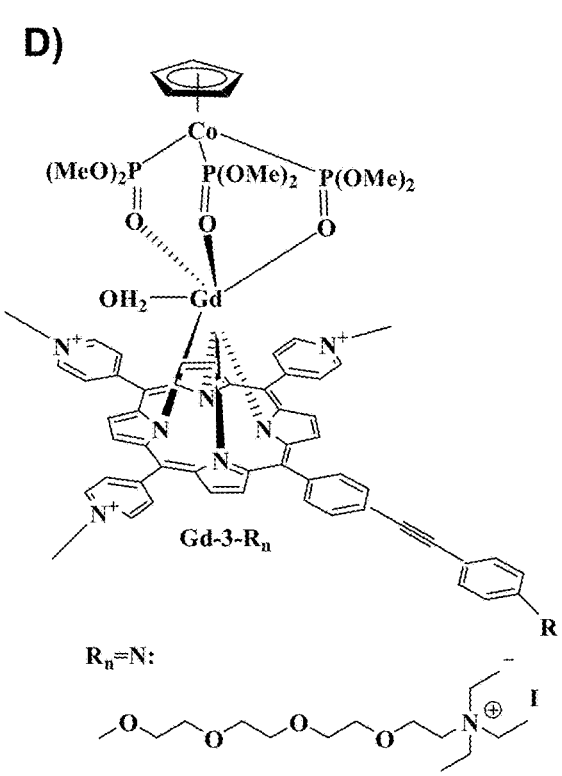

Herein, the inventors have designed and synthesized 4 water-soluble, cell-permeable porphyrin-based gadolinium complexes, Gd-1, Gd-2, Gd-3-R1, Gd-3-N (FIG. 40), which has the same general chemical formula as FIG. 12 *a*). These complexes for use as multi-modal PDT agents are examined (1. Bio-stability—P$_M$; 2. PDT and in-situ imaging—$^1O_2$ and emission quantum yield; 3. MR imaging—t$_1$ relaxivity; and 4. Cancer or bladder cells specific—ex vivo toxicity)

Figure 41:
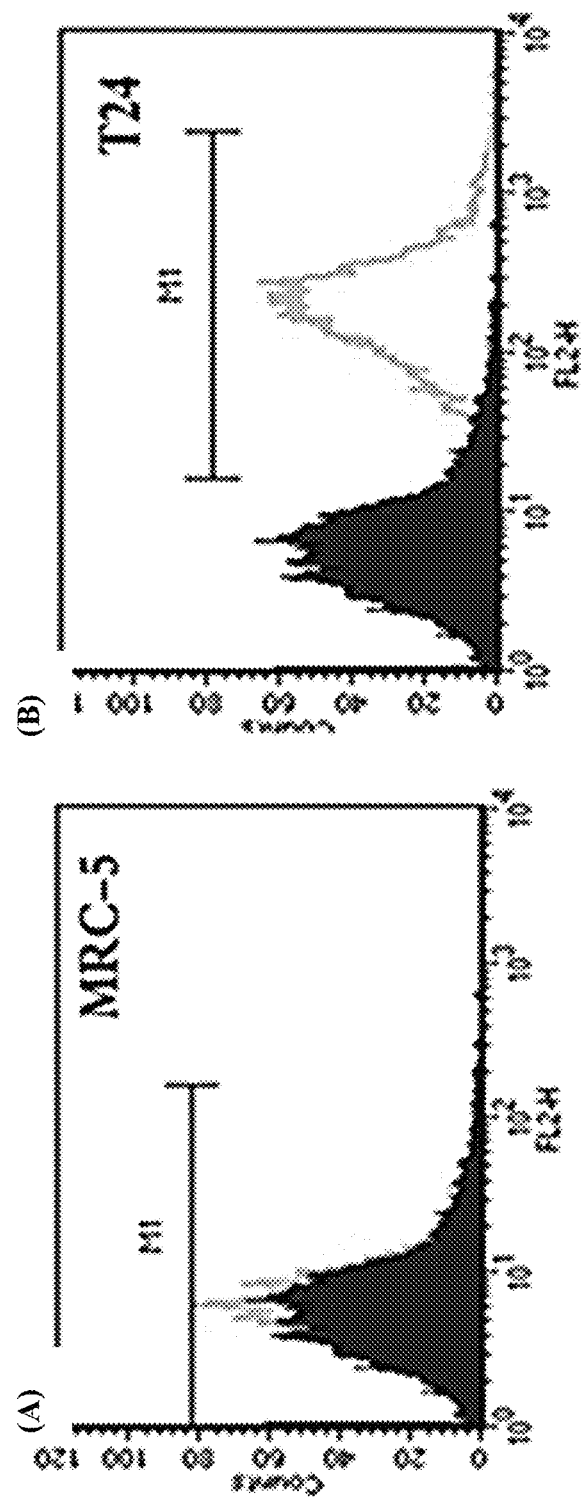
FIG. 41 shows flow cytometry analysis of cellular uptake of Gd-3-R$_1$.Gd-3-R$_1$ has the fastest uptake rate among the four porphyrin complexes in the cancer cells and also with the better selectivity towards (B) bladder cancer T24 cells rather than (A) normal MRC-5 cells.

(a) The Stability, Solubility and Uptake Profile of Gadolinium Complexes, Gd-1, Gd-2, Gd-3-R$_1$, Gd-3-N The protonation of the substituent groups on the porphyrin of Gd-1, Gd-2, Gd-3-R$_1$, Gd-3-N demonstrates an improvement of the water solubility. All the complexes have been purified by HPLC. The organometallic system Gd-2, Gd-3-R$_1$ and Gd-3-N show better stability than Gd-1, with the P$_m$ values of Gd-2. Gd-3-R$_1$ and Gd-3-N being around 8.15. P$_m$ value is the negative log of the concentration of free metal ion left uncomplexed by a given chelator, pM=−log [M]$_{free}$. The cellular uptake profile from flow cytometry also shows that Gd-3-R$_1$ has the fastest uptake rate among the four complexes in the cancer cells and also with the better selectivity towards bladder cancer T24 cells rather than normal MRC-5 cells (FIG. 41).

(b) The $^1O_2$ and NIR Emission Quantum Yield

Figure 42:
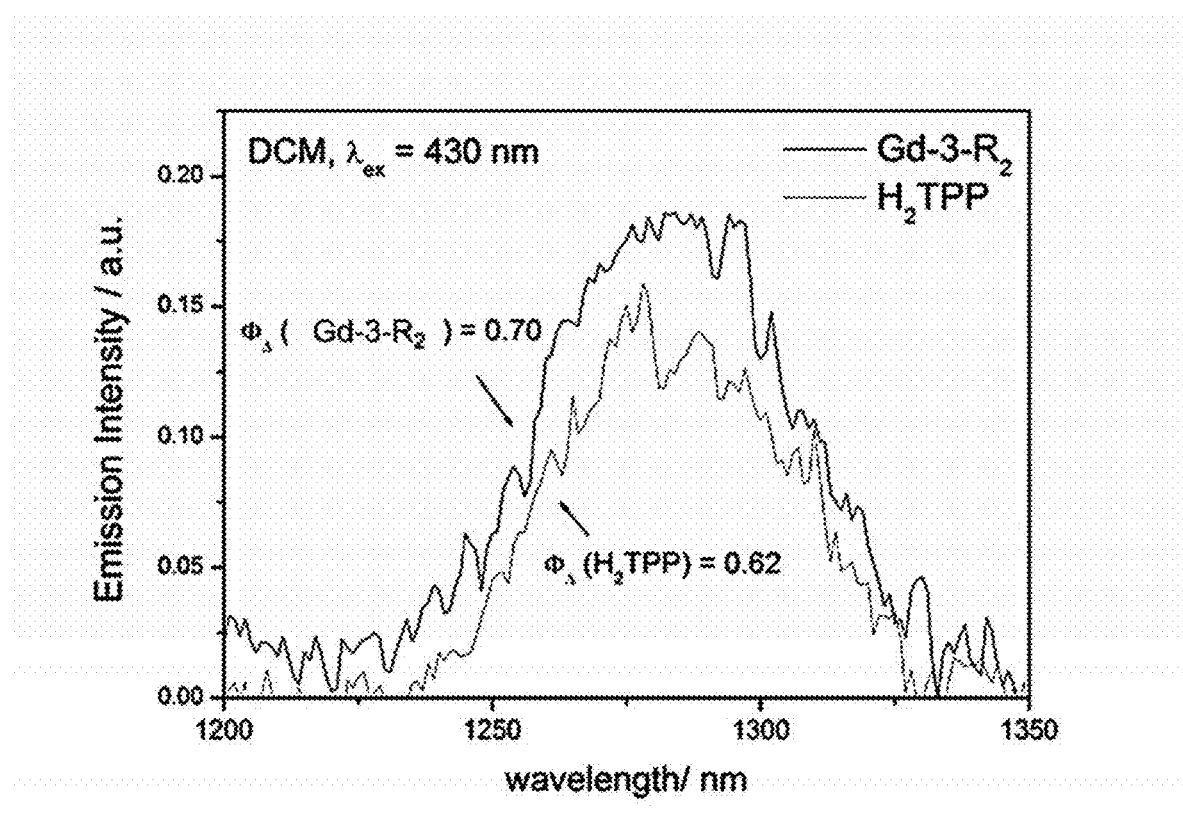
FIG. 42 shows emission intensities of Gd-3-R$_1$ complex and H$_2$TPP irradiated at 430 nm excitation; similar $^1$O$_2$ and emission quantum yield upon protonation of the Gd-3-R$_1$ complex compared with H$_2$TPP reported in PNAS, 2014, E5492-E5497, which are around ~70% $^1$O$_2$ quantum yield and 46% emission quantum yield with the excitation at 430 nm respectively.
Figure 43:
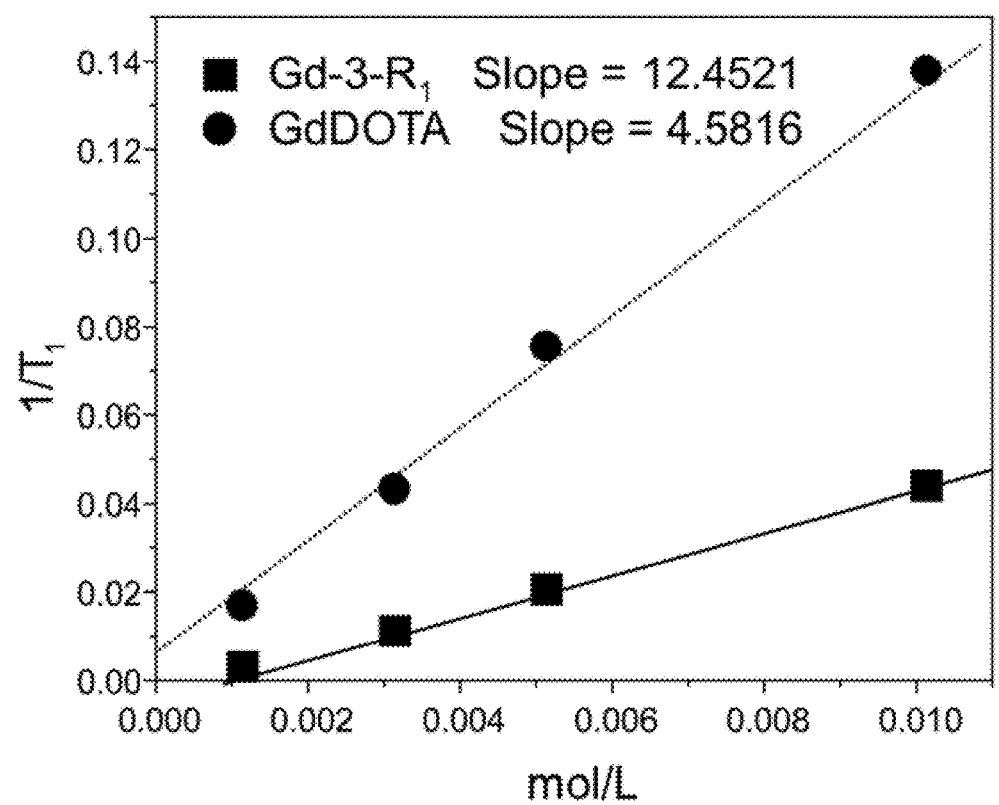
FIG. 43 shows the t$_1$ relaxivity of Gd-3-R$_1$ and Gd-DOTA of various concentrations; t$_1$ relaxivity of Gd-3-R$_1$ is three times greater than Gd-DOTA.
Figure 44:
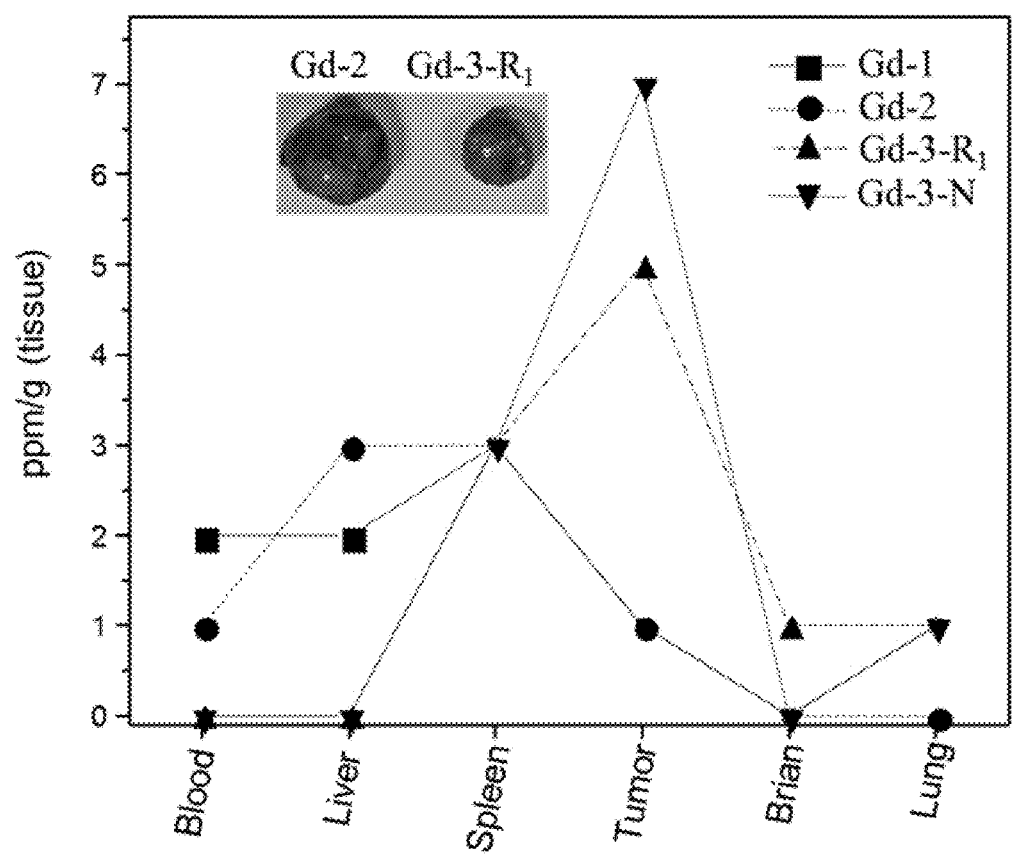
FIG. 44 shows concentration of Gd-1, Gd-2, Gd-3-R$_1$ and Gd-3-N in ppm level per gram of different tissues.

Upon protonation of the complexes, similar $^1O_2$ and emission quantum yield are shown and compared with the existing complex, H$_2$TPP, which are around ~70% $^1O_2$ quantum yield (FIG. 42) and 46% emission quantum yield with the excitation at 430 nm respectively I the $t_1$ Relaxivity and Ex Vivo Toxicity/Distribution of Gd-1, Gd-2, Gd-3-R$_1$, Gd-3-N With an aim to develop them as MR contrast agents, the water exchange rate of the complexes is one of key preliminary studied. The $t_1$ relaxivity of Gd-1, Gd-2, Gd-3-R$_1$, Gd-3-N are evaluated and Gd-3-R$_1$ has three times $t_1$ relaxivity greater than Gd-DOTA (FIG. 43). The effectiveness ex vivo tumor toxicity of Gd-3-R$_1$ has been compared with the control (Gd-2) (FIG. 44).

(d) The In Vivo Magnetic Resonance Imaging (MRI)

Figure 49A:
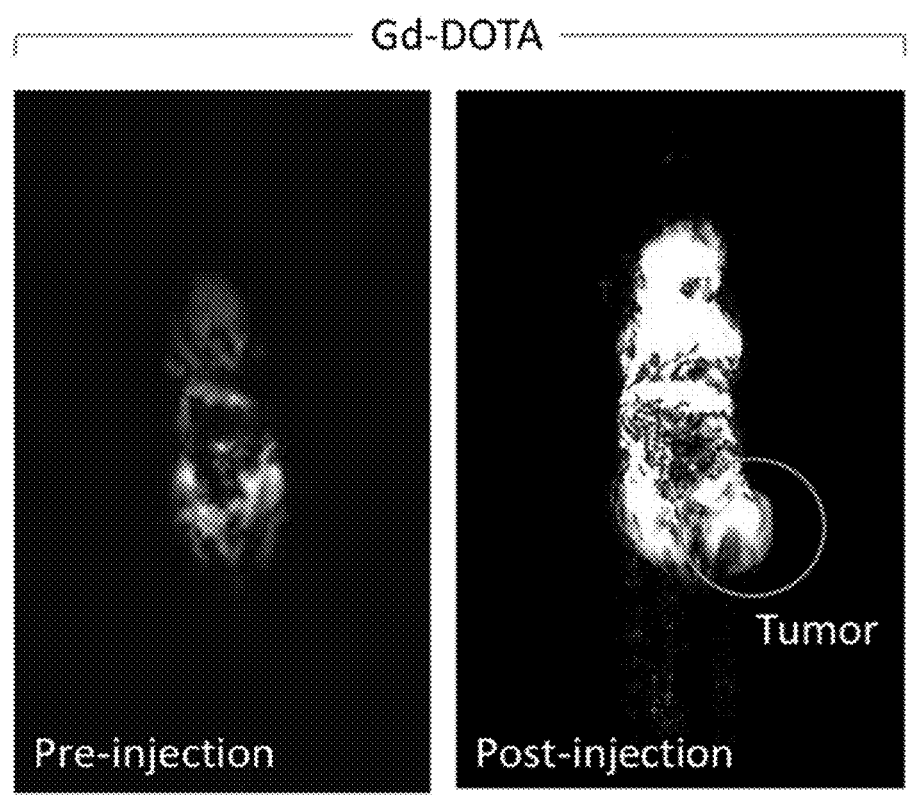
FIG. 49A shows the selectivity towards (T24 bladder cancer, xenograft tumor) by comparing the in vivo magnetic resonance images of Gd-DOTA and Gd-3-R$_1$ (FIG. 49B).
Figure 49B:
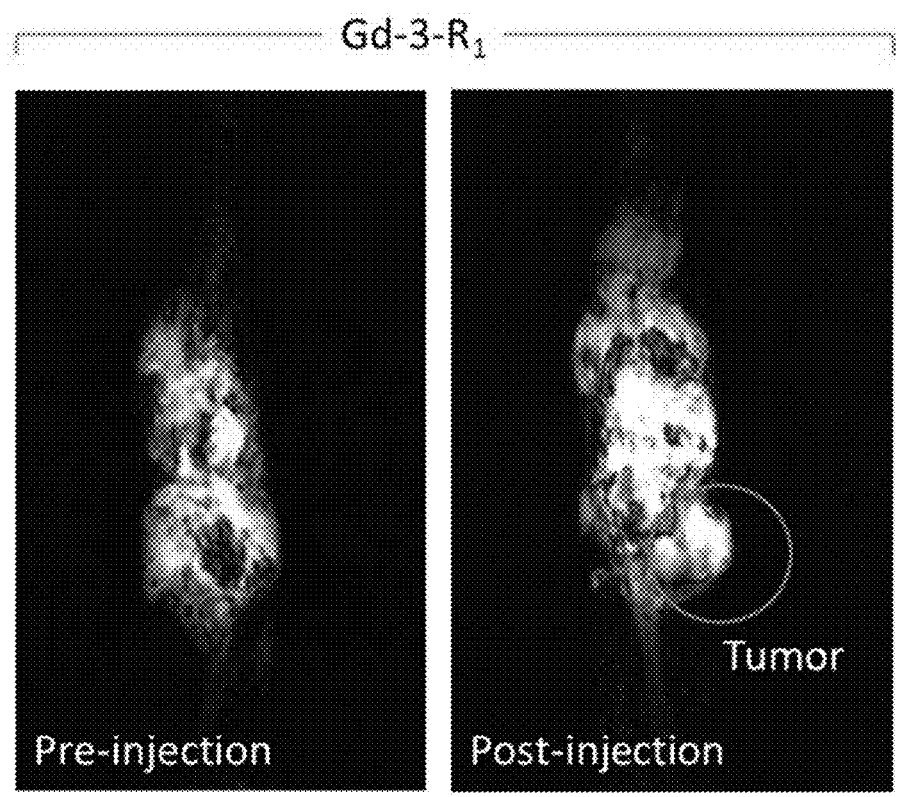

After tail vein injection of Gd-3-R$_1$ and Gd-DOTA into the mice, MRI experiment is conducted immediately. As shown in FIGS. 49A and 49B, the contrast effect of Gd-3-R$_1$ on the xenograft tumor (T24 bladder cancer cells) is enhanced significantly and specifically, while the Gd-DOTA enhances the whole body signal without selectivity toward the tumor.

Multi-Modal Lanthanide-Based Bio-Probes with Integrin $\alpha_v\beta_3$ Isoform, Specific Peptide Coatings as a Simultaneous Imaging (Optical and MR) and Anti-Cancer Agent In Vitro and In Vivo.

Task 1—Synthesis of "Smart" Organometallic Complexes that can Selectively Differentiate Tumor Cells for Effective PDT and Available for MR and Optical Imaging There are two major problems associated with commercially or literature available photosensitizers in photodynamic treatment: (i) the recognition of cancer cells and (ii) the monitoring of their effectiveness. Studies show that newly developed lanthanide complex, Gd-3-R$_1$, is able to identify cancer cells through its anionic PS membrane, generate $^1O_2$ with certain laser wavelength, and display two-photon induced NIR emissions and MR availability. The inventors extend their previous findings and run a comprehensive program to obtain new lanthanide complexes (on top of cancer cell selectivity with better $^1O_2$ yield) as a new generation of PDT agents specifically for cancer disease, especially for bladder cancer. The new development agents are able to treat tumors that are deeper under the skin or in body tissues, more selective for cancer cells as opposed to normal cells and removed from the body more quickly, reducing the time people need to worry about photosensitivity reactions. Selection criteria for the best photosensitizers. There are a number of criteria for the selection of photosensitizers. First of all, it must be water soluble. The photosensitizer(s) should be able to be excited in the near infrared region, especially between 800 nm to 900 nm. Also, the $^1O_2$ quantum yield of the best photosensitizers should be >20% and with specific mitochondria subcellular localization. The photocytotoxicity of valid bladder cancer specific photosensitizer (i.e. LC$_{50}$ in 1J laser dosed is 1M) must be 100 times lower than dark cytotoxicity. (IC50 have to be >0.1 mM).

Absorption and Fluorescence Details of Porphyrin-Based Compounds

Porphyrin is a highly conjugated molecule with 11 delocalized double bonds. The electronic absorption bands of metalloporphyrins are found at ~410-430 nm (the Soret band or B band) and 550-650 nm (Q bands) with strong one photon absorption coefficients (>100K M$^{-1}$ cm$^{-1}$). The emission band of porphyrin is always located at ~650 to 700 nm. As a result, the emission and excitation bands of metalloporphyrins are always located within biological windows. In addition, the strong two photon absorption cross section of metalloporphyrins are recorded with >100 GM, which indicates that the porphyrin can be excited at 860 nm and give two photon induced emission at 650 nm to 700 nm for molecular imaging, as well as generation of $^1O_2$ and PDT.

Figure 45:
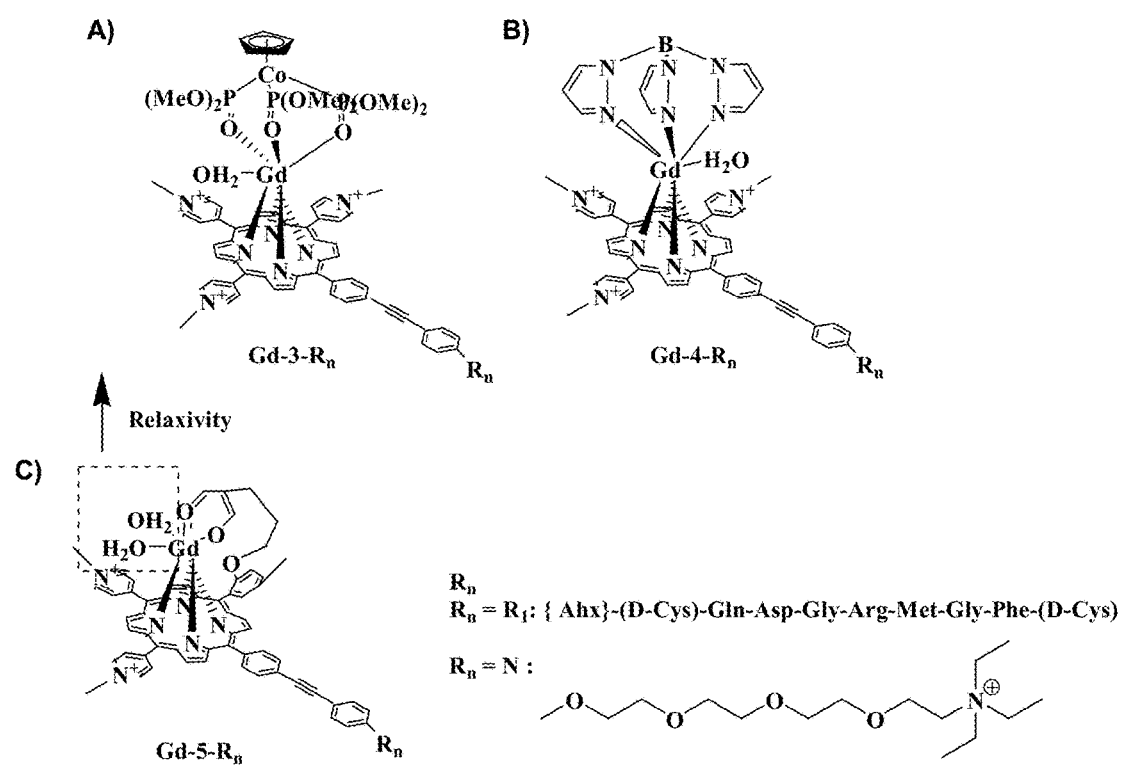
FIG. 45 shows the structures (A) Gd-3-R$_n$, (B) Gd-4-R$_n$ and (C) Gd-5-R$_n$ with the change of different substituent groups (improve water solubility), and organometallic/molecular caps (for stability/relaxivity).
Figure 46:
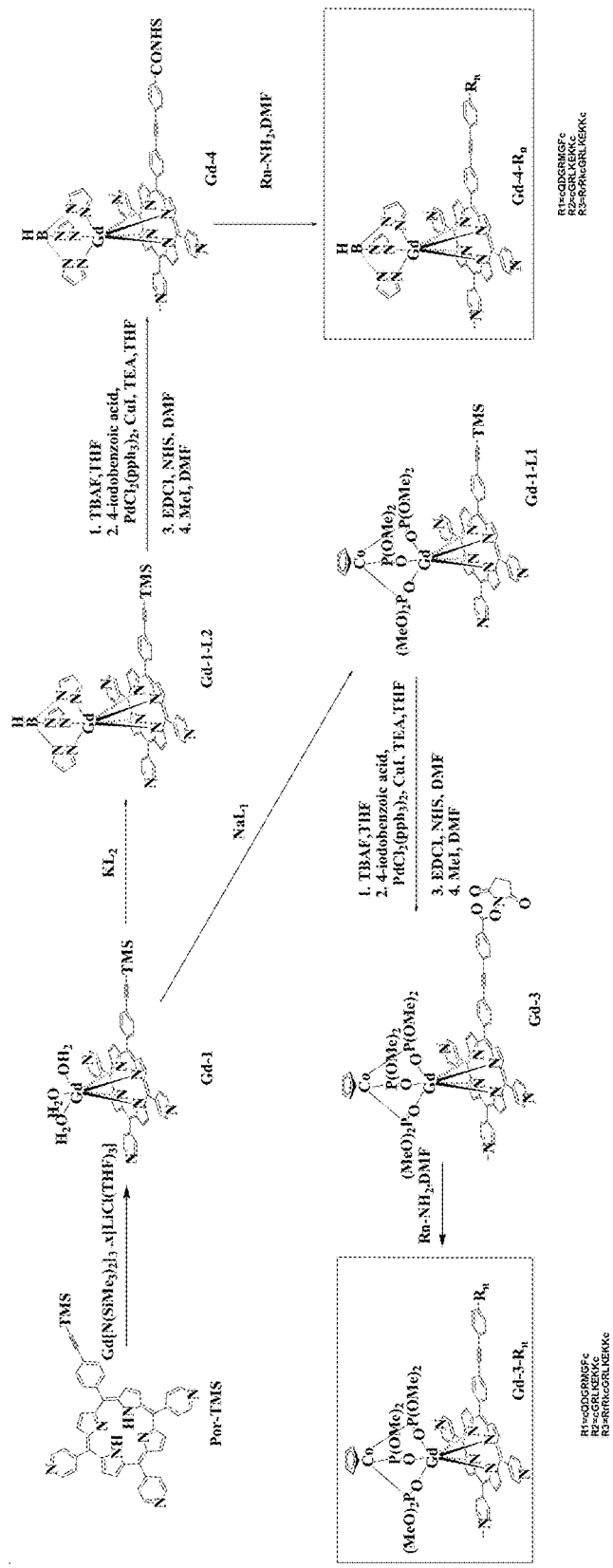
FIG. 46 shows the reaction scheme of the complexes Gd-3-R$_n$ and Gd-4-R$_n$ intermediates for FIGS. 40 and 45.

1.1 Synthesis of Water-Soluble, Highly Emissive, MR and $^1O_2$ Available Porphyrin-Based Gadolinium (III) Complexes which Target Anionic Phospholipid Membrane Water-soluble porphyrin-based gadolinium complex (Gd—N) exhibits strong selectivity toward the cancer cell membrane, emits strong visible-to-NIR emission, and undergoes high metabolism that can be removed from the body quickly. To improve the relaxivity and stability of the complexes as multi-modal agents, the present invention provides two more types of organometallic complexes in which the Gd ions are stabilized by other organometallic compounds (Gd-4-R$_n$) or with carboxylic pendant arm (Gd-5-R$_n$) (FIGS. 45 and 46).

Figure 47:
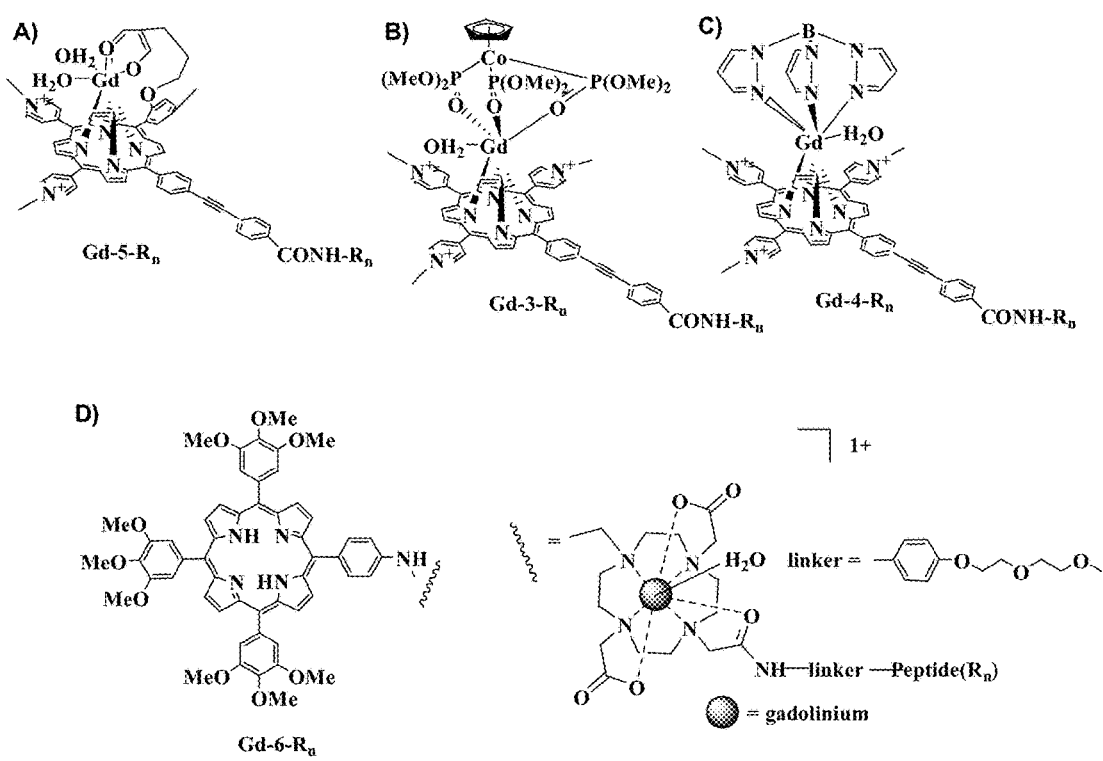
FIG. 47 shows structures of (A) Gd-5-R$_n$, (B) Gd-3-R$_n$, (C) Gd-4-R$_n$, (D) Gd-6-R$_n$ that achieve better MRI and PDT effects. (With better cellular permeability, t$_1$ relaxivity and NIR emission for optical imaging).

1.2 Synthesis of Water-Soluble, Highly Emissive, MR and $^1O_2$ Available Porphyrin-Based Gadolinium (III) Complexes which Target Bladder Cancer Cell/Tumor For bladder cancer diagnosis, the physical examination on the detection of bladder cancer has high risk to damage the bladder function. When it comes to specific treatment, PDT is a newer treatment method that is now being studied to see if it is useful in treating especially early stage bladder cancers. The limitations of using the traditional PDT are the poor penetration power of light and the difficulty to monitor the performance in real time. The present invention provides multi-modal PDT agents for comprehensive diagnosis and treatment on bladder cancer—MR for diagnosis, NIR induced $^1O_2$ for PDT and NIR induced NIR emission for real time monitoring the effectiveness of PDT. In the inventors' publication (PNSA, 2014, E5492-E5497) and the above examples, the stability, relaxivity, NIR-induced emission, $^1O_2$ ability and selectivity of the present porphyrin based complexes in cancer cells are shown. The design of the theranostic complexes targeting bladder cancer is shown in the FIG. 45 (Gd-3-R$_1$/Gd-4-R$_1$/Gd-5-R$_1$) and the several bladder cancer specific peptide(s) as vector(s) (Gd-3-R$_n$/Gd-4-R$_n$/Gd-5-R$_n$/Gd-6-R$_n$) in FIG. 47 for the $\alpha_v\beta_3$ isoform of integrin protein will be conjugated to the multi-modal complexes in the section 1.1.

Preparation of Compound Por-TMS 4-((trimethylsilyl)ethynyl)benzaldehyde (2.02 g, 10 mmol) was mixed with Pyridine-4-carboxaldehyde (3.21 g, 30 mmol) in propionic acid (700 mL) and the mixture was stirred for half an hour in 130° C. Then pyrrole (2.64 g, 40 mmol) was added dropwise into the reaction mixture with the temperature increased to 140° C. Then the mixture continued to be stirred for 30 minutes in open air. After cooled down to room temperature, the solvent was removed under reduce pressure to afford black solid. The crude product was dissolved in minimum amount of $CH_2Cl_2$ and purified by column chromatography on silica gel column $CH_2Cl_2$/Methanol (12:1) to give purple color solid. Yield 8%.

$Gd[N(SiMe_3)_2]_3 \cdot x[LiCl(THF)_3]$:

$HN(SiMe_3)_2$ (10.8 ml, 0.050 mol) was dissolved 20 ml of THF in ice bath, then n-BuLi (1.6M in hexane) was added slowly over 30-min period. The resulting solution was magnetically stirred for 12 hours until a clear pale yellow solution was obtained. Then the solution was transferred slowly to a Schlenk flask with $GdCl_3$ (4.47 g, 0.017 mol) suspended in 20 ml THF. The resulting mixture was magnetically stirred for 24 h until all of the solid $GdCl_3$ was disappeared. The resultant solution $Gd[N(SiMe_3)_2]_3 \cdot x[LiCl(THF)_3]$ (x=3~5) was referred to as solution C Gd-1-L1:

Solution C (2.5 ml, 0.52 mmol of Gd) prepared above was transferred to a Schlenk flask and the solvent was removed under vacuum. Then 10 ml $CH_2Cl_2$ was added for the precipitation of LiCl. The mixture was centrifuged and the clear layer was transferred to another Schlenk flask with dry Por-TMS (0.099 g, 0.14 mmol) dissolved in 15 ml toluene. The resulting solution was refluxed until most of the free base coordinated with the metal ion. Dry $NaL_1$ (0.1 g, 0.22 mmol) $[L_1$-((cyclopentadienyl)tris(dimethylphosphito)-cobaltate, an anionic tripodal ligand] was then added and magnetically stirred for another 12 hours before the reaction solution was cooled down to room temperature. Upon completion of the reaction, the solvent was removed in vacuum and the residue dissolved in $CHCl_3$, filtered and chromatographed on silica gel using $CHCl_3/CH_3OH$ ether (V/V 200:1) as eluent. The product was dissolved in $CH_2Cl_2$ (5 ml) and the solution was filtered. Yield: 61%

Gd-1-L2:

The similar procedure with Gd-1-L1, replace $NaL_1$ with $KL_2$ (potassium tris(1-pyrazolyl) borohydride, 0.055 g, 0.22 mmol). Yield: 50%.

Gd-3:

TBAF (1.0M in THF, 0.2 mL, 0.2 mmol) was added to a solution of Gd-1-L1 (0.133 mg, 0.1 mmol) in 10 ml DCM, and the solution was stirred for 30 min. The progress of the reaction was monitored by TLC. After completion of the reaction, the mixture was passed through a short of silica gel column using DCM After removal of solvent, pure product was obtained, the pure product (33.2. mg, 0.02 mmol) and $Pd(PPh_3)_4$ (2.2 mg 0.008 mmol), CuI (0.77 mg, 0.004 mmol), 4-iodobenzoic acid 5.1 mg were placed in a dried flask and under nitrogen. THF (15 mL) and $Net_3$ (5 mL) were added and the reaction mixture degassed with nitrogen. The reaction mixture was stirred at 40° C. for 12 h. After that, the solvent was removed under reduced pressure. The residue was purified by chromatography. Elution with $CH_2Cl_2$/Methanol (10:1) afforded the pure product, the pure product (30 mg, 23.75 mmol), EDCI (9.02 g, 0.048 mmol), NHS (5.52 mg, 0.048 mmol) were placed in a dried flask and under nitrogen, 10 mL dry DMF was added. Stirred at room temperature for 48 h. then remove the solvent, The residue was recrystallized by diethyl ether and dried to give the title product, the product (33.37 mg, 0.025 mol) was dissolved in DMF (10 ml), Then $CH_3I$ (0.25 mmol) was added and stirred for 5 h, After completion of the reaction, solvent was removed. The residue was washed with ether .DCM. afforded the pure product. Yield 52%.

Gd-4:

The similar procedure with Gd-3, replace Gd-1-L1 with Gd-1-L2. Yield 50%.

Gd-3-Rn:

A stirred solution of Gd-3 (20 mg, 1 equiv) in anhydrous DMF was mixed with N,N'-diisopropylethylamine (DIPEA) (1 equiv.). the mixture solution was added into a vial which containing peptide (1.3 equiv.) ($R_n$). It was then reacted at RT overnight, after that, the solvent was removed under vacuum to get the dry compound. The residue was recrystallized by diethyl ether three times and dried to give the titled product. Yield 70%.

Gd-4-Rn:

The same procedure with Gd-3-Rn, replace Gd-3 with Gd-4. Yield 68%.

Figure 48:
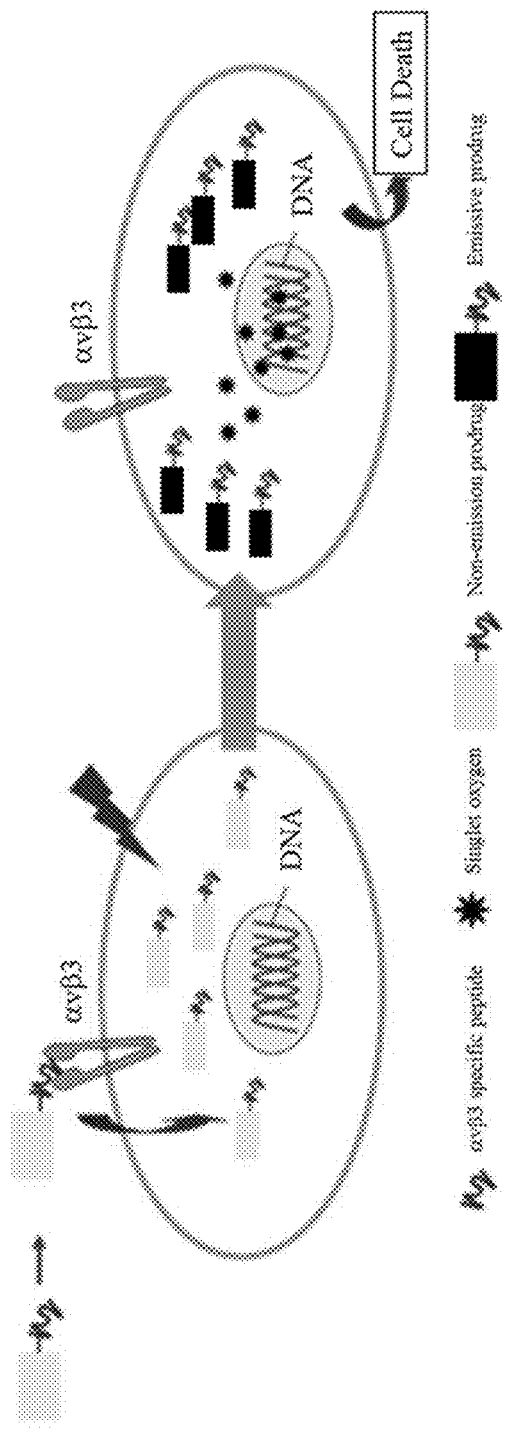
FIG. 48 shows the development of multi-modal water-soluble, lanthanide-based PDT agents for optical imaging and inhibition of bladder cancer.

Task 2: Examination of the Selectivity and Relaxivity of Gd-3-$R_1$ with Bladder Cancer The general photophysical properties, such as emission quantum efficiency and emission lifetime are examined. The magnetic properties of these gadolinium porphyrin complexes are measured. The binding affinity between the $\alpha_v\beta_3$ isoform and the present invented porphyrin complexes Gd-3-$R_1$, is the prime factor for developing the multi-modal probe for monitoring $\alpha_v\beta_3$ isoform bladder cancer. The binding affinities of the present invented complexes for $\alpha_v\beta_3$ isoform bladder cancer are determined by enthalpy changes and electrostatic interactions. The cell-permeable and water-soluble porphyrin-based gadolinium porphyrin complexes are to be bioconjugated with a cancer-specific vector (peptide). The tailored peptide can be used to trace the integrin $\alpha_v\beta_3$ isoform in bladder cancer cell membrane. Bladder cancer (T24) model are under studied and other cancer cell models such as HeLa, SK-N-SH, A549, C666-1 and normal cells: MRC-5 are served as control (FIG. 48).

2.1 Photophysical Properties and Stability of the Newly Synthesized Gadolinium (III) Complex, Gd-3-$R_1$ The linear, multi-photon photophysical properties (i.e. emission spectra, emission lifetime, quantum yield and two-photon absorption cross section) and $^1O_2$ yield and also photo-bleaching quantum yield (compared with standard, such as uroporphyrin) of Gd-3-$R_1$ is measured following the literature protocols. Titration experiments are conducted to investigate the stabilities of the synthesized porphyrin complexes toward several common biological anions and human serum albumin (HSA); $P_M$ and $P_{Ka}$ are determined. Liquid-concentrated stock solutions of each anion, as well as HSA, are added gradually to a solution of the complexes concerned separately. Absorption, fluorescence as well as $^{31}P$ NMR spectroscopy are used to monitor the stability of the complexes in aqueous solution upon the addition of various biological small molecules such as HSA, citrate etc.

2.2 Binding Affinity Via Electrophoretic Mobility Shift Assay

Electrophoretic Mobility Shift Assay is a powerful method for determining the binding affinity of the inventors' gadolinium porphyrin complexes to $\alpha_v\beta_3$ isoform cancer cell which is specific for bladder cancer. The $\alpha_v\beta_3$ isoform cell are expressed in an E. coli system and further purified by glutathione affinity chromatography before carrying out agarose gel electrophoresis. Experiments are to confirm physical structure of the $\alpha_v\beta_3$ isoform would not be altered by the binding of the lanthanide bio-probes.

2.3 Evaluation the Binding Affinity Via Emission and Isothermal Titration Calorimetric The binding affinity of the complexes and $\alpha_v\beta_3$ isoform is studied by isothermal titration calorimetry (ITC), a solution state method that measures the interactions between molecules, e.g. macro-proteins and ligands. The binding affinity ($K_a$), binding stoichiometry (N) and the enthalpy changes (H) of the interaction could all be determined by ITC experiments directly. From the enthalpy change, the Gibbs energy and entropy change are determined by established equations. Advantages of ITC include a real-time observation of inter-molecule interactions without limitation on molecular weight in, most importantly, a nondestructive manner.

2.4 Relaxivity Determination of Gadolinium Porphyrin Complex, Gd-3-$R_1$

The relaxivity of the inventors' synthesized complexes will be calculated from the relaxation time obtained by a Bruker DPX300 NMR spectrometer in D20 solutions. An inversion-recovery pulse sequence is used and a ten×$T_1$ delay is maintained between successive pulses. The relaxivity (r1) is obtained by a plot of the inverse of longitudinal time (1/$T_1$) versus Gd concentrations:

$$\frac{1}{T1obs} = r1 \times [Gd] + \frac{1}{T1b}$$

where $T_{1obs}$ and $T_{1b}$ are the longitudinal relaxation times of the sample and the solvent background respectively.

2.5 Tumour Models or Cell Lines Will be Used, and Details of Biological Studies

Bladder cancer (T24) model is under studied and other cancer cell models such as HeLa, SK-N-SH, A549, C666-1 and normal cells: MRC-5 are served as control. Cancer/normal cells (Cancer cells: T24-bladder cancer, HeLa, SK-N-SH, A549, C666-1 and normal cells: MRC-5, ($2\times10^4$/well) are incubated in 96-well plates overnight. In vitro imaging for selective binding—the cells are treated with Gd-3-$R_1$ (Task 1) for 6, 12 and 24 hours in the dark. The culture medium is replaced by fresh medium and the cells are exposed to light (1-8 J/cm$^2$) produced from a laser (linear and multi-photon femtosecond Ti:sapphire laser) in the multi-photon confocal microscope. The time-lapse confocal images of Gd-3-$R_1$ in cells are carried out and their in vitro subcellular localization are compared. The subcellular localization of Gd-3-$R_1$ are different in bladder cell T24 and other non-bladder cancer cell lines, such as HeLa, C666-1 and SK-N-SH.

In Vitro Photo-Cytotoxicity—

Bladder cancer T24 cells are treated with several concentrations of complex and incubated for 12 hours. The free complex in the medium will be removed by changing the medium several times. The cells will be irradiated by laser to initiate the release of $^1O_2$ from the complex and MTT assay is performed to measure the cell viability after a number of incubation time points. Control experiment is performed with the same experimental condition, such as light dosed amount, incubation time and concentration of proposed complexes in non-bladder cancer cell lines.

The in vitro dark toxicity of the invented complexes are tested. After 24 hours, the water-soluble complexes and the targeted cells are incubated further with 3-(4, 5-dimethyl-thiazol-2-yl)-2,5-diphenyltetrazolium bromide (0.5 mg/ml), otherwise known as MTT, for 4 hours, so that formazan can be formed along with the cell's metabolic pathways. Then, the formazan is extracted and dissolved by dimethyl sulfoxide (DMSO), with the absorbance of the subsequent solutions measured in a Bio-Rad iMark microplate reader (490 nm). Quadruplicates are performed and the data are interpreted and analyzed using the GraphPad Prism 5 software.

The photocytotoxicity of valid bladder cancer specific photosensitizer (i.e. $LC_{50}$ in 1J laser dosed is 1M) must be 100 times lower than its dark cytotoxicity. (IC50 have to be >0.1 mM).

Task 3—Structure and Biological Activity (In Vitro/-Vivo Imaging and Specific PDT Effect)

In this section, effectiveness of the Gd-3-$R_1$ in vivo are evaluated. Comprehensive in vitro and in vivo examinations are employed, such as multi-confocal in vivo real time studies, MR imaging and metabolism studies (FIG. 49B).

3.1 Determine the Stability of Lanthanide Complexes for Biological Assays

There is great challenge of the coordination stability lanthanide complexes for cellular studies. Therefore, the aqueous/tissue culture medium stability must be carried out. The aqueous stability of the present complexes in the presence of various biomolecules, including citrate and human serum albumin (HSA), and in varies pH are examined as well by simple UV-vis absorption/fluorescence titration via the aforementioned procedures. Liquid concentrated stock solutions of each anion, as well as HSA, are added individually and gradually to a solution of the complex concerned. Addition is ceased either when the volume of added anion totaled 5% of the complex solution or the influence on complex absorption/luminescence was saturated.

3.2 In Vitro Cytotoxicity Studies and Rate of Cellular Uptake

For the establishment of the mouse tumor xenograft mode, bladder cancer cells (T24) or non-bladder cancer cells (HeLa) are trypsinized, harvested and suspended in serum-free culture medium. $5\times10^6$ cells in a 100 µL volume is injected subcutaneously into the flanks of female athymic nude mice (5-week old) When the tumor volume reaches the size of around 100 mm$^3$, animals are divided randomly into four experimental group with SEVEN mice in each group, as follows: group 1, vehicle control group; group 2, cisplatin treatment group; group 3, Gd—N low dose treatment group; group 4, Gd—N high dose treatment group. Treatments is administered via intratumoral injection once every 5 days, for 21-28 days. The experiment is repeated three times. The tumor volume is measured every 2 days with electronic calipers (accuracy of 0.02 mm) and then calculated independently on the basis of the equation V=(L×W$^2$)/2, where L and W correspond to the larger and smaller dimensions respectively. All animal experiments is carried out in accordance with the guidelines of the Committee on Use of Human and Animal Subjects in Teaching and Research, Hong Kong Baptist University. One-way analysis of variance towards statistical significances between groups was assessed by the GraphPad Prism 5.0 software.

3.3 Real Time Analysis of $\alpha_v\beta_3$ Isoform and Evaluation of Effectiveness (Tumorigenically Assays) of Tumor Inhibition-Days/Week Tracing of Tumor Development of Xenograft Mouse Via Multi-Photon Confocal and Magnetic Resonance Imaging for Pharmacokinetic Studies The development of xenograft mice is achieved by transplanting human bladder tumor cells (T24) to mice which are allowed to grow. The complexes is injected at the tail vein, the peritoneum or buccally delivered and after 24 to 48 hours, the xenograft are surgically extracted for two-photon confocal microscopy and MRI experiments, with the peritumor cells extracted being the control (no lanthanide complexes signals should be obtained). In vivo MM experiments are carried out on the xenograft in a Co—I institute with a Bruker Biospec 4.7 T/30 cm scanner (Bruker Inc., MA). Moreover, the tumor sizes will be measured weekly.

3.4 In Vivo Bio-Distribution Evaluation of Proposed Gadolinium Complexes

Gd-3-$R_1$ is injected intravenously to BALB/c athymic mice bearing xenografted cancer tumors. After 24 hours of incubation, the mice are sacrificed and its main organs including the tumor is removed and fixed in 10% PBS buffered formalin. Control models are athymic mice with only the buffered formalin injected. The tissue samples are frozen and lyophilized for 24 h before being digested by conc. $HNO_3$ at 70° C. for 4 hours. The gadolinium content, reflective of the quantity of the complexes, are determined by ICP-MS. The gadolinium content in urine of the mouse are evaluated to confirm the metabolism of these complexes in vivo. The results in 3.3 and 3.4 should be correlated (FIG. 44).

INDUSTRIAL APPLICABILITY

The present invention relates to a new generation of PDT agents based on porphyrin-lanthanide complexes with specific functional groups which can specifically localize on particular tumors, and their PDT processes can be monitored via NIR emission from erbium. In particular, the present invention provides a multi-modal lanthanide-porphyrin PDT agent (Er—$R_3$) that are capable of killing the bladder tumor cells selectivity via $^1O_2$ from porphyrin moiety and affording the fluorescence imaging simultaneously upon Er—$R_3$ binding with the integrin $\alpha_v\beta_3$ isoform in bladder cancer cells.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

---

What we claim is:

1. A composition for photodynamic therapy and imaging of cancer cells comprising an Erbium porphyrin based complex, Ytterbium porphyrin based complex, or Gadolinium porphyrin based complex represented by the molecular formula:

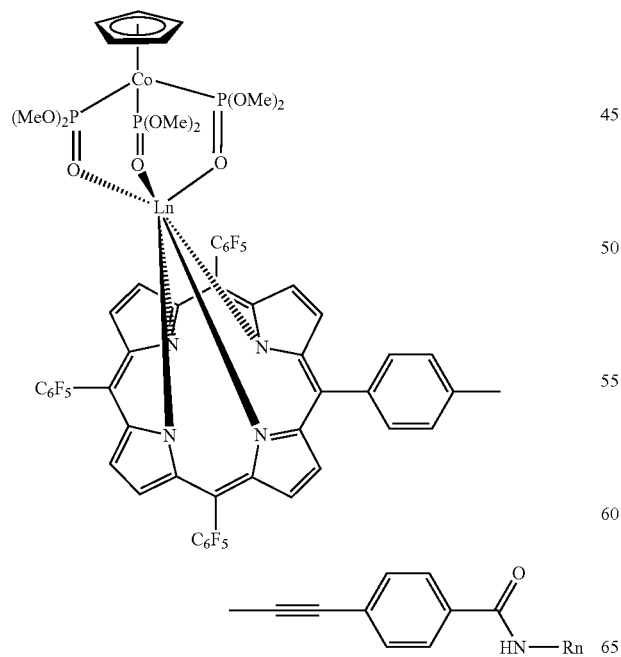

wherein Ln is Er, Yb, or Gd; and $R_n$ is a polypeptide having an amino acid sequence selected from the group consisting of SEQ ID NO: 1; SEQ ID NO: 2; and SEQ ID NO: 3; or a water-soluble porphyrin-based Gadolinium complex represented by a molecular formula selected from the group consisting of $Gd_1$, $Gd_2$, $Gd_3$, $Gd_4$, and $Gd_5$:

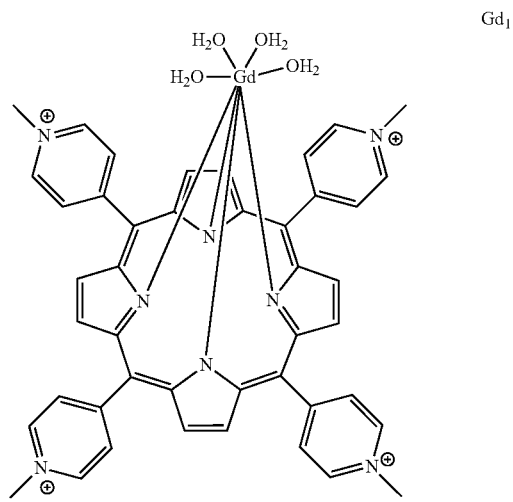

-continued

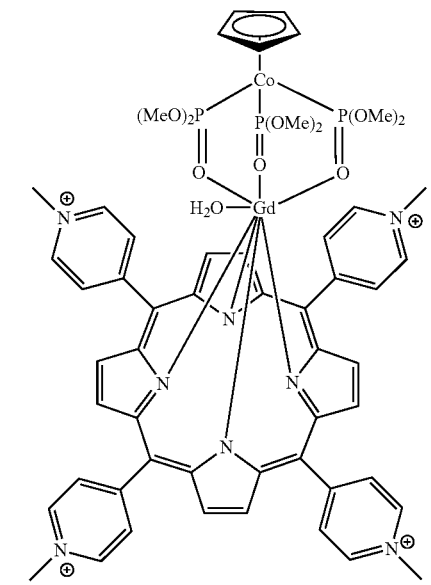
Gd₂

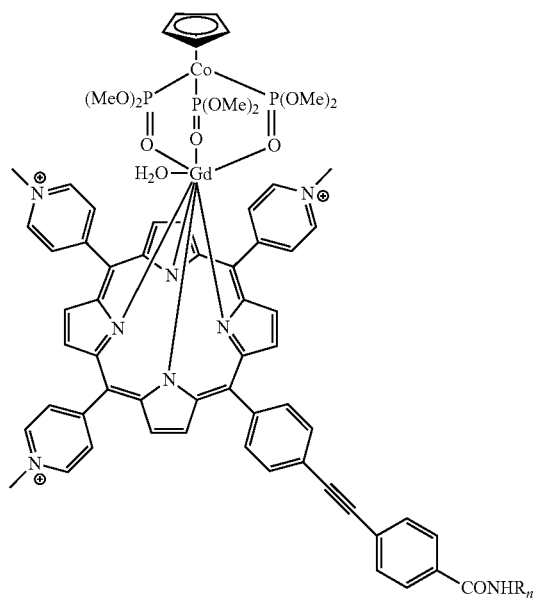

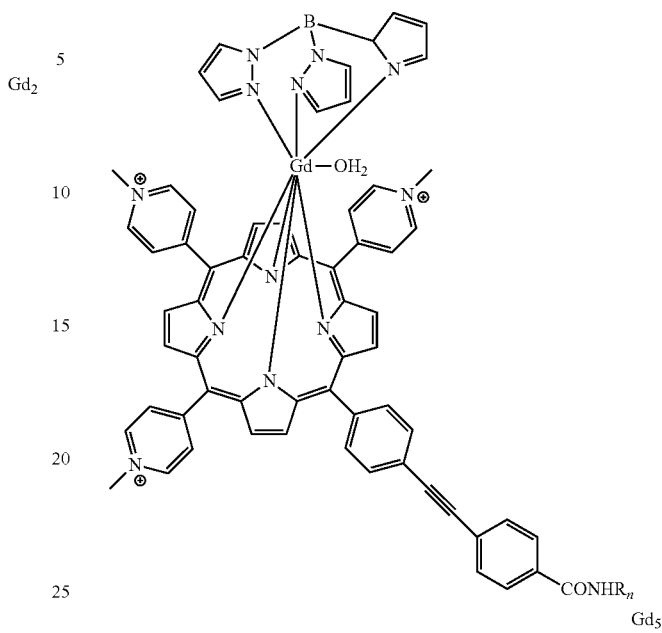
Gd₄

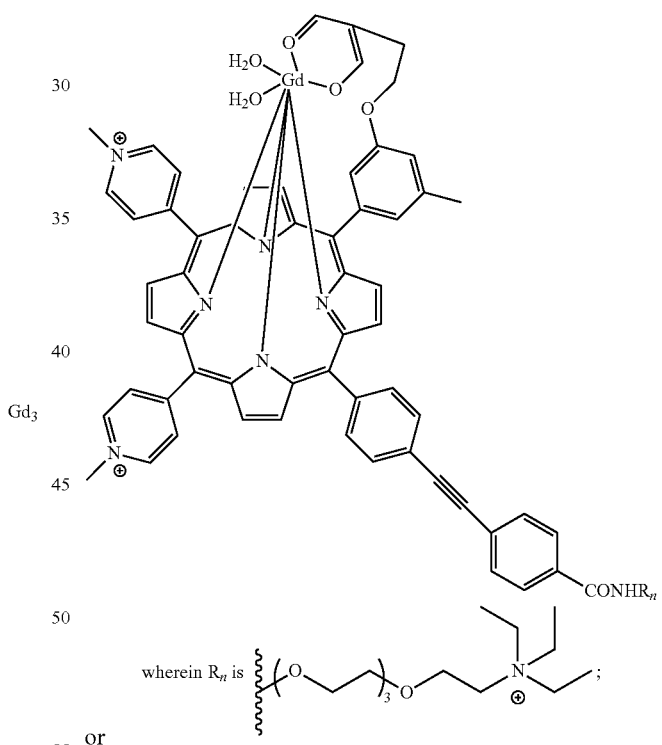
Gd₃

Gd₅ wherein $R_n$ is or
a polypeptide having an amino acid sequence selected from the group consisting of SEQ ID NO: 1; SEQ ID NO: 2; SEQ ID NO: 3; SEQ ID NO: 4; and SEQ ID NO: 5 or a pharmaceutically acceptable salt thereof.

2. The composition according to claim 1 wherein the Erbium porphyrin based complexes are conjugated with integrin $\alpha_v\beta_3$ isoform-specific peptides.

3. The composition according to claim 1, wherein the composition comprises the Erbium porphyrin based complex and $R_n$ is SEQ ID NO: 4.

4. The composition according to claim 1, wherein the composition comprises the Erbium porphyrin based complex and $R_n$ is SEQ ID NO: 5.

5. The composition according to claim 1, wherein the composition comprises the Erbium porphyrin based complex and $R_n$ is SEQ ID NO: 3.

6. The composition according to claim 1, wherein the composition comprises the Erbium porphyrin based complex represented by the molecular formula of:

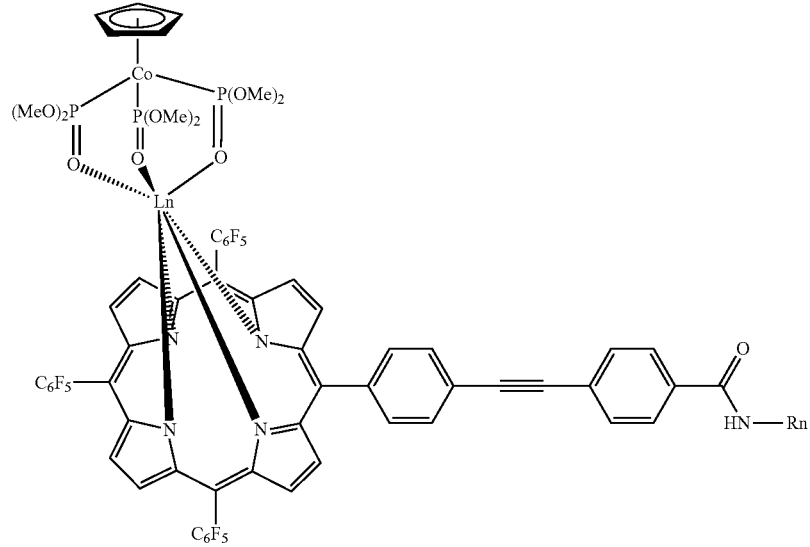

wherein Ln is Er and $R_n$ is a polypeptide having an amino acid sequence of SEQ ID NO: 3.

7. The composition according to claim 1 wherein the cancer cells comprising of bladder cancer cells, cervical cancer cells and lung cancer.

8. A method of photodynamic therapy and imaging of cancer cells comprising administering to a subject in need thereof the composition according to claim 1 and irradiating the cancer cells in the subject in need thereof with a radiation source.

9. The method according to claim 8 wherein the administration of said composition is performed intravenously or by injection to site of said cancer cells.

10. The method according to claim 8, wherein said radiation source is a light source with a wavelength in the Q band of porphyrin.

11. The method according to claim 8, wherein said radiation source is a light source with a wavelength beyond 550 nm.

12. The method according to claim 8, wherein said radiation source is a light source with a wavelength is at 860 nm.

13. The method according to claim 8 wherein the imaging is performed using fluorescent imaging.

14. The method according to claim 8 wherein the imaging is performed using NIR imaging.

15. The method according to claim 8 wherein the imaging is performed using MRI imaging.

16. The method according to claim 8 wherein the composition comprises the Gadolinium porphyrin based complex and Ln is Gd; or the composition comprises a compound selected from the group consisting of $Gd_1$, $Gd_2$, $Gd_3$, $Gd_4$, and $Gd_5$.

17. A method of synthesizing the composition according to claim 1 wherein Ln=Er or Ln=Yb comprising steps according to the following scheme:

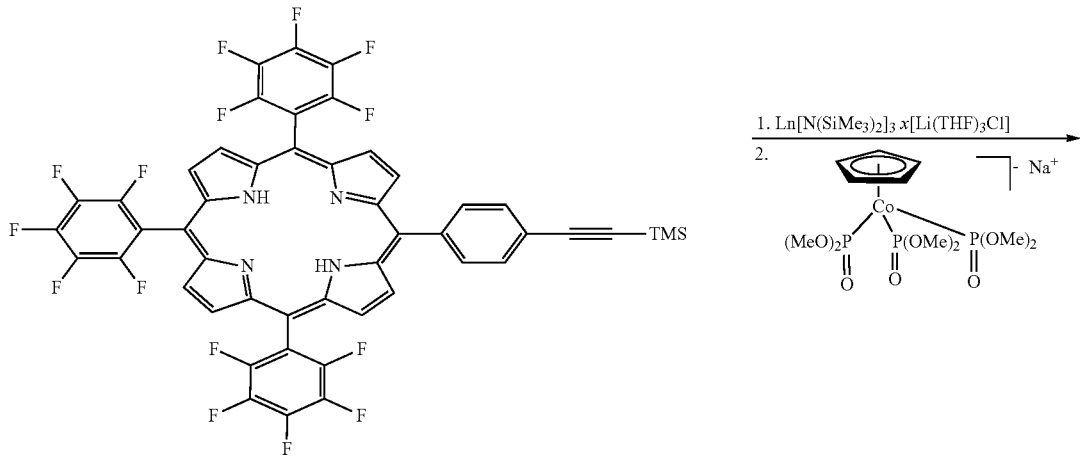

Por(THP—TMS)

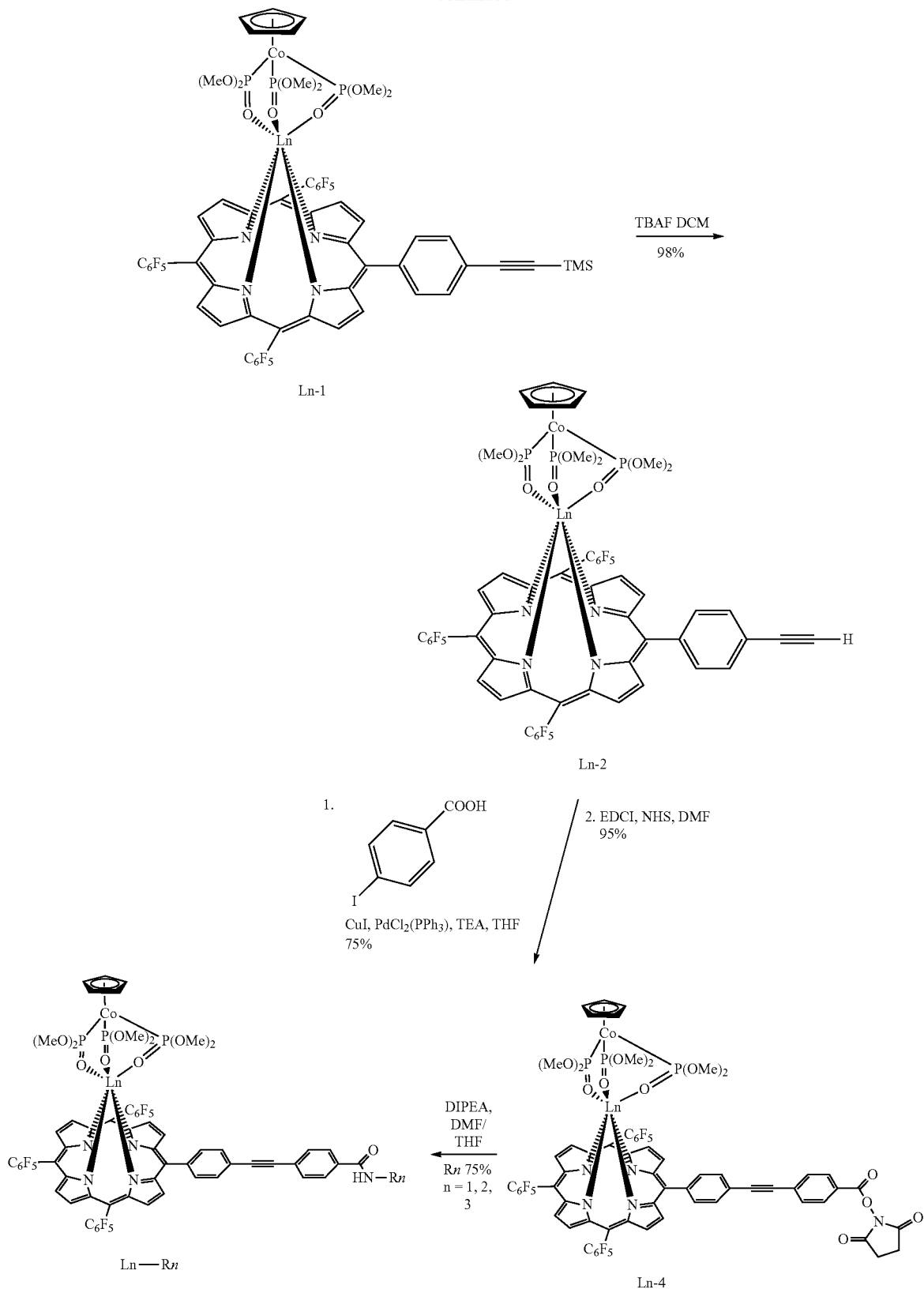

wherein said compound Por(THP-TMS) is synthesized via steps comprising:
dissolving Pyrrole, pentafluorobenzaldehyde and 4-[2-(trimethylsilyl)ethynyl]benzaldehyde 6 in $CH_2Cl_2$ under an argon atmosphere to produce a first solution;
leaving the first solution for at least 10 minutes;
adding $BF_3.O(Et)_2$ to the first solution;
stirring the first solution for at least 1 hour at room temperature;
adding DDQ (2,3-Dichloro-5,6-dicyano-1,4-benzoquinone) to the first solution;
stirring the first solution for at least another 1 hour at room temperature;
removing the solvent from the first solution in vacuo to produce a first mixture;
passing the first mixture through a silica column (hexanes-$CH_2Cl_2$) concentrated under reduced pressure to produce 5,10,15-Tris(pentafluorophenyl)-20-[4-{2-(trimethylsilyl)ethynyl}phenylporphyrin] or Por(THP-TMS);
said compound Ln-1 is synthesized via steps comprising:
dissolving $Ln[N(SiMe_3)2]_3.x[LiCl(THF)_3]$: $HN(SiMe_3)_2$ in THF at about 0 degrees Celcius to produce a second solution;
adding n-BuLi slowly over at least 30-minutes period to the second solution;
stirring the second solution for at least 12 hours;
transferring the second solution to a Schlenk flask with $LnCl_3$ suspended in THF to produce a second mixture;
stirring the second mixture for at least 24 hours until all of the solid $LnCl_3$ disappeared to produce $Ln[N(SiMe_3)2]_3.x[Li(THF)_3Cl]$ (x=3~5) wherein Ln=Er or Ln=Yb;
said compound Yb-1 is further synthesized via steps comprising:
transferring $Yb[N(SiMe_3)2]_3.x[Li(THF)_3Cl]$ (x=3~5) to a Schlenk flask;
removing the solvent from $Yb[N(SiMe_3)2]_3.x[Li(THF)_3Cl]$ (x=3~5) under vacuum to produce a first residue;
adding $CH_2Cl_2$ to the first residue for the precipitation of LiCl to produce a third mixture;
centrifuging the third mixture until a clear layer is produced;
transferring the clear layer to another Schlenk flask with dry Por(THP-TMS) free base dissolved in toluene to produce a third solution;
refluxing the third solution until most of the free base coordinated with the metal ion;
adding dry NaLOMe [LOMe-((cyclopentadienyl)tris(dimethylphosphito)-cobaltate or an anionic tripodalligand) to the third solution to produce a fourth mixture;
stirring the fourth mixture for at least another 12 hours;
cooling down the fourth mixture to room temperature;
removing the solvent from the fourth mixture in vacuum to produce a second residue;
dissolving the second residue in $CHCl_3$;
filtering and chromatographing the dissolved second residue on silica gel using $CHCl_3$/petroleum ether as eluent;
further dissolving the output from chromatography in $CH_2Cl_2$; and filtering the solution to produce compound Yb-1;
Said compound Er-1 is further synthesized via steps comprising:
the same steps as for Yb-1, replacing $Yb[N(SiMe_3)2]_3.x[Li(THF)_3Cl]$ (x=3~5) with $Er[N(SiMe_3)2]_3.x[Li(THF)_3Cl]$ (x=3~5);

said compound Ln-2 wherein Ln=Yr is synthesized via steps comprising:
adding TBAF to a solution of Yb-1 in $CH_2Cl2$ to produce a fifth solution;
stirring the fifth solution for at least 30 minutes;
monitoring the progress of the reaction of the fifth solution by TLC;
after completion of the reaction, passing the fifth solution through a short of silica gel column;
removing the solvent from the fifth solution to produce Yr-2;
said compound Er-2 is further synthesized via steps comprising:
the same steps as for Yb-2, replacing Yb-1 with Er-1;
said compound Ln-4 wherein Ln=Yr is synthesized via steps comprising:
mixing $Pd(PPh_3)_4$, CuI, Yb-2 and 4-iodobenzoic acid in a dried flask under nitrogen to produce a fifth mixture;
adding THF and $Net_3$ to the fifth mixture and degassing said fifth mixture with nitrogen;
stirring said fifth mixture at least 40° C. for at least 12 hours;
removing the solvent from said fifth mixture under reduced pressure to produce a third residue;
purifying the third residue by chromatography;
eluting the purified third residue with $CH_2Cl_2$/Methanol to produce an eluted compound;
mixing the eluted compound, EDCI, NHS in a dried flask and under nitrogen to produce a sixth mixture;
adding dry DMF to the sixth mixture;
stirring the sixth mixture at room temperature for at least 48 hours;
removing the solvent from the stirred sixth mixture to produce a fourth residue;
recrystallizing the fourth residue by diethyl ether and drying the crystals to produce Yb-4;
said compound Er-4 is further synthesized via steps comprising:
the same steps as for Yb-4, replacing Yb-2 with Er-2;
said compound Yb—$R_1$ is synthesized via steps comprising:
mixing a stirred solution of Yb-4 in anhydrous DMF with N,N'-diisopropylethylamine (DIPEA) to produce a seventh mixture;
adding peptide $R_1$ to the seventh mixture;
leaving the seventh mixture to react at room temperature for at least 24 hours;
removing the solvent from the seventh mixture under vacuum to produce a dry fifth residue;
recrystallizing the dry fifth residue by diethyl ether for at least three times;
drying the recrystallized dry fifth residue to produce Yb—$R_1$;
said compound Yb—$R_2$ is further synthesized via steps comprising:
the same steps as for Yb—$R_1$, replacing $R_1$ with $R_2$;
said compound Yb—$R_3$ is further synthesized via steps comprising:
the same steps as for Yb—$R_1$, replacing $R_1$ with $R_3$;
said compound Er—$R_1$ is further synthesized via steps comprising:
the same steps as for Yb—$R_1$, replacing Yb-4 with Er-4;
said compound Er—$R_2$ is further synthesized via steps comprising:
the same steps as for Yb—$R_2$, replacing Yb-4 with Er-4;
said compound Er—$R_3$ is further synthesized via steps comprising:
the same steps as for Yb—$R_3$, replacing Yb-4 with Er-4.

18. A method of synthesizing a composition comprising steps according to the following scheme:

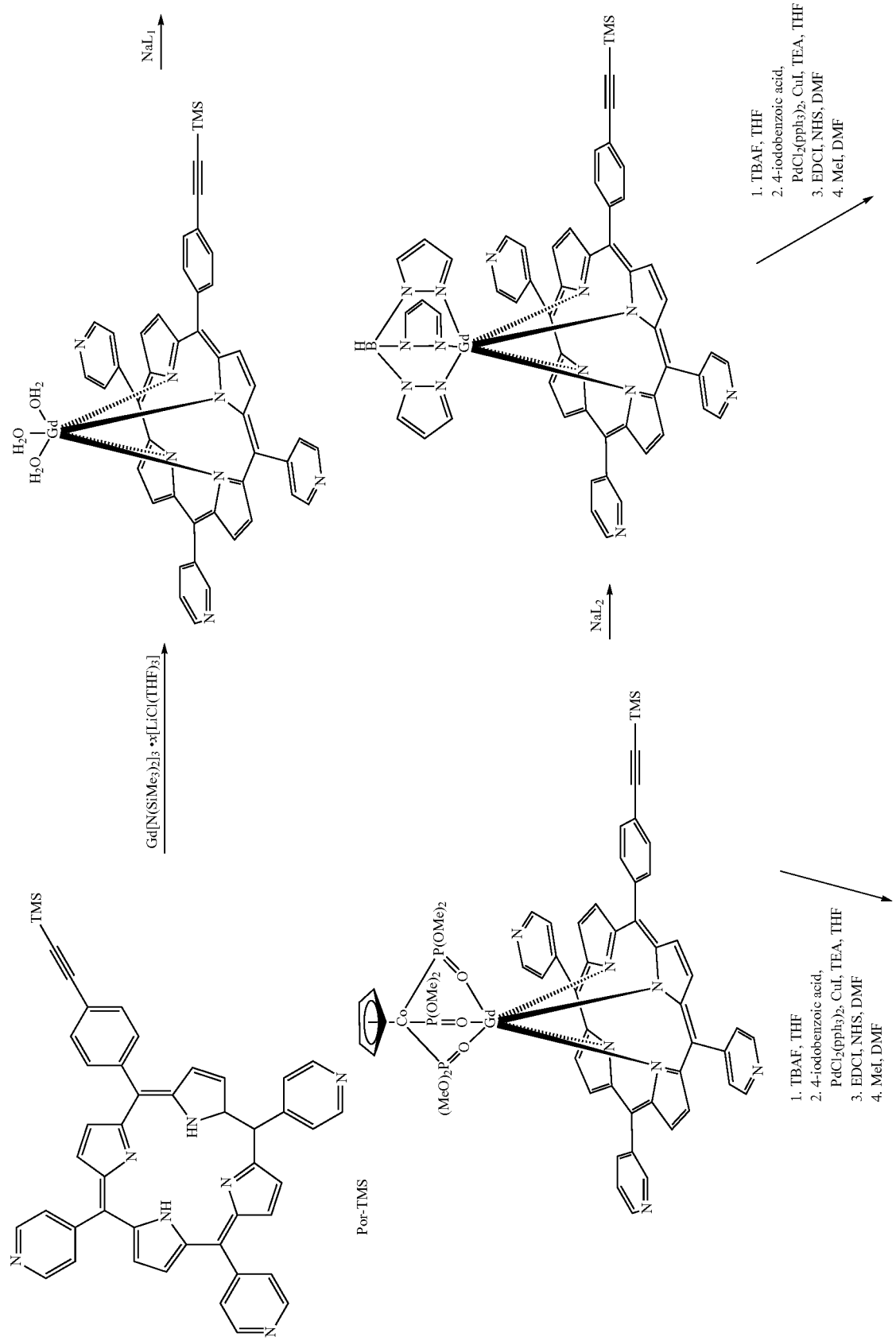

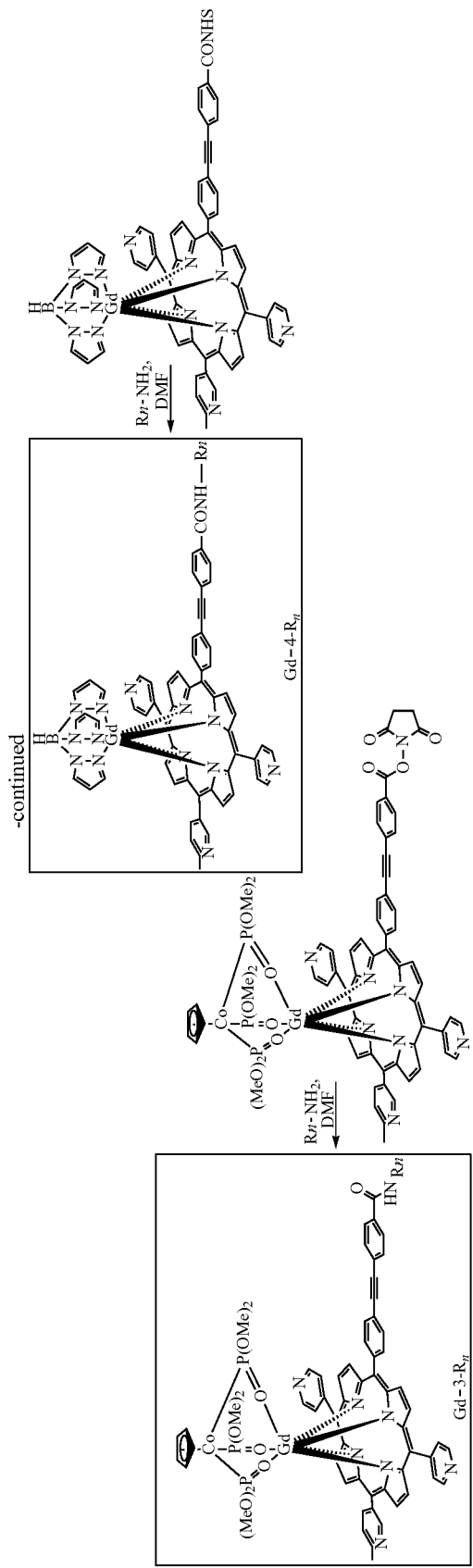

wherein said compound Por-TMS is synthesized via steps comprising:

mixing 4-((trimethylsilyl)ethynyl)benzaldehyde with Pyridine-4-carboxaldehyde in propionic acid to produce an eighth mixture;

stirring the eighth mixture for at least half an hour in at least 130° C.;

adding pyrrole dropwise into the eighth mixture with the temperature increased to at least 140° C.;

stirring the eighth mixture for at least 30 minutes in open air;

cooling down the eighth mixture to room temperature;

removing the solvent from the eighth mixture under reduce pressure to produce a crude product;

dissolving the crude product in $CH_2Cl_2$ to produce a sixth solution;

purifying the sixth solution by column chromatography on silica gel column $CH_2Cl_2$/Methanol to produce Por-TMS;

said compound $Gd[N(SiMe_3)_2]3.x[LiCl(THF)_3]$ is synthesized via steps comprising:

dissolving $HN(SiMe_3)_2$ in THF at about 0 degrees Celcius to produce a seventh solution;

adding n-BuLi to the seventh solution over at least a 30-minutes period;

stirring the seventh solution at least for 12 hours until a clear pale yellow solution was obtained;

transferring the seventh solution a Schlenk flask with $GdCl_3$ suspended in THF to produce a ninth mixture;

stirring the ninth mixture for at least 24 hours until all of the solid $GdCl_3$ disappeared to produce the resultant solution $Gd[N(SiMe_3)_2]_3.x[LiCl(THF)_3]$ (x=3~5);

said compound Gd-1-L1 is synthesized via steps comprising:

transferring $Gd[N(SiMe_3)_2]_3.x[LiCl(THF)_3]$ (x=3~5) to a Schlenk flask and removing the solvent therein under vacuum to produce a sixth residue;

adding $CH_2Cl_2$ to the sixth residue for the precipitation of LiCl to produce a tenth mixture;

centrifuging the tenth mixture until a clear layer is produced;

transferring the clear layer to another Schlenk flask with dry Por-TMS free base dissolved in toluene to produce an eighth solution;

refluxing the eighth solution until most of the free base coordinated with the metal ion;

adding dry $NaL_1$ (0.1 g, 0.22 mmol) [$L_1$-((cyclopentadienyl)tris(dimethylphosphito)-cobaltate, an anionic tripodal ligand) to the eighth solution to produce an eleventh mixture;

stirring the eleventh mixture for at least another 12 hours;

cooling down the eleventh mixture to room temperature;

removing the solvent from the eleventh mixture in vacuum to produce a seventh residue;

dissolving the seventh residue in $CHCl_3$;

filtering and chromatographing the dissolved second residue on silica gel using $CHCl_3$/$CH_3OH$ ether as eluent;

further dissolving the output from chromatography in $CH_2Cl_2$; and filtering the dissolved output to produce compound Gd-1-L1;

Said compound Gd-1-L2 is synthesized via steps comprising:

the same steps as for Gd-1-L1, replacing $NaL_1$ with $KL_2$ (potassium tris(1-pyrazolyl) borohydride);

said compound Gd-3 is synthesized via steps comprising:

adding TBAF to a solution of Gd-1-L1 in DCM to produce a ninth solution;

stirring the ninth solution for at least 30 minutes;

monitoring the reaction of the ninth solution by TLC;

passing the ninth solution through a short of silica gel column using DCM to remove the solvent therein to produce a pure product;

placing the pure product and $Pd(PPh_3)_4$, CuI, 4-iodobenzoic acid in a dried flask and under nitrogen to produce a twelfth mixture;

adding THF and $Net_3$ to the twelfth mixture;

degassing the twelfth mixture with nitrogen;

stirring the twelfth mixture at a temperature at least 40° C. for at least 12 hours;

removing the solvent from the twelfth mixture under reduced pressure to produce an eighth residue;

purifying the eighth residue by chromatography;

eluting the purified eighth residue with $CH_2Cl_2$/Methanol;

placing the eluted purified eighth residue, EDCI, NHS in a dried flask and under nitrogen to produce a thirteenth mixture;

adding dry DMF to the thirteenth mixture;

stirring the thirteenth mixture at room temperature for at least 48 hours;

removing the solvent from the thirteenth mixture to produce a ninth residue;

recrystallizing the ninth residue by diethyl ether and dried said crystals to produce Gd-3;

dissolving the Gd-3 in DMF;

adding $CH_3I$ to the dissolved Gd-3;

stirring the dissolved Gd-3 for at least 5 hours;

removing the solvent from the stirred dissolved Gd-3 to produce a tenth residue;

washing the tenth residue with ether .DCM. to produce pure Gd-3;

said compound Gd-4 is synthesized via steps comprising:

the same steps as for Gd-3, replacing Gd-1-L1 with Gd-1-L2;

said compound Gd-3-Rn is synthesized via steps comprising:

mixing a stirred solution of Gd-3 in anhydrous DMF with N,N'-diisopropylethylamine (DIPEA) to produce a fourteenth mixture;

adding peptide Rn to the fourteenth mixture;

reacting the fourteenth mixture at room temperature for at least 24 hours;

removing the solvent from the fourteenth mixture under vacuum to produce a dry eleventh residue;

recrystallizing the dry eleventh residue by diethyl ether for at least three times and further dry the result to produce Gd-3-Rn;

said compound Gd-4-Rn is synthesized via steps comprising:

the same steps as for Gd-3-Rn, replacing Gd-3 with Gd-4.

* * * * *